United States Patent
Bachmann et al.

(10) Patent No.: US 7,128,911 B2
(45) Date of Patent: *Oct. 31, 2006

(54) ANTIGEN ARRAYS FOR TREATMENT OF BONE DISEASE

(75) Inventors: Martin F. Bachmann, Seuzach (CH); Patrik Maurer, Winterthur (CH); Gunther Spohn, Zürich (CH)

(73) Assignee: Cytos Biotechnology AG, Zurich-Schlieren (CH)

( * ) Notice: Subject to any disclaimer, the term of this patent is extended or adjusted under 35 U.S.C. 154(b) by 509 days.

This patent is subject to a terminal disclaimer.

(21) Appl. No.: 10/289,456

(22) Filed: Nov. 7, 2002

(65) Prior Publication Data

US 2004/0033211 A1 Feb. 19, 2004

Related U.S. Application Data

(63) Continuation-in-part of application No. PCT/IB02/00166, filed on Jan. 21, 2002, and a continuation-in-part of application No. 10/050,902, filed on Jan. 18, 2002.

(60) Provisional application No. 60/396,635, filed on Jul. 19, 2002, provisional application No. 60/331,045, filed on Nov. 7, 2001, provisional application No. 60/326,998, filed on Oct. 5, 2001, provisional application No. 60/288,549, filed on May 4, 2001, provisional application No. 60/262,379, filed on Jan. 19, 2001.

(51) Int. Cl.
*A61K 39/385* (2006.01)
*A61K 38/22* (2006.01)
*A61K 9/00* (2006.01)
*C07K 17/00* (2006.01)

(52) U.S. Cl. .............................. 424/185.1; 424/193.1; 424/194.1; 424/195.11; 424/400; 530/403; 530/404

(58) Field of Classification Search ................ 424/400, 424/185.1, 193.1, 194.1, 195.11, 198.1, 278.1, 424/288.1, 281.1; 530/350, 403, 404
See application file for complete search history.

(56) References Cited

U.S. PATENT DOCUMENTS

| | | |
|---|---|---|
| 4,722,840 A | 2/1988 | Valenzuela et al. |
| 5,071,651 A | 12/1991 | Sabara et al. |
| 5,143,726 A | 9/1992 | Thornton et al. |
| 5,334,394 A | 8/1994 | Kossovsky et al. |
| 5,374,426 A | 12/1994 | Sabara et al. |
| 5,580,859 A | 12/1996 | Felgner et al. |
| 5,698,424 A | 12/1997 | Mastico et al. |
| 5,739,026 A | 4/1998 | Garoff et al. |
| 5,766,602 A | 6/1998 | Xiong et al. |
| 5,770,380 A | 6/1998 | Hamilton et al. |
| 5,789,245 A | 8/1998 | Dubensky, Jr. et al. |
| 5,792,462 A | 8/1998 | Johnston et al. |
| 5,814,482 A | 9/1998 | Dubensky, Jr. et al. |
| 5,843,678 A | 12/1998 | Boyle |
| 5,935,821 A | 8/1999 | Chatterjee et al. |
| 5,939,598 A | 8/1999 | Kucherlapati et al. |
| 6,231,864 B1 | 5/2001 | Birkett |
| 6,242,213 B1 | 6/2001 | Anderson |
| 6,242,586 B1 | 6/2001 | Gorman et al. |
| 6,380,364 B1 | 4/2002 | Mueller et al. |
| 2002/0064533 A1 | 5/2002 | Murray |
| 2002/0081295 A1 | 6/2002 | Schiller et al. |
| 2003/0175290 A1 | 9/2003 | Renner et al. |
| 2003/0175711 A1* | 9/2003 | Renner et al. .................. 435/6 |
| 2004/0033211 A1 | 2/2004 | Bachmann et al. |
| 2004/0059094 A1 | 3/2004 | Bachmann et al. |
| 2004/0076611 A1 | 4/2004 | Bachmann et al. |
| 2004/0076645 A1 | 4/2004 | Bachmann et al. |
| 2004/0141984 A1 | 7/2004 | Bachmann et al. |

FOREIGN PATENT DOCUMENTS

| | | |
|---|---|---|
| EP | 0 259 149 B1 | 12/1993 |
| EP | 0 385 610 B1 | 3/1994 |
| EP | 0 283 505 B1 | 7/1994 |
| EP | 0 421 635 B1 | 7/1995 |
| EP | 0 677 111 B1 | 5/1997 |
| JP | 2000-102390 | 4/2000 |
| WO | WO 92/11291 A1 | 7/1992 |
| WO | WO 92/13081 | 8/1992 |
| WO | WO 94/06472 A1 | 3/1994 |
| WO | WO 96/05293 A1 | 2/1996 |
| WO | WO 96/30523 A2 | 10/1996 |

(Continued)

OTHER PUBLICATIONS

Hertz et al. Journal of Bone and Mineral Research Suppl. 1, p. S222, abstract F422, Sep. 2001.*

(Continued)

*Primary Examiner*—Mary E. Mosher
(74) *Attorney, Agent, or Firm*—Sterne, Kessler, Goldstein & Fox PLLC

(57) ABSTRACT

The present invention is related to the fields of molecular biology, virology, immunology and medicine. The invention provides a composition comprising an ordered and repetitive antigen or antigenic determinant array, and in particular a RANKL protein, RANKL fragment or RANKL peptide-VLP-array. More specifically, the invention provides a composition comprising a virus-like particle and at least one RANKL protein, RANKL fragment or RANKL peptide bound thereto. The invention also provides a process for producing the conjugates and the ordered and repetitive arrays, respectively. The compositions of the invention are useful in the production of vaccines for the treatment of bone diseases and as a pharmaccine to prevent or cure bone diseases and to efficiently induce immune responses, in particular antibody responses. Furthermore, the compositions of the invention are particularly useful to efficiently induce self-specific immune responses within the indicated context.

55 Claims, 12 Drawing Sheets

FOREIGN PATENT DOCUMENTS

| WO | WO 98/46751 | | 10/1998 |
|---|---|---|---|
| WO | WO 99/29865 | A2 | 6/1999 |
| WO | WO 99/29865 | A3 | 6/1999 |
| WO | WO 99/40934 | A1 | 8/1999 |
| WO | WO 99/57289 | | 11/1999 |
| WO | WO 00/15807 | | 3/2000 |
| WO | WO 00/23955 | * | 4/2000 |
| WO | WO 01/77158 | A1 | 10/2001 |
| WO | WO 01/85208 | A2 | 11/2001 |
| WO | WO 01/98333 | A2 | 12/2001 |
| WO | WO 01/98333 | A3 | 12/2001 |
| WO | WO 02/14478 | A2 | 2/2002 |
| WO | WO 2005/117963 | A1 | 12/2005 |
| WO | WO 2005/117983 | A2 | 12/2005 |

OTHER PUBLICATIONS

Abraham, J.M., et al., "An invertible element of DNA controls phase variation of type 1 fimbriae of *Escherichia coli*,"*Proc. Natl. Acad. Sci. USA* 82:5724-5727, National Academy Press (1985).

Abraham, S.N., et al., "Glycerol-Induced Unraveling of the Tight Helical Conformation of *Escherichia coli* Type 1 Fimbriae," *J. Bacteriol.* 174:5145-5148, American Society for Microbiology (1992).

Adhin, M.R., et al., "Nucleotide Sequence from the ssRNA Bacteriophage JP34 Resolves the Discrepancy between Serological and Biophysical Classification," *Virology* 170:238-242, Academic Press, Inc. (1989).

Aguzzi, A., "Prion diseases, blood and the immune system: concerns and reality," *Haematologica* 85:3-10, Il Pensiero Scientifico Editore (Jan. 2000).

Ansel, K.M., et al., "In Vivo-activated CD4 T Cells Upregulate CXC Cheomkine Receptor 5 and Reprogram Their Response to Lymphoid Chemokines," *J. Exp. Med.* 190:1123-1134, The Rockefeller University Press (1999).

Ansel, K.M., et al., "A chemokine-driven positive feedback loop organizes lymphoid follicles," *Nature* 406:309-314, Nature Publishing Group (Jul. 2000).

Antonysamy, M.A., et al., "Evidence for a Role of IL-17 in Organ Allograft Rejection: IL-17 Promotes the Functional Differentiation of Dendritic Cell Progenitors," *J. Immunol.* 162:577-584, The American Association of Immunologists (1999).

Arenberg, D.A., et al., "The murine CC chemokine, 6C-kine, inhibits tumor growth and angiogenesis in a human lung cancer SCID mouse model," *Cancer Immunol. Immunother.* 49:587-592, Springer-Verlag (Jan. 2001).

Arnon, R., et al., "A mimotope peptide-based vaccine against *Schistosoma mansoni*: synthesis and characterization," *Immunology* 101:555-562, Blackwell Science, Ltd. (Dec. 2000).

Bachmann, M.F., and Zinkernagel, R.M., "The influence of virus structure on antibody responses and virus serotype formation," *Immunol. Today* 17:553-558, Elsevier Science, Ltd. (1996).

Bachmann, M.F., and Zinkernagel, R.M., "Neutralizing Antiviral B Cell Responses," *Annu. Rev. Immunol.* 15:235-270, Annual Reviews, Inc. (1997).

Bachmann, M.F., et al., "TRANCE, a Tumor Necrosis Factor Family Member Critical for CD40 Ligand-independent T Helper Cell Activation," *J. Exp. Med.* 189:1025-1031, The Rockefeller University Press (1999).

Banerjee, R.R., and Lazar, M.A., "Dimerization of Resistin and Resistin-like Molecules Is Determined by a Single Cysteine," *J. Biol. Chem.* 276:25970-25973, The American Society for Biochemistry and Molecular Biology, Inc. (Jul. 2001).

Bard, F. et al., "Peripherally administered antibodies against amyloid β-peptide enter the central nervous system and reduce pathology in a mouse model of Alzheimer disease," *Nat. Med.* 6:916-919, Nature Publishing Company (Aug. 2000).

Bass, S., and Yang, M., "Expressing cloned genes in *Escherichia coli*," in *Protein Function: A Practical Approach*, 2nd ed., Creighton, T.E., ed., IRL Press, Oxford, Great Britain, pp. 29-55 (1997).

Bernhagen, J., et al., "Purification, Bioactivity, and Secondary Structure Analysis of Mouse and Human Macrophage Migration Inhibitory Factor (MIF)," *Biochemistry* 33:14144-14155, American Chemical Society (1994).

Biaselle, C.J., and Millar, D.B., "Studies on Triton X-100 detergent micelles," *Biophys. Chem.* 3:355-361, North-Holland Publushing Company (1975).

Bleul, C.C., et al., "The lymphocyte chemoattractant SDF-1 is a ligand for LESTR/fusin and blocks HIV-1 entry," *Nature* 382:829-833, Nature Publishing Group (1996).

Blomfield, I.C., et al., "Type 1 Fimbriation and *fimE* Mutants of *Escherichia coli* K-12," *J. Bacteriol.* 173:5298-5307, American Society for Microbiology (1991).

Blomfield, I.C., et al., "Integration host factor stimulates both FimB- and FimE- mediated site-specific DNA inversion that controls phase variation of type 1 fimbriae expression in *Escherichia coli*," *Mol. Microbiol.* 23:705-717, Blackwell Science, Ltd. (1997).

Boder, E.T., and Wittrup, K.D., "Yeast Surface Display for Directed Evolution of Protein Expression, Affinity, and Stability," *Methods Enzymol.* 328:430-444, Academic Press (Oct. 2000).

Adams, S.E., et al., "The expression of hybrid HIV:Ty virus-like particles in yeast," *Nature* 329:68-70, Macmillan Publishers Ltd (1987).

Anderson, D.M., et al., "A homologue of the TNF receptor and its ligand enhance T-cell growth and dendritic-cell function," *Nature* 390(6656):175-179, Macmillan Publishers Ltd. (1997).

Bachmann, M.F., et al., "Dendritic cells process exogenous viral proteins and virus-like particles for class I presentation to CD8+ cytotoxic T lymphocytes," *Eur. J. Immunol.* 26:2595-2600, VCH Verlagsgesellschaft mbH (1996).

Bachmann, M.F., et al., "The influence of antigen organization on B cell responsiveness," *Science* 262(5138):1448-1451, American Association for the Advancement of Science (1993).

Bekker, P.J., et al., "The effect of a single dose of osteoprotegerin in postmenopausal women," *J Bone Miner Res* 16(2):348-360, American Society for Bone and Mineral Research (Feb. 2001).

Body, J.J., et al., "A phase I study of AMGN-0007, a recombinant osteoprotegerin construct, in patients with multiple myeloma or breast carcinoma related bone metastases," *Cancer* 97(3 Suppl):887-892, American cancer Society (Feb. 2003).

Borisova, G., et al., "Hybrid Hepatitis B Virus Nucleocapsid Bearing an Immunodominant Region from Hepatitis B Virus Surface Antigen," *J. Virol.* 67:3696-3701, American Society for Microbiology (1993).

Brown, W.L., et al., "RNA bacteriophage capsid-mediated drug delivery and epitope presentation," *Intervirology* 45(4-6):371-80, S. Karger AG, Basel (Jul.-Dec. 2002).

Bucay, N., et al., "*Osteoprotegerin*-deficient mice develop early onset osteoporosis and arterial calcification," *Genes & Develop.* 12:1260-1268, Cold Spring Laboratory Press (1998).

Chackerian, B., et al., "Conjugation of a self-antigen to papillomavirus-like particles allows for efficient induction of protective autoantibodies," *J Clin Invest* 108(3):415-23, High Wire Press (Aug. 2001).

Chackerian, B., et al., "Determinants of autoantibody induction by conjugated papillomavirus virus-like particles," *J. Immunol.* 169:6120-6126, The American Association of Immunologists (Dec. 2002).

Chackerian, B., et al., "Induction of autoantibodies to mouse CCR5 with recombinant papillomavirus particles," *Proc. Natl. Acad. Sci. USA* 96:2373-2378, National Academy of Sciences (1999).

Cielens, I., et al., "Mutilation of RNA phage Qbeta virus-like particles: from icosahedrons to rods," *FEBS Lett* 482(3):261-4, Elsevier Science (Oct. 2000).

Dougall, W.C., et al., "RANK is essential for osteoclast and lymph node development," *Genes & Develop.* 13:2412-2424, Cold Spring Harbor Laboratory Press (1999).

Emery, J.G., et al., "Osteoprotegerin is a receptor for the cytotoxic ligand TRAIL," *J Biol Chem* 273(23):14363-7, The American Society for Biochemistry and Molecular Biology (1998).

Fata, J.E., et al.,"The osteoclast differentiation factor osteoprotegerin-ligand is essential for mammary gland development," *Cell* 103(1):41-50, Cell Press (Sep. 2000).

Fehr, T., et al., "Role of Repetitive Antigen Patterns for Induction of Antibodies Against Antibodies," *J Exp. Med.* 185:1785-1792, The Rockefeller University Press (1997).

Fehr, T., et al., "T cell-independent type I antibody response against B cell epitopes expressed repetitively on recombinant virus particles," *Proc. Natl. Acad. Sci. USA* 95:9477-9481, National Academy Press (1998).

Goater, J.J., et al., "Efficacy of ex vivo OPG gene therapy in preventing wear debris induced osteolysis," *J. Orth. Res.* 20:169-173, Elsevier Science Ltd (Mar. 2002).

Golmohammadi, R., et al., "The crystal structure of bacteriophage Qβ at 3.5Å resolution," *Structure* 4:543-554, Current Biology, Ltd. (1996).

Gowen, M., et al., "Emerging therapies for osteoporosis," *Expert Opin Emerg Drugs* 5:1-43, Ashley Publications Ltd. (Feb. 2000).

Groom, J., et al., "Association of BAFF/BLyS overexpression and altered B cell differentiation with Sjogren's syndrome," *J Clin Invest* 109(1):59-68, American Society for Clinical Investigation (Jan. 2002).

Hofbauer, L.C and Heufelder, A.E., "The Role of Receptor Activator of Nuclear Factor-6B Ligand and Osteoprotegerin in the Pathogenesis and Treatment of Metabolic Bone Diseases," *J. Clin. Endocrin. Meta.* 85:2355-2363, The Endocrine Society (Jul. 2000).

Hui, E. K-W. et al., "Hepatitis B viral core proteins with an N-terminal extension can assemble into core-like particles but cannot be enveloped," *J. Gen. Virol.* 80:2647-2659, Society for General Microbiology (1999).

Ikeda, T., et al., "Determination of Three Isoforms of the Receptor Activator of Nuclear Factor-κB Ligand and Their Differential Expression in Bone and Thymus," *Endocrinology* 142:1419-1426, The Endocrine Society (Apr. 2001).

Jegerlehner, A., et al., "A molecular assembly system that renders antigens of choice highly repetitive for induction of protective B cell responses," *Vaccine* 20:3104-3112, Elsevier Science, Ltd. (Aug. 2002).

Josien, R., et al., "TRANCE, a Tumor Necrosis Factor Family Member, Enhances the Longevity and Adjuvant Properties of Dendritic Cells In Vivo," *J. Exp. Med.* 191:495-501, The Rockefeller University Press (Feb. 2000).

Juji, T., et al., "A novel therapeutic vaccine approach, targeting RANKL, prevents bone destruction in bone-related disorders," *J. Bone Miner. Metab.* 20:266-268, Springer-Verlag (Sep. 2002).

Kastelein, R.A. et al., "Effect of the sequence upstream from the ribosome-binding site on the yield of protein from the cloned gene for phage MS2 coat protein," *Gene* 23:245-254, Elsevier (1983).

Kim, D., et al., "Regulation of peripheral lymph node genesis by the tumor necrosis factor family member TRANCE," *J Exp Med* 192(10):1467-1478, Rockefeller University Press (Nov. 2000).

Kim, N., et al., "Diverse roles of the tumor necrosis factor family member TRANCE in skeletal physiology revealed by TRANCE deficiency and partial rescue by a lymphocyte-expressed TRANCE transgene," *Proc. Natl. Acad. Sci.* 97:10905-10910, National Academy of Sciences (Sep. 2000).

Kimbauer, R., et al., "Papillomavirus L1 major capsid protein self-assembles into virus-like particles that are highly immunogenic," *Proc. Natl. Acad. Sci. USA* 89:12180-12184, National Academy of Sciences (1992).

Klovins, J., et al., "Nucleotide sequence of a ssRNA phage from *Acinetobacter*: kinship to coliphages," *J. Gen. Virol.* 83:1523-1533, Society for General Microbiology (Jun. 2002).

Kong, Y.-Y., et al., "Activated T cells regulate bone loss and joint destruction in adjuvant arthritis through osteoprotegerin ligand," *Nature* 402:304-309, Nature Publishing Group (1999).

Kong, Y.-Y., et al., "OPGL is a key regulator of osteoclastogenesis, lymphocyte development and lymph-node organogenesis," *Nature* 397:315-323, Nature Publishing Group (1999).

Koschel, M., et al., "Extensive Mutagenesis of the Hepatitis B Virus Core Gene and Mapping of Mutations That Allow Capsid Formation," *J. Virol* 73:2153-2160, American Society for Microbiology (1999).

Kozlovska, T.M., et al., "Recombinant RNA phage Qβ capsid particles synthesized and self-assembled in *Escherichia coli*," *Gene* 137:133-137, Elsevier Science Publishers B.V. (1993).

Kozlovska, T.M., et al., "RNA Phage Qβ Coat Protein as a Carrier for Foreign Epitopes," *Intervirology* 39:9-15, S. Karger AG (1996).

Kozlovskaya, T.M., et al., "Formation of capsid-like structures as a result of the expression of a cloned envelope protein gene from RNA-containing bacteriophage fr," *Dokl. Akad. Nauk. SSSR* 287:452-455, Erivan Akademiia Nauk Armianskoi Ssr (1986); and unverified English-language abstract from STNEasy/CAPlus.

Kratz, P.A., et al., "Native display of complete foreign protein domains on the surface of hepatitis B virus capsids," *Proc. Natl. Acad. Sci. USA* 96:1915-1920, National Academy of Sciences (1999).

Lacey, D.L., et al., "Osteoprotegerin Ligand Is a Cytokine that Regulates Osteoclast Differentiation and Activation," *Cell* 93:165-176, Cell Press (1998).

Lam, J., et al., "Crystal structure of the TRANCE/RANKL cytokine reveals determinants of receptor-ligand specificity," *J. Clin. Invest.* 108:971-979, American Society for Clinical Investigation (Oct. 2001).

Lamhamedi-Cherradi, S.-E., et al., "Defective thymocyte apoptosis and accelerated autoimmune diseases in TRAIL-/- mice," *Nat Immunol* 4(3):255-260, Nature Publishing Group (Mar. 2003).

Lechner, F., et al., "Virus-like particles as a modular system for novel vaccines," *Intervirology* 45 (4-6):212-217, S. Karger AG, Basel (Jul.-Dec. 2002).

Li, J., et al., "RANK is the intrinsic hematopoietic cell surface receptor that controls osteoclastogenesis and regulation of bone mass and calcium metabolism," *Proc. Natl. Acad. Sci. USA* 97:1566-1571, National Academy of Sciences (Feb. 2000).

Lim, F., et al., "The RNA-binding Site of Bacteriophage Qβ Coat Protein," *J. Biol. Chem.* 271:31839-31845, The American Society for Biochemistry and Molecular Biology, Inc. (1996).

Lo-Man, R., et al., "A recombinant virus-like particle system derived from parvovirus as an efficient antigen carrier to elicit a polarized Th1 immune response without adjuvant," *Eur. J. Immunol.* 28:1401-1407, Wiley-VCH Verlag GmbH (1998).

Luger, N.M., et al., "Osteoprotegerin Diminishes Advanced Bone Cancer Pain," *Cancer Res.* 61:4038-4047, American Association for Cancer Research (May 2001).

Lum, L., et al., "Evidence for a Role of a Tumor Necrosis Factor-α(TNF-α)-converting Enzyme-like Protease in Shedding of TRANCE, a TNF Family Member Involved in Osteoclastogenesis and Dendritic Cell Survival," *J. Biol. Chem.* 274:13613-13618, The American Society for Biochemistry and Molecular Biology, Inc. (1999).

Mackay, F., and Kalled, S.L., "TNF ligands and receptors in autoimmunity: an update," *Curr Opin Immunol* 14(6):783-790, Elsevier Science Ltd. (Dec. 2002).

Min, H., et al., "Osteoprotegerin Reverses Osteoporosis by Inhibiting Endosteal Osteoclasts and Prevents Vascular Calcification by Blocking a Process Resembling Osteoclastogenesis," *J. Exp. Med.* 192:463-474, The Rockefeller University Press (Aug. 2000).

Neurath, A.R., et al., "Hepatitis B Virus surface antigen (HBsAg) as carrier for synthetic peptides having an attached hydrophobic tail," *Mol. Immunol.* 26:53-62, Pergamon Press (1989).

Ni, C.-Z., et al., "Crystal structure of the coat protein from the GA bacteriophage: Model of the unassembled dimer," *Protein Sci.* 5:2485-2493, Cambridge University Press (1996).

Nieland, J.D., et al., "Chimeric Papillomavirus Virus-like Particles Induce a Murine Self-Antigen-Specific Protective and Therapeutic Antitumor Immune Response," *J. Cell. Biochem.* 73:145-152, Wiley-Liss, Inc. (1999).

Pearse, R.N., et al., "Multiple myeloma disrupts the TRANCE/osteoprotegerin cytokine axis to trigger bone destruction and promote tumor progression," *Proc. Natl. Acad. Sci. USA* 98:11581-11586, National Academy of Sciences (Sep. 2001).

Priano, C., et al., "A Complete Plasmid-based Complementation System for RNA Coliphage Qβ: Three Proteins of Bacteriophages Qβ (Group III) and SP (Group IV) can be Interchanged," *J. Mol. Biol.* 249:283-297, Academic Press, Ltd. (1995).

Pumpens, P. and Grens, E., "HBV Core Particles as a Carrier for B Cell/T Cell Epitopes," *Intervirol.* 44:98-114, Karger AG (Mar.-Jun. 2001).

Pumpens, P. and Grens, E., "Hepatitis B core particles as a universal display model: a structure-function basis for development," *FEBS Lett. 442*:1-6, Elsevier Science B.V. on behalf of the Federation of European Biochemical Societies (1999).

Pushko, P., et al., "Analysis of RNA phage *fr* coat protein assembly by insertion, deletion and substitution mutagenesis," *Prot. Eng. 6*:883-891, IRL Press at Oxford University Press (1993).

Redlich, K., et al., "Tumor necrosis factor alpha-mediated joint destruction is inhibited by targeting osteoclasts with osteoprotegerin," *Arthritis Rheum 46*(3):785-792, American College of Rheumatology (Mar. 2002).

Romagnani, S., "The Th1/Th2 paradigm," *Immunol. Today 18*:263-266, Elsevier Science, Ltd. (1997).

Roschke, V., et al., "BLyS and APRIL form biologically active heterotrimers that are expressed in patients with systemic immune-based rheumatic diseases," *J Immunol 169*(8):4314-4321, The American Association of Immunologists (Oct. 2002).

Roth, J.-F., "The yeast Ty virus-like particles," *Yeast 16*:785-795, John Wiley & Sons, Ltd. (Jun. 2000).

Rueda, P., et al., "Minor Displacements in the Insertion Site Provoke Major Differences in the Induction of Antibody Responses by Chimeric Parvovirus-like Particles," *Virol. 263*:89-99, Academic Press (1999).

Sedlik, C., et al., "Recombinant parvovirus-like particles as an antigen carrier: A novel nonreplicative exogenous antigen to elicit protective antiviral cytotoxic T cells," *Proc. Natl. Acad. Sci. USA 94*:7503-7508, National Academy Press (1997).

Senior, K., "Vaccinating against bone destruction," *Drug Discov. Today 6*:1243-1244, Elsevier Science, Ltd. (Dec. 2001).

Simonet, W.S., et al., "Osteoprotegerin: A Novel Secreted Protein Involved in the Regulation of Bone Density," *Cell 89*:309-319, Cell Press (1997).

Stoll, E., et al., "Revised Amino Acid Sequence of Qbeta Coat Protein between Positions 1 and 60," *J. Biol. Chem. 252*:990-993, The American Society of Biological Chemists, Inc. (1977).

Stomi, T., et al., "Critical role for activation of antigen-presenting cells in priming of cytotoxic T cell responses after vaccination with virus-like particles," *J Immunol 168*(6):2880-2886, The American Association of Immunologists (Mar. 2002).

Taylor, K.M., et al., "Position-Dependent Processing of Peptides Presented on the Surface of Cowpea Mosaic Virus," *Biol. Chem. 380*:387-392, Walter de Gruyter (1999).

Teng, Y.-T.A., et al., "Functional human T-cell immunity and osteoprotegerin ligand alveolar bone destruction in periodontal infection," *J. Clin. Invest. 106*:R59-R67, American Society for Clinical Investigation (Sep. 2000).

Theill, L.E., et al., "RANK-L and RANK: T cells, bone loss, and mammalian evolution," *Annu Rev Immunol 20*:795-823, Annual Reviews (first available online Oct. 2001).

Twomey, T., et al., "Structure and immunogenicity of experimental foot-and-mouth disease and poliomyelitis vaccines," *Vaccine 13*:1603-1610, Elsevier Science, Ltd. (1995).

Ulrich, R., et al., "Core particles of hepatitis B virus as carrier for foreign epitopes," *Adv. Virus Res. 50*:141-182, Academic Press (1998).

Vasiljeva, I., et al., "Mosaic Qbeta coats as a new presentation model," *FEBS Lett. 431*:7-11, Federation of European Biochemical Societies (1998).

Walsh, M.C., and Choi, Y., "Biology of the TRANCE axis," *Cytokine Growth Factor Rev.* 14(3-4):251-263, Elsevier Science Ltd. (Jun.-Aug. 2003).

Warnes, A., et al., "Expression of the measles virus nucleoprotein gene in *Escherichia coli* and assembly of nucleocapsid-like structures," *Gene 160*:173-178, Elsevier Science B.V. (1995).

Wiley, S.R., et al., "Identification and characterization of a new member of the TNF family that induces apoptosis," *Immunity 3*(6):673-682, Cell Press (1995).

Willard, D., et al., "Expression, Purification, and Characterization of the Human Receptor Activator of NF-6B Ligand (RANKL) Extracellular Domain," *Protein Expr. Purif. 20*:48-57, Academic Press (Oct. 2000).

Witherell, G.W., and Uhlenbeck, O.C., "Specific RNA Binding by Qβ Coat Protein," *Biochemistry 28*:71-76, American Chemical Society (1989).

Wong, B.R., et al., "TRANCE Is a Novel Ligand of the Tumor Necrosis Factor Receptor Family That Activates c-Jun N-terminal Kinase in T Cells," *J. Biol. Chem. 272*:25190-25194, The American Society of Biochemistry and Molecular Biology, Inc. (1997).

Wynne, S.A., et al., "The Crystal Structure of the Human Hepatitis B Virus Capsid," *Mol. Cell 3*:771-780, Cell Press (1999).

Xu, J., et al., "Cloning, Sequencing, and Functional Characterization of the Rat Homologue of Receptor Activator of NF-6B Ligand," *J. Bone Miner. Res. 15*:2178-2186, American Society for Bone and Mineral Research (Nov. 2000).

Yasuda, H., et al., "Osteoclast differentiation factor is a ligand for osteoprotegerin/osteoclastogenesis-inhibitory factor and is identical to TRANCE/RANKL," *Proc. Natl. Acad. Sci. USA 95*:3597-3602, National Academy of Sciences (1998).

Yuan, T-T., et al., "Subtype-Independent Immature Secretion and Subtype-Dependent Replication Deficiency of a Highly Frequent, Naturally Occurring Mutation of Human Hepatitis B Virus Core Antigen," *J. Virol. 73*:10122-10128, American Society for Microbiology (1999).

Zhang, J., et al., "Osteoprotegerin inhibits prostate cancer-induced osteoclastogenesis and prevents prostate tumor growth in the bone," *J. Clin. Invest. 107*:1235-1244, American Society for Clinical Investigation (May 2001).

Zhou, S., and Standring, D.N., "Cys Residues of the Hepatitis B Virus Capsid Protein Are Not Essential for the Assembly of Viral Core Particles but Can Influence Their Stability," *J. Virol. 66*:5393-5398, American Society for Microbiology (1992).

* cited by examiner

ANTIGEN ARRAYS FOR TREATMENT OF BONE DISEASE

CROSS REFERENCE TO RELATED APPLICATIONS

The present application claims the benefit of the filing dates of U.S. Provisional Appl. Nos. 60/331,045, filed Nov. 7, 2001, and 60/396,635, filed Jul. 19, 2002. The present application also is a continuation-in-part of, and claims priority to, U.S. application Ser. No. 10/050,902, filed Jan. 18, 2002, and International Appl. No. PCT/IB02/00166, filed Jan. 21, 2002, the latter of which was published under PCT Article 21(2) in the English language as WO 02/056905 on Jul. 25, 2002, both of which applications claim the benefit of the filing dates of U.S. application Ser. Nos. 60/262,379, 60/288,549, 60/326,998 and 60/331,045, filed Jan. 19, 2001, May 4, 2001, Oct. 5, 2001, and Nov. 7, 2001, respectively. The disclosures of all of the above-referenced applications are incorporated by reference herein in their entireties.

BACKGROUND OF THE INVENTION

1. Field of the Invention

The present invention is related to the fields of molecular biology, virology, immunology and medicine. The invention provides a composition comprising an ordered and repetitive antigen or antigenic determinant array, and in particular a RANKL protein, RANKL fragment or RANKL peptide-array. More specifically, the invention provides a composition comprising a virus-like particle and at least one RANKL protein, RANKL fragment or RANKL peptide bound thereto. The invention also provides a process for producing the conjugates and the ordered and repetitive arrays, respectively. The compositions of the invention are useful in the production of vaccines for the treatment of bone diseases and as a pharmaccine to prevent or cure bone diseases and to efficiently induce immune responses, in particular antibody responses. Furthermore, the compositions of the invention are particularly useful to efficiently induce self-specific immune responses within the indicated context.

2. Related Art

Living bone is permanently turned over by balanced and coordinated remodeling processes. Primarily two cell types contribute to this remodeling: osteoblasts are essential for the formation of bone while osteoclasts promote dissolution of bone matrix and solubilization of the hydroxyapatite. In young individuals with growing bone, the rate of bone formation exceeds the rate of bone resorption, while in older individuals the rate of resorption can exceed formation and result in a net loss of bone mineral density and/or bone mass. In the latter case the bone strength is weakened and leads to an increased risk of fracture as well as slow or incomplete repair of broken bones. Multiple conditions in humans are known to be associated with an imbalance in bone remodeling.

Recently three proteins have been described that are crucially involved in the formation of osteoclasts from hematopoietic precursor cells and regulation of bone remodeling. RANKL (Receptor activator of NFkB Ligand) which is also known as TNFSF11 (Tumor necrosis factor superfamily member 11), TRANCE (TNF-related activation induced cytokine), ODF (Osteoclast differentiation factor) or OPGL (Osteoprotegerin ligand) is a transmembrane protein of 245 amino acids that forms homotrimers. Part of the extracellular region of RANKL can be shed by a TACE-like protease. In addition, splice variants lacking the transmembrane region have been described. The shed part of RANKL contains the domain that is highly homologous to the TNF-α (Lum, L., et al., *J. Biol. Chem.* 274: 13613–13618 (2000)).

Processes how to produce RANKL protein and RANKL fragments have been disclosed in WO 9846751, U.S. Pat. No. 5,843,678, WO 98259958, U.S. Pat. No. 6,242,586, WO 9828426, U.S. Pat. No. 6,242,213, WO 9929865, JP 2000102390 and WO 0015807.

RANKL interacts with a transmembrane molecule on osteoclasts, termed RANK (Receptor activator of NFkB). This interaction leads to activation of the osteoclast precursor and ends in the formation of active, bone-resorbing osteoclasts. In vivo, a soluble decoy receptor termed osteoprotegerin, is involved in the regulation of osteoclastogenesis by its ability to bind to RANKL and inhibit the interaction of RANKL with its receptor RANK. This inhibition leads to a suppression of osteoclastogenesis and thus provides a means to stop excessive bone resorption. The interaction of RANKL with its receptor RANK can be suppressed by recombinant osteoprotegerin and by a soluble RANK-Fc fusion protein. In accordance with these findings, RANKL- and RANK-deficient mice develop osteopetrosis while RANKL-overexpressing transgenic mice as well as osteoprotegerin-deficient mice develop osteoporosis (Kong Y Y., et al., Nature 397:315–322 (1999), Kim, N., et al., Proc. Natl. Acad. Sci USA 97:10905–10910 (2000), Dougall, B., et al., Proc. Natl. Acad. Sci USA 97:1566–1571 (1999), Bucay, N., et al., Genes Dev. 12: 1260–1268 (1998)).

The importance of the RANKL-RANK-osteoprotegerin system is further confirmed in an rodent model for osteoporosis induced by estrogen-deficiency. Recombinant osteoprotegerin completely abolished ovariectomy-induced bone loss (Simonet, W. S., et al. Cell 89:309–319 (1997).

In an adjuvant-induced arthritis model osteoprotegerin injection was able to prevent bone loss and cartilage destruction, but not inflammation (paw swelling). Beside its expression on stromal cells RANKL is also expressed on T cells, and RANK is found on antigen-presenting cells. It is assumed that during an arthritic reaction activated T cells with enhanced RANKL expression mediate an increase in osteoclastogenesis and subsequent bone loss. The interaction of RANKL with RANK also enhances the longevity and adjuvant properties of dendritic cells (Kong Y. Y., et al., Nature 402:304–309 (1999)).

Alveolar bone destruction and subsequent tooth loss is observed in periodontal infections. In vivo inhibition of RANKL function with osteoprotegerin diminished alveolar bone destruction and reduced the number of periodontal osteoclasts after microbial challenge (Teng, Y. T. A., et al., J. Clin. Invest. 106:R59–R67 (2000).

Bone tumors and certain tumor metastases are characterized by increased bone resorption due to an increased osteoclastogenesis (Hofbauer, L. C. and Heufelder A. E., J. Clin Endocrin. Met. 85:2355–2363 (2000). Osteoprotegerin was shown to inhibit prostate-cancer induced osteoclastogenesis and prevent prostate tumor growth in the bone of mice (Zhang Y., et al., J. Clin. Invest. 107:1219–1220 (2001). It also diminished advanced bone cancer pain in mice (Luger N. M., et al., Cancer Res. 61:4038–4047 (2001)). Multiple myeloma is a B cell malignancy characterized by the accumulation of plasma cells in the bone marrow and the development of osteolytic bone disease. In mouse models for multiple myeloma injection of osteoprotegerin or RANK-Fc fusion protein prevented the development of lytic bone lesions and interfered with mycloma progression (Pearse R N., et al., Proc. Natl. Acad. Sci USA 98:11581–11586 (2001).

Central to the etiology of aseptic loosening of prostethic implants is periprostethic osteolysis at the bone-implant interface, which is caused by wear-debris-induced inflammation. Fibroblast-like synoviocytes, transfected with osteoprotegerin, were able to prevent wear debris induced osteoclastogenesis in a mouse model (Gouter J. J., et al., J. Orthop. Res. 202:169–173 (2002)).

Vascular calcification is found with high clinical incidence in the osteoporotic patient population. An involvement of the RANKL-RANK-osteoprotegerin system is demonstrated by the finding that osteoprotegerin-deficient mice showed arterial calcification which could be reversed by recombinant osteoprotegerin (Min, H., et al., J. Exp. Med. 192:463–474 (2000)).

All these finding point to a crucial importance of the RANKL-RANK-osteoprotegerin system in regulation bone resorption in a variety of pathological conditions. So far, inhibition of bone loss has been mainly shown by injection of recombinant osteoprotegerin or a RANK-Fc fusion protein. Conceptually, immunization of an animal with RANKL should allow the production of RANKL-specific antibodies which, by binding to the RANK binding site or steric inhibition, should interfere with osteoclastogenesis.

However, so far no vaccination with a RANKL protein or peptide has been reported. Moreover, there has been no evidence that vaccines might be effective for protection against bone diseases, in particular, since it is usually difficult to induce antibody responses to self-molecules by conventional vaccination.

One way to improve the efficiency of vaccination is to increase the degree of repetitiveness of the antigen applied. Unlike isolated proteins, viruses induce prompt and efficient immune responses in the absence of any adjuvants both with and without T-cell help (Bachmann and Zinkernagel, *Ann. Rev. Immunol:* 15:235–270 (1991)). Although viruses often consist of few proteins, they are able to trigger much stronger immune responses than their isolated components. For B-cell responses, it is known that one crucial factor for the immunogenicity of viruses is the repetitiveness and order of surface epitopes. Many viruses exhibit a quasi-crystalline surface that displays a regular array of epitopes which efficiently crosslinks epitope-specific immunoglobulins on B cells (Bachmann and Zinkernagel, *Immunol. Today* 17:553–558 (1996)). This crosslinking of surface immunoglobulins on B cells is a strong activation signal that directly induces cell-cycle progression and the production of IgM antibodies. Further, such triggered B cells are able to activate T helper cells, which in turn induce a switch from IgM to IgG antibody production in B cells and the generation of long-lived B cell memory—the goal of any vaccination (Bachmann and Zinkernagel, *Ann. Rev. Immunol.* 15:235–270 (1997)). Viral structure is even linked to the generation of anti-antibodies in autoimmune disease and as a part of the natural response to pathogens (see Fehr, T., et al., *J Exp. Med.* 185:1785–1792 (1997)). Thus, antibodies presented by a highly organized viral surface are able to induce strong anti-antibody responses.

As indicated, however, the immune system usually fails to produce antibodies against self-derived structures. For soluble antigens present at low concentrations, this is due to tolerance at the Th cell level. Under these conditions, coupling the self-antigen to a carrier that can deliver T help may break tolerance. For soluble proteins present at high concentrations or membrane proteins at low concentration, B and Th cells may be tolerant. However, B cell tolerance may be reversible (anergy) and can be broken by administration of the antigen in a highly organized fashion coupled to a foreign carrier (Bachmann and Zinkernagel, *Ann. Rev. Immunol.* 15:235–270 (1997)).

BRIEF SUMMARY OF THE INVENTION

We have now found that RANKL proteins, RANKL fragments or RANKL peptides, which are bound to a core particle having a structure with an inherent repetitive organization, and hereby in particular to virus-like-particles (VLPs) and subunits of VLPs, respectively, leading to highly ordered and repetitive conjugates represent potent immunogens for the induction of antibodies specific for RANKL. The antibodies are able to block and neutralize, respectively, the interaction of RANKL with its receptor RANK. Therefore, the present invention provides a therapeutic mean for the treatment of bone diseases, which is based on an ordered and repetitive RANKL-core particle array, and in particular a VLP-RANKL-conjugate and -array, respectively. This therapeutic is able to induce high titers of anti-RANKL antibodies in a vaccinated animal.

The present invention, thus, provides for a composition comprising: (a) a core particle with at least one first attachment site; and (b) at least one antigen or antigenic determinant with at least one second attachment site, wherein said antigen or antigenic determinant is a RANKL protein, RANKL fragment or RANKL peptide, and wherein said second attachment site being selected from the group consisting of (i) an attachment site not naturally occurring with said antigen or antigenic determinant; and (ii) an attachment site naturally occurring with said antigen or antigenic determinant, wherein said second attachment site is capable of association to said first attachment site; and wherein said antigen or antigenic determinant and said core particle interact through said association to form an ordered and repetitive antigen array. Preferred embodiments of core particles suitable for use in the present invention are a virus, a virus-like particle, a bacteriophage, a bacterial pilus or flagella or any other core particle having an inherent repetitive structure capable of forming an ordered and repetitive antigen array in accordance with the present invention.

More specifically, the invention provides a composition comprising an ordered and repetitive antigen or antigenic determinant array, and hereby in particular RANKL protein-, RANKL fragment- or RANKL peptide-VLP conjugates. More specifically, the invention provides a composition comprising a virus-like particle and at least one RANKL protein, RANKL fragment or RANKL peptide bound thereto. The invention also provides a process for producing the conjugates and the ordered and repetitive arrays, respectively. The compositions of the invention are useful in the production of vaccines for the treatment of bone diseases and as a pharmaccine to prevent or cure bone diseases and to efficiently induce immune responses, in particular antibody responses. Furthermore, the compositions of the invention are particularly useful to efficiently induce self-specific immune responses within the indicated context.

In the present invention, a RANKL protein, RANKL fragment or RANKL peptide is bound to a core particle and VLP, respectively, typically in an oriented manner, yielding an ordered and repetitive RANKL protein, RANKL fragment or RANKL peptide antigen array. Furthermore, the highly repetitive and organized structure of the core particles and VLPs, respectively, mediates the display of the RANKL protein, RANKL fragment or RANKL peptide in a highly ordered and repetitive fashion leading to a highly organized and repetitive antigen array. Furthermore, binding of the RANKL protein, RANKL fragment or RANKL peptide to the core particle and VLP, respectively, provides T helper cell epitopes, since the core particle and VLP is foreign to the host immunized with the core particle-RANKL protein, -RANKL fragment or -RANKL peptide array and VLP-RANKL protein, -RANKL fragment or -RANKL peptide array, respectively. Those arrays differ from prior art conjugates in their highly organized structure, dimensions, and in the repetitiveness of the antigen on the surface of the array.

In one aspect of the invention, the RANKL protein, RANKL fragment or RANKL peptide is expressed in a suitable expression host compatible with proper folding of the RANKL protein or RANKL fragment, or synthesized, while the core particle and the VLP, repespectively, is expressed and purified from an expression host suitable for the folding and assembly of the core particle and the VLP, repespectively. RANKL protein, RANKL fragment or RANKL peptide may also be chemically synthesized. The RANKL protein, RANKL fragment or RANKL peptide array is then assembled by binding the RANKL protein, RANKL fragment or RANKL peptide to the core particle and the VLP, respectively.

In another aspect, the present invention provides for a composition comprising (a) a virus-like particle, and (b) at least one antigen or antigenic determinant, wherein said antigen or said antigenic determinant is a RANKL protein, RANKL fragment or RANKL peptide, and wherein said at least one antigen or antigenic determinant is bound to the virus-like particle.

In a further aspect, the present invention provides for a pharmaceutical composition comprising (a) the compositions of the invention, and (b) an acceptable pharmaceutical carrier.

In still a further aspect, the present invention provides for a vaccine composition comprising a composition comprising: (a) a core particle with at least one first attachment site; and (b) at least one antigen or antigenic determinant with at least one second attachment site, wherein said antigen or antigenic determinant is a RANKL protein, RANKL fragment or RANKL peptide, and wherein said second attachment site being selected from the group consisting of (i) an attachment site not naturally occurring with said antigen or antigenic determinant; and (ii) an attachment site naturally occurring with said antigen or antigenic determinant, wherein said second attachment site is capable of association to said first attachment site; and wherein said antigen or antigenic determinant and said core particle interact through said association to form an ordered and repetitive antigen array.

In a further aspect, the present invention provides for a vaccine composition comprising a composition, wherein said composition comprising (a) a virus-like particle; and (b) at least one antigen or antigenic determinant, wherein said antigen or said antigenic determinant is a RANKL protein, RANKL fragment or RANKL peptide; and wherein said at least one antigen or antigenic determinant is bound to said virus-like particle.

In still a further aspect, the present invention provides for a process for producing a composition of claim 1 comprising (a) providing a virus-like particle; and (b) providing at least one antigen or antigenic determinant, wherein said antigen or said antigenic determinant is a RANKL protein, RANKL fragment or RANKL peptide; (c) combining said virus-like particle and said at least one antigen or antigenic determinant so that said at least one antigen or antigenic determinant is bound to said virus-like particle.

In still a further aspect, the present invention provides a process for producing a composition of the invention comprising: (a) providing a core particle with at least one first attachment site; (b) providing at least one antigen or antigenic determinant with at least one second attachment site, wherein said antigen or antigenic determinant is a RANKL protein, RANKL fragment or RANKL peptide, and wherein said second attachment site being selected from the group consisting of (i) an attachment site not naturally occurring with said antigen or antigenic determinant; and (ii) an attachment site naturally occurring with said antigen or antigenic determinant; and wherein said second attachment site is capable of association to said first attachment site; and (c) combining said core particle and said at least one antigen or antigenic determinant, wherein said antigen or antigenic determinant and said core particle interact through said association to form an ordered and repetitive antigen array.

In another aspect, the present invention provides for a method of immunization comprising administering the compositions of the invention to an animal or human.

In a further aspect, the present invention provides for a use of the compositions of the invention for the manufacture of a medicament for treatment of bone diseases.

In a still further aspect, the present invention provides for a use of the compositions of the invention for the preparation of a medicament for the therapeutic or prophylactic treatment of bone diseases, preferably of mammalian encephalopathies. Furthermore, in a still further aspect, the present invention provides for a use of the compositions of the invention, either in isolation or in combination with other agents, for the manufacture of a composition, vaccine, drug or medicament for therapy or prophylaxis of bone diseases, in particular mammalian encephalopathies, and/or for stimulating the mammalian immune system.

Therefore, the invention provides, in particular, vaccine compositions which are suitable for preventing and/or attenuating bone diseases or conditions related thereto. The invention further provides and immunization and vaccination methods, respectively, for preventing and/or attenuating bone diseases or conditions related thereto, in animals, and in particular in cows, sheep and cattles as well as in humans. The inventive compositions may be used prophylactically or therapeutically.

In specific embodiments, the invention provides methods for preventing and/or attenuating bone diseases or conditions related thereto which are caused or exacerbated by "self" gene products, i.e. "self antigens" as used herein. In related embodiments, the invention provides methods for inducing immunological responses in animals and individuals, respectively, which lead to the production of antibodies that prevent and/or attenuate bone diseases or conditions related thereto, which are caused or exacerbated by "self" gene products.

As would be understood by one of ordinary skill in the art, when compositions of the invention are administered to an animal or a human, they may be in a composition which contains salts, buffers, adjuvants, or other substances which are desirable for improving the efficacy of the composition. Examples of materials suitable for use in preparing pharmaceutical compositions are provided in numerous sources including *Remington's Pharmaceutical Sciences* (Osol, A, ed., Mack Publishing Co. (1990)).

Compositions of the invention are said to be "pharmacologically acceptable" if their administration can be tolerated by a recipient individual. Further, the compositions of the invention will be administered in a "therapeutically effective amount" (i.e., an amount that produces a desired physiological effect).

The compositions of the present invention may be administered by various methods known in the art, but will normally be administered by injection, infusion, inhalation, oral administration, or other suitable physical methods. The compositions may alternatively be administered intramuscularly, intravenously, or subcutaneously. Components of compositions for administration include sterile aqueous (e.g., physiological saline) or non-aqueous solutions and suspensions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption.

Other embodiments of the present invention will be apparent to one of ordinary skill in light of what is known in the art, the following drawings and description of the invention, and the claims.

Purification of C-RANKL was analysed on a SDS gel under reducing conditions. The gel was stained with Coomassie Brilliant Blue. Molecular weights of marker proteins are given on the left margin. Lane 1: low molecular weight marker. Lanes 2 and 3: the supernatant of the cell lysates of the BL21/DE3 cells transformed with the empty vector pGEX6p1 and pGEX-RANKL, respectively, after sixteen hours of induction with IPTG 0.4 mM. Lane 4: the purified GST-PS-C-RANKL protein after GST-Trap FF column. Lane 5: the GST-Trap FF column unbound fraction. Lane 6: the purified GST-PS-C-RANKL protein after the cleavage with the PreScission protease. Lane 7: the unbound fraction of the GST-Trap FF column loaded with the GST-RANKL digestion, which contains the purified C-RANKL. Lane 8: the bound fraction of the GST-Trap FF column loaded with the GST-PS-C-RANKL digestion and eluted with GSH.

FIG. 2 shows the expression and purification of RANKL-C.

Figure 2A:
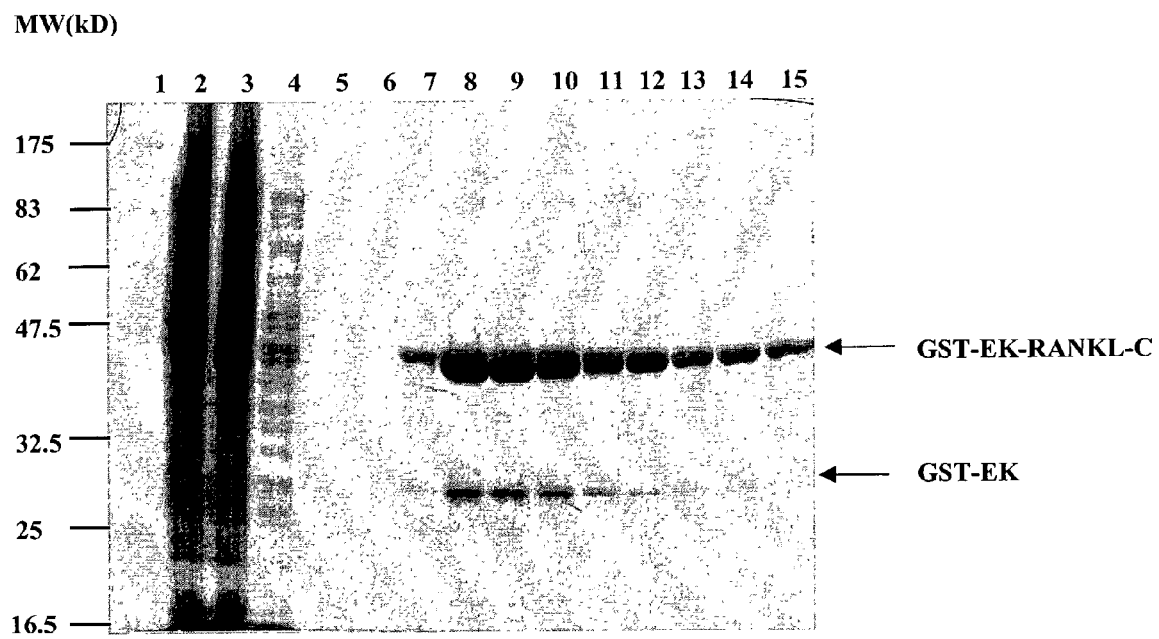

FIG. 2A shows purification of GST-EK-RANKL-C. Proteins samples were analyzed on a SDS-PAGE under reducing conditions. The gel was stained with Coomassie Brilliant Blue. Molecular weights of marker proteins are given on the left margin. Lane 1: Prestained protein marker, broad range (New England Biolabs). Lane 2: cleared cell lysate of BL21/DE3 cells transformed with the pMod-GST-EK-mRANKL-C1 plasmid after overnight induction with 0.1 mM IPTG. Lane 3: flow through of the GST-Trap FF column loaded with the cleared lysate of lane 2. Lane 4: first wash of GST-Trap FF column. Lane 5: second wash of GST-Trap FF column. Lane 6: third wash of GST-Trap FF column. Lanes 7–15: elution fractions 1 to 9 of the GST-Trap FF column containing the purified GST-EK-RANKL-C fusion protein and a minor amount of GST-EK protein.

Figure 2B:
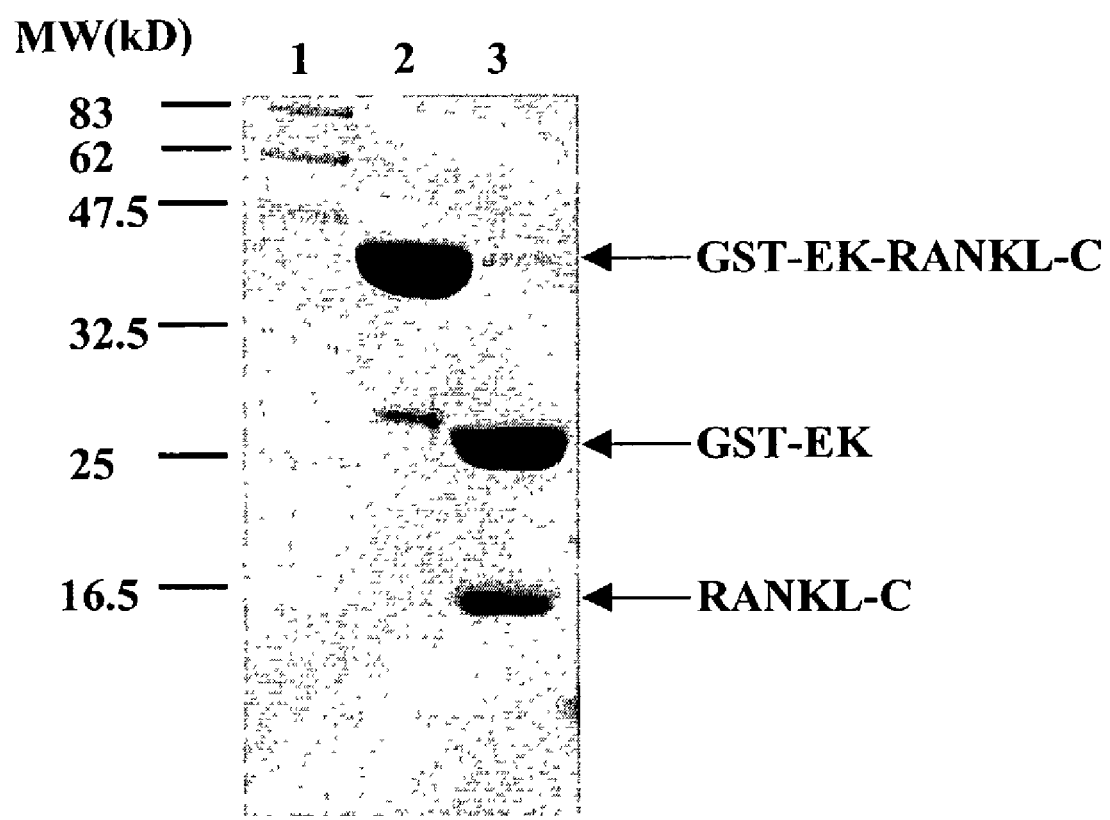

FIG. 2B shows cleavage of GST-EK-RANKL-C with EnterokinaseMax™.

Digestion of GST-EK-RANKL-C was analysed on SDS-PAGE under reducing conditions. The gel was stained with Coomassie Brilliant Blue. Molecular weights of marker proteins are given on the left margin. Lane 1: Prestained protein marker, broad range (New England Biolabs). Lane 2: Purified GST-EK-RANKL-C fusion protein. Lane 3: cleavage products after 16 h incubation at 4° C. with EnterokinaseMax™.

Figure 2C:
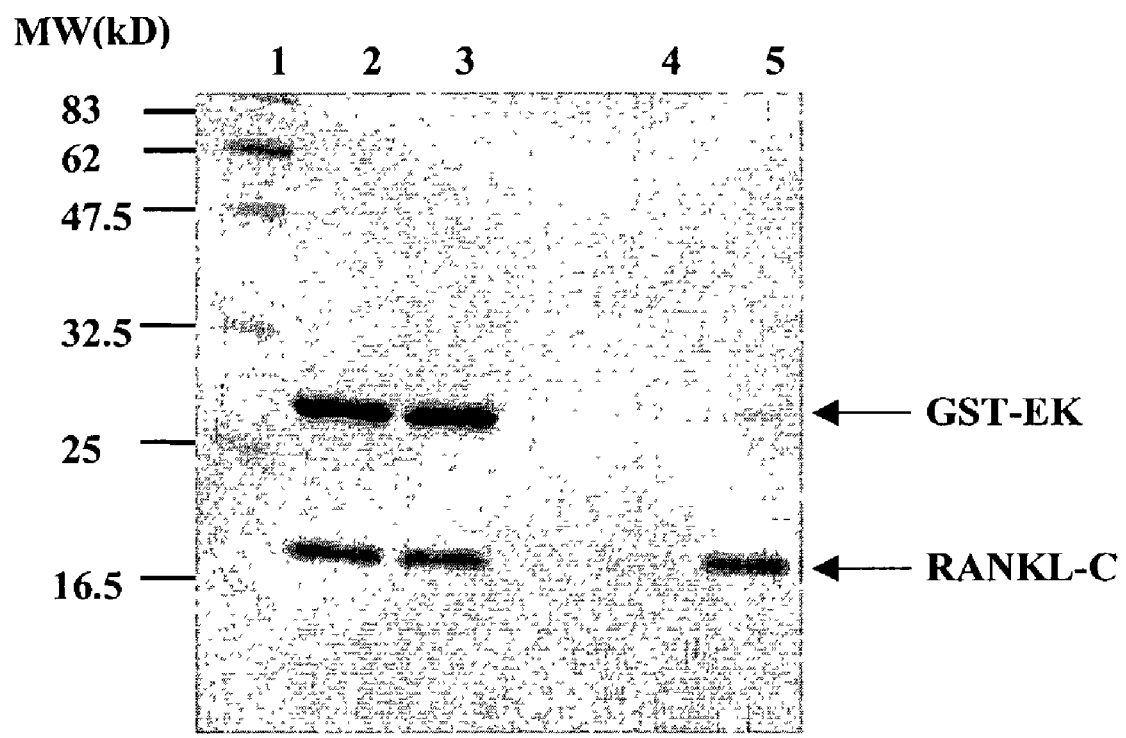

FIG. 2C shows purification of RANKL-C.

Purification of RANKL-C after removal of GST-EK by affinity chromatography on glutathione sepharose was analysed on SDS-PAGE under reducing conditions. The gel was stained with Coomassie Brilliant Blue. Molecular weights of marker proteins are given on the left margin. Lane 1: Prestained protein marker, broad range (New England Biolabs). Lane 2 and 3: cleavage products GST-EK and RANKL-C after 16 h incubation of GST-EK-RANKL-C at 4° C. with EnterokinaseMax™ Lane 4 and 5: different amounts of the unbound fraction of the GST-Trap FF column, which contains the RANKL-C protein in high purity.

FIG. 3 shows coupling of C-RANKL to Qβ capsid protein.

Figure 3A:
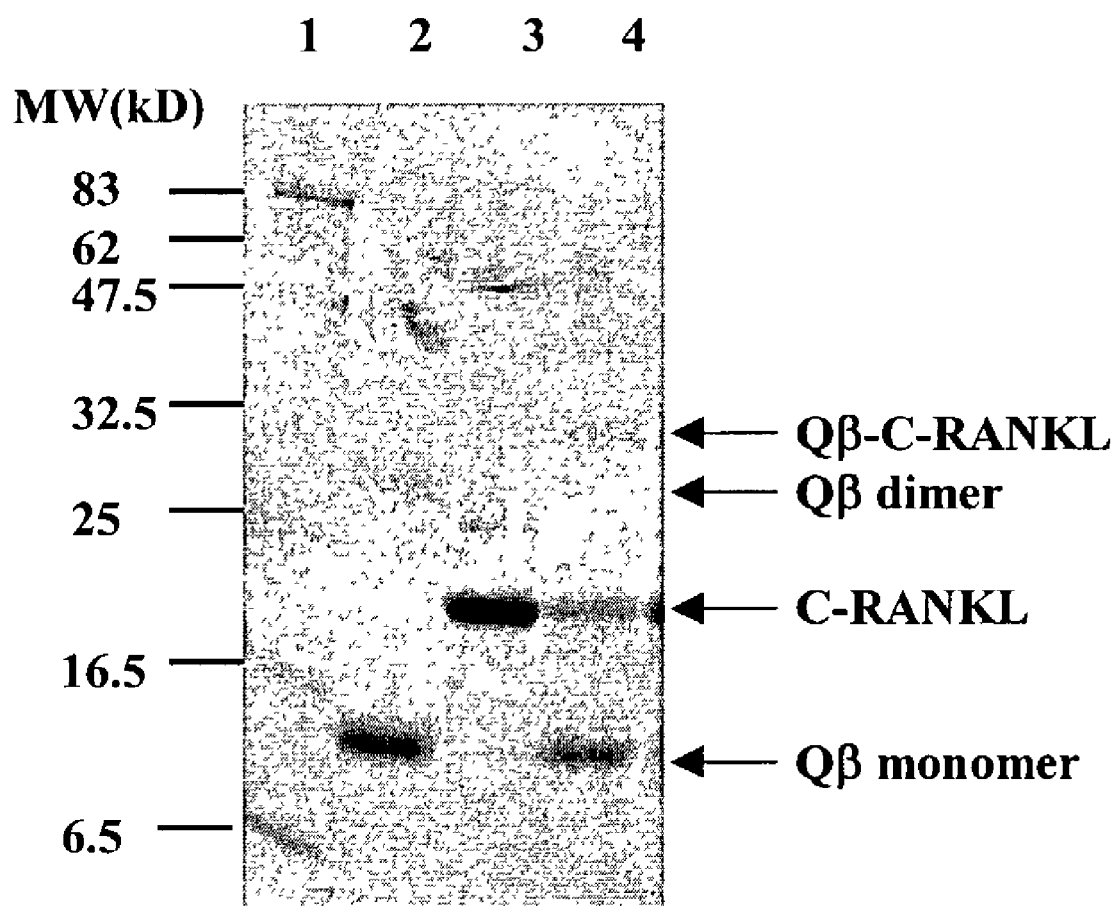

FIG. 3A shows SDS-PAGE analysis of coupling products: Proteins were analysed on 16% SDS gels under reducing conditions. The gel was stained with Coomassie Brilliant Blue. Molecular weights of marker proteins are given on the left margin. Identity of protein bands is indicated on the right margin. Lane 1: Prestained protein marker, broad range (New England Biolabs). Lane 2: derivatized Qβ capsid protein. Lane 3: purified C-RANKL protein. Lane 4: C-RANKL/Qβ coupling reaction.

Figure 3B:
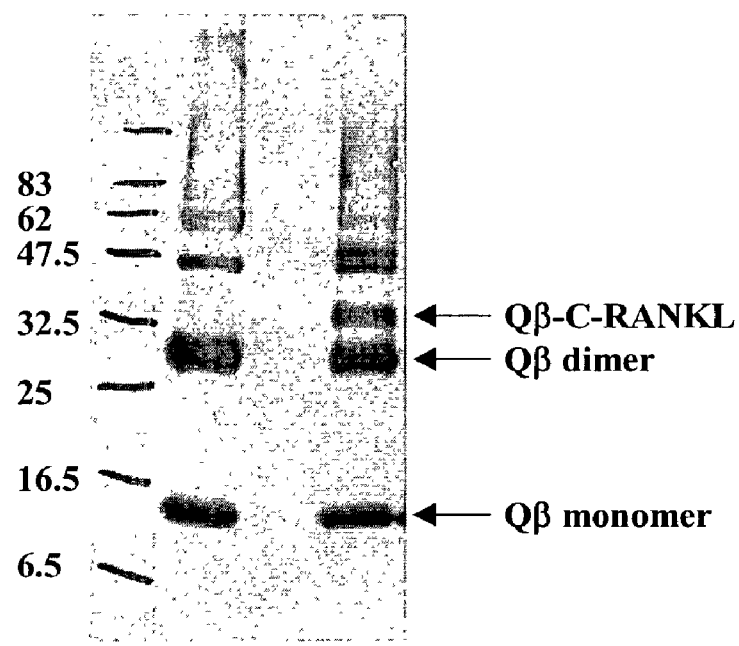
Figure 3C:
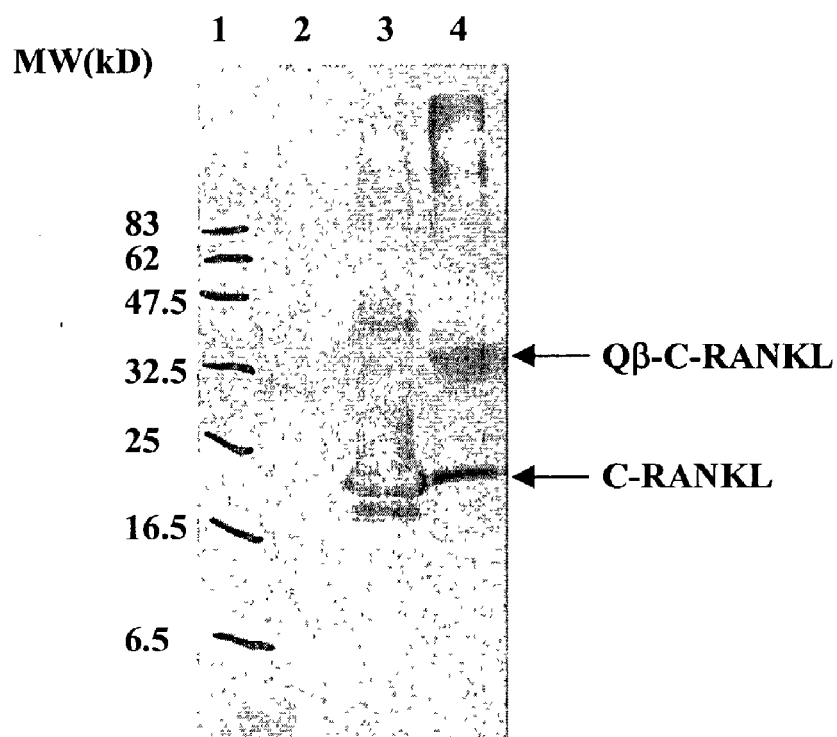

FIG. 3B and FIG. 3C: Western Blot analysis of coupling products.

Proteins were run on 16% SDS gels under reducing conditions, blotted to nitrocellulose membranes and detected with anti-Qβ antiserum (FIG. 3B) or anti-RANKL antibody (FIG. 3C). Molecular weights of marker proteins are given on the left margin. Identity of protein bands is indicated on the right margin. Lane 1: Prestained protein marker, broad range (New England Biolabs). Lane 2: derivatized Qβ capsid protein. Lane 3: purified C-RANKL protein. Lane 4: C-RANKL/Qβ coupling reaction.

Figure 4:
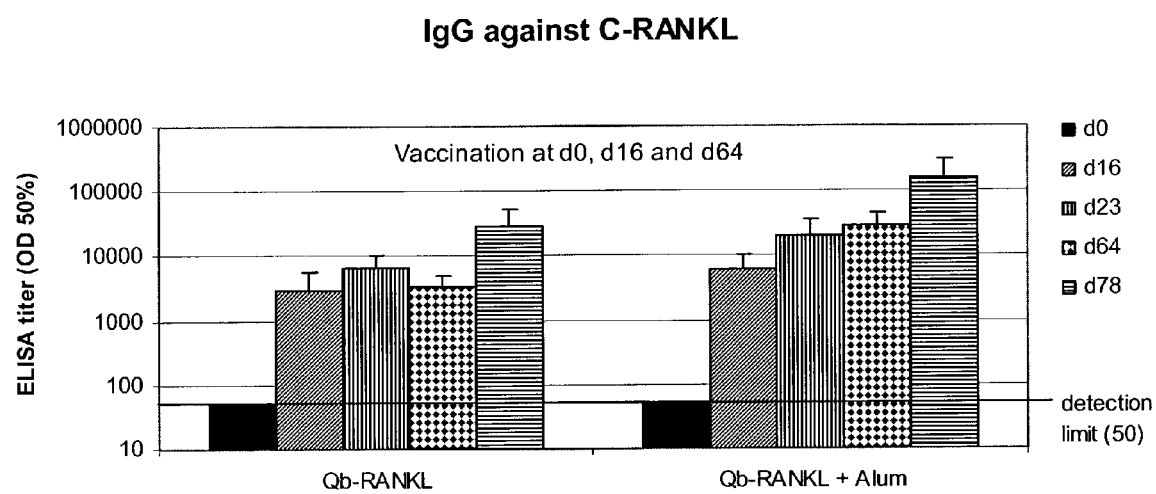

FIG. 4 shows ELISA for RANKL-specific IgG in mice immunized with C-RANKL coupled to Qβ.

Female Balb/c mice were vaccinated subcutaneously with 25 µg of C-RANKL coupled to Qβ in PBS on day 0, day 16 and day 64 with or without the addition of alum. Sera from days 0, 16, 23, 64, and 78 were analysed for antibodies specific for RANKL. ELISA titers are expressed as the average of those sera dilutions which lead to half maximal OD420 in the ELISA assay.

FIG. 5 shows neutralizing activity of antibodies induced in mice immunized with C-RANKL coupled to Qβ.

Figure 5A:
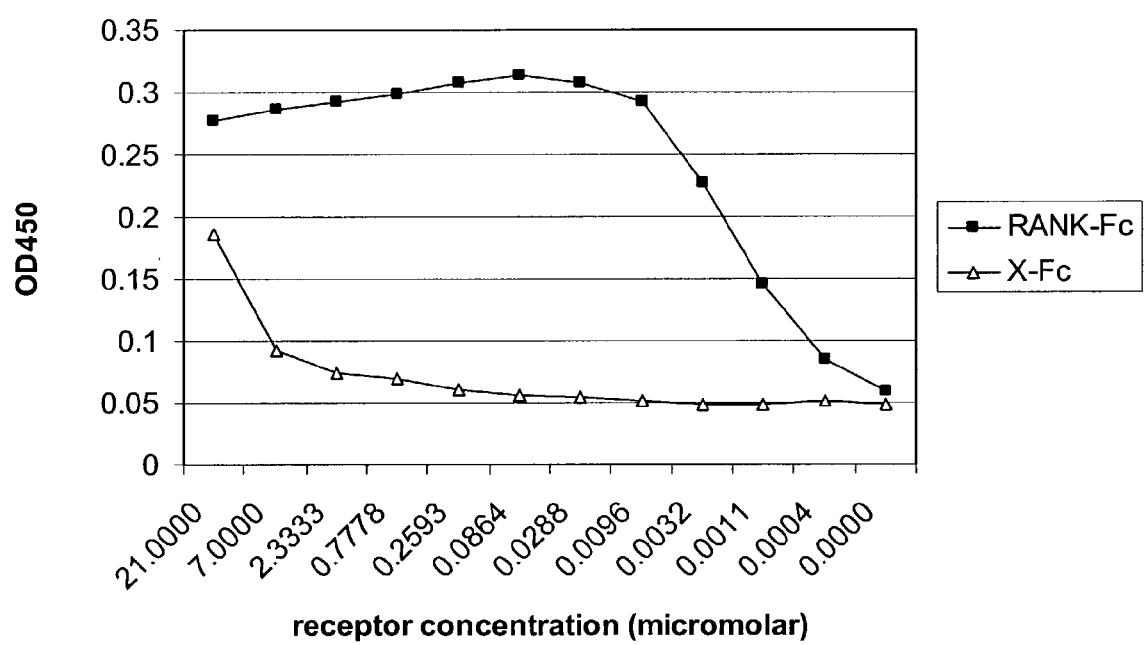

FIG. 5A shows binding assay of C-RANKL and its cognate ligand RANK. ELISA plates were coated with 10 µg/ml C-RANKL and incubated with serial dilutions of RANK-Fc fusion protein or an unrelated Fc-fusion protein. Detection of bound RANK was performed with HRP-conjugated anti-Fc antibodies.

Figure 5B:
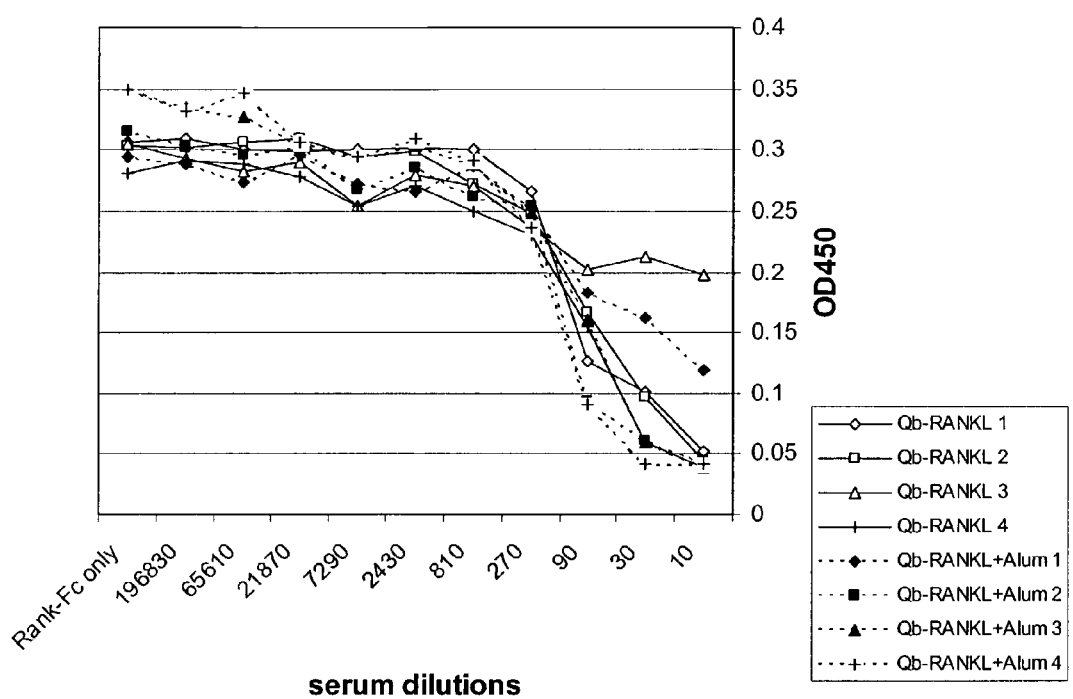

FIG. 5B shows inhibition of C-RANKL/RANK-Fc binding by serum antibodies of mice vaccinated with C-RANKL coupled to Qβ Elisa plates were coated with 10 µg/ml C-RANKL and co-incubated with serial dilutions of mouse sera from day 78 and 1 nM RANK-Fc fusion protein. Binding of fusion protein to C-RANKL was detected with horse raddish peroxidase conjugated anti-Fc antibody.

Figure 6A:
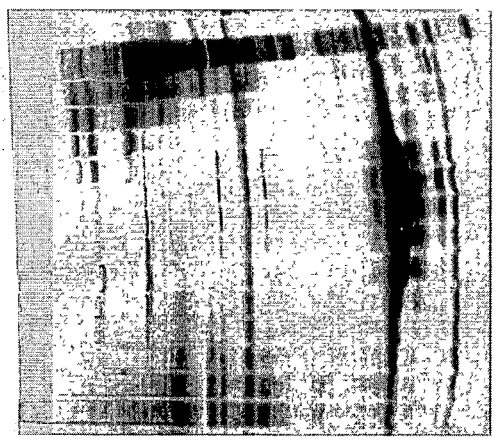
Figure 6B:
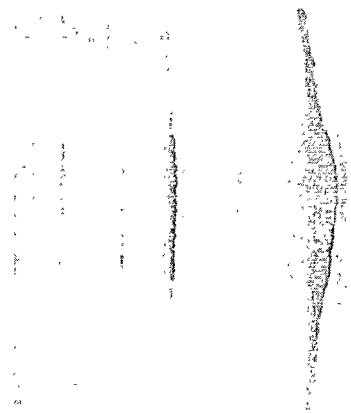
Figure 6C:
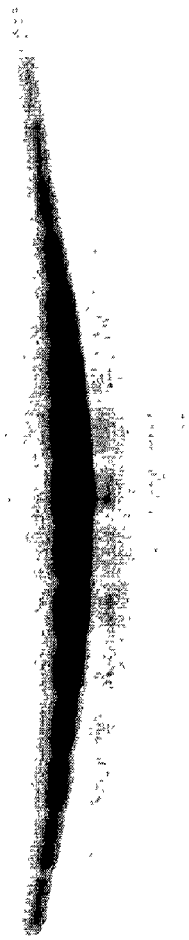

FIG. 6A–C depict the purification of AP205 proteins for use in VLPs, as analysed by SDS PAGE and Western-blotting.

Figure 7B:
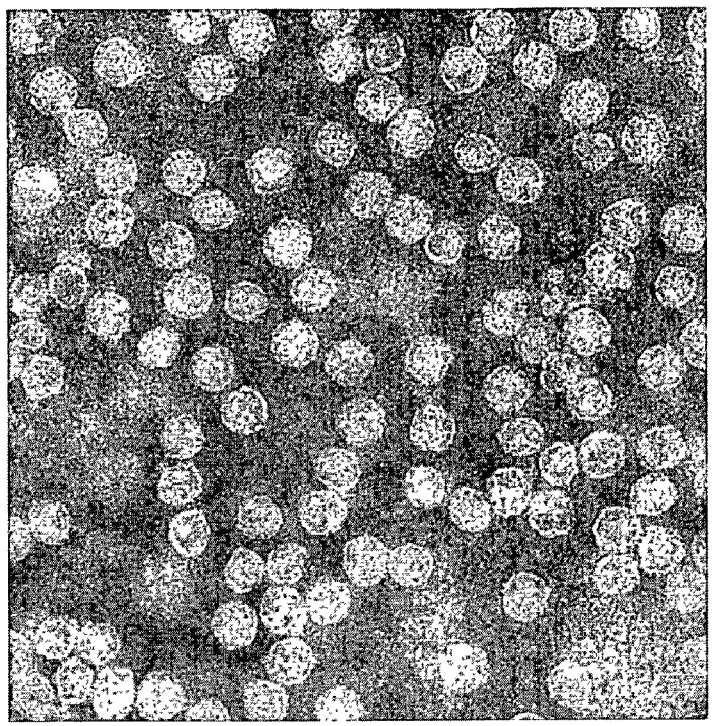
Figure 7A:
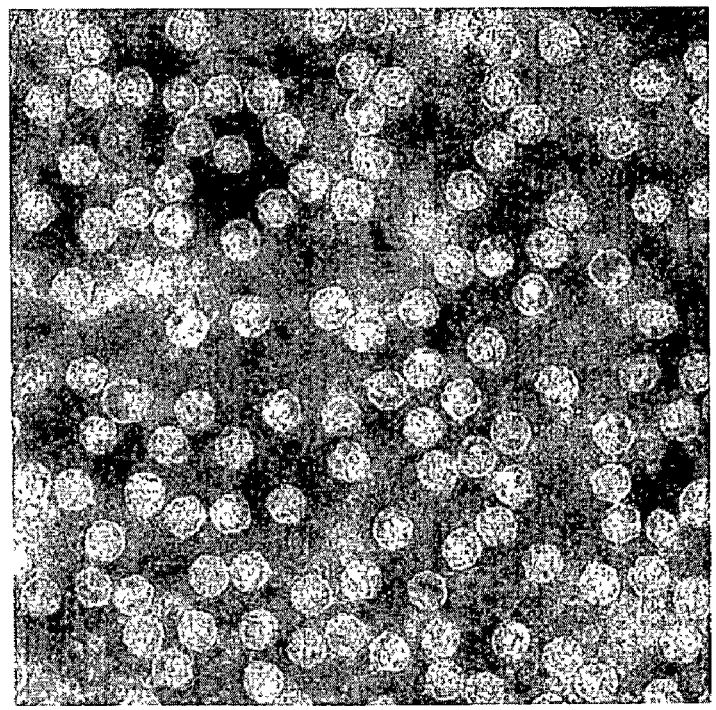

FIG. 7A–B depict electron micrographs comparing AP205 phage particles to AP205 virus like particles spontaneously assembled from recombinant protein expressed in *E. coli* and purified.

DETAILED DESCRIPTION OF THE INVENTION

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are hereinafter described.

1. Definitions

Amino acid linker: An "amino acid linker", or also just termed "linker" within this specification, as used herein, either associates the antigen or antigenic determinant with the second attachment site, or more preferably, already comprises or contains the second attachment site, typically—but not necessarily—as one amino acid residue, preferably as a cysteine residue. The term "amino acid linker" as used herein, however, does not intend to imply that such an amino acid linker consists exclusively of amino acid residues, even if an amino acid linker consisting of amino acid residues is a preferred embodiment of the present invention. The amino acid residues of the amino acid linker are, preferably, composed of naturally occuring amino acids or unnatural amino acids known in the art, all-L or all-D or mixtures thereof. However, an amino acid linker comprising a molecule with a sulfhydryl group or cysteine residue is also encompassed within the invention. Such a molecule comprise preferably a C1–C6 alkyl-, cycloalkyl (C5,C6), aryl or heteroaryl moiety. However, in addition to an amino acid linker, a linker comprising preferably a C1–C6 alkyl-, cycloalkyl- (C5, C6), aryl- or heteroaryl-moiety and devoid of any amino acid(s) shall also be encompassed within the scope of the invention. Association between the antigen or antigenic determinant or optionally the second attachment site and the amino acid linker is preferably by way of at least one covalent bond, more preferably by way of at least one peptide bond.

Animal: As used herein, the term "animal" is meant to include, for example, humans, sheep, elk, deer, mule deer, minks, mammals, monkeys, horses, cattle, pigs, goats, dogs, cats, rats, mice, birds, chicken, reptiles, fish, insects and arachnids.

Antibody: As used herein, the term "antibody" refers to molecules which are capable of binding an epitope or antigenic determinant. The term is meant to include whole antibodies and antigen-binding fragments thereof, including single-chain antibodies. Most preferably the antibodies are human antigen binding antibody fragments and include, but are not limited to, Fab, Fab' and F(ab')2, Fd, single-chain Fvs (scFv), single-chain antibodies, disulfide-linked Fvs (sdFv) and fragments comprising either a $V_L$ or $V_H$ domain. The antibodies can be from any animal origin including birds and mammals. Preferably, the antibodies are human, murine, rabbit, goat, guinea pig, camel, horse or chicken. As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described, for example, in U.S. Pat. No. 5,939,598 by Kucherlapati et al.

Antigen: As used herein, the term "antigen" refers to a molecule capable of being bound by an antibody or a T cell receptor (TCR) if presented by MHC molecules. The term "antigen", as used herein, also encompasses T-cell epitopes. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a Th cell epitope and is given in adjuvant. An antigen can have one or more epitopes (B- and T-epitopes). The specific reaction referred to above is meant to indicate that the antigen will preferably react, typically in a highly selective manner, with its corresponding antibody or TCR and not with the multitude of other antibodies or TCRs which may be evoked by other antigens. Antigens as used herein may also be mixtures of several individual antigens.

Antigenic determinant: As used herein, the term "antigenic determinant" is meant to refer to that portion of an antigen that is specifically recognized by either B- or T-lymphocytes. B-lymphocytes responding to antigenic determinants produce antibodies, whereas T-lymphocytes respond to antigenic determinants by proliferation and establishment of effector functions critical for the mediation of cellular and/or humoral immunity.

Association: As used herein, the term "association" as it applies to the first and second attachment sites, refers to the binding of the first and second attachment sites that is preferably by way of at least one non-peptide bond. The nature of the association may be covalent, ionic, hydrophobic, polar or any combination thereof, preferably the nature of the association is covalent.

Attachment Site, First: As used herein, the phrase "first attachment site" refers to an element of non-natural or natural origin, to which the second attachment site located on the antigen or antigenic determinant may associate. The first attachment site may be a protein, a polypeptide, an amino acid, a peptide, a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof. The first attachment site is located, typically and preferably on the surface, of the core particle such as, preferably the virus-like particle. Multiple first attachment sites are present on the surface of the core and virus-like particle, respectively, typically in a repetitive configuration.

Attachment Site, Second: As used herein, the phrase "second attachment site" refers to an element associated with the antigen or antigenic determinant to which the first attachment site located on the surface of the core particle and virus-like particle, respectively, may associate. The second attachment site of the antigen or antigenic determinant may be a protein, a polypeptide, a peptide, a sugar, a polynucleotide, a natural or synthetic polymer, a secondary metabolite or compound (biotin, fluorescein, retinol, digoxigenin, metal ions, phenylmethylsulfonylfluoride), or a combination thereof, or a chemically reactive group thereof. At least one second attachment site is present on the antigen or antigenic determinant. The term "antigen or antigenic determinant with at least one second attachment site" refers, therefore, to an antigen or antigenic construct comprising at least the antigen or antigenic determinant and the second attachment site. However, in particular for a second attachment site, which is of non-natural origin, i.e. not naturally occurring within the antigen or antigenic determinant, these antigen or antigenic constructs comprise an "amino acid linker".

Bone diseases: The term "bone diseases", as used herein, encompasses, in particular, conditions characterized by increased bone resorption. The term "bone diseases" includes, but is not limited, to osteoporosis in its different forms such as primary osteoporosis (such as idiopathic, postmenopausal, involutional or senile osteoporosis) and secondary osteoporosis. The latter include osteoporosis caused by glucocorticoid excess, hyperparathyroidism, hyperthyroidism, hypergonadism, hyperprolactinemia, diabetes mellitus, drug-induced osteoporosis such as the one caused by glucocorticosteroids, ethanol, dilantin, tobacco, barbiturates or heparin), disuse-induced osteoporosis and miscellaneous conditions associated with increased bene resorption such as chronic renal failure, liver disease, malabsorption syndromes, chronic obstructive lung disease, sarcoidosi. Further conditions with increased bone resorption include Paget's disease, familial expansile osteolysis, spontaneous osteolysis, bone loss associated with rheumatoid arthritis, bone resorption and tooth loss during periodontal disease, osteomyelitis, hypercalcemia of malignancy, bone tumors, cancers associated by bone metastases and bone loss caused by weigthlessness as found in space flight. Those skilled in the art can recognize further conditions characterized by increased bone resorption.

Bound: As used herein, the term "bound" refers to binding or attachment that may be covalent, e.g., by chemically coupling, or non-covalent, e.g., ionic interactions, hydrophobic interactions, hydrogen bonds, etc. Covalent bonds can be, for example, ester, ether, phosphoester, amide, peptide, imide, carbon-sulfur bonds, carbon-phosphorus bonds, and the like. The term "bound" is broader than and includes terms such as "coupled," "fused" and "attached".

Coat protein(s): As used herein, the term "coat protein(s)" refers to the protein(s) of a bacteriophage or a RNA-phage capable of being incorporated within the capsid assembly of the bacteriophage or the RNA-phage. However, when referring to the specific gene product of the coat protein gene of RNA-phages the term "CP" is used. For example, the specific gene product of the coat protein gene of RNA-phage Qβ is referred to as "Qβ CP", whereas the "coat proteins" of bacteriophage Qβ comprise the "Qβ CP" as well as the A1 protein. The capsid of Bacteriophage Qβ is composed mainly of the Qβ CP, with a minor content of the A1 protein. Likewise, the VLP Qβ coat protein contains mainly Qβ CP, with a minor content of A1 protein.

Core particle: As used herein, the term "core particle" refers to a rigid structure with an inherent repetitive organization. A core particle as used herein may be the product of a synthetic process or the product of a biological process.

Coupled: The term "coupled", as used herein, refers to attachment by covalent bonds or by strong non-covalent interactions, typically and preferably to attachment by covalent bonds. Any method normally used by those skilled in the art for the coupling of biologically active materials can be used in the present invention.

Effective Amount: As used herein, the term "effective amount" refers to an amount necessary or sufficient to realize a desired biologic effect. An effective amount of the composition would be the amount that achieves this selected result, and such an amount could be determined as a matter of routine by a person skilled in the art. For example, an effective amount for treating an immune system deficiency could be that amount necessary to cause activation of the immune system, resulting in the development of an antigen specific immune response upon exposure to antigen. The term is also synonymous with "sufficient amount."

The effective amount for any particular application can vary depending on such factors as the disease or condition being treated, the particular composition being administered, the size of the subject, and/or the severity of the disease or condition. One of ordinary skill in the art can empirically determine the effective amount of a particular composition of the present invention without necessitating undue experimentation.

Epitope: As used herein, the term "epitope" refers to continuous or discontinuous portions of a polypeptide having antigenic or immunogenic activity in an animal, preferably a mammal, and most preferably in a human. An epitope is recognized by an antibody or a T cell through its T cell receptor in the context of an MHC molecule. An "immunogenic epitope," as used herein, is defined as a portion of a polypeptide that elicits an antibody response or induces a T-cell response in an animal, as determined by any method known in the art. (See, for example, Geysen et al., *Proc. Natl. Acad. Sci. USA* 81:3998–4002 (1983)). The term "antigenic epitope," as used herein, is defined as a portion of a protein to which an antibody can immunospecifically bind its antigen as determined by any method well known in the art. Immunospecific binding excludes non-specific binding but does not necessarily exclude cross-reactivity with other antigens. Antigenic epitopes need not necessarily be immunogenic. Antigenic epitopes can also be T-cell epitopes, in which case they can be bound immunospecifically by a T-cell receptor within the context of an MHC molecule.

An epitope can comprise 3 amino acids in a spatial conformation which is unique to the epitope. Generally, an epitope consists of at least about 5 such amino acids, and more usually, consists of at least about 8–10 such amino acids. If the epitope is an organic molecule, it may be as small as Nitrophenyl.

Fusion: As used herein, the term "fusion" refers to the combination of amino acid sequences of different origin in one polypeptide chain by in-frame combination of their coding nucleotide sequences. The term "fusion" explicitly encompasses internal fusions, i.e., insertion of sequences of different origin within a polypeptide chain, in addition to fusion to one of its termini.

Immune response: As used herein, the term "immune response" refers to a humoral immune response and/or cellular immune response leading to the activation or proliferation of B- and/or T-lymphocytes and/or and antigen presenting cells. In some instances, however, the immune responses may be of low intensity and become detectable only when using at least one substance in accordance with the invention. "Immunogenic" refers to an agent used to stimulate the immune system of a living organism, so that one or more functions of the immune system are increased and directed towards the immunogenic agent. An "immunogenic polypeptide" is a polypeptide that elicits a cellular and/or humoral immune response, whether alone or linked to a carrier in the presence or absence of an adjuvant. Preferably, antigen presenting cell may be activated.

A substance which "enhances" an immune response refers to a substance in which an immune response is observed that is greater or intensified or deviated in any way with the addition of the substance when compared to the same immune response measured without the addition of the substance. For example, the lytic activity of cytotoxic T cells can be measured, e.g. using a $^{51}$Cr release assay, in samples obtained with and without the use of the substance during immunization. The amount of the substance at which the CTL lytic activity is enhanced as compared to the CTL lytic activity without the substance is said to be an amount sufficient to enhance the immune response of the animal to the antigen. In a preferred embodiment, the immune response in enhanced by a factor of at least about 2, more preferably by a factor of about 3 or more. The amount or type of cytokines secreted may also be altered. Alternatively, the amount of antibodies induced or their subclasses may be altered.

Immunization: As used herein, the terms "immunize" or "immunization" or related terms refer to conferring the ability to mount a substantial immune response (comprising antibodies and/or cellular immunity such as effector CTL) against a target antigen or epitope. These terms do not require that complete immunity be created, but rather that an immune response be produced which is substantially greater than baseline. For example, a mammal may be considered to be immunized against a target antigen if the cellular and/or humoral immune response to the target antigen occurs following the application of methods of the invention.

Natural origin: As used herein, the term "natural origin" means that the whole or parts thereof are not synthetic and exist or are produced in nature.

Non-natural: As used herein, the term generally means not from nature, more specifically, the term means from the hand of man.

Non-natural origin: As used herein, the term "non-natural origin" generally means synthetic or not from nature; more specifically, the term means from the hand of man.

Ordered and repetitive antigen or antigenic determinant array: As used herein, the term "ordered and repetitive antigen or antigenic determinant array" generally refers to a repeating pattern of antigen or antigenic determinant, characterized by a typically and preferably uniform spacial arrangement of the antigens or antigenic determinants with respect to the core particle and virus-like particle, respectively. In one embodiment of the invention, the repeating pattern may be a geometric pattern. Typical and preferred examples of suitable ordered and repetitive antigen or antigenic determinant arrays are those which possess strictly repetitive paracrystalline orders of antigens or antigenic determinants, preferably with spacings of 1 to 30 nanometers, preferably 5 to 15 nanometers.

Pili: As used herein, the term "pili" (singular being "pilus") refers to extracellular structures of bacterial cells composed of protein monomers (e.g., pilin monomers) which are organized into ordered and repetitive patterns. Further, pili are structures which are involved in processes such as the attachment of bacterial cells to host cell surface receptors, inter-cellular genetic exchanges, and cell-cell recognition. Examples of pili include Type-1 pili, P-pili, F1C pili, S-pili, and 987P-pili. Additional examples of pili are set out below.

Pilus-like structure: As used herein, the phrase "pilus-like structure" refers to structures having characteristics similar to that of pili and composed of protein monomers. One example of a "pilus-like structure" is a structure formed by a bacterial cell which expresses modified pilin proteins that do not form ordered and repetitive arrays that are identical to those of natural pili.

Polypeptide: As used herein, the term "polypeptide" refers to a molecule composed of monomers (amino acids) linearly linked by amide bonds (also known as peptide bonds). It indicates a molecular chain of amino acids and does not refer to a specific length of the product. Thus, peptides, dipeptides, tripeptides, oligopeptides and proteins are included within the definition of polypeptide. This term is also intended to refer to post-expression modifications of the polypeptide, for example, glycosolations, acetylations, phosphorylations, and the like. A recombinant or derived polypeptide is not necessarily translated from a designated nucleic acid sequence. It may also be generated in any manner, including chemical synthesis.

RANKL protein: The term "RANKL protein" as used herein refers to a protein encoded by a RANKL gene. Different variants of the RANKL protein may be caused by nucleotide point mutations and polymorphisms, respectively, as well as insertions, deletions and/or substitutions of one or more nucleotides, and shall be explicitly encompassed within the scope of the present invention. Further variablity can be caused by posttranslational modifications, such as differentially glycosylated forms of RANKL as well as proteolytically cleaved forms of RANKL (Lum, L., et al., J. Biol. Chem. 274: 13613–13618 (2000). There are a number of at present known splice variants of the human RANKL gene and the RANKL gene of other species which, with the possible variants mentioned above, are also within the scope of the invention. Therefore, the term "RANKL protein", as used herein, shall also encompass the RANKL protein variants, including but not limiting to the above indicated preferred examples.

As used herein, the term "RANKL fragment" is broadly defined as any polypeptide of at least 50 amino acids length which represents part of a RANKL protein, most preferably of a folded part of RANKL, and most preferably of the extracellular part of RANKL, even more preferably of the region homologous to the TNF-α. The term RANKL fragment also encompasses recombinantly produced proteins and polypeptides, respectively, corresponding to splicing isoforms and proteolytically cleaved forms of RANKL, and all variants, as described above, thereof.

As used herein, the term "RANKL peptide" is broadly defined as any peptide which represents a fraction of a RANKL protein or a RANKL fragment and containing at least two, preferably at least three, more prefereably at least four, more prefereably at least five, more prefereably at least six consecutive amino acids of the original RANKL protein or RANKL fragment, most preferably of the extracellular part of RANKL. Moreover, the term "RANKL peptide" shall preferably encompass any fraction of said RANKL peptide, wherein said fraction may be, preferably, derived by deletion of one or more amino acids at the N and/or C terminus. The RANKL peptide can be obtained by recombinant expression in eucaryotic or procaryotic expression systems as RANKL peptide alone or as a fusion with other amino acids or proteins, e.g. to facilitate folding, expression or solubility of the RANKL peptide or to facilitate purification of the RANKL peptide. To enable coupling of RANKL peptides and subunit proteins of VLPs or capsids, at least one second attachment site may be added to the RANKL peptide. Alternatively RANKL peptides may be synthesized using methods known to the art. The term RANKL peptide as used herein shall also preferably encompass a peptide which simulates the three dimensional surface structure of RANKL. Such RANKL peptide is not necessarily derived from a continuous amino acid sequence of RANKL, but may be formed by discontinuous amino acid residues from RANKL. Such peptides may even contain amino acids which are not present in the corresponding RANKL protein.

Residue: As used herein, the term "residue" is meant to mean a specific amino acid in a polypeptide backbone or side chain.

Self antigen: As used herein, the term "self antigen" refers to proteins encoded by the host's DNA and products generated by proteins or RNA encoded by the host's DNA are defined as self. In addition, proteins that result from a combination of two or several self-molecules or that represent a fraction of a self-molecule and proteins that have a high homology two self-molecules as defined above (>95%, preferably >97%, more preferably >99%) may also be considered self.

Treatment: As used herein, the terms "treatment", "treat", "treated" or "treating" refer to prophylaxis and/or therapy. When used with respect to an infectious disease, for example, the term refers to a prophylactic treatment which increases the resistance of a subject to infection with a pathogen or, in other words, decreases the likelihood that the subject will become infected with the pathogen or will show signs of illness attributable to the infection, as well as a treatment after the subject has become infected in order to fight the infection, e.g., reduce or eliminate the infection or prevent it from becoming worse. When used with respect to bone disease, the term "treatment" refers to a prophylactic or therapeutic treatment which inhibits or reduces the increased bone resorption that is associated to bone diseases.

Vaccine: As used herein, the term "vaccine" refers to a formulation which contains the composition of the present invention and which is in a form that is capable of being administered to an animal. Typically, the vaccine comprises a conventional saline or buffered aqueous solution medium in which the composition of the present invention is suspended or dissolved. In this form, the composition of the present invention can be used conveniently to prevent, ameliorate, or otherwise treat a condition. Upon introduction into a host, the vaccine is able to provoke an immune response including, but not limited to, the production of antibodies and/or cytokines and/or the activation of cytotoxic T cells, antigen presenting cells, helper T cells, dendritic cells and/or other cellular responses.

Optionally, the vaccine of the present invention additionally includes an adjuvant which can be present in either a minor or major proportion relative to the compound of the present invention. The term "adjuvant" as used herein refers to non-specific stimulators of the immune response or substances that allow generation of a depot in the host which when combined with the vaccine of the present invention provide for an even more enhanced immune response. A variety of adjuvants can be used. Examples include complete and incomplete Freund's adjuvant, aluminum hydroxide and modified muramyldipeptide.

Virus-like particle (VLP): As used herein, the term "virus-like particle" refers to a structure resembling a virus particle. Moreover, a virus-like particle in accordance with the invention is non replicative and noninfectious since it lacks all or part of the viral genome, in particular the replicative and infectious components of the viral genome. A virus-like particle in accordance with the invention may contain nucleic acid distinct from their genome. A typical and preferred embodiment of a virus-like particle in accordance with the present invention is a viral capsid such as the viral capsid of the corresponding virus, bacteriophage, or RNA-phage. The terms "viral capsid" or "capsid", as interchangeably used herein, refer to a macromolecular assembly composed of viral protein subunits. Typically and preferably, the viral protein subunits assemble into a viral capsid and capsid, respectively, having a structure with an inherent repetitive organization, wherein said structure is, typically, spherical or tubular. For example, the capsids of RNA-phages or HBcAg's have a spherical form of icosahedral symmetry. The term "capsid-like structure" as used herein, refers to a macromolecular assembly composed of viral protein subunits ressembling the capsid morphology in the above defined sense but deviating from the typical symmetrical assembly while maintaining a sufficient degree of order and repetitiveness.

Virus-like particle of a bacteriophage: As used herein, the term "virus-like particle of a bacteriophage" refers to a virus-like par structure of a bacteriophage, being non replicative and noninfectious, and lacking at least the gene or genes encoding for the replication machinery of the bacteriophage, and typically also lacking the gene or genes encoding the protein or proteins responsible for viral attachment to or entry into the host. This definition should, however, also encompass virus-like particles of bacteriophages, in which the aforementioned gene or genes are still present but inactive, and, therefore, also leading to non-replicative and noninfectious virus-like particles of a bacteriophage.

VLP of RNA phage coat protein: The capsid structure formed from the self-assembly of 180 subunits of RNA phage coat protein and optionally containing host RNA is referred to as a "VLP of RNA phage coat protein". A specific example is the VLP of Qβ coat protein. In this particular case, the VLP of Qβ coat protein may either be assembled exclusively from Qβ CP subunits (generated by expression of a Qβ CP gene containing, for example, a TAA stop codon precluding any expression of the longer A1 protein through suppression, see Kozlovska, T. M., et al., *Intervirology* 39: 9–15 (1996)), or additionally contain A1 protein subunits in the capsid assembly.

Virus particle: The term "virus particle" as used herein refers to the morphological form of a virus. In some virus types it comprises a genome surrounded by a protein capsid; others have additional structures (e.g., envelopes, tails, etc.).

One, a, or an: When the terms "one," "a," or "an" are used in this disclosure, they mean "at least one" or "one or more," unless otherwise indicated.

As will be clear to those skilled in the art, certain embodiments of the invention involve the use of recombinant nucleic acid technologies such as cloning, polymerase chain reaction, the purification of DNA and RNA, the expression of recombinant proteins in prokaryotic and eukaryotic cells, etc. Such methodologies are well known to those skilled in the art and can be conveniently found in published laboratory methods manuals (e.g., Sambrook, J. et al., eds., *Molecular Cloning, A Laboratory Manual*, 2nd. edition, Cold Spring Harbor Laboratory Press, Cold Spring Harbor, N.Y. (1989); Ausubel, F. et al., eds., *Current Protocols in Molecular Biology*, John H. Wiley & Sons, Inc. (1997)). Fundamental laboratory techniques for working with tissue culture cell lines (Celis, J., ed., *Cell Biology*, Academic Press, $2^{nd}$ edition, (1998)) and antibody-based technologies (Harlow, E. and Lane, D., *Antibodies: A Laboratory Manual*, Cold Spring Harbor Laboratory, Cold Spring Harbor, N.Y. (1988); Deutscher, M. P., "Guide to Protein Purification," *Meth. Enzymol.* 128, Academic Press San Diego (1990); Scopes, R. K., *Protein Purification Principles and Practice,* 3rd ed., Springer-Verlag, New York (1994)) are also adequately described in the literature, all of which are incorporated herein by reference.

2. Compositions and Methods for Enhancing an Immune Response

The disclosed invention provides compositions and methods for enhancing an immune response against RANKL protein, RANKL fragment or RANKL peptide in an animal. Compositions of the invention comprise, or alternatively consist of (a) a core particle with at least one first attachment site; and (b) at least one antigen or antigenic determinant with at least one second attachment site, wherein said antigen or antigenic determinant is a RANKL protein, RANKL fragment or RANKL peptide, and wherein said second attachment site being selected from the group consisting of (i) an attachment site not naturally occurring with said antigen or antigenic determinant; and (ii) an attachment site naturally occurring with said antigen or antigenic determinant, wherein said second attachment site is capable of association to said first attachment site; and wherein said antigen or antigenic determinant and said core particle interact through said association to form an ordered and repetitive antigen array. More specifically, compositions of the invention comprise, or alternatively consist of, a virus-like particle and at least one antigen or antigenic determinant, wherein the antigen or antigenic determinant is a RANKL protein, RANKL fragment or RANKL peptide, and wherein the at least one antigen or antigenic determinant is bound to the virus-like particle so as to form an ordered and repetitive antigen-VLP-array. Furthermore, the invention conveniently enables the practitioner to construct such a composition, inter alia, for treatment and/or prophylactic prevention of bone diseases characterized by increased bone resorption.

In one embodiment, the core particle comprises a virus, a bacterial pilus, a structure formed from bacterial pilin, a bacteriophage, a virus-like particle, a viral capsid particle or a recombinant form thereof. Any virus known in the art having an ordered and repetitive coat and/or core protein structure may be selected as a core particle of the invention; examples of suitable viruses include sindbis and other alphaviruses, rhabdoviruses (e.g. vesicular stomatitis virus), picornaviruses (e.g., human rhino virus, Aichi virus), togaviruses (e.g., rubella virus), orthomyxoviruses (e.g., Thogoto virus, Batken virus, fowl plague virus), polyomaviruses (e.g., polyomavirus BK, polyomavirus JC, avian polyomavirus BFDV), parvoviruses, rotaviruses, Norwalk virus, foot and mouth disease virus, a retrovirus, Hepatitis B virus, Tobacco mosaic virus, Flock House Virus, and human Papilomavirus, and preferably a RNA phage, bacteriophage Qβ, bacteriophage R17, bacteriophage M11, bacteriophage MX1, bacteriophage NL95, bacteriophage fr, bacteriophage GA, bacteriophage SP, bacteriophage MS2, bacteriophage f2, bacteriophage PP7 (for example, see Table 1 in Bachmann, M. F. and Zinkernagel, R. M., *Immunol. Today* 17:553–558 (1996)).

In a further embodiment, the invention utilizes genetic engineering of a virus to create a fusion between an ordered and repetitive viral envelope protein and a first attachment site comprising a heterologous protein, peptide, antigenic determinant or a reactive amino acid residue of choice. Other genetic manipulations known to those in the art may be included in the construction of the inventive compositions; for example, it may be desirable to restrict the replication ability of the recombinant virus through genetic mutation. Furthermore, the virus used for the present invention is replication incompetent due to chemical or physical inactivation or, as indicated, due to lack of a replication competent genome. The viral protein selected for fusion to the first attachment site should have an organized and repetitive structure. Such an organized and repetitive structure includes paracrystalline organizations with a spacing of 5–30 nm, preferably 5–15 nm, on the surface of the virus. The creation of this type of fusion protein will result in multiple, ordered and repetitive first attachment sites on the surface of the virus and reflect the normal organization of the native viral protein. As will be understood by those in the art, the first attachment site may be or be a part of any suitable protein, polypeptide, sugar, polynucleotide, peptide (amino acid), natural or synthetic polymer, a secondary metabolite or combination thereof that may serve to specifically attach the antigen or antigenic determinant leading an ordered and repetitive antigen array.

In another embodiment of the invention, the core particle is a recombinant alphavirus, and more specifically, a recombinant Sinbis virus. Alphaviruses are positive stranded RNA viruses that replicate their genomic RNA entirely in the cytoplasm of the infected cell and without a DNA intermediate (Strauss, J. and Strauss, E., *Microbiol. Rev.* 58:491–562 (1994)). Several members of the alphavirus family, Sindbis (Xiong, C. et al., *Science* 243:1188–1191 (1989); Schlesinger, S., *Trends Biotechnol.* 11:18–22 (1993)), Semliki Forest Virus (SFV) (Liljeström, P. & Garoff, H., *Bio/Technology* 9:1356–1361 (1991)) and others (Davis, N. L. et al., *Virology* 171:189–204 (1989)), have received considerable attention for use as virus-based expression vectors for a variety of different proteins (Lundstrom, K., *Curr. Opin. Biotechnol.* 8:578–582 (1997); Liljeström, P., *Curr. Opin. Biotechnol.* 5:495–500 (1994)) and as candidates for vaccine development. Recently, a number of patents have issued directed to the use of alphaviruses for the expression of heterologous proteins and the development of vaccines (see U.S. Pat. Nos. 5,766,602; 5,792,462; 5,739,026; 5,789,245 and 5,814,482). The construction of the alphaviral core particles of the invention may be done by means generally known in the art of recombinant DNA technology, as described by the aforementioned articles, which are incorporated herein by reference.

A variety of different recombinant host cells can be utilized to produce a viral-based core particle for antigen or antigenic determinant attachment. For example, alphaviruses are known to have a wide host range; Sindbis virus infects cultured mammalian, reptilian, and amphibian cells, as well as some insect cells (Clark, H., *J. Natl. Cancer Inst.* 51:645 (1973); Leake, C., *J. Gen. Virol.* 35:335 (1977); Stollar, V. in The Togaviruses, R. W. Schlesinger, Ed., Academic Press, (1980), pp.583–621). Thus, numerous recombinant host cells can be used in the practice of the invention. BHK, COS, Vero, HeLa and CHO cells are particularly suitable for the production of heterologous proteins because they have the potential to glycosylate heterologous proteins in a manner similar to human cells (Watson, E. et al., *Glycobiology* 4:227, (1994)) and can be selected (Zang, M. et al., *Bio/Technology* 13:389 (1995)) or genetically engineered (Renner W. et al., *Biotech. Bioeng.* 4:476 (1995); Lee K. et al. *Biotech. Bioeng.* 50:336 (1996)) to grow in serum-free medium, as well as in suspension.

Introduction of the polynucleotide vectors into host cells can be effected by methods described in standard laboratory manuals (see, e.g., Sambrook, J. et al., eds., Molecular Cloning, A Laboratory Manual, 2nd. edition, Cold Spring Harbor Laboratory Press, Cold Spring Harbor, N.Y. (1989), Chapter 9; Ausubel, F. et al., eds., Current Protocols in Molecular Biology, John H. Wiley & Sons, Inc. (1997), Chapter 16), including methods such as electroporation, DEAE-dextran mediated transfection, transfection, microinjection, cationic lipid-mediated transfection, transduction, scrape loading, ballistic introduction, and infection. Methods for the introduction of exogenous DNA sequences into host cells are discussed in Felgner, P. et al., U.S. Pat. No. 5,580,859.

Packaged RNA sequences can also be used to infect host cells. These packaged RNA sequences can be introduced to host cells by adding them to the culture medium. For example, the preparation of non-infective alpahviral particles is described in a number of sources, including "Sindbis Expression System", Version C (*Invitrogen* Catalog No. K750-1).

When mammalian cells are used as recombinant host cells for the production of viral-based core particles, these cells will generally be grown in tissue culture. Methods for growing cells in culture are well known in the art (see, e.g., Celis, J., ed., CELL BIOLOGY, Academic Press, $2^{nd}$ edition, (1998); Sambrook, J. et al., eds., MOLECULAR CLONING, A LABORATORY MANUAL, 2nd. edition, Cold Spring Harbor Laboratory Press, Cold Spring Harbor, N.Y. (1989); Ausubel, F. et al., eds., CURRENT PROTOCOLS IN MOLECULAR BIOLOGY, John H. Wiley & Sons, Inc. (1997); Freshney, R., CULTURE OF ANIMAL CELLS, Alan R. Liss, Inc. (1983)).

Further examples of RNA viruses suitable for use as core particles in the present invention include, but are not limited to, the following: members of the family Reoviridae, including the genus Orthoreovirus (multiple serotypes of both mammalian and avian retroviruses), the genus Orbivirus (Bluetongue virus, Eugenangee virus, Kemerovo virus, African horse sickness virus, and Colorado Tick Fever virus), the genus Rotavirus (human rotavirus, Nebraska calf diarrhea virus, murine rotavirus, simian rotavirus, bovine or ovine rotavirus, avian rotavirus); the family Picornaviridae, including the genus Enterovirus (poliovirus, Coxsackie virus A and B, enteric cytopathic human orphan (ECHO) viruses, hepatitis A, C, D, E and G viruses, Simian enteroviruses, Murine encephalomyelitis (ME) viruses, Poliovirus muris, Bovine enteroviruses, Porcine enteroviruses, the genus Cardiovirus (Encephalomyocarditis virus (EMC), Mengovirus), the genus Rhinovirus (Human rhinoviruses including at least 113 subtypes; other rhinoviruses), the genus Apthovirus (Foot and Mouth disease (FMDV); the family Calciviridae, including Vesicular exanthema of swine virus, San Miguel sea lion virus, Feline picornavirus and Norwalk virus; the family Togaviridae, including the genus Alphavirus (Eastern equine encephalitis virus, Semliki forest virus, Sindbis virus, Chikungunya virus, O'Nyong-Nyong virus, Ross river virus, Venezuelan equine encephalitis virus, Western equine encephalitis virus), the genus Flavirius (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever virus), the genus Nairovirus (Crimean-Congo hemorrhagic fever virus, Nairobi sheep disease virus), and the genus Uukuvirus (Uukuniemi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type C (possible separate genus); the family paramyxoviridae, including the genus Paramyxovirus (Parainfluenza virus type 1, Sendai virus, Hemadsorption virus, Parainfluenza viruses types 2 to 5, Newcastle Disease Virus, Mumps virus), the genus Morbillivirus (Measles virus, subacute sclerosing panencephalitis virus, distemper virus, Rinderpest virus), the genus Pneumovirus (respiratory syncytial virus (RSV), Bovine respiratory syncytial virus and Pneumonia virus of mice); forest virus, Sindbis virus, Chikungunya virus, O'Nyong-Nyong virus, Ross river virus, Venezuelan equine encephalitis virus, Western equine encephalitis virus), the genus Flavirius (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever virus), the genus Nairovirus (Crimean-Congo hemorrhagic fever virus, Nairobi sheep disease virus), and the genus Uukuvirus (Uukuniemi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type C (possible separate genus); the family paramyxoviridae, including the genus Paramyxovirus (Parainfluenza virus type 1, Sendai virus, Hemadsorption virus, Parainfluenza viruses types 2 to 5, Newcastle Disease Virus, Mumps virus), the genus Morbillivirus (Measles virus, subacute sclerosing panencephalitis virus, distemper virus, Rinderpest virus), the genus Pneumovirus (respiratory syncytial virus (RSV), Bovine respiratory syncytial virus and Pneumonia virus of mice); the family Rhabdoviridae, including the genus Vesiculovirus (VSV), Chandipura virus, Flanders-Hart Park virus), the genus Lyssavirus (Rabies virus), fish Rhabdoviruses and, filoviruses (Marburg virus and Ebola virus); the family Arenaviridae, including Lymphocytic choriomeningitis virus (LCM), Tacaribe virus complex, and Lassa virus; the family Coronoaviridae, including Infectious Bronchitis Virus (IBV), Mouse Hepatitis virus, Human enteric corona virus, and Feline infectious peritonitis (Feline coronavirus).

Illustrative DNA viruses that may be used as core particles include, but are not limited to: the family Poxviridae, including the genus Orthopoxvirus (Variola major, Variola minor, Monkey pox Vaccinia, Cowpox, Buffalopox, Rabbitpox, Ectromelia), the genus Leporipoxvirus (Myxoma, Fibroma), the genus Avipoxvirus (Fowlpox, other avian poxvirus), the genus Capripoxvirus (sheeppox, goatpox), the genus Suipoxvirus (Swinepox), the genus Parapoxvirus (contagious postular dermatitis virus, pseudocowpox, bovine papular stomatitis virus); the family Iridoviridae (African swine fever virus, Frog viruses 2 and 3, Lymphocystis virus of fish); the family Herpesviridae, including the alpha-Herpesviruses (Herpes Simplex Types 1 and 2, Varicella-Zoster, Equine abortion virus, Equine herpes virus 2 and 3, pseudorabies virus, infectious bovine keratoconjunctivitis virus, infectious bovine rhinotracheitis virus, feline rhinotracheitis virus, infectious laryngotracheitis virus) the Beta-herpesviruses (Human cytomegalovirus and cytomegaloviruses of swine, monkeys and rodents); the gamma-herpesviruses (Epstein-Barr virus (EBV), Marek's disease virus, Herpes saimiri, Herpesvirus ateles, Herpesvirus sylvilagus, guinea pig herpes virus, Lucke tumor virus); the family Adenoviridae, including the genus Mastadenovirus (Human subgroups A, B, C, D and E and ungrouped; simian adenoviruses (at least 23 serotypes), infectious canine hepatitis, and adenoviruses of cattle, pigs, sheep, frogs and many other species, the genus Aviadenovirus (Avian adenoviruses); and non-cultivatable adenoviruses; the family Papoviridae, including the genus Papillomavirus (Human papilloma viruses, bovine papilloma viruses, Shope rabbit papilloma virus, and various pathogenic papilloma viruses of other species), the genus Polyomavirus (polyomavirus, Simian vacuolating agent (SV-40), Rabbit vacuolating agent (RKV), K virus, BK virus, JC virus, and other primate polyoma viruses such as Lymphotrophic papilloma virus); the family Parvoviridae including the genus Adeno-associated viruses, the genus Parvovirus (Feline panleukopenia virus, bovine parvovirus, canine parvovirus, Aleutian mink disease virus, etc.). Finally, DNA viruses may include viruses such as chronic infectious neuropathic agents (CHINA virus).

In other embodiments, a bacterial pilin, a subportion of a bacterial pilin, or a fusion protein which contains either a bacterial pilin or subportion thereof is used to prepare compositions and vaccine compositions, respectively, of the invention. Examples of pilin proteins include pilins produced by *Escherichia coli, Haemophilus influenzae, Neisseria meningitidis, Neisseria gonorrhoeae, Caulobacter crescentus, Pseudomonas stutzeri, and Pseudomonas aeruginosa*. The amino acid sequences of pilin proteins suitable for use with the present invention include those set out in GenBank reports AJ000636 (SEQ ID NO:1), AJ132364 (SEQ ID NO:2), AF229646 (SEQ ID NO: 3), AF051814 (SEQ ID NO:4), AF051815 (SEQ ID NO:5), and X00981 (SEQ ID NO:6), the entire disclosures of which are incorporated herein by reference.

Bacterial pilin proteins are generally processed to remove N-terminal leader sequences prior to export of the proteins into the bacterial periplasm. Further, as one skilled in the art would recognize, bacterial pilin proteins used to prepare compositions and vaccine compositions, respectively, of the invention will generally not have the naturally present leader sequence.

One specific example of a pilin protein suitable for use in the present invention is the P-pilin of *E. coli* (GenBank report AF237482 (SEQ ID NO:7)). An example of a Type-1 *E. coli* pilin suitable for use with the invention is a pilin having the amino acid sequence set out in GenBank report P04128 (SEQ ID NO:8), which is encoded by nucleic acid having the nucleotide sequence set out in GenBank report M27603 (SEQ ID NO:9). The entire disclosures of these GenBank reports are incorporated herein by reference. Again, the mature form of the above referenced protein would generally be used to prepare compositions and vaccine compositions, respectively, of the invention.

Bacterial pilins or pilin subportions suitable for use in the practice of the present invention will generally be able to associate to form ordered and repetitive antigen arrays.

Methods for preparing pili and pilus-like structures in vitro are known in the art. Bullitt et al., *Proc. Natl. Acad. Sci. USA* 93:12890–12895 (1996), for example, describe the in vitro reconstitution of *E. coli* P-pili subunits. Furthermore, Eshdat et al., *J. Bacteriol.* 148:308–314 (1981) describe methods suitable for dissociating Type-1 pili of *E. coli* and the reconstitution of pili. In brief, these methods are as follows: pili are dissociated by incubation at 37° C. in saturated guanidine hydrochloride. Pilin proteins are then purified by chromatography, after which pilin dimers are formed by dialysis against 5 mM tris(hydroxymethyl) aminomethane hydrochloride (pH 8.0). Eshdat et al. also found that pilin dimers reassemble to form pili upon dialysis against the 5 mM tris(hydroxymethyl) aminomethane (pH 8.0) containing 5 mM $MgCl_2$.

Further, using, for example, conventional genetic engineering and protein modification methods, pilin proteins may be modified to contain a first attachment site to which an antigen or antigenic determinant is linked through a second attachment site. Alternatively, antigens or antigenic determinants can be directly linked through a second attachment site to amino acid residues which are naturally resident in these proteins. These modified pilin proteins may then be used in vaccine compositions of the invention.

Bacterial pilin proteins used to prepare compositions and vaccine compositions, respectively, of the invention may be modified in a manner similar to that described herein for HBcAg. For example, cysteine and lysine residues may be either deleted or substituted with other amino acid residues and first attachment sites may be added to these proteins. Further, pilin proteins may either be expressed in modified form or may be chemically modified after expression. Similarly, intact pili may be harvested from bacteria and then modified chemically.

In another embodiment, pili or pilus-like structures are harvested from bacteria (e.g., *E. coli*) and used to form compositions and vaccine compositions of the invention. One example of pili suitable for preparing compositions and vaccine compositions is the Type-1 pilus of *E. coli*, which is formed from pilin monomers having the amino acid sequence set out in SEQ ID NO:8.

A number of methods for harvesting bacterial pili are known in the art. Bullitt and Makowski (*Biophys. J.* 74:623–632 (1998)), for example, describe a pilus purification method for harvesting P-pili from *E. coli*. According to this method, pili are sheared from hyperpiliated *E. coli* containing a P-pilus plasmid and purified by cycles of solubilization and $MgCl_2$ (1.0 M) precipitation.

Once harvested, pili or pilus-like structures may be modified in a variety of ways. For example, a first attachment site can be added to the pili to which antigens or antigen determinants may be attached through a second attachment site. In other words, bacterial pili or pilus-like structures can be harvested and modified to lead to ordered and repetitive antigen arrays.

Antigens or antigenic determinants could be linked to naturally occurring cysteine resides or lysine residues present in Pili or pilus-like structures. In such instances, the high order and repetitiveness of a naturally occurring amino acid residue would guide the coupling of the antigens or antigenic determinants to the pili or pilus-like structures. For example, the pili or pilus-like structures could be linked to the second attachment sites of the antigens or antigenic determinants using a heterobifunctional cross-linking agent.

When structures which are naturally synthesized by organisms (e.g., pili) are used to prepare compositions and vaccine compositions of the invention, it will often be advantageous to genetically engineer these organisms so that they produce structures having desirable characteristics. For example, when Type-1 pili of *E. coli* are used, the *E. coli* from which these pili are harvested may be modified so as to produce structures with specific characteristics. Examples of possible modifications of pilin proteins include the insertion of one or more lysine residues, the deletion or substitution of one or, more of the naturally resident lysine residues, and the deletion or substitution of one or more naturally resident cysteine residues (e.g., the cysteine residues at positions 44 and 84 in SEQ ID NO:8).

Further, additional modifications can be made to pilin genes which result in the expression products containing a first attachment site other than a lysine residue (e.g., a FOS or JUN domain). Of course, suitable first attachment sites will generally be limited to those which do not prevent pilin proteins from forming pili or pilus-like structures suitable for use in vaccine compositions of the invention.

Pilin genes which naturally reside in bacterial cells can be modified in vivo (e.g., by homologous recombination) or pilin genes with particular characteristics can be inserted into these cells. For examples, pilin genes could be introduced into bacterial cells as a component of either a replicable cloning vector or a vector which inserts into the bacterial chromosome. The inserted pilin genes may also be linked to expression regulatory control sequences (e.g., a lac operator).

In most instances, the pili or pilus-like structures used in compositions and vaccine compositions, respectively, of the invention will be composed of single type of a pilin subunit. Pili or pilus-like structures composed of identical subunits will generally be used because they are expected to form structures which present highly ordered and repetitive antigen arrays.

However, the compositions of the invention also include compositions and vaccines comprising pili or pilus-like structures formed from heterogenous pilin subunits. The pilin subunits which form these pili or pilus-like structures can be expressed from genes naturally resident in the bacterial cell or may be introduced into the cells. When a naturally resident pilin gene and an introduced gene are both expressed in a cell which forms pili or pilus-like structures, the result will generally be structures formed from a mixture of these pilin proteins. Further, when two or more pilin genes are expressed in a bacterial cell, the relative expression of each pilin gene will typically be the factor which determines the ratio of the different pilin subunits in the pili or pilus-like structures.

When pili or pilus-like structures having a particular composition of mixed pilin subunits is desired, the expression of at least one of the pilin genes can be regulated by a heterologous, inducible promoter. Such promoters, as well as other genetic elements, can be used to regulate the relative amounts of different pilin subunits produced in the bacterial cell and, hence, the composition of the pili or pilus-like structures.

In additional, the antigen or antigenic determinant can be linked to bacterial pili or pilus-like structures by a bond which is not a peptide bond, bacterial cells which produce pili or pilus-like structures used in the compositions of the invention can be genetically engineered to generate pilin proteins which are fused to an antigen or antigenic determinant. Such fusion proteins which form pili or pilus-like structures are suitable for use in vaccine compositions of the invention.

Virus-like particles in the context of the present application refer to structures resembling a virus particle but which are not pathogenic. In general, virus-like particles lack the viral genome and, therefore, are noninfectious. Also, viruslike particles can be produced in large quantities by heterologous expression and can be easily purified.

In a preferred embodiment, the virus-like particle is a recombinant virus-like particle. The skilled artisan can produce VLPs using recombinant DNA technology and virus coding sequences which are readily available to the public. For example, the coding sequence of a virus envelope or core protein can be engineered for expression in a baculovirus expression vector using a commercially available baculovirus vector, under the regulatory control of a virus promoter, with appropriate modifications of the sequence to allow functional linkage of the coding sequence to the regulatory sequence. The coding sequence of a virus envelope or core protein can also be engineered for expression in a bacterial expression vector, for example.

Examples of VLPs include, but are not limited to, the capsid proteins of Hepatitis B virus (Ulrich, et al., *Virus Res.* 50:141–182 (1998)), measles virus (Warnes, et al., *Gene* 160:173–178 (1995)), Sindbis virus, rotavirus (U.S. Pat. No. 5,071,651 and U.S. Pat. No. 5,374,426), foot-and-mouth-disease virus (Twomey, et al., *Vaccine* 13:1603–1610, (1995)), Norwalk virus (Jiang, X., et al., *Science* 250: 1580–1583 (1990); Matsui, S. M., et al., *J. Clin. Invest.* 87:1456–1461 (1991)), the retroviral GAG protein (WO 96/30523), the retrotransposon Ty protein p1, the surface protein of Hepatitis B virus (WO 92/11291), human papilloma virus (WO 98/15631), RNA phages, Ty, fr-phage, GA-phage and Qβ-phage.

As will be readily apparent to those skilled in the art, the VLP of the invention is not limited to any specific form. The particle can be synthesized chemically or through a biological process, which can be natural or non-natural. By way of example, this type of embodiment includes a virus-like particle or a recombinant form thereof.

In a more specific embodiment, the VLP can comprise, or alternatively essentially consist of, or alternatively consist of recombinant polypeptides, or fragments thereof, being selected from recombinant polypeptides of Rotavirus, recombinant polypeptides of Norwalk virus, recombinant polypeptides of Alphavirus, recombinant polypeptides of Foot and Mouth Disease virus, recombinant polypeptides of measles virus, recombinant polypeptides of Sindbis virus, recombinant polypeptides of Polyoma virus, recombinant polypeptides of Retrovirus, recombinant polypeptides of Hepatitis B virus (e.g., a HBcAg), recombinant polypeptides of Tobacco mosaic virus, recombinant polypeptides of Flock House Virus, recombinant polypeptides of human Papillomavirus, recombinant polypeptides of bacteriophages, recombinant polypeptides of RNA phages, recombinant polypeptides of Ty, recombinant polypeptides of fr-phage, recombinant polypeptides of GA-phage and recombinant polypeptides of Qβ-phage. The virus-like particle can further comprise, or alternatively essentially consist of, or alternatively consist of, one or more fragments of such polypeptides, as well as variants of such polypeptides. Variants of polypeptides can share, for example, at least 80%, 85%, 90%, 95%, 97%, or 99% identity at the amino acid level with their wild-type counterparts.

In a preferred embodiment, the virus-like particle comprises, consists essentially of, or alternatively consists of recombinant proteins, or fragments thereof, of a RNA-phage. Preferably, the RNA-phage is selected from the group consisting of a) bacteriophage Qβ; b) bacteriophage R17; c) bacteriophage fr; d) bacteriophage GA; e) bacteriophage SP; f) bacteriophage MS2; g) bacteriophage M11; h) bacteriophage MX1; i) bacteriophage NL95; k) bacteriophage f2; and l) bacteriophage PP7.

In another preferred embodiment of the present invention, the virus-like particle comprises, or alternatively consists essentially of, or alternatively consists of recombinant proteins, or fragments thereof, of the RNA-bacteriophage Qβ or of the RNA-bacteriophage fr.

In a further preferred embodiment of the present invention, the recombinant proteins comprise, or alternatively consist essentially of, or alternatively consist of coat proteins of RNA phages.

RNA-phage coat proteins forming capsids or VLPs, or fragments of the bacteriophage coat proteins compatible with self-assembly into a capsid or a VLP, are, therefore, further preferred embodiments of the present invention. Bacteriophage Qβ coat proteins, for example, can be expressed recombinantly in *E. coli*. Further, upon such expression these proteins spontaneously form capsids. Additionally, these capsids form a structure with an inherent repetitive organization.

Specific preferred examples of bacteriophage coat proteins which can be used to prepare compositions of the invention include the coat proteins of RNA bacteriophages such as bacteriophage Qβ (SEQ ID NO:10; PIR Database, Accession No. VCBPQβ referring to Qβ CP and SEQ ID NO: 11; Accession No. AAA16663 referring to Qβ A1 protein), bacteriophage R17 (SEQ ID NO:12; PIR Accession No. VCBPR7), bacteriophage fr (SEQ ID NO:13; PIR Accession No. VCBPFR), bacteriophage GA (SEQ ID NO:14; GenBank Accession No. NP-040754), bacteriophage SP (SEQ ID NO:15; GenBank Accession No. CAA30374 referring to SP CP and SEQ ID NO: 16; Accession No. referring to SP A1 protein), bacteriophage MS2 (SEQ ID NO:17; PIR Accession No. VCBPM2), bacteriophage M11 (SEQ ID NO:18; GenBank Accession No. AAC06250), bacteriophage MX1 (SEQ ID NO:19; GenBank Accession No. AAC14699), bacteriophage NL95 (SEQ ID NO:20; GenBank Accession No. AAC14704), bacteriophage f2 (SEQ ID NO: 21; GenBank Accession No. P03611), bacteriophage PP7 (SEQ ID NO: 22). Furthermore, the A1 protein of bacteriophage Qβ or C-terminal truncated forms missing as much as 100, 150 or 180 amino acids from its C-terminus may be incorporated in a capsid assembly of Qβ coat proteins. Generally, the percentage of Qβ A1 protein relative to Qβ CP in the capsid assembly will be limited, in order to ensure capsid formation.

Qβ coat protein has also been found to self-assemble into capsids when expressed in *E. coli* (Kozlovska T M. et al., *GENE* 137: 133–137 (1993)). The obtained capsids or virus-like particles showed an icosahedral phage-like capsid structure with a diameter of 25 nm and T=3 quasi symmetry. Further, the crystal structure of phage Qβ has been solved. The capsid contains 180 copies of the coat protein, which are linked in covalent pentamers and hexamers by disulfide bridges (Golmohammadi, R. et al., *Structure* 4: 543–5554 (1996)) leading to a remarkable stability of the capsid of Qβ coat protein. Capsids or VLPs made from recombinant Qβ coat protein may contain, however, subunits not linked via disulfide links to other subunits within the capsid, or incompletely linked. Thus, upon loading recombinant Qβ capsid on non-reducing SDS-PAGE, bands corresponding to monomeric Qβ coat protein as well as bands corresponding to the hexamer or pentamer of Qβ coat protein are visible. Incompletely disulfide-linked subunits could appear as dimer, trimer or even tetramer band in non-reducing SDS-PAGE. Qβ capsid protein also shows unusual resistance to organic solvents and denaturing agents. Surprisingly, we have observed that DMSO and acetonitrile concentrations as high as 30%, and Guanidinium concentrations as high as 1 M do not affect the stability of the capsid. The high stability of the capsid of Qβ coat protein is an advantageous feature, in particular, for its use in immunization and vaccination of mammals and humans in accordance of the present invention.

Upon expression in *E. coli*, the N-terminal methionine of Qβ coat protein is usually removed, as we observed by N-terminal Edman sequencing as described in Stoll, E. et al. *J. Biol. Chem.* 252:990–993 (1977). VLP composed from Qβ coat proteins where the N-terminal methionine has not been removed, or VLPs comprising a mixture of Qβ coat proteins where the N-terminal methionine is either cleaved or present are also within the scope of the present invention.

Further RNA phage coat proteins have also been shown to self-assemble upon expression in a bacterial host (Kastelein, R A. et al., *Gene* 23: 245–254 (1983), Kozlovskaya, T M. et al., *Dokl. Akad. Nauk SSSR* 287: 452–455 (1986), Adhin, M R. et al., *Virology* 170: 238–242 (1989), Ni, C Z., et al., *Protein Sci.* 5: 2485–2493 (1996), Priano, C. et al., *J. Mol. Biol.* 249: 283–297 (1995)). The Qβ phage capsid contains, in addition to the coat protein, the so called read-through protein A1 and the maturation protein A2. A1 is generated by suppression at the UGA stop codon and has a length of 329 aa. The capsid of phage Qβ recombinant coat protein used in the invention is devoid of the A2 lysis protein, and contains RNA from the host. The coat protein of RNA phages is an RNA binding protein, and interacts with the stem loop of the ribosomal binding site of the replicase gene acting as a translational repressor during the life cycle of the virus. The sequence and structural elements of the interaction are known (Witherell, G W. & Uhlenbeck, O C. *Biochemistry* 28: 71–76 (1989); Lim F. et al., *J. Biol. Chem.* 271: 31839–31845 (1996)). The stem loop and RNA in general are known to be involved in the virus assembly (Golmohammadi, R. et al., *Structure* 4: 543–5554 (1996)).

In a further preferred embodiment of the present invention, the virus-like particle comprises, or alternatively consists essentially of, or alternatively consists of recombinant proteins, or fragments thereof, of a RNA-phage, wherein the recombinant proteins comprise, consist essentially of or alternatively consist of mutant coat proteins of a RNA phage, preferably of mutant coat proteins of the RNA phages mentioned above. In another preferred embodiment, the mutant coat proteins of the RNA phage have been modified by removal of at least one lysine residue by way of substitution, or by addition of at least one lysine residue by way of substitution; alternatively, the mutant coat proteins of the RNA phage have been modified by deletion of at least one lysine residue, or by addition of at least one lysine residue by way of insertion.

In another preferred embodiment, the virus-like particle comprises, or alternatively consists essentially of, or alternatively consists of recombinant proteins, or fragments thereof, of the RNA-bacteriophage Qβ, wherein the recombinant proteins comprise, or alternatively consist essentially of, or alternatively consist of coat proteins having an amino acid sequence of SEQ ID NO:10, or a mixture of coat proteins having amino acid sequences of SEQ ID NO:10 and of SEQ ID NO: 11 or mutants of SEQ ID NO: 11 and wherein the N-terminal methionine is preferably cleaved.

In a further preferred embodiment of the present invention, the virus-like particle comprises, consists essentially of or alternatively cons recombinant proteins of Qβ, or fragments thereof, wherein the recombinant proteins comprise, or alternatively consist essentially of, or alternatively consist of mutant Qβ coat proteins. In another preferred embodiment, these mutant coat proteins have been modified by removal of at least one lysine residue by way of substitution, or by addition of at least one lysine residue by way of substitution. Alternatively, these mutant coat proteins have been modified by deletion of at least one lysine residue, or by addition of at least one lysine residue by way of insertion.

Four lysine residues are exposed on the surface of the capsid of Qβ coat protein. Qβ mutants, for which exposed lysine residues are replaced by arginines can also be used for the present invention. The following Qβ coat protein mutants and mutant Qβ VLPs can, thus, be used in the practice of the invention: "Qβ-240" (Lys13-Arg; SEQ ID NO:23), "Qβ-243" (Asn 10-Lys; SEQ ID NO:24), "Qβ-250" (Lys 2-Arg, Lys13-Arg; SEQ ID NO:25), "Qβ-251" (SEQ ID NO:26) and "Qβ-259" (Lys 2-Arg, Lys16-Arg; SEQ ID NO:27). Thus, in further preferred embodiment of the present invention, the virus-like particle comprises, consists essentially of or alternatively consists of recombinant proteins of mutant Qβ coat proteins, which comprise proteins having an amino acid sequence selected from the group of a) the amino acid sequence of SEQ ID NO:23; b) the amino acid sequence of SEQ ID NO:24; c) the amino acid sequence of SEQ ID NO:25; d) the amino acid sequence of SEQ ID NO:26; and e) the amino acid sequence of SEQ ID NO:27. The construction, expression and purification of the above indicated Qβ coat proteins, mutant Qβ coat protein VLPs and capsids, respectively, are disclosed in pending U.S. application Ser. No. 10/050,902 filed by the present assignee on Jan. 18, 2002. In particular is hereby referred to Example 18 of above mentioned application.

In a further preferred embodiment of the present invention, the virus-like particle comprises, or alternatively consists essentially of, or alternatively consists of recombinant proteins of Qβ, or fragments thereof, wherein the recombinant proteins comprise, consist essentially of or alternatively consist of a mixture of either one of the foregoing Qβ mutants and the corresponding A1 protein.

In a further preferred embodiment of the present invention, the virus-like particle comprises, or alternatively essentially consists of, or alternatively consists of recombinant proteins, or fragments thereof, of RNA-phage AP205.

The AP205 genome consists of a maturation protein, a coat protein, a replicase and two open reading frames not present in related phages; a lysis gene and an open reading frame playing a role in the translation of the maturation gene (Klovins,J., et al., *J. Gen. Virol.* 83: 1523–33 (2002)). AP205 coat protein can be expressed from plasmid pAP283-58 (SEQ ID NO: 111), which is a derivative of pQb10 (Kozlovska, T. M. et al., *Gene* 137:133–37 (1993)), and which contains an AP205 ribosomal binding site. Alternatively, AP205 coat protein may be cloned into pQb185, downstream of the ribosomal binding site present in the vector. Both approaches lead to expression of the protein and formation of capsids as described in the US provisional patent application with the title "Molecular Antigen Arrays"and having filed by the present assignee on Jul. 16, 2002, which is incorporated by reference in its entirety. Vectors pQb10 and pQb185 are vectors derived from pGEM vector, and expression of the cloned genes in these vectors is controlled by the trp promoter (Kozlovska, T. M. et al., *Gene* 137:133–37 (1993)). Plasmid pAP283-58 (SEQ ID NO:111) comprises a putative AP205 ribosomal binding site in the following sequence, which is downstream of the XbaI site, and immediately upstream of the ATG start codon of the AP205 coat protein: tctagaATTTTCTGCGCACCCATC-CCGGGTGGCGCCCAAAGTGAGGAAAATCACat g (SEQ ID NO: 115). The vector pQb185 comprises a Shine Delagamo sequence downstream from the XbaI site and upstream of the start codon (tctagaTTAACCCAACGCGT AGGAG TCAGGCCatg (SEQ ID NO: 116), Shine Delagarno sequence underlined).

In a further preferred embodiment of the present invention, the virus-like particle comprises, or alternatively essentially consists of, or alternatively consists of recombinant coat proteins, or fragments thereof, of the RNA-phage AP205.

This preferred embodiment of the present invention, thus, comprises AP205 coat proteins that form capsids. Such proteins are recombinantly expressed, or prepared from natural sources. AP205 coat proteins produced in bacteria spontaneously form capsids, as evidenced by Electron Microscopy (EM) and immunodiffusion. The structural properties of the capsid formed by the AP205 coat protein (SEQ ID NO: 112) and those formed by the coat protein of the AP205 RNA phage are nearly indistinguishable when seen in EM. AP205 VLPs are highly immunogenic, and can be linked with antigens and/or antigenic determinants to generate vaccine constructs displaying the antigens and/or antigenic determinants oriented in a repetitive manner. High titers are elicited against the so displayed antigens showing that bound antigens and/or antigenic determinants are accessible for interacting with antibody molecules and are immunogenic.

In a further preferred embodiment of the present invention, the virus-like particle comprises, or alternatively essentially consists of, or alternatively consists of recombinant mutant coat proteins, or fragments thereof, of the RNA-phage AP205.

Assembly-competent mutant forms of AP205 VLPs, including AP205 coat protein with the subsitution of proline at amino acid 5 to threonine (SEQ ID NO: 113), may also be used in the practice of the invention and leads to a further preferred embodiment of the invention. These VLPs, AP205 VLPs derived from natural sources, or AP205 viral particles, may be bound to antigens to produce ordered repetitive arrays of the antigens in accordance with the present invention.

AP205 P5-T mutant coat protein can be expressed from plasmid pAP281-32 (SEQ ID No. 114), which is derived directly from pQb185, and which contains the mutant AP205 coat protein gene instead of the Qβ coat protein gene. Vectors for expression of the AP205 coat protein are transfected into *E. coli* for expression of the AP205 coat protein.

Methods for expression of the coat protein and the mutant coat protein, respectively, leading to self-assembly into VLPs are described in co-pending US provisional patent application with the title "Molecular Antigen Arrays" and having filed by the present assignee on Jul. 17, 2002, which is incorporated by reference in its entirety. Suitable *E. coli* strains include, but are not limited to, *E. coli* K802, JM 109, RR1. Suitable vectors and strains and combinations thereof can be identified by testing expression of the coat protein and mutant coat protein, respectively, by SDS-PAGE and capsid formation and assembly by optionally first purifying the capsids by gel filtration and subsequently testing them in an immunodiffusion assay (Ouchterlony test) or Electron Microscopy (Kozlovska, T. M. et al., *Gene* 137:133–37 (1993)).

AP205 coat proteins expressed from the vectors pAP283-58 and pAP281-32 may be devoid of the initial Methionine amino-acid, due to processing in the cytoplasm of *E. coli*. Cleaved, uncleaved forms of AP205 VLP, or mixtures thereof are further preferred embodiments of the invention.

In a further preferred embodiment of the present invention, the virus-like particle comprises, or alternatively essentially consists of, or alternatively consists of a mixture of recombinant coat proteins, or fragments thereof, of the RNA-phage AP205 and of recombinant mutant coat proteins, or fragments thereof, of the RNA-phage AP205.

In a further preferred embodiment of the present invention, the virus-like particle comprises, or alternatively essentially consists of, or consists of fragments of recombinant coat proteins or recombinant mutant coat proteins of the RNA-phage AP205.

Recombinant AP205 coat protein fragments capable of assembling into a VLP and a capsid, respectively are also useful in the practice of the invention. These fragments may be generated by deletion, either internally or at the termini of the coat protein and mutant coat protein, respectively. Insertions in the coat protein and mutant coat protein sequence or fusions of antigen sequences to the coat protein and mutant coat protein sequence, and compatible with assembly into a VLP, are further embodiments of the invention and lead to chimeric AP205 coat proteins, and particles, respectively. The outcome of insertions, deletions and fusions to the coat protein sequence and whether it is compatible with assembly into a VLP can be determined by electron microscopy.

The particles formed by the AP205 coat protein, coat protein fragments and chimeric coat proteins described above, can be isolated in pure form by a combination of fractionation steps by precipitation and of purification steps by gel filtration using e.g. Sepharose CL-4B, Sepharose CL-2B, Sepharose CL-6B columns and combinations thereof as described in the co-pending US provisional patent application with the title "Molecular Antigen Arrays" and having filed by the present assignee on Jul. 17, 2002, which is incorporated by reference in its entirety. Other methods of isolating virus-like particles are known in the art, and may be used to isolate the virus-like particles (VLPs) of bacteriophage AP205. For example, the use of ultracentrifugation to isolate VLPs of the yeast retrotransposon Ty is described in U.S. Pat. No. 4,918,166, which is incorporated by reference herein in its entirety.

The crystal structure of several RNA bacteriophages has been determined (Golmohammadi, R. et al., *Structure* 4:543–554 (1996)). Using such information, surface exposed residues can be identified and, thus, RNA-phage coat proteins can be modified such that one or more reactive amino acid residues can be inserted by way of insertion or substitution. As a consequence, those modified forms of bacteriophage coat proteins can also be used for the present invention. Thus, variants of proteins which form capsids or capsid-like structures (e.g., coat proteins of bacteriophage Qβ, bacteriophage R17, bacteriophage fr, bacteriophage GA, bacteriophage SP, and bacteriophage MS2) can also be used to prepare compositions of the present invention.

Although the sequence of the variants proteins discussed above will differ from their wild-type counterparts, these variant proteins will generally retain the ability to form capsids or capsid-like structures. Thus, the invention further includes compositions and vaccine compositions, respectively, which further includes variants of proteins which form capsids or capsid-like structures, as well as methods for preparing such compositions and vaccine compositions, respectively, individual protein subunits used to prepare such compositions, and nucleic acid molecules which encode these protein subunits. Thus, included within the scope of the invention are variant forms of wild-type proteins which form capsids or capsid-like structures and retain the ability to associate and form capsids or capsid-like structures.

As a result, the invention further includes compositions and vaccine compositions, respectively, comprising proteins, which comprise, or alternatively consist essentially of, or alternatively consist of amino acid sequences which are at least 80%, 85%, 90%, 95%, 97%, or 99% identical to wild-type proteins which form ordered arrays and having an inherent repetitive structure, respectively.

Further included within the scope of the invention are nucleic acid molecules which encode proteins used to prepare compositions of the present invention.

In other embodiments, the invention further includes compositions comprising proteins, which comprise, or alternatively consist essentially of, or alternatively consist of amino acid sequences which are at least 80%, 85%, 90%, 95%, 97%, or 99% identical to any of the amino acid sequences shown in SEQ ID NOs:10–27.

Proteins suitable for use in the present invention also include C-terminal truncation mutants of proteins which form capsids or capsid-like structures, or VLPs. Specific examples of such truncation mutants include proteins having an amino acid sequence shown in any of SEQ ID NOs:10–27 where 1, 2, 5, 7, 9, 10, 12, 14, 15, or 17 amino acids have been removed from the C-terminus. Typically, theses C-terminal truncation mutants will retain the ability to form capsids or capsid-like structures.

Further proteins suitable for use in the present invention also include N-terminal truncation mutants of proteins which form capsids or capsid-like structures. Specific examples of such truncation mutants include proteins having an amino acid sequence shown in any of SEQ ID NOs:10–27 where 1, 2, 5, 7, 9, 10, 12, 14, 15, or 17 amino acids have been removed from the N-terminus. Typically, these N-terminal truncation mutants will retain the ability to form capsids or capsid-like structures.

Additional proteins suitable for use in the present invention include N- and C-terminal truncation mutants which form capsids or capsid-like structures. Suitable truncation mutants include proteins having an amino acid sequence shown in any of SEQ ID NOs:10–27 where 1, 2, 5, 7, 9, 10, 12, 14, 15, or 17 amino acids have been removed from the N-terminus and 1, 2, 5, 7, 9, 10, 12, 14, 15, or 17 amino acids have been removed from the C-terminus. Typically, these N-terminal and C-terminal truncation mutants will retain the ability to form capsids or capsid-like structures.

The invention further includes compositions comprising proteins which comprise, or alternatively consist essentially of, or alternatively consist of, amino acid sequences which are at least 80%, 85%, 90%, 95%, 97%, or 99% identical to the above described truncation mutants.

The invention thus includes compositions and vaccine compositions prepared from proteins which form capsids or VLPs, methods for preparing these compositions from individual protein subunits and VLPs or capsids, methods for preparing these individual protein subunits, nucleic acid molecules which encode these subunits, and methods for vaccinating and/or eliciting immunological responses in individuals using these compositions of the present invention.

As previously stated, the invention includes virus-like particles or recombinant forms thereof. In one further preferred embodiment, the particles used in compositions of the invention are composed of a Hepatitis B core protein (HBcAg) or a fragment of a HBcAg. In a further embodiment, the particles used in compositions of the invention are composed of a Hepatitis B core protein (HBcAg) or a fragment of a HBcAg protein, which has been modified to either eliminate or reduce the number of free cysteine residues. Zhou et al. (*J. Virol.* 66:5393–5398 (1992)) demonstrated that HBcAgs which have been modified to remove the naturally resident cysteine residues retain the ability to associate and form capsids. Thus, VLPs suitable for use in compositions of the invention include those comprising modified HBcAgs, or fragments thereof, in which one or more of the naturally resident cysteine residues have been either deleted or substituted with another amino acid residue (e.g., a serine residue).

The HBcAg is a protein generated by the processing of a Hepatitis B core antigen precursor protein. A number of isotypes of the HBcAg have been identified and their amino acids sequences are readily available to those skilled in the art. In most instances, compositions and vaccine compositions, respectively, of the invention will be prepared using the processed form of a HBcAg (i.e., a HBcAg from which the N-terminal leader sequence of the Hepatitis B core antigen precursor protein have been removed).

Further, when HBcAgs are produced under conditions where processing will not occur, the HBcAgs will generally be expressed in "processed" form. For example, when an *E. coli* expression system directing expression of the protein to the cytoplasm is used to produce HBcAgs of the invention, these proteins will generally be expressed such that the N-terminal leader sequence of the Hepatitis B core antigen precursor protein is not present.

The preparation of Hepatitis B virus-like particles, which can be used for the present invention, is disclosed, for example, in WO 00/32227, and hereby in particular in Examples 17 to 19 and 21 to 24, as well as in WO 01/85208, and hereby in particular in Examples 17 to 19, 21 to 24, 31 and 41, and in pending U.S. application Ser. No. 10/050,902 filed by the present assignee on Jan. 18, 2002. For the latter application, it is in particular referred to Example 23, 24, 31 and 51. All three documents are explicitly incorporated herein by reference.

The present invention also includes HBcAg variants which have been modified to delete or substitute one or more additional cysteine residues. It is known in the art that free cysteine residues can be involved in a number of chemical side reactions. These side reactions include disulfide exchanges, reaction with chemical substances or metabolites that are, for example, injected or formed in a combination therapy with other substances, or direct oxidation and reaction with nucleotides upon exposure to UV light. Toxic adducts could thus be generated, especially considering the fact that HBcAgs have a strong tendency to bind nucleic acids. The toxic adducts would thus be distributed between a multiplicity of species, which individually may each be present at low concentration, but reach toxic levels when together.

In view of the above, one advantage to the use of HBcAgs in vaccine compositions which have been modified to remove naturally resident cysteine residues is that sites to which toxic species can bind when antigens or antigenic determinants are attached would be reduced in number or eliminated altogether.

A number of naturally occurring HBcAg variants suitable for use in the practice of the present invention have been identified. Yuan et al., (*J. Virol.* 73:10122–10128 (1999)), for example, describe variants in which the isoleucine residue at position corresponding to position 97 in SEQ ID NO:28 is replaced with either a leucine residue or a phenylalanine residue. The amino acid sequences of a number of HBcAg variants, as well as several Hepatitis B core antigen precursor variants, are disclosed in GenBank reports AAF121240 (SEQ ID NO:29), AF121239 (SEQ ID NO:30), X85297 (SEQ ID NO:31), X02496 (SEQ ID NO:32), X85305 (SEQ ID NO:33), X85303 (SEQ ID NO:34), AF151735 (SEQ ID NO:35), X85259 (SEQ ID NO:36), X85286 (SEQ ID NO:37), X85260 (SEQ ID NO:38), X85317 (SEQ ID NO:39), X85298 (SEQ ID NO:40), AF043593 (SEQ ID NO:41), M20706 (SEQ ID NO:42), X85295 (SEQ ID NO:43), X80925 (SEQ ID NO:44), X85284 (SEQ ID NO:45), X85275 (SEQ ID NO:46), X72702 (SEQ ID NO:47), X85291 (SEQ ID NO:48), X65258 (SEQ ID NO:49), X85302 (SEQ ID NO:50), M32138 (SEQ ID NO:51), X85293 (SEQ ID NO:52), X85315 (SEQ ID NO:53), U95551 (SEQ ID NO:54), X85256 (SEQ ID NO:55), X85316 (SEQ ID NO:56), X85296 (SEQ ID NO:57), AB033559 (SEQ ID NO:58), X59795 (SEQ ID NO:59), X85299 (SEQ ID NO:60), X85307 (SEQ ID NO:61), X65257 (SEQ ID NO:62), X85311 (SEQ ID NO:63), X85301 (SEQ ID NO:64), X85314 (SEQ ID NO:65), X85287 (SEQ ID NO:66), X85272 (SEQ ID NO:67), X85319 (SEQ ID NO:68), AB010289 (SEQ ID NO:69), X85285 (SEQ ID NO:70), AB010289 (SEQ ID NO:71), AF121242 (SEQ ID NO:72), M90520 (SEQ ID NO:73), P03153 (SEQ ID NO:74), AF110999 (SEQ ID NO:75), and M95589 (SEQ ID NO:76), the disclosures of each of which are incorporated herein by reference. These HBcAg variants differ in amino acid sequence at a number of positions, including amino acid residues which corresponds to the amino acid residues located at positions 12, 13, 21, 22, 24, 29, 32, 33, 35, 38, 40, 42, 44, 45, 49, 51, 57, 58, 59, 64, 66, 67, 69, 74, 77, 80, 81, 87, 92, 93, 97, 98, 100, 103, 105, 106, 109, 113, 116, 121, 126, 130, 133, 135, 141, 147, 149, 157, 176, 178, 182 and 183 in SEQ ID NO:77. Further HBcAg variants suitable for use in the compositions of the invention, and which may be further modified according to the disclosure of this specification are described in WO 00/198333, WO 00/177158 and WO 00/214478.

As noted above, generally processed HBcAgs (i.e., those which lack leader sequences) will be used in the compositions and vaccine compositions, respectively, of the invention. The present invention includes vaccine compositions, as well as methods for using these compositions, which employ the above described variant HBcAgs.

Whether the amino acid sequence of a polypeptide has an amino acid sequence that is at least 80%, 85%, 90%, 95%, 97% or 99% identical to one of the above wild-type amino acid sequences, or a subportion thereof, can be determined conventionally using known computer programs such the Bestfit program. When using Bestfit or any other sequence alignment program to determine whether a particular sequence is, for instance, 95% identical to a reference amino acid sequence, the parameters are set such that the percentage of identity is calculated over the full length of the reference amino acid sequence and that gaps in homology of up to 5% of the total number of amino acid residues in the reference sequence are allowed.

The HBcAg variants and precursors having the amino acid sequences set out in SEQ ID NOs: 29–72 and 73–76 are relatively similar to each other. Thus, reference to an amino acid residue of a HBcAg variant located at a position which corresponds to a particular position in SEQ ID NO:77, refers to the amino acid residue which is present at that position in the amino acid sequence shown in SEQ ID NO:77. The homology between these HBcAg variants is for the most part high enough among Hepatitis B viruses that infect mammals so that one skilled in the art would have little difficulty reviewing both the amino acid sequence shown in SEQ ID NO:77 and that of a particular HBcAg variant and identifying "corresponding" amino acid residues. Furthermore, the HBcAg amino acid sequence shown in SEQ ID NO:73, which shows the amino acid sequence of a HBcAg derived from a virus which infect woodchucks, has enough homology to the HBcAg having the amino acid sequence shown in SEQ ID NO:77 that it is readily apparent that a three amino acid residue insert is present in SEQ ID NO:64 between amino acid residues 155 and 156 of SEQ ID NO:77.

The invention also includes vaccine compositions which comprise HBcAg variants of Hepatitis B viruses which infect birds, as wells as vaccine compositions which comprise fragments of these HBcAg variants. For these HBcAg variants one, two, three or more of the cysteine residues naturally present in these polypeptides could be either substituted with another amino acid residue or deleted prior to their inclusion in vaccine compositions of the invention.

As discussed above, the elimination of free cysteine residues reduces the number of sites where toxic components can bind to the HBcAg, and also eliminates sites where cross-linking of lysine and cysteine residues of the same or of neighboring HBcAg molecules can occur. Therefore, in another embodiment of the present invention, one or more cysteine residues of the Hepatitis B virus capsid protein have been either deleted or substituted with another amino acid residue.

In other embodiments, compositions and vaccine compositions, respectively, of the invention will contain HBcAgs from which the C-terminal region (e.g., amino acid residues 145–185 or 150–185 of SEQ ID NO:77) has been removed. Thus, additional modified HBcAgs suitable for use in the practice of the present invention include C-terminal truncation mutants. Suitable truncation mutants include HBcAgs where 1, 5, 10, 15, 20, 25, 30, 34, 35, amino acids have been removed from the C-terminus.

HBcAgs suitable for use in the practice of the present invention also include N-terminal truncation mutants. Suitable truncation mutants include modified HBcAgs where 1, 2, 5, 7, 9, 10, 12, 14, 15, or 17 amino acids have been removed from the N-terminus.

Further HBcAgs suitable for use in the practice of the present invention include N- and C-terminal truncation mutants. Suitable truncation mutants include HBcAgs where 1, 2, 5, 7, 9, 10, 12, 14, 15, and 17 amino acids have been removed from the N-terminus and 1, 5, 10, 15, 20, 25, 30, 34, 35 amino acids have been removed from the C-terminus.

The invention further includes compositions and vaccine compositions, respectively, comprising HBcAg polypeptides comprising, or alternatively essentially consisting of, or alternatively consisting of, amino acid sequences which are at least 80%, 85%, 90%, 95%, 97%, or 99% identical to the above described truncation mutants.

In certain embodiments of the invention, a lysine residue is introduced into a HBcAg polypeptide, to mediate the binding of the RANKL protein, RANKL fragment or RANKL peptide to the VLP of HBcAg. In preferred embodiments, compositions of the invention are prepared using a HBcAg comprising, or alternatively consisting of, amino acids 1–144, or 1–149, 1–185 of SEQ ID NO:77, which is modified so that the amino acids corresponding to positions 79 and 80 are replaced with a peptide having the amino acid sequence of Gly-Gly-Lys-Gly-Gly (SEQ ID NO:117). In further preferred embodiments, the cysteine residues at positions 48 and 107 of SEQ ID NO:77 are mutated to serine. The invention further includes compositions comprising the corresponding polypeptides having amino acid sequences shown in any of SEQ ID NOs:29–74, which also have above noted amino acid alterations. Further included within the scope of the invention are additional HBcAg variants which are capable of associating to form a capsid or VLP and have the above noted amino acid alterations. Thus, the invention further includes compositions and vaccine compositions, respectively, comprising HBcAg polypeptides which comprise, or alternatively consist of, amino acid sequences which are at least 80%, 85%, 90%, 95%, 97% or 99% identical to any of the wild-type amino acid sequences, and forms of these proteins which have been processed, where appropriate, to remove the N-terminal leader sequence and modified with above noted alterations.

Compositions or vaccine compositions of the invention may comprise mixtures of different HBcAgs. Thus, these vaccine compositions may be composed of HBcAgs which differ in amino acid sequence. For example, vaccine compositions could be prepared comprising a "wild-type" HBcAg and a modified HBcAg in which one or more amino acid residues have been altered (e.g., deleted, inserted or substituted). Further, preferred vaccine compositions of the invention are those which present highly ordered and repetitive antigen array, wherein the antigen is a RANKL protein, RANKL fragment or RANKL peptide.

In a further preferred embodiment of the present invention, the at least one RANKL protein, RANKL fragment or RANKL peptide is bound to said core particle and virus-like particle, respectively, by at least one covalent bond. Preferably, the least one RANKL protein, RANKL fragment or RANKL peptide is bound to the core particle and virus-like particle, respectively, by at least one covalent bond, said covalent bond being a non-peptide bond leading to a core particle-RANKL ordered and repetitive array and a RANKL-VLP-array or -conjugate, respectively. This RANKL-VLP array and conjugate, respectively, has typically and preferably a repetitive and ordered structure since the at least one, but usually more than one, RANKL protein, RANKL fragment or RANKL peptide is bound to the VLP in an oriented manner. Preferably, more than 10, 20, 40, 80, 120 RANKL proteins, RANKL fragments or RANKL peptides are bound to the VLP. The formation of a repetitive and ordered RANKL-VLP array and conjugate, respectively, is ensured by an oriented and directed as well as defined binding and attachment, respectively, of the at least one RANKL protein, RANKL fragment or RANKL peptide to the VLP as will become apparent in the following. Furthermore, the typical inherent highly repetitive and organized structure of the VLPs advantageously contributes to the display of the RANKL protein, RANKL fragment or RANKL peptide in a highly ordered and repetitive fashion leading to a highly organized and repetitive RANKL-VLP array and conjugate, respectively.

Therefore, the preferred inventive conjugates and arrays, respectively, differ from prior art conjugates in their highly organized structure, dimensions, and in the repetitiveness of the antigen on the surface of the array. The preferred embodiment of this invention, furthermore, allows expression of both the particle and the antigen in an expression host guaranteeing proper folding of the antigen, i.e. the at least one RANKL protein, RANKL fragment or RANKL peptide, and proper folding and assembly of the VLP.

The present invention discloses methods of binding of RANKL protein, RANKL fragment or RANKL peptide to core particles and VLPs, repectively. As indicated, in one aspect of the invention, the RANKL protein, RANKL fragment or RANKL peptide is bound to the core particle and VLP, respectively, by way of chemical cross-linking, typically and preferably by using a heterobifunctional cross-linker. Several hetero-bifunctional cross-linkers are known to the art. In preferred embodiments, the hetero-bifunctional cross-linker contains a functional group which can react with preferred first attachment sites, i.e. with the side-chain amino group of lysine residues of the core particle and the VLP or at least one VLP subunit, respectively, and a further functional group which can react with a preferred second attachment site, i.e. a cysteine residue naturally present, made available for reaction by reduction, or engineered on the RANKL protein, RANKL fragment or RANKL peptide, and optionally also made available for reaction by reduction. The first step of the procedure, typically called the derivatization, is the reaction of the core particle or the VLP with the cross-linker. The product of this reaction is an activated core particle or activated VLP, also called activated carrier. In the second step, unreacted cross-linker is removed using usual methods such as gel filtration or dialysis. In the third step, the RANKL protein, RANKL fragment or RANKL peptide is reacted with the activated carrier, and this step is typically called the coupling step. Unreacted RANKL protein, RANKL fragment or RANKL peptide may be optionally removed in a fourth step, for example by dialysis. Several hetero-bifunctional cross-linkers are known to the art. These include the preferred cross-linkers SMPH (Pierce), Sulfo-MBS, Sulfo-EMCS, Sulfo-GMBS, Sulfo-SIAB, Sulfo-SMPB, Sulfo-SMCC, SVSB, SIA and other cross-linkers available for example from the Pierce Chemical Company (Rockford, Ill., USA), and having one functional group reactive towards amino groups and one functional group reactive towards cysteine residues. The above mentioned cross-linkers all lead to formation of a thioether linkage. Another class of cross-linkers suitable in the practice of the invention is characterized by the introduction of a disulfide linkage between the RANKL protein, RANKL fragment or RANKL peptide and the core particle or VLP upon coupling. Preferred cross-linkers belonging to this class include for example SPDP and Sulfo-LC-SPDP (Pierce). The extent of derivatization of the core particle and VLP, respectively, with cross-linker can be influenced by varying experimental conditions such as the concentration of each of the reaction partners, the excess of one reagent over the other, the pH, the temperature and the ionic strength. The degree of coupling, i.e. the amount of RANKL protein, RANKL fragment or RANKL peptides per subunits of the core particle and VLP, respectively, can be adjusted by varying the experimental conditions described above to match the requirements of the vaccine. Solubility of the RANKL protein, RANKL fragment or RANKL peptide may impose a limitation on the amount of RANKL protein, RANKL fragment or RANKL peptide that can be coupled on each subunit, and in those cases where the obtained vaccine would be insoluble, reducing the amount of RANKL protein, RANKL fragment or RANKL peptides per subunit is beneficial.

A particularly favored method of binding of RANKL protein, RANKL fragment or RANKL peptides to the core particle and the VLP, respectively, is the linking of a lysine residue on the surface of the core particle and the VLP, respectively, with a cysteine residue on the RANKL protein, RANKL fragment or RANKL peptide. Thus, in a preferred embodiment of the present invention, the first attachment site is a lysine residue and the second attachment site is a cysteine residue. In some embodiments, engineering of an amino acid linker containing a cysteine residue, as a second attachment site or as a part thereof, to the RANKL protein, RANKL fragment or RANKL peptide for coupling to the core particle and VLP, respectively, may be required. Alternatively, a cysteine may be introduced either by insertion or mutation within the RANKL protein, RANKL fragment or RANKL peptide. Alternatively, the cysteine residue or a thiol group may be introduced by chemical coupling.

The selection of the amino acid linker will be dependent on the nature of the antigen and self-antigen, respectively, i.e. on the nature of the RANKL protein, RANKL fragment or RANKL peptide, on its biochemical properties, such as pI, charge distribution and glycosylation. In general, flexible amino acid linkers are favored. Preferred embodiments of the amino acid linker are selected from the group consisting of: (a) CGG; (b) N-terminal gamma 1-linker; (c) N-terminal gamma 3-linker; (d) Ig hinge regions; (e) N-terminal glycine linkers; (f) $(G)_kC(G)_n$ with n=0–12 and k=0–5; (g) N-terminal glycine-serine linkers; (h) $(G)_kC(G)_m(S)_l(GGGGS)_n$ (SEQ ID NO: 118) with n=0–3, k=0–5, m=0–10, 1=0–2; (i) GGC; (k) GGC-NH2; (l) C-terminal gamma 1-linker; (m) C-terminal gamma 3-linker; (n) C-terminal glycine linkers; (o) $(G)_nC(G)_k$ with n=0–12 and k=0–5; (p) C-terminal glycine-serine linkers; (q) $(G)_m(S)_l(GGGGS)_n(G)_oC(G)_k$ (SEQ ID NO: 119) with n=0–3, k=0–5, m=0–10, 1=0–2, and o=0–8.

Further preferred examples of amino acid linkers are the hinge region of Immunoglobulins, glycine seine linkers (GGGGS)$_n$ (SEQ ID NO: 120), and glycine linkers $(G)_n$ all further containing a cysteine residue as second attachment site and optionally further glycine residues. Typically preferred examples of said amino acid linkers are N-terminal gamma1: CGDKTHTSPP (SEQ ID NO: 121); C-terminal gamma 1: DKTHTSPPCG (SEQ ID NO: 122); N-terminal gamma 3: CGGPKPSTPPGSSGGAP (SEQ ID NO: 123); C-terminal gamma 3: PKPSTPPGSSGGAPGGCG (SEQ ID NO: 124); N-terminal glycine linker: GCGGGG (SEQ ID NO: 125); C-terminal glycine linker: GGGGCG (SEQ ID NO: 126); C-terminal glycine-lysine linker: GGKKGC (SEQ ID NO: 127); N-terminal glycine-lysine linker: CGKKGG (SEQ ID NO: 128).

In a further preferred embodiment of the present invention, and in particular if the antigen is a RANKL peptide, GGCG, GGC or GGC-NH2 ("NH2" stands for amidation) linkers at the C-terminus of the peptide or CGG at its N-terminus are preferred as amino acid linkers. In general, glycine residues will be inserted between bulky amino acids and the cysteine to be used as second attachment site, to avoid potential steric hindrance of the bulkier amino acid in the coupling reaction.

The cysteine residue present on the RANKL protein, RANKL fragment or RANKL peptide has to be in its reduced state to react with the hetero-bifunctional cross-linker on the activated VLP, that is a free cysteine or a cysteine residue with a free sulfhydryl group has to be available. In the instance where the cysteine residue to function as binding site is in an oxidized form, for example if it is forming a disulfide bridge, reduction of this disulfide bridge with e.g. DTT, TCEP or β-mercaptoethanol is required.

Binding of the RANKL protein, RANKL fragment or RANKL peptide to the core particle and VLP, respectively, by using a hetero-bifunctional cross-linker according to the preferred methods described above, allows coupling of the RANKL protein, RANKL fragment or RANKL peptide to the core particle and the VLP, respectively, in an oriented fashion. Other methods of binding the RANKL protein, RANKL fragment or RANKL peptide to the core particle and the VLP, respectively, include methods wherein the RANKL protein, RANKL fragment or RANKL peptide is cross-linked to the core particle and the VLP, respectively, using the carbodiimide EDC, and NHS. The RANKL protein, RANKL fragment or RANKL peptide may also be first thiolated through reaction, for example with SATA, SATP or iminothiolane. The RANKL protein, RANKL fragment or RANKL peptide, after deprotection if required, may then be coupled to the core particle and the VLP, respectively, as follows. After separation of the excess thiolation reagent, the RANKL protein, RANKL fragment or RANKL peptide is reacted with the core particle and the VLP, respectively, previously activated with a hetero-bifunctional cross-linker comprising a cysteine reactive moiety, and therefore displaying at least one or several functional groups reactive towards cysteine residues, to which the thiolated RANKL protein, RANKL fragment or RANKL peptide can react, such as described above. Optionally, low amounts of a reducing agent are included in the reaction mixture. In further methods, the RANKL protein, RANKL fragment or RANKL peptide is attached to the core particle and the VLP, respectively, using a homo-bifunctional cross-linker such as glutaraldehyde, DSG, BM[PEO]$_4$, BS$^3$, (Pierce Chemical Company, Rockford, Ill., USA) or other known homo-bifunctional cross-linkers whith functional groups reactive towards amine groups or carboxyl groups of the core particle and the VLP, respectively,.

In a further embodiment, the RANKL protein, RANKL fragment or RANKL peptide is bound to the core particle and the VLP, respectively, through modification of the carbohydrate moieties present on glycosylated RANKL protein, RANKL fragment or RANKL peptide and subsequent reaction with the core particle and the VLP, respectively. In one embodiment, the glycosylated RANKL protein, RANKL fragment or RANKL peptide is reacted with sodium periodate in a mild oxidation reaction of the carbohydrate moiety, to yield an activated RANKL protein, RANKL fragment or RANKL peptide with one or more aldehyde functional groups. The so activated RANKL protein, RANKL fragment or RANKL peptide is separated from excess sodium periodate, and further reacted with the core particle and the VLP, respectively, wherein lysine residues of the core particle and the VLP, respectively, or of at least one VLP subunit are reacting with the previously formed aldehyde functional group on the RANKL protein, RANKL fragment or RANKL peptide, for example as described by Hermanson, G. T. in *Bioconjugate Techniques*, Academic Press Inc., San Diego, Calif., USA Self polymerization of the activated RANKL protein, RANKL fragment or RANKL peptide may be controlled by adjusting the pH as described in the aforementioned publication. The formed Schiff base is preferably further reduced with sodium cyanoborohydride, which is subsequently removed by gel filtration or dialysis. Alternatively, the core particle and the VLP, respectively, may be reacted with EDC at carboxyl groups of the core particle and the VLP, respectively, or at least one VLP subunit and a dihydrazide, such as adipic acid dihydrazide, to yield a hydrazide moiety available for reaction with the one or more aldehyde functional groups present on the activated RANKL protein, RANKL fragment or RANKL peptide. The so formed hydrazone may be further reduced with sodium cyanoborohydride. Alternatively, the activated RANKL protein, RANKL fragment or RANKL peptide with one or more aldehyde functional groups is reacted with cysteamine, resulting in the introduction of a cysteine group in the RANKL protein, RANKL fragment or RANKL peptide. Additional cross-linking methods and cross-linkers, suitable for binding a RANKL protein, RANKL fragment or RANKL peptide to a core particle and a VLP, respectively, as well as guidance on performing the coupling reactions and on the use of chemical cross-linkers and chemical cross-linking procedures can be found in Hermanson, G. T. in *Bioconjugate Techniques*, Academic Press Inc., San Diego, Calif., USA.

Other methods of binding the VLP to a RANKL protein, RANKL fragment or RANKL peptide include methods where the core particle and the VLP, respectively, is biotinylated, and the RANKL protein, RANKL fragment or RANKL peptide expressed as a streptavidin-fusion protein, or methods wherein both the RANKL protein, RANKL fragment or RANKL peptides and the core particle and the VLP, respectively, are biotinylated, for example as described in WO 00/23955. In this case, the RANKL protein, RANKL fragment or RANKL peptide may be first bound to streptavidin or avidin by adjusting the ratio of RANKL protein, RANKL fragment or RANKL peptide to streptavidin such that free binding sites are still available for binding of the core particle and the VLP, respectively, which is added in the next step. Alternatively, all components may be mixed in a "one pot" reaction. Other ligand-receptor pairs, where a soluble form of the receptor and of the ligand is available, and are capable of being cross-linked to the core particle and the VLP, respectively, or the RANKL protein, RANKL fragment or RANKL peptide, may be used as binding agents for binding the RANKL protein, RANKL fragment or RANKL peptide to the core particle and the VLP, respectively,. Alternatively, either the ligand or the receptor may be fused to the RANKL protein, RANKL fragment or RANKL peptide, and so mediate binding to the core particle and the VLP, respectively, chemically bound or fused either to the receptor, or the ligand respectively. Fusion may also be effected by insertion or substitution.

As already indicated, in a favored embodiment of the present invention, the VLP is the VLP of a RNA phage, and in a more preferred embodiment, the VLP is the VLP of RNA phage Qβ coat protein.

One or several antigen molecules, i.e. a RANKL protein, RANKL fragment or RANKL peptide, can be attached to one subunit of the capsid or VLP of RNA phages coat proteins, preferably through the exposed lysine residues of the VLP of RNA phages, if sterically allowable. A specific feature of the VLP of the coat protein of RNA phages and in particular of the Qβ coat protein VLP is thus the possibility to couple several antigens per subunit. This allows for the generation of a dense antigen array.

In a preferred embodiment of the invention, the binding and attachment, respectively, of the at least RANKL protein, RANKL fragment or RANKL peptide to the core particle and the virus-like particle, respectively, is by way of interaction and association, respectively, between at least one first attachment site of the virus-like particle and at least one second attachment of the antigen or antigenic determinant.

VLPs or capsids of Qβ coat protein display a defined number of lysine residues on their surface, with a defined topology with three lysine residues pointing towards the interior of the capsid and interacting with the RNA, and four other lysine residues exposed to the exterior of the capsid. These defined properties favor the attachment of antigens to the exterior of the particle, rather than to the interior of the particle where the lysine residues interact with RNA. VLPs of other RNA phage coat proteins also have a defined number of lysine residues on their surface and a defined topology of these lysine residues.

In further preferred embodiments of the present invention, the first attachment site is a lysine residue and/or the second attachment comprises sulfhydryl group or a cysteine residue. In a very preferred embodiment of the present invention, the first attachment site is a lysine residue and the second attachment is a cysteine residue.

In very preferred embodiments of the invention, the RANKL protein, RANKL fragment or RANKL peptide is bound via a cysteine residue, either naturally present on the RANKL protein, RANKL fragment or RANKL peptide or engineered, to lysine residues of the VLP of RNA phage coat protein, and in particular to the VLP of Qβ coat protein.

Another advantage of the VLPs derived from RNA phages is their high expression yield in bacteria that allows production of large quantities of material at affordable cost.

As indicated, the inventive conjugates and arrays, respectively, differ from prior art conjugates in their highly organized structure, dimensions, and in the repetitiveness of the antigen on the surface of the array. Moreover, the use of the VLPs as carriers allow the formation of robust antigen arrays and conjugates, respectively, with variable antigen density. In particular, the use of VLPs of RNA phages, and hereby in particular the use of the VLP of RNA phage Qβ coat protein allows to achieve very high epitope density. The preparation of compositions of VLPs of RNA phage coat proteins with a high epitope density can be effected by using the teaching of this application.

The second attachment site, as defined herein, may be either naturally or non-naturally present with the antigen or the antigenic determinant. In the case of the absence of a suitable natural occurring second attachment site on the antigen or antigenic determinant, such a, then non-natural second attachment has to be engineered to the antigen.

As described above, four lysine residues are exposed on the surface of the VLP of Qβ coat protein. Typically these residues are derivatized upon reaction with a cross-linker molecule. In the instance where not all of the exposed lysine residues can be coupled to an antigen, the lysine residues which have reacted with the cross-linker are left with a cross-linker molecule attached to the ε-amino group after the derivatization step. This leads to disappearance of one or several positive charges, which may be detrimental to the solubility and stability of the VLP. By replacing some of the lysine residues with arginines, as in the disclosed Qβ coat protein mutants described below, we prevent the excessive disappearance of positive charges since the arginine residues do not react with the cross-linker. Moreover, replacement of lysine residues by arginines may lead to more defined antigen arrays, as fewer sites are available for reaction to the antigen.

Accordingly, exposed lysine residues were replaced by arginines in the following Qβ coat protein mutants and mutant Qβ VLPs disclosed in this application: Qβ-240 (Lys13-Arg; SEQ ID NO:23), Qβ-250 (Lys 2-Arg, Lys13-Arg; SEQ ID NO:25) and Qβ-259 (Lys 2-Arg, Lys16-Arg; SEQ ID NO:27). The constructs were cloned, the proteins expressed, the VLPs purified and used for coupling to peptide and protein antigens. Qβ-251; (SEQ ID NO:26) was also constructed, and guidance on how to express, purify and couple the VLP of Qβ-251 coat protein can be found throughout the application.

In a further embodiment, we disclose a Qβ mutant coat protein with one additional lysine residue, suitable for obtaining even higher density arrays of antigens. This mutant Qβ coat protein, Qβ-243 (Asn 10-Lys; SEQ ID NO:24), was cloned, the protein expressed, and the capsid or VLP isolated and purified, showing that introduction of the additional lysine residue is compatible with self-assembly of the subunits to a capsid or VLP. Thus, RANKL protein, RANKL fragment or RANKL peptide arrays and conjugates, respectively, may be prepared using VLP of Qβ coat protein mutants. A particularly favored method of attachment of antigens to VLPs, and in particular to VLPs of RNA phage coat proteins is the linking of a lysine residue present on the surface of the VLP of RNA phage coat proteins with a cysteine residue naturally present or engineered on the antigen, i.e. the RANKL protein, RANKL fragment or RANKL peptide. In order for a cysteine residue to be effective as second attachment site, a sulfhydryl group must be available for coupling. Thus, a cysteine residue has to be in its reduced state, that is, a free cysteine or a cysteine residue with a free sulfhydryl group has to be available. In the instant where the cysteine residue to function as second attachment site is in an oxidized form, for example if it is forming a disulfide bridge, reduction of this disulfide bridge with e.g. DTT, TCEP or β-mercaptoethanol is required. The concentration of reductand, and the molar excess of reductand over antigen has to be adjusted for each antigen. A titration range, starting from concentrations as low as 10 μM or lower, up to 10 to 20 mM or higher reductand if required is tested, and coupling of the antigen to the carrier assessed. Although low concentrations of reductand are compatible with the coupling reaction as described in pending U.S. application Ser. No. 10/050,902 filed by the present assignee on Jan. 18, 2002, higher concentrations inhibit the coupling reaction, as a skilled artisan would know, in which case the reductand has to be removed by dialysis or gel filtration. Advantageously, the pH of the dialysis or equilibration buffer is lower than 7, preferably 6. The compatibility of the low pH buffer with antigen activity or stability has to be tested.

Epitope density on the VLP of RNA phage coat proteins can be modulated by the choice of cross-linker and other reaction conditions. For example, the cross-linkers Sulfo-GNBS and SMPH typically allow reaching high epitope density. Derivatization is positively influenced by high concentration of reactands, and manipulation of the reaction conditions can be used to control the number of antigens coupled to VLPs of RNA phage coat proteins, and in particular to VLPs of Qβ coat protein.

Prior to the design of a non-natural second attachment site the position at which it should be fused, inserted or generally engineered has to be chosen. The selection of the position of the second attachment site may, by way of example, be based on a crystal structure of the antigen. Such a crystal structure of the antigen may provide information on the availability of the C- or N-termini of the molecule (determined for example from their accessibilty to solvent), or on the exposure to solvent of residues suitable for use as second attachment sites, such as cysteine residues. Exposed disulfide bridges, as is the case for Fab fragments, may also be a source of a second attachment site, since they can be generally converted to single cysteine residues through mild reduction. Mild reduction conditions not affecting the immunogenicity of RANKL protein, RANKL fragment or RANKL peptide will be choosen. In general, in the case where immunization with a self-antigen is aiming at inhibiting the interaction of this self-antigen with its natural ligands, the second attachment site will be added such that it allows generation of antibodies against the site of interaction with the natural ligands. Thus, the location of the second attachment site will be selected such that steric hindrance from the second attachment site or any amino acid linker containing the same is avoided. In further embodiments, an antibody response directed at a site distinct from the interaction site of the self-antigen with its natural ligand is desired. In such embodiments, the second attachment site may be selected such that it prevents generation of antibodies against the interaction site of the self-antigen with its natural ligands.

Other criteria in selecting the position of the second attachment site include the oligomerization state of the antigen, the site of oligomerization, the presence of a cofactor, and the availability of experimental evidence disclosing sites in the antigen structure and sequence where modification of the antigen is compatible with the function of the self-antigen, or with the generation of antibodies recognizing the self-antigen.

In the most preferred embodiments, the RANKL protein, RANKL fragment or RANKL peptide comprises a single second attachment site or a single reactive attachment site capable of association with the first attachment sites on the core particle and the VLPs or VLP subunits, respectively. This ensures a defined and uniform binding and association, respectively, of the at least one, but typically more than one, preferably more than 10, 20, 40, 80, 120 antigens to the core particle and VLP, respectively. The provision of a single second attachment site or a single reactive attachment site on the antigen, thus, ensures a single and uniform type of binding and association, respectively leading to a very highly ordered and repetitive array. For example, if the binding and association, respectively, is effected by way of a lysine- (as the first attachment site) and cysteine- (as a second attachment site) interaction, it is ensured, in accordance with this preferred embodiment of the invention, that only one cysteine residue per antigen, independent whether this cysteine residue is naturally or non-naturally present on the antigen, is capable of binding and associating, respectively, with the VLP and the first attachment site of the core particle, respectively.

In some embodiments, engineering of a second attachment site onto the antigen require the fusion of an amino acid linker containing an amino acid suitable as second attachment site according to the disclosures of this invention. Therefore, in a preferred embodiment of the present invention, an amino acid linker is bound to the antigen or the antigenic determinant by way of at least one covalent bond. Preferably, the amino acid linker comprises, or alternatively consists of, the second attachment site. In a further preferred embodiment, the amino acid linker comprises a sulfhydryl group or a cysteine residue. In another preferred embodiment, the amino acid linker is cysteine. Some criteria of selection of the amino acid linker as well as further preferred embodiments of the amino acid linker according to the invention have already mentioned above.

In a further preferred embodiment of the invention, the at least one antigen or antigenic determinant, i.e. the RANKL protein, RANKL fragment or RANKL peptide arrays is fused to the core particle and the virus-like particle, respectively. As outlined above, a VLP is typically composed of at least one subunit assembling into a VLP. Thus, in again a further preferred embodiment of the invention, the antigen or antigenic determinant, preferably the at least one RANKL protein, RANKL fragment or RANKL peptide, is fused to at least one subunit of the virus-like particle or of a protein capable of being incorporated into a VLP generating a chimeric VLP-subunit-RANKL protein, RANKL fragment or RANKL peptide fusion.

Fusion of the RANKL protein, RANKL fragment or RANKL peptide can be effected by insertion into the VLP subunit sequence, or by fusion to either the N- or C-terminus of the VLP-subunit or protein capable of being incorporated into a VLP. Hereinafter, when referring to fusion proteins of a peptide to a VLP subunit, the fusion to either ends of the subunit sequence or internal insertion of the peptide within the subunit sequence are encompassed.

Fusion may also be effected by inserting the RANKL protein, RANKL fragment or RANKL peptide sequences into a variant of a VLP subunit where part of the subunit sequence has been deleted, that are further referred to as truncation mutants. Truncation mutants may have N- or C-terminal, or internal deletions of part of the sequence of the VLP subunit. For example, the specific VLP HBcAg with, for example, deletion of amino acid residues 79 to 81 is a truncation mutant with an internal deletion. Fusion of RANKL protein, RANKL fragment or RANKL peptide to either the N- or C-terminus of the truncation mutants VLP-subunits also lead to embodiments of the invention. Likewise, fusion of an epitope into the sequence of the VLP subunit may also be effected by substitution, where for example for the specific VLP HBcAg, amino acids 79–81 are replaced with a foreign epitope. Thus, fusion, as referred to hereinafter, may be effected by insertion of the RANKL protein, RANKL fragment or RANKL peptide sequence in the sequence of a VLP subunit, by substitution of part of the sequence of the VLP subunit with the RANKL protein, RANKL fragment or RANKL peptide sequence, or by a combination of deletion, substitution or insertions.

The chimeric RANKL protein, RANKL fragment or RANKL peptide-VLP subunit will be in general capable of self-assembly into a VLP. VLP displaying epitopes fused to their subunits are also herein referred to as chimeric VLPs. As indicated, the virus-like particle comprises or alternatively is composed of at least one VLP subunit. In a further embodiment of the invention, the virus-like particle comprises or alternatively is composed of a mixture of chimeric VLP subunits and non-chimeric VLP subunits, i.e. VLP subunits not having an antigen fused thereto, leading to so called mosaic particles. This may be advantageous to ensure formation of and assembly to a VLP. In those embodiments, the proportion of chimeric VLP-subunits may be 1, 2, 5, 10, 20, 30, 40, 50, 60, 70, 80, 90, 95% or higher.

Flanking amino acid residues may be added to either end of the sequence of the peptide or epitope to be fused to either end of the sequence of the subunit of a VLP, or for internal insertion of such peptidic sequence into the sequence of the subunit of a VLP. Glycine and serine residues are particularly favored amino acids to be used in the flanking sequences added to the RANKL protein, RANKL fragment or RANKL peptide to be fused. Glycine residues confer additional flexibility, which may diminish the potentially destabilizing effect of fusing a foreign sequence into the the sequence of a VLP subunit.

In a specific embodiment of the invention, the VLP is a Hepatitis B core antigen VLP. Fusion proteins to either the N-terminus of a HBcAg (Neyrinck, S. et al., *Nature Med.* 5:1157–1163 (1999)) or insertions in the so called major immunodominant region (MIR) have been described (Pumpens, P. and Grens, E., *Intervirology* 44:98–114 (2001)), WO 01/98333), and are preferred embodiments of the invention. Naturally occurring variants of HBcAg with deletions in the MIR have also been described (Pumpens, P. and Grens, E., *Intervirology* 44:98–114 (2001), which is expressly incorporated by reference in their entirety), and fusions to the N- or C-terminus, as well as insertions at the position of the MIR corresponding to the site of deletion as compared to a wt HBcAg are further embodiments of the invention. Fusions to the C-terminus have also been described (Pumpens, P. and Grens, E., *Intervirology* 44:98–114 (2001)). One skilled in the art will easily find guidance on how to construct fusion proteins using classical molecular biology techniques (Sambrook, J. et al., eds., *Molecular Cloning, A Laboratory Manual*, 2nd. edition, Cold Spring Habor Laboratory Press, Cold Spring Harbor, N.Y. (1989), Ho et al., *Gene* 77:51 (1989)). Vectors and plasmids encoding HBcAg and HBcAg fusion proteins and useful for the expression of a HBcAg and HBcAg fusion proteins have been described (Pumpens, P. & Grens, E. Intervirology 44: 98–114 (2001), Neyrinck, S. et al., *Nature*

*Med.* 5:1157–1163 (1999)) and can be used in the practice of the invention. We also describe by way of example (Example 6) the insertion of an epitope into the MIR of HBcAg, resulting in a chimeric self-assembling HBcAg. An important factor for the optimization of the efficiency of self-assembly and of the display of the epitope to be inserted in the MIR of HBcAg is the choice of the insertion site, as well as the number of amino acids to be deleted from the HBcAg sequence within the MIR (Pumpens, P. and Grens, E., *Intervirology* 44:98–114 (2001); EP 421,635; U.S. Pat. No. 6,231,864) upon insertion, or in other words, which amino acids form HBcAg are to be substituted with the new epitope. For example, substitution of HBcAg amino acids 76–80, 79–81, 79–80, 75–85 or 80–81 with foreign epitopes has been described (Pumpens, P. and Grens, E., *Intervirology* 44:98–114 (2001); EP0421635; U.S. Pat. No. 6,231, 864). HBcAg contains a long arginine tail (Pumpens, P. and Grens, E., *Intervirology* 44:98–114 (2001)) which is dispensable for capsid assembly and capable of binding nucleic acids (Pumpens, P. and Grens, E., *Intervirology* 44:98–114 (2001)). HBcAg either comprising or lacking this arginine tail are both embodiments of the invention.

In a further preferred embodiment of the invention, the VLP is a VLP of a RNA phage. The major coat proteins of RNA phages spontaneously assemble into VLPs upon expression in bacteria, and in particular in *E. coli*. Specific examples of bacteriophage coat proteins which can be used to prepare compositions of the invention include the coat proteins of RNA bacteriophages such as bacteriophage Qβ (SEQ ID NO:10; PIR Database, Accession No. VCBPQβ referring to Qβ CP and SEQ ID NO: 11; Accession No. AAA16663 referring to Qβ A1 protein) and bacteriophage fr (SEQ ID NO:4; PIR Accession No. VCBPFR).

In a more preferred embodiment, the at least one RANKL protein, RANKL fragment or RANKL peptide is fused to a Qβ coat protein. Fusion protein constructs wherein epitopes have been fused to the C-terminus of a truncated form of the A1 protein of Qβ, or inserted within the A1 protein have been described (Kozlovska, T. M., et al., *Intervirology*, 39:9–15 (1996)). The A1 protein is generated by suppression at the UGA stop codon and has a length of 329 aa, or 328 aa, if the cleavage of the N-terminal methionine is taken into account. Cleavage of the N-terminal methionine before an alanine (the second amino acid encoded by the Qβ CP gene) usually takes place in *E. coli*, and such is the case for N-termini of the Qβ coat proteins CP. The part of the A1 gene, 3' of the UGA amber codon encodes the CP extension, which has a length of 195 amino acids. Insertion of the at least one RANKL protein, RANKL fragment or RANKL peptide between position 72 and 73 of the CP extension leads to further embodiments of the invention (Kozlovska, T. M., et al., *Intervirology* 39:9–15 (1996)). Fusion of a RANKL protein, RANKL fragment or RANKL peptide at the C-terminus of a C-terminally truncated Qβ A1 protein leads to further preferred embodiments of the invention. For example, Kozlovska et al., (*Intervirology*, 39: 9–15 (1996)) describe Qβ A1 protein fusions where the epitope is fused at the C-terminus of the Qβ CP extension truncated at position 19.

As described by Kozlovska et al. (*Intervirology*, 39: 9–15 (1996)), assembly of the particles displaying the fused epitopes typically requires the presence of both the A1 protein-RANKL protein, RANKL fragment or RANKL peptide fusion and the wt CP to form a mosaic particle. However, embodiments comprising virus-like particles, and hereby in particular the VLPs of the RNA phage Qβ coat protein, which are exclusively composed of VLP subunits having at least one RANKL protein, RANKL fragment or RANKL peptide fused thereto, are also within the scope of the present invention.

Figure 1:
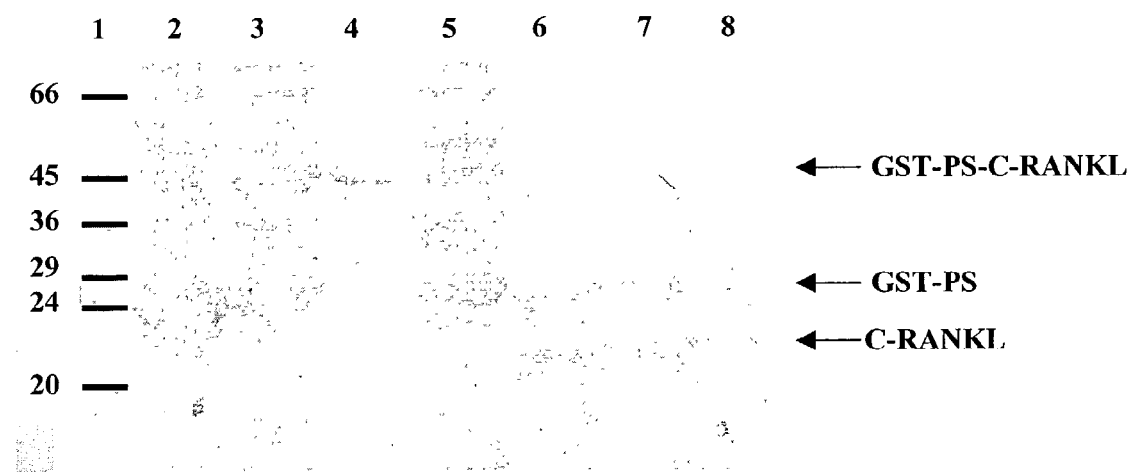
FIG. 1 shows the expression and purification of C-RANKL.

The production of mosaic particles may be effected in a number of ways. Kozlovska et al., *Intervirolog*, 39:9–15 (1996), describe two methods, which both can be used in the practice of the invention. In the first approach, efficient display of the fused epitope on the VLPs is mediated by the expression of the plasmid encoding the Qβ A1 protein fusion having a UGA stop codong between CP and CP extension in a *E. coli* strain harboring a plasmid encoding a cloned UGA suppressor tRNA which leads to translation of the UGA codon into Trp (pISM3001 plasmid (Smiley B.K., et al., *Gene* 134:33–40 (1993))). In another approach, the CP gene stop codon is modified into UAA, and a second plasmid expressing the A1 protein-RANKL protein, RANKL fragment or RANKL peptide fusion is cotransformed. The second plasmid encodes a different antibiotic resistance and the origin of replication is compatible with the first plasmid (Kozlovska, T. M., et al., *Intervirology* 39:9–15 (1996)). In a third approach, CP and the A1 protein-RANKL protein, RANKL fragment or RANKL peptide fusion are encoded in a bicistronic manner, operatively linked to a promoter such as the Trp promoter, as described in FIG. 1 of Kozlovska et al., *Intervirology*, 39:9–15 (1996).

In a further embodiment, the RANKL protein, RANKL fragment or RANKL peptide is inserted between amino acid 2 and 3 (numbering of the cleaved CP, that is wherein the N-terminal methionine is cleaved) of the fr CP, thus leading to a RANKL protein, RANKL fragment or RANKL peptide -fr CP fusion protein. Vectors and expression systems for construction and expression of fr CP fusion proteins self-assembling to VLP and useful in the practice of the invention have been described (Pushko P. et al., *Prot. Eng.* 6:883–891 (1993)). In a specific embodiment, the RANKL protein, RANKL fragment or RANKL peptide sequence is inserted into a deletion variant of the fr CP after amino acid 2, wherein residues 3 and 4 of the fr CP have been deleted (Pushko P. et al., *Prot. Eng.* 6:883–891 (1993)).

Fusion of epitopes in the N-terminal protuberant β-hairpin of the coat protein of RNA phage MS-2 and subsequent presentation of the fused epitope on the self-assembled VLP of RNA phage MS-2 has also been described (WO 92/13081), and fusion of RANKL protein, RANKL fragment or RANKL peptide by insertion or substitution into the coat protein of MS-2 RNA phage is also falling under the scope of the invention.

In another embodiment of the invention, the RANKL protein, RANKL fragment or RANKL peptide are fused to a capsid protein of papillomavirus. In a more specific embodiment, the RANKL protein, RANKL fragment or RANKL peptide are fused to the major capsid protein L1 of bovine papillomavirus type 1 (BPV-1). Vectors and expression systems for construction and expression of BPV-1 fusion proteins in a baculovirus/insect cells systems have been described (Chackerian, B. et al., *Proc. Natl. Acad. Sci. USA* 96:2373–2378 (1999), WO 00/23955). Substitution of amino acids 130–136 of BPV-1 L1 with a RANKL protein, RANKL fragment or RANKL peptide leads to a BPV-1 L1-RANKL protein, RANKL fragment or RANKL peptide fusion protein, which is a preferred embodiment of the invention. Cloning in a baculovirus vector and expression in baculovirus infected Sf9 cells has been described, and can be used in the practice of the invention (Chackerian, B. et al., *Proc. Natl. Acad. Sci. USA* 96:2373–2378 (1999), WO 00/23955). Purification of the assembled particles displaying the fused RANKL protein, RANKL fragment or RANKL peptide can be performed in a number of ways, such as for example gel filtration or sucrose gradient ultracentrifugation (Chackerian, B. et al., *Proc. Natl. Acad. Sci. USA* 96:2373–2378 (1999), WO 00/23955).

In a further embodiment of the invention, the RANKL protein, RANKL fragment or RANKL peptide are fused to a Ty protein capable of being incorporated into a Ty VLP. In a more specific embodiment, the RANKL protein, RANKL fragment or RANKL peptide are fused to the p1 or capsid protein encoded by the TYA gene (Roth, J. F., *Yeast* 16:785–795 (2000)). The yeast retrotransposons Ty1, 2, 3 and 4 have been isolated from *Saccharomyces Serevisiae*, while the retrotransposon Tf1 has been isolated from *Schizosaccharomyces Pombae* (Boeke, J. D. and Sandmeyer, S. B., "Yeast Transposable elements," in *The molecular and Cellular Biology of the Yeast Saccharomyces: Genome dynamics, Protein Synthesis, and Energetics.*, p. 193, Cold Spring Harbor Laboratory Press (1991)). The retrotransposons Ty1 and 2 are related to the copia class of plant and animal elements, while Ty3 belongs to the gypsy family of retrotransposons, which is related to plants and animal retroviruses. In the Ty1 retrotransposon, the p1 protein, also referred to as Gag or capsid protein, has a length of 440 amino acids. P1 is cleaved during maturation of the VLP at position 408, leading to the p2 protein, the essential component of the VLP.

Fusion proteins to p1 and vectors for the expression of said fusion proteins in Yeast have been described (Adams, S. E., et al., *Nature* 329:68–70 (1987)). So, for example, a RANKL protein, RANKL fragment or RANKL peptide may be fused to p1 by inserting a sequence coding for the RANKL protein, RANKL fragment or RANKL peptide into the BamHI site of the pMA5620 plasmid (Adams, S. E., et al., *Nature* 329:68–70 (1987)). The cloning of sequences coding for foreign epitopes into the pMA5620 vector leads to expression of fusion proteins comprising amino acids 1–381 of p1 of Ty1-15, fused C-terminally to the N-termiinus of the foreign epitope. Likewise, N-terminal fusion of RANKL protein, RANKL fragment or RANKL peptide s, or internal insertion into the p1 sequence, or substitution of part of the p1 sequence is also meant to fall within the scope of the invention. In particular, insertion of RANKL protein, RANKL fragment or RANKL peptide into the Ty sequence between amino acids 30–31, 67–68, 113–114 and 132–133 of the Ty protein p1 (EP0677111) leads to preferred embodiments of the invention.

Further VLPs suitable for fusion of RANKL protein, RANKL fragment or RANKL peptide are, for example, Retrovirus-like-particles (W09630523), HIV2 Gag (Kang, Y. C., et al, *Biol. Chem.* 380:353–364 (1999)), Cowpea Mosaic Virus (Taylor, K. M. et al., *Biol. Chem.* 380:387–392 (1999)), parvovirus VP2 VLP (Rueda, P. et al., *Virology* 263:89–99 (1999)), HBsAg (U.S. Pat. No. 4,722,840, EP0020416B1).

Examples of chimeric VLPs suitable for the practice of the invention are also those described in *Intervirology* 39:1 (1996). Further examples of VLPs contemplated for use in the invention are: HPV-1, HPV-6, HPV-11, HPV-16, HPV-18, HPV-33, HPV-45, CRPV, COPV, HIV GAG, Tobacco Mosaic Virus. Virus-like particles of SV-40, Polyomavirus, Adenovirus, Herpes Simplex Virus, Rotavirus and Norwalk virus have also been made, and chimeric VLPs of those VLPs are also within the scope of the present invention.

In a further preferred embodiment of the present invention, the antigen or antigenic determinant is a RANKL protein, RANKL fragment or RANKL peptide.

In a further very preferred embodiment of the invention, the antigen or antigenic determinant is a human RANKL protein, RANKL fragment or RANKL peptide.

In a further very preferred embodiment of the invention, the antigen or antigenic determinant comprises, alternatively essentially consists of, or alternatively consists of an amino acid sequence selected from the group consisting of a) the amino acid sequence of SEQ ID NO: 79; b) the amino acid sequence of any fragment of SEQ ID NO: 79.

In a further preferred embodiment of the invention, the antigen or antigenic determinant is a RANKL protein, RANKL fragment or RANKL peptide variant, e.g. in particular containing amino acid substitutions or peptide insertions or polymorphisms. As already indicated, compositions and vaccine compositions, respectively, comprising RANKL protein, RANKL fragment or RANKL peptide variants are included within the scope of the present invention.

In a further preferred embodiment of the invention, the antigen or antigenic determinant is a RANKL fragment. Preferably, the antigen or antigenic determinant is human RANKL fragment selected from the group of a) the extracellular region of human RANKL, b) the splice isoform 1 of human RANKL, c) the splice isoform 2 resulting in a secreted human RANKL, d) the proteolytically produced soluble region of human RANKL, and e) the TNF-α homolog region. .

In a further very preferred embodiment of the invention, the antigen or antigenic determinant comprises, alternatively essentially consists of, or alternatively consists of an amino acid sequence selected from the group consisting a) the amino acid sequence of SEQ ID NO: 79; b) the amino acid sequence of SEQ ID NO: 80; c) the amino acid sequence of SEQ ID NO: 81; d) the amino acid sequence of SEQ ID NO: 82; e) the amino acid sequence of SEQ ID NO: 83; f) the amino acid sequence of SEQ ID NO: 84; g) the amino acid sequence of SEQ ID NO: 100; h) the amino acid sequence of SEQ ID NO: 101; i) the amino acid sequence of any fragment of any of SEQ ID NO:79–84,100,101.

RANKL protein and RANKL fragments can be produced by expression of the RANKL cDNA in procaryotic or eucaryotic expression systems. Various examples hereto have been described in the literature and can be used, possibly after modifications, to express any RANKL protein, RANKL fragment or RANKL peptide of any desired species. RANKL protein and RANKL fragments have been expressed in mammalian cells (Anderson, D. M., et al., *Nature* 390: 175–179 (1997), Lacey, D. L., et al., *Cell* 93: 165–176 (1998), Wong B. R., et al., *J. Biol. Chem.* 272: 25190–25194 (1997), Lum, L., et al., *J. Biol. Chem.* 274: 13613–13618 (2000)), in insect cells (Willard, D., et al., *Prot. Express. Purif* 20: 48–57 (2000)), and procaryotic cells (Xu, J., et al., *J. Bone Mineral Res.* 15: 2178–86 (2000), Yasuda et al., *Proc. Natl. Acad. Sci. USA* 95: 3597–3602 (1998)). Disclosures how to produce RANKL proteins and fragments are also given in WO 9846751, U.S. Pat. No. 5,843,678, WO 98259958, U.S. Pat. No. 6,242,586, WO 9828426, U.S. Pat. No. 6,242,213, WO 9929865, JP 2000102390 and WO 0015807.

In a further preferred embodiment of the invention, the antigen or antigenic determinant is a RANKL peptide. Such RANKL peptides or fragments thereof can be produced using standard molecular biological technologies where the nucleotide sequence coding for the fragment of interest is amplified by PCR and is cloned as a fusion to a polypeptide tag, such as the histdine tag, the Flag tag, myc tag or the constant region of an antibody (Fc region). By introducing a protease cleavage site between the RANKL fragment and the tag, the RANKL fragment can be separated from the tag after purification by digestion with corresponding protease. In another approach the RANKL fragment can be synthesized in vitro using standard peptide synthesis reactions known to a person skilled in the art. In a further approach RANKL peptides or RANKL fragments can be produced by protease digestion or chemical cleavage of the full length RANKL protein or RANKL fragments, both methods which are well known to people trained in the art.

In a still further preferred embodiment of the present invention, the antigen or antigenic determinant further comprise at least one second attachment site being selected from the group consisting of: (i) an attachment site not naturally occurring with said antigen or antigenic determinant; and (ii) an attachment site naturally occurring with said antigen or antigenic determinant. Guidance on how to modify RANKL protein, RANKL fragment or RANKL peptide for binding to the virus-like particle is given throughout the application. Preferred second attachment sites contain a cysteine residue for binding to the derivatized VLP and examples are given in the above description and in Example 12 and 13.

We have built a model for the 3-dimensional structure of the region of human RANKL that is homologous to TNF-α. We found that the naturally occuring cysteine may not be accessible in the folded structure for interaction with a first attachment site on the VLP in accordance with the present invention. Our model was confirmed by the X-ray structure of mouse RANKL that was recently solved (Lam, J., et al., J. Clin. Invest., 108: 971–979 (2002)). The N-terminus is preferred for attaching a second attachment site comprising an amino acid linker with an additional cysteine residue as shown in Example 12. However, an amino-acid linker containing a cysteine residue as second attachment site and being fused at the C-terminus of the RANKL construct leads to a further preferred embodiment of the invention as shown in EXAMPLE 13. A human RANKL construct with an N-terminal amino acid linker containing a cysteine residue fused to the extracellular region of RANKL is a very preferred embodiment of the invention.

Mouse RANKL fragment constructs (SEQ ID NO:96 and SEQ ID NO:99) are disclosed, and preferred human RANKL fragment constructs can also be generated and have, for example, the sequence of SEQ ID NO:100–104. Further preferred constructs comprise the whole human RANKL protein, a human RANKL fragment selected from the group of a) the extracellular region of RANKL (SEQ ID NO:82), b) the splice isoform 1 of RANKL (SEQ ID NO: 80), c) the splice isoform 2 resulting in a secreted RANKL (SEQ ID NO:81), d) the proteolytically produced soluble region of RANKL (SEQ ID NO:83), and e) the TNF-α homolog region (SEQ ID NO:84) or human RANKL peptide sequences. Immunization against RANKL protein, RANKL fragment or RANKL peptide using the inventive compositions comprising, preferably a human RANKL protein, RANKL fragment or RANKL peptide bound to a VLP may provide a way of treatment or prevention of bone diseases.

In a further preferred embodiment of the present invention, the RANKL protein, RANKL fragment or RANKL peptide comprises at least one antigenic site of a RANKL protein. The skilled person in the art knows how to identify the corresponding peptides and amino acid sequences, respectively.

In a further preferred embodiment of the present invention, the antigen or antigenic determinant is a RANKL peptide that is crucial for interaction with the receptor RANK. Our modeling of the human RANKL structure and the published crystal structure of the mouse RANKL showed that the RANKL monomer consists of a β-sandwich, composed of two flat antiparallel β-sheets. The first sheet is formed by β-strands A", A, H, C and F while the second sheet is formed by β-strands B', B, G, D, and E. The inner A"AHCF β-sheet is involved in intersubunit association, whereas the B'BGDE β-sheet contributes largely to the outer surface. β-strands are connected via the AA" loop, the CD loop, the DE loop, the EF loop. The homotrimer is assembled such that one edge of the β-sandwich in each RANKL monomer packs against the inner hydrophobic face of the AHCF β-sheet of the neighbouring monomer. The RANK binding site is thought to encompass the cleft formed by neighbouring monomers of the homotrimer. Based on the homology between the mouse and the human sequence peptides are selected which encompass the RANK binding site. In a preferred embodiment peptides from the interaction site of RANKL with RANK are selected from the group consisting of a) the AA" loop encompassing amino acids 171–194 (SEQ ID NO: 87), b) the DE loop encompassing amino acids 246–253 (SEQ ID NO:88), c) the β-strand D encompassing amino acids 235–245 (SEQ ID NO: 89), d) the CD loop encompassing amino acids 223–234 (SEQ ID NO:90), e) the EF loop encompassing 262–272 (SEQ ID NO:91), f) β-strand B'-loop B'B encompassing amino acids 200–207 (SEQ ID NO:92), g) loop GH encompassing amino acids 300–305 (SEQ ID NO:93), h) any fragment of said peptides a–g, i) any N- and/or C-terminal extensions of said peptides a–g of at least one amino acid and up to 25 amino acids, j) any fusion of peptides a–i). Further RANKL peptides suitable for use in the present invention can be experimentally determined by their intrinsic property to induce a T cell or an antibody response. This is generally achieved by immunizing an experimental animal separately with selected peptides in an immunologically suitable formulation and by measuring T cell and B cell, i.e. antibody responses, using methods known to a person trained in the art. In the case where the antigen is a protein, a polypeptide or a peptide, this region can be formed by a continuous amino acid sequence. Alternatively, the antibody epitope can be formed by a discontinuous amino acid sequence in which, after three dimensional folding of the protein, polypeptide or peptide, the aminoacids are arranged in such a manner that they spatially come close together and form the epitope. Continuous peptide fragments of interest can identified by immunization experiments as described above.

Further preferred RANKL peptides suitable for use for the present invention can be identified by using existing or future monoclonal or polyclonal antibodies, the procedures hereto are know to those skilled in the art.

Further RANKL peptides suitable for use for the present invention may be identified by screening phage display peptide libraries with antibodies specific for RANKL, a method well known to a person trained in the art.

In a further preferred embodiment of the invention, the antigen or antigenic determinant is isolated RANKL of any animal as well as any antigenic fragments of RANKL of any animal. Those skilled in the art know how to produce fragments and peptides from those isolated RANKL protein or fragments.

It will be understood by one of ordinary skill in the relevant arts that other suitable modifications and adaptations to the methods and applications described herein are readily apparent and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLE 1

Construction and Expression of Mutant Qβ Coat Proteins, and Purification of Mutant Qβ Coat Protein VLPS or Capsids Plasmid Construction and Cloning of Mutant Coat Proteins Construction of pQβ-240:

The plasmid pQβ10 (Kozlovska, T M, et al., *Gene* 137: 133–137) was used as an initial plasmid for the construction of pQβ-240. The mutation Lys13→Arg was created by inverse PCR. The inverse primers were designed in inverted tail-to-tail directions:

(SEQ ID NO: 129)
5'-GGTAACATCGGTCGAGATGGAAAACAAACTCTGGTCC-3' and (SEQ ID NO: 130)
5'-GGACCAGAGTTTGTTTTCCATCTCGACCGATGTTACC-3'.

The products of the first PCR were used as templates for the second PCR reaction, in which an upstream primer (SEQ ID NO: 131)
5'-AGCTCGCCCGGGGATCCTCTAG-3' and a downstream primer (SEQ ID NO: 132)
5'-CGATGCATTTCATCCTTAGTTATCAATACGCTGGGTTCAG-3' were used. The product of the second PCR was digested with XbaI and Mph1103I and cloned into the pQβ10 expression vector, which was cleaved by the same restriction enzymes. The PCR reactions were performed with PCR kit reagents and according to producer protocol (MBI Fermentas, Vilnius, Lithuania).

Sequencing using the direct label incorporation method verified the desired mutations. *E.coli* cells harbouring pQβ-240 supported efficient synthesis of 14-kD protein co migrating upon SDS-PAGE with control Qβ coat protein isolated from Qβ phage particles.

Resulting Amino Acid Sequence:

(SEQ ID NO:23)
AKLETVTLGNIGRDGKQTLVLNPRGVNPTNGVASLSQAGAVPALEKRVTV

SVSQPSRNRKNYKVQVKIQNPTACTANGSCDPSVTRQKYADVTFSFTQYS

TDEERAFVRTELAALLASPLLIDAIDQLNPAY

Construction of pQβ-243:

The plasmid pQβ10 was used as an initial plasmid for the construction of pQβ-243. The mutation Asn10→Lys was created by inverse PCR. The inverse primers were designed in inverted tail-to-tail directions:

(SEQ ID NO: 133)
5'-GGCAAAATTAGAGACTGTTACTTTAGGTAAGATCGG-3' and (SEQ ID NO: 134)
5'-CCGATCTTACCTAAAGTAACAGTCTCTAATTTTGCC-3'.

The products of the first PCR were used as templates for the second PCR reaction, in which an upstream primer (SEQ ID NO: 135)
5'-AGCTCGCCCGGGGATCCTCTAG-3' and a downstream primer (SEQ ID NO: 136)
5'-CGATGCATTTCATCCTTAGTTATCAATACGCTGGGTTCAG-3' were used. The product of the second PCR was digested with XbaI and Mph1103I and cloned into the pQβ10 expression vector, which was cleaved by the same restriction enzymes. The PCR reactions were performed with PCR kit reagents and according to producer protocol (MBI Fermentas, Vilnius, Lithuania).

Sequencing using the direct label incorporation method verified the desired mutations. *E.coli* cells harbouring pQβ-243 supported efficient synthesis of 14-kD protein co migrating upon SDSD-PAGE with control Qβ coat protein isolated from Qβ phage particles.

Resulting amino acid sequence:

(SEQ ID NO: 24)
AKLETVTLGKIGKDGKQTLVLNPRGVNPTNGVASLSQAGAVPALEKRVTV

SVSQPSRNRKNYKVQVKIQNPTACTANGSCDPSVTRQKYADVTFSFTQYS

TDEERAFVRTELAALLASPLLIDAIDQLNPAY

Construction of pQβ-250:

The plasmid pQβ-240 was used as an initial plasmid for the construction of pQβ-250. The mutation Lys2→Arg was created by site-directed mutagenesis. An upstream primer (SEQ ID NO: 137)
5'-GGCCATGGCACGACTCGAGACTGTTACTTTAGG-3' and a downstream primer (SEQ ID NO: 138)
5'-GATTTAGGTGACACTATAG-3' were used for the synthesis of the mutant PCR-fragment, which was introduced into the pQβ-185 expression vector at the unique restriction sites NcoI and HindIII. The PCR reactions were performed with PCR kit reagents and according to producer protocol (MBI Fermentas, Vilnius, Lithuania).

Sequencing using the direct label incorporation method verified the desired mutations. *E.coli* cells harbouring pQβ-250 supported efficient synthesis of 14-kD protein co migrating upon PAGE with control Qβ coat protein isolated from Qβ phage particles.

Resulting Amino Acid Sequence:

(SEQ ID NO:25)
ARLETVTLGNIGRDGKQTLVLNPRGVNPTNGVASLSQAGAVPALEKRVTV

SVSQPSRNRKNYKVQVKIQNPTACTANGSCDPSVTRQKYADVTFSFTQYS

TDEERAFVRTELAALLASPLLIDAIDQLNPAY

Construction of pQβ-251:

The plasmid pQβ10 was used as an initial plasmid for the construction of pQβ-251. The mutation Lys16→Arg was created by inverse PCR. The inverse primers were designed in inverted tail-to-tail directions:

(SEQ ID NO: 139)
5'-GATGGACGTCAAACTCTGGTCCTCAATCCGCGTGGGG-3' and (SEQ ID NO: 140)
5'-CCCCACGCGGATTGAGGACCAGAGTTTGACGTCCATC-3'.

The products of the first PCR were used as templates for the second PCR reaction, in which an upstream primer (SEQ ID NO: 141)
5'-AGCTCGCCCGGGGATCCTCTAG-3' and a downstream primer (SEQ ID NO: 142)
5'-CGATGCATTTCATCCTTAGTTATCAATACGCTGGGTTCAG-3' were used. The product of the second PCR was digested with XbaI and Mph1103I and cloned into the pQβ10 expression vector, which was cleaved by the same restriction enzymes. The PCR reactions were performed with PCR kit reagents and according to producer protocol (MBI Fermentas, Vilnius, Lithuania).

Sequencing using the direct label incorporation method verified the desired mutations. E.coli cells harbouring pQβ-251 supported efficient synthesis of 14-kD protein co migrating upon SDS-PAGE with control Qβ coat protein isolated from Qβ phage particles. The resulting amino acid sequence encoded by this construct is shown in SEQ. ID NO: 26.

Construction of pQβ-259:

The plasmid pQβ-251 was used as an initial plasmid for the construction of pQβ-259. The mutation Lys2→Arg was created by site-directed mutagenesis. An upstream primer (SEQ ID NO: 143)
5'-GGCCATGGCACGACTCGAGACTGTTACTTTAGG-3' and a downstream primer (SEQ ID NO: 143)
5'-GATTTAGGTGACACTATAG-3' were used for the synthesis of the mutant PCR-fragment, which was introduced into the pQβ-185 expression vector at the unique restriction sites NcoI and HindIII. The PCR reactions were performed with PCR kit reagents and according to producer protocol (MBI Fermentas, Vilnius, Lithuania).

Sequencing using the direct label incorporation method verified the desired mutations. E.coli cells harbouring pQβ-259 supported efficient synthesis of 14-kD protein co migrating upon SDS-PAGE with control Qβ coat protein isolated from Qβ phage particles.

Resulting Amino Acid Sequence:

(SEQ ID NO: 27)
AKLETVTLGNIGKDGKQTLVLNPRGVNPTNGVASLSQAGAVPALEKRVTV

SVSQPSRNRKNYKVQVKIQNPTACTANGSCDPSVTRQKYADVTFSFTQYS

TDEERAFVRTELAALLASPLLIDATDQLNPAY

General Procedures for Expression and Purification of Qβ and Qβ Mutants

Expression

E.coli JM109 was transformed with Qβ coat protein expression plasmids. 5 ml of LB liquid medium containing 20 μg/ml ampicillin were inoculated with clones transformed with with Qβ coat protein expression plasmids. The inoculated culture was incubated at 37° C. for 16–24 h without shaking. The prepared inoculum was subsequently diluted 1:100 in 100–300 ml of fresh LB medium, containing 20 μg/ml ampicillin, and incubated at 37° C. overnight without shaking. The resulting second inoculum was diluted 1:50 in M9 medium containing 1% Casamino acids and 0.2% glucose in flasks, and incubated at 37° C. overnight under shaking.

Purification

Solutions and buffers for the purification procedure:
1. Lysis buffer LB
   50 mM Tris-HCl pH8,0 with 5 mM EDTA, 0,1% triton X-100 and freshly prepared PMSF at a concentration of 5 micrograms per ml. Without lysozyme and DNAse.
2. SAS
   Saturated ammonium sulphate in water
3. Buffer NET.
   20 mM Tris-HCl, pH 7.8 with 5 mM EDTA and 150 mM NaCl.
4. PEG
   40% (w/v) polyethylenglycol 6000 in NET Disruption and Lysis Frozen cells were resuspended in LB at 2 ml/g cells. The mixture was sonicated with 22 kH five times for15 seconds, with intervals of 1 min to cool the solution on ice. The lysate was then centrifuged at 14 000 rpm, for 1 h using a Janecki K 60 rotor. The centrifugation steps described below were all performed using the same rotor, except otherwise stated. The supernatant was stored at 4° C., while cell debris were washed twice with LB. After centrifugation, the supernatants of the lysate and wash fractions were pooled.

Fractionation

A saturated ammonium sulphate solution was added dropwise under stirring to the above pooled lysate. The volume of the SAS was adjusted to be one fifth of total volume, to obtain 20% of saturation. The solution was left standing overnight, and was centrifuged the next day at 14 000 rpm, for 20 min. The pellet was washed with a small amount of 20% ammonium sulphate, and centrifuged again. The obtained supernatants were pooled, and SAS was added dropwise to obtain 40% of saturation. The solution was left standing overnight, and was centrifuged the next day at 14 000 rpm, for 20 min. The obtained pellet was solubilised in NET buffer.

Chromatography

The capsid or VLP protein resolubilized in NET buffer was loaded on a Sepharose CL-4B column. Three peaks eluted during chromatography. The first one mainly contained membranes and membrane fragments, and was not collected. Capsids were contained in the second peak, while the third one contained other E.coli proteins.

The peak fractions were pooled, and the NaCl concentration was adjusted to a final concentration of 0.65 M. A volume of PEG solution corresponding to one half of the pooled peak fraction was added dropwise under stirring. The solution was left to stand overnight without stirring. The capsid protein was sedimented by centrifugation at 14 000 rpm for 20 min. It was then solubilized in a minimal volume of NET and loaded again on the Sepharose CL-4B column. The peak fractions were pooled, and precipitated with ammonium sulphate at 60% of saturation (w/v). After centrifugation and resolubilization in NET buffer, capsid protein was loaded on a Sepharose CL-6B column for rechromatography.

Dialysis and Drying

The peak fractions obtained above were pooled and extensively dialysed against sterile water, and lyophilized for storage.

Expression and Purification Qβ-240

Cells (*E. coli* JM 109, transformed with the plasmid pQβ-240) were resuspended in LB, sonicated five times for 15 seconds (water ice jacket) and centrifuged at 13000 rpm for one hour. The supernatant was stored at 4° C. until further processing, while the debris were washed 2 times with 9 ml of LB, and finally with 9 ml of 0,7 M urea in LB. All supernatants were pooled, and loaded on the Sepharose CL-4B column. The pooled peak fractions were precipitated with ammonium sulphate and centrifuged. The resolubilized protein was then purified further on a Sepharose 2B column and finally on a Sepharose 6B column. The capsid peak was finally extensively dialyzed against water and lyophilized as described above. The assembly of the coat protein into a capsid was confirmed by electron microscopy.

Expression and Purification Qβ-243

Cells (*E. coli* RR1) were resuspended in LB and processed as described in the general procedure. The protein was purified by two successive gel filtration steps on the sepharose CL-4B column and finally on a sepharose CL-2B column. Peak fractions were pooled and lyophilized as described above. The assembly of the coat protein into a capsid was confirmed by electron microscopy.

Expression and Purification of Qβ-250

Cells (*E. coli* JM 109, transformed with pQβ-250) were resuspended in LB and processed as described above. The protein was purified by gel filtration on a Sepharose CL-4B and finally on a Sepharose CL-2B column, and lyophilized as described above. The assembly of the coat protein into a capsid was confirmed by electron microscopy.

Expression and Purification of Qβ-259

Cells (*E. coli* JM 109, transformed with pQβ-259) were resuspended in LB and sonicated. The debris were washed once with 10 ml of LB and a second time with 10 ml of 0,7 M urea in LB. The protein was purified by two gel-filtration chromatogaphy steps, on a Sepharose CL-4 B column. The protein was dialyzed and lyophilized, as described above. The assembly of the coat protein into a capsid was confirmed by electron microscopy.

EXAMPLE 2

Insertion of a Peptide Containing a Lysine Residue into the C/E1 Epitope of HBCAG(1–149)

The c/e1 epitope (residues 72 to 88) of HBcAg is located in the tip region on the surface of the Hepatitis B virus capsid (HBcAg). A part of this region (Proline 79 and Alanine 80) was genetically replaced by the peptide Gly-Gly-Lys-Gly-Gly (HBcAg-Lys construct: SEQ ID NO: 117). The introduced Lysine residue contains a reactive amino group in its side chain that can be used for intermolecular chemical crosslinking of HBcAg particles with any antigen containing a free cysteine group.

HBcAg-Lys DNA, having the amino acid sequence shown in SEQ ID NO:78, was generated by PCRs: The two fragments encoding HBcAg fragments (amino acid residues 1 to 78 and 81 to 149) were amplified separately by PCR. The primers used for these PCRs also introduced a DNA sequence encoding the Gly-Gly-Lys-Gly-Gly peptide. The HBcAg (1 to 78) fragment was amplified from pEco63 using primers EcoRIHBcAg(s) and Lys-HBcAg(as). The HBcAg (81 to 149) fragment was amplified from pEco63 using primers Lys-HBcAg(s) and HBcAg(1–149)Hind(as). Primers Lys-HBcAg(as) and Lys-HBcAg(s) introduced complementary DNA sequences at the ends of the two PCR products allowing fusion of the two PCR products in a subsequent assembly PCR. The assembled fragments were amplified by PCR using primers EcoRIHBcAg(s) and HbcAg(1–149)Hind(as).

For the PCRs, 100 pmol of each oligo and 50 ng of the template DNAs were used in the 50 ml reaction mixtures with 2 units of Pwo polymerase, 0.1 mM dNTPs and 2 mM MgSO4. For both reactions, temperature cycling was carried out as follows: 94° C. for 2 minutes; 30 cycles of 94° C. (1 minute), 50° C. (1 minute), 72° C. (2 minutes).

Primer Sequences:

EcoRIHBcAg(s):
(SEQ ID NO: 145)
(5'-CCGGAATTCATGGACATTGACCCTTATAAAG-3');

Lys-HBcAg(as):
(SEQ ID NO: 146)
(5'-CCTAGAGCCACCTTTGCCACCATCTTCTAAATTAGTACCCACCCAG GTAGC-3');

Lys-HBcAg(s):
(SEQ ID NO: 147)
(5'-GAAGATGGTGGCAAAGGTGGCTCTAGGGACCTAGTAGTCAGTTATG TC-3');

HBcAg(1-149)Hind(as):
(SEQ ID NO: 148)
(5'-CGCGTCCCAAGCTTCTAAACAACAGTAGTCTCCGGAAG-3').

For fusion of the two PCR fragments by PCR 100 pmol of primers EcoRIHBcAg(s) and HBcAg(1–149)Hind(as) were used with 100 ng of the two purified PCR fragments in a 50 ml reaction mixture containing 2 units of Pwo polymerase, 0.1 mM dNTPs and 2 mM MgSO$_4$. PCR cycling conditions were: 94° C. for 2 minutes; 30 cycles of 94° C. (1 minute), 50° C. (1 minute), 72° C. (2 minutes). The assembled PCR product was analyzed by agarose gel electrophoresis, purified and digested for 19 hours in an appropriate buffer with EcoRI and HindIII restriction enzymes. The digested DNA fragment was ligated into EcoRI/HindIII-digested pKK vector to generate pKK-HBcAg-Lys expression vector. Insertion of the PCR product into the vector was analyzed by EcoRI/HindIII restriction analysis and DNA sequencing of the insert.

EXAMPLE 3

Expression and Purification of HBcAg-Lys

*E. coli* strains K802 or JM109 were transformed with pKK-HBcAg-Lys. 1 ml of an overnight culture of bacteria was used to innoculate 100 ml of LB medium containing 100 μg/ml ampicillin. This culture was grown for 4 hours at 37° C. until an OD at 600 nm of approximately 0.8 was reached. Induction of the synthesis of HBcAg-Lys was performed by addition of IPTG to a final concentration of 1 mM. After induction, bacteria were further shaken at 37° C. for 4 hours. Bacteria were harvested by centrifugation at 5000×g for 15 minutes. The pellet was frozen at −80° C. The pellet was thawed and resuspended in bacteria lysis buffer (10 mM $Na_2HPO_4$, pH 7.0, 30 mM NaCl, 0.25% Tween-20, 10 mM EDTA) supplemented with 200 μg/ml lysozyme and 10 μl of Benzonase (Merck). Cells were incubated for 30 minutes at room temperature and disrupted by sonication. *E. coli* cells harboring pKK-HBcAg-Lys expression plasmid or a control plasmid were used for induction of HBcAg-Lys expression with IPTG. Prior to the addition of IPTG, a sample was removed from the bacteria culture carrying the pKK-HBcAg-Lys plasmid and from a culture carrying the control plasmid. Four hours after addition of IPTG, samples were again removed from the culture containing pKK-HBcAg-Lys and from the control culture. Protein expression was monitored by SDS-PAGE followed by Coomassie staining.

The lysate was then centrifuged for 30 minutes at 12,000×g in order to remove insoluble cell debris. The supernatant and the pellet were analyzed by Western blotting using a monoclonal antibody against HBcAg (YVS1841, purchased from Accurate Chemical and Scientific Corp., Westbury, N.Y., USA), indicating that a significant amount of HBcAg-Lys protein was soluble. Briefly, lysates from *E. coli* cells expressing HBcAg-Lys and from control cells were centrifuged at 14,000×g for 30 minutes. Supernatant (=soluble fraction) and pellet (=insoluble fraction) were separated and diluted with SDS sample buffer to equal volumes. Samples were analyzed by SDS-PAGE followed by Western blotting with anti-HBcAg monoclonal antibody YVS 1841.

The cleared cell lysate was used for step-gradient centrifugation using a sucrose step gradient consisting of a 4 ml 65% sucrose solution overlaid with 3 ml 15% sucrose solution followed by 4 ml of bacterial lysate. The sample was centrifuged for 3 hrs with 100,000×g at 4° C. After centrifugation, 1 ml fractions from the top of the gradient were collected and analyzed by SDS-PAGE followed by Coomassie staining. The HBcAg-Lys protein was detected by Coomassie staining.

The HBcAg-Lys protein was enriched at the interface between 15 and 65% sucrose indicating that it had formed a capsid particle. Most of the bacterial proteins remained in the sucrose-free upper layer of the gradient, therefore step-gradient centrifugation of the HBcAg-Lys particles led both to enrichment and to a partial purification of the particles.

Expression and purification of HBcAg-Lys in large scale was performed as follows. An overnight culture was prepared by inoculating a single colony in 100 ml LB, 100 μg/ml Ampicillin and growing the culture overnight at 37° C. 25 ml of the preculture were diluted in 800 ml LB Ampicillin medium the next day, and the culture gorwn to an optical density $OD^{600}$ of 0.6–0.8. The culture was then induced with 1 mM IPTG, and left to grow for another 4 hours. The cells were harvested and lysed essentially as described above.

HBcAg-Lys was then purified by first precipitating the protein with ammonium sulphate (30% saturation) from the cleared cell lysate, then loading the resolubilized pellet on a gel filtration column (Sephacryl S-400, Pharmacia). The pooled fractions were precipitated again with ammonium sulphate, the pellet resolubilized and loaded a second time on the same gel filtration column. The fractions were finally pooled and concentrated, and the concentration assessed using a Bradford test (BioRad).

EXAMPLE 4

Construction of a HBcAG Devoid of Free Cysteine Residues and Containing an Inserted Lysine Residue A Hepatitis core Antigen (HBcAg), referred to herein as HBcAg-lys-2cys-Mut, devoid of cysteine residues at positions corresponding to 48 and 107 in SEQ ID NO:77 and containing an inserted lysine residue was constructed using the following methods.

The two mutations were introduced by first separately amplifying three fragments of the HBcAg-Lys gene prepared as described above in Example 2 with the following PCR primer combinations. PCR methods and conventional cloning techniques were used to prepare the HBcAg-lys-2cys-Mut gene.

In brief, the following primers were used to prepare fragment 1:

```
Primer 1: EcoRIHBcAg(s)
                                          (SEQ ID NO: 145)
CCGGAATTCATGGACATTGACCCTTATAAAG Primer 2: 48as
                                          (SEQ ID NO: 149)
GTGCAGTATGGTGAGGTGAGGAATGCTCAGGAGACTC.
```

The following primers were used to prepare fragment 2:

```
Primer 3: 48s
                                          (SEQ ID NO: 150)
GSGTCTCCTGAGCATTCCTCACCTCACCATACTGCAC Primer 4: 107as
                                          (SEQ ID NO: 151)
CTTCCAAAAGTGAGGGAAGAAATGTGAAACCAC
```

The following primers were used to prepare fragment 3:

```
Primer 5: HBcAg149hind-as
                                          (SEQ ID NO: 152)
CGCGTCCCAAGCTTCTAAACAACAGTAGTCTCCGGAAGCGTTGATAG Primer 6: 107s
                                          (SEQ ID NO: 153)
GTGGTTTCACATTTCTTCCCTCACTTTTGGAAG
```

Fragments 1 and 2 were then combined with PCR primers EcoRIHBcAg(s) and 107as to give fragment 4. Fragment 4 and fragment 3 were then combined with primers EcoRIHBcAg(s) and HBcAg149hind—as to produce the full length gene. The full length gene was then digested with the EcoRI (GAATTC) and HindIII (AAGCTT) enzymes and cloned into the pKK vector (Pharmacia) cut at the same restriction sites. Expression and purification of HBcAg-lys-2cys-Mut were performed as set out in Example 3.

EXAMPLE 5

Construction of HBcAG1–185-Lys

Hepatitis core Antigen (HBcAg) 1–185 was modified as described in Example 2. A part of the c/e1 epitope (residues 72 to 88) region (Proline 79 and Alanine 80) was genetically replaced by the peptide Gly-Gly-Lys-Gly-Gly (HBcAg1–185-Lys construct, SEQ ID NO: 117). The introduced Lysine residue contains a reactive amino group in its side chain that can be used for intermolecular chemical crosslinking of HBcAg particles with any antigen containing a free cysteine group. PCR methods and conventional cloning techniques were used to prepare the HBcAg1–185-Lys gene.

The Gly-Gly-Lys-Gly-Gly sequence (SEQ ID NO: 117) was inserted by amplifying two separate fragments of the HBcAg gene from pEco63, as described above in Example 2 and subsequently fusing the two fragments by PCR to assemble the full length gene. The following PCR primer combinations were used:

fragment 1:
Primer 1: EcoRIHBcAg(s) (see Example 2)

```
CεH3fwd:
5' GTT AAC TTG ACC TGG TCT CGT GCT TCT GGT  GCA TCC AGG GAT CTA GTA GTC 3'   (SEQ ID NO: 156)
    V   N   L   T   W   S   R   A   S   G   A80 S   R   D   L   V   V86     (SEQ ID NO: 157)

CεH3rev:
5' ACC AGA AGC ACG AGA CCA GGT CAA GTT AAC  ATC TTC CAA ATT ATT ACC CAC 3'   (SEQ ID NO: 158)
                                            D78 E   L   N   N   G   V72     (SEQ ID NO: 159)

HBcAg-wt EcoRI fwd:
5' CCGgaattcATGGACATTGACCCTTATAAAG                                           (SEQ ID NO: 160)

HBcAg-wt Hind III rev:
5' CGCGTCCCaagcttCTAACATTGAGATTCCCGAGATTG                                    (SEQ ID NO: 161)
```

Primer 2: Lys-HBcAg(as) (see Example 2)
fragment 2:
Primer 3: Lys-HBcAg(s) (see Example 2)
Primer 4: HBcAgwtHindIIhI CGCGTCCCAAGCTTCTAACATTGAGATTCCCGAGATTG (SEQ ID NO: 154)
assembly:
Primer 1: EcoRIHBcAg(s) (see example 2)
Primer 2: HBcAgwtHindIII The assembled full length gene was then digested with the EcoRI (GAATTC) and HindIII (AAGCTT) enzymes and cloned into the pKK vector (Pharmacia) cut at the same restriction sites.

EXAMPLE 6

Fusion of a Peptide Epitope in the MIR Region of HBcAg

The residues 79 and 80 of HBcAg1–185 were substituted with the epitope CεH3 of sequence VNLTWSRASG (SEQ ID NO: 155). The CεH3 sequence stems from the sequence of the third constant domain of the heavy chain of human IgE. The epitope was inserted in the HBcAg1–185 sequence using an assembly PCR method. In the first PCR step, the HBcAg1–185 gene originating from ATCC clone pEco63 and amplified with primers HBcAg-wt EcoRI fwd and HBcAg-wt HindIII rev was used as template in two separate reactions to amplify two fragments containing sequence elements coding for the CεH3 sequence. These two fragments were then assembled in a second PCR step, in an assembly PCR reaction.

Primer combinations in the first PCR step: CεH3fwd with HBcAg-wt HindIII rev, and HBcAg-wt EcoRI fwd with CεH3rev. In the assembly PCR reaction, the two fragments isolated in the first PCR step were first assembled during 3 PCR cycles without outer primers, which were added afterwards to the reaction mixture for the next 25 cycles. Outer primers: HBcAg-wt EcoRI fwd and HBcAg-wt HindIII rev.

The PCR product was cloned in the pKK223.3 using the EcoRI and HindIII sites, for expression in E. coli (see Example 2). The chimeric VLP was expressed in E. coli and purified as described in Example 2. The elution volume at which the HBcAg1–185-CεH3 eluted from the gel filtration showed assembly of the fusion proteins to a chimeric VLP.

EXAMPLE 7

Fusion of a RANKL Peptide Epitope in the MIR Region of HBcAG

Primer Sequences:

The residues 79 and 80 of HBcAg1–185 are substituted with the RANKL peptide epitope of sequence: SIKIPSSH (SEQ ID NO: 162). Two overlapping primers are designed using the same strategy described in Example 6, and the fusion protein constructed by assembly PCR. The PCR product is cloned in the pKK223.3 vector, and expressed in E. coli K802. The chimeric VLPs are expressed and purified as described in Example 3.

A primer annealing to the 5' end of the Qβ A1 gene and a primer annealing to the 3' end of the A1 gene and comprising additionally a sequence element coding for the RANKL peptide epitope of sequence: SIKIPSSH (SEQ ID NO: 162), are used in a PCR reaction with pQβ10 as template. The PCR product is cloned in pQβ10 (Kozlovska T. M. et al., Gene 137: 133–37 (1993)), and the chimeric VLP expressed and purified as described in Example 1.

Complementary primers coding for the sequence of the RANKL peptide epitope of sequence: SIKIPSSH (SEQ ID NO: 162), and containing Bsp119I compatible ends and additional nucleotides enabling in frame insertion, are inserted in the Bsp119I site of the pFrd8 vector (Pushko, P. et al., Prot. Eng. 6: 883–91 (1993)) by standard molecular biology techniques. Alternatively, the overhangs of the pFrd8 vector are filled in with Klenow after digestion with Bsp119I, and oligonucleotides coding for the sequence of the RANKL protein, RANKL fragment or RANKL peptide and additional nucleotides for in frame cloning are ligated in pFrd8 after the Klenow treatment. Clones with the insert in the right orientation are analysed by sequencing. Expression and purification of the chimeric fusion protein in E. coli JM109 or E. coli K802 is performed as described in Pushko, P. et al, Prot. Eng. 6:883–91 (1993), but for the chromatography steps which are performed using a Sepharose CL-4B or Sephacryl S-400 (Pharmacia). The cell lysate is precipitated with ammonium sulphate, and purified by two successive gel filtration purification steps, similarly to the procedure described for Qβ in Example 1.

Two complementary oligonucleotides coding for the RANKL peptide epitope of sequence: SIKIPSSH (SEQ ID NO: 162), with ends compatible with the NheI site of pOGS8111 are synthesized. Additional nucleotides are added to allow for in frame insertion of a sequence coding for the RANKL epitope according to the description of EP06777111. The amino acids AS and SS flanking the inserted epitope are encoded by the altered NheI sites resulting from the insertion of the oligonucleotide in the TyA(d) gene of pOGS8111.

EXAMPLE 10

Insertion of a RANKL Peptide Epitope Between Positions 67 and 68 of Ty1 Protein P1 in the Vector pOGS8111

Two complementary oligonucleotides coding for the RANKL peptide epitope of sequence: SIKIPSSH, with ends compatible with the NheI site of pOGS8111 are synthesized. Additional nucleotides are added to allow for in frame insertion of a sequence coding for the RANKL epitope according to the description of EP06777111. The amino acids AS and SS flanking the inserted epitope are encoded by the altered NheI sites resulting from the insertion of the oligonucleotide in the TyA(d) gene of pOGS8111.

POGS8111 is transformed into S. cervisiae strain MC2, for expression of the chimeric Ty VLP as described in EP0677111 and references therein. The chimeric Ty VLP is purified by sucrose gradient ultracentrifugation as described in EP0677111.

EXAMPLE 11

Insertion of a RANKL Peptide Epitope in to the Major Capsid Protein L1 of Papillomavirus Type 1 (BPV-1)

A sequence coding for the RANKL peptide epitope of sequence SIKIPSSH (SEQ ID NO: 162) is substituted to the sequence coding for amino acids 130–136 of the BPV-1 L1 gene cloned in the pFastBac1 (GIBCO/BRL) vector as described (Chackerian, B. et al., Proc. Natl. Acad. USA 96: 2373–2378 (1999)). The sequence of the construct is verified by nucleotide sequence analysis. Recombinant baculovirus is generated using the GIBCO/BRL baculovirus system as described by the manufacturer. The chimeric VLPs are purified from baculovirus infected Sf9 cells as described by Kirnbauer, R. et al., Proc. Natl. Acad. Sci. 89:12180–84 (1992) and Greenstone, H. L., et al., Proc. Natl. Acad. Sci. 95:1800–05 (1998).

EXAMPLE 12

Introduction of an N-Terminal Cys-Containing Linker, Expression and Purification of RANKL A fragment of RANKL was recombinantly expressed with an N-terminal linker containing one cysteine for coupling to VLP.

Construction of Expression Plasmid

The C-terminal coding region of the RANKL gene was amplified by PCR with oligos RANKL-UP and RANKL-DOWN (Oligos: RANKL-UP: 5'CTGCCAGGGGC-CCGGGTGCGGCGGTGGCCATCATCACCACCAT-CACCAGCGCTTCTCAGGAG-3' (SEQ ID NO: 163); RANKL-DOWN: 5'-CCGCTCGAGT-TAGTCTATGTCCT-GAACTTTGAAAG-3' (SEQ ID NO: 164)). RANKL-UP had an internal ApaI site and RANKL-DOWN had an internal XhoI site. The PCR product was digested with ApaI and XhoI and ligated into pGEX-6p1 (Amersham Pharmacia). The resulting plasmid was named pGEX-RANKL. All steps were performed by standard molecular biology protocols and the sequence was verified. The plasmid pGEX-RANKL codes for a fusion protein of a glutathione S-transferase-Prescission cleavage site-cysteine-containing amino acid linker-RANKL (GST-PS-C-RANKL). The cysteine-containing amino acid linker had the sequence GPGCGGG (SEQ ID NO: 165). The construct also contains a hexahistidine tag between the cysteine containing amino acid linker and the RANKL sequence. Sequences of the resulting cDNA and protein constructs are given as SEQ-ID NO: 94 and SEQ-ID NO: 95.

Expression and Purification of C-RANKL

Competent Escherichia coli BL21 (DE3) Gold pLys cells were transformed with the plasmid pGEX-RANKL. Single colonies from ampicillin-containing agar plates were expanded in liquid culture (LB medium, 100 µg/ml ampicillin) and incubated at 30° C. with 220 rpm shaking overnight. One litre of LB (with 100 µg/ml ampicillin) was then inoculated 1:100 v/v with the overnight culture and grown at 24° C. to $OD_{600}$=1. Expression was induced with 0.4 mM IPTG. Cells were harvested after 16 h and centrifuged at 5000 rpm. Cell pellet was suspended in lysis buffer (50 mM Tris-HCl, pH 8.0; 25% sucrose; 1 mM EDTA, 1% $NaN_3$; 10 mM DTT; 5 mM $MgCl_2$; 1 mg/ml Lysozyme; 0.4 U/ml DNAse) for 30 min. Then 2.5 volumes of buffer A (50 mM Tris-HCl, pH 8.0; 1% Triton 100; 100 mM NaCl; 0.1% $NaN_3$; 10 mM DTT;1 mM PMSF) were added and incubated at 37° C. for 15 min. The cells were sonicated and pelleted at 9000 rpm for 15 min. The supernatant was immediately used for GST-affinity chromatography.

A GST-Trap FF column of 5 ml (Amersham Pharmacia) was equilibrated in PBS, pH 7.3 (140 mM NaCl, 2.7 mM KCl, 10 mM $Na_2HPO_4$, 1.8 mM $KH_2PO_4$). The supernatant was loaded on the 5 ml GST-Trap FF column and subsequently the column was rinsed with 5 column volumes of PBS. The protein GST-PS-C-RANKL was eluted with 50 mM Tris-HCl, pH 8.0 containing 10 mM reduced glutathione.

The purified GST-PS-C-RANKL protein was digested using the protease PreScission (Amersham Pharmacia). The digestion was performed at 37° C. for 1 hour using a molar ratio of 500/1 of GST-PS-C-RANKL to PreScission.

Furthermore, the reaction of protease digestion was buffer exchanged using a HiPrep 26/10 desalting column (Amersham Pharmacia), the fractions containing the proteins were pooled and immediately used for another step of GST affinity chromatography using the same conditions reported before. Purification of C-RANKL was analysed on a SDS-PAGE gel under reducing conditions, shown in FIG. 1. The cleaved C-RANKL is present in the flow-through (unbound fraction) while the uncleaved GST-PS-C-RANKL, the cleaved GST-PS and the PreScission remain bound to the column. C-RANKL protein (SEQ ID NO:96) of the expected size of 22 kDa was obtained in high purity.

EXAMPLE 13

Introduction of a C-Terminal Cys-Containing Linker, Expression and Purification of RANKL A fragment of the RANKL was recombinantly expressed with a C-terminal linker containing one cysteine for coupling to VLP.

Construction of Expression Plasmid

The MCS of pET22b(+) (Novagen, Inc.) was changed to GTTTAACTTTAAGAAGGAGATATA-CATATGGATCCGGCTAGCGCTCGAGGGT TTAAACG-GCGGCCGCATGCACC (SEQ ID NO: 166) by replacing the original sequence from the NdeI site to XhoI site with annealed oligos primerMCS-1F and primerMCS-1R (annealing in 15 mM TrisHCl pH 8 buffer). The resulting plasmid was termed pMod00, which had NdeI,BamHI,NheI, XhoI,PmeI and NotI restriction sites in its MCS. The annealed pair of oligos Bamhis6-EK-Nhe-F and Bamhis6-EKNhe-R and the annealed pair of oligo1F-C-glycine-linker and oligo1R-C-glycine-linker were together ligated into BamHI-NotI digested pMod00 plasmid to get pModEC1, which had an N terminal hexahistidine tag, an enterokinase cleavage site and a C-terminal amino acid glycine linker containing one cysteine residue.

A DNA fragment comprising the glutathione S transferase gene with a C-terminal enterokinase cleavage site was amplified by PCR with oligonucleotides GST-UP and GST-EK from plasmid SP-GST-EK-pCEP-Pu (Wuttke, M., et al., *J. Biol. Chem.*, 276: 36839–36848), digested with NheI and BamHI and cloned into the pModEC1 vector.

The resulting plasmid pMod-GST-EK-C1 comprises the gene coding for glutathione S transferase fused to an enterokinase cleavage site and a C-terminal cys-containing linker. The C-terminal coding sequence of RANKL was then amplified by PCR with oligonucleotides mRANKL-1 and mRANKL-2, digested with NheI and XhoI, and cloned into plasmid pMod-GST-EK-C1. The resulting plasmid pMod-GST-EK-mRANKL-C1 encodes a fusion protein consisting of glutathione S-transferase, an enterokinase cleavage site, the RANKL fragment, and a cysteine-containing amino acid linker (GST-EK-RANKL-C). Sequences of the resulting cDNA and protein constructs are given as SEQ ID NO:97 and SEQ ID NO: 98.

Sequence of Oligonucleotides:

```
                                         (SEQ ID NO: 167)
GST-UP:   5'-ATATATGGATCCTATACTAGGTTATTGGAAAAT-3';

(SEQ ID NO: 168)
GST-EK:   5'-ATATATGCTAGCTTATCGTCATCGTCG-3';

(SEQ ID NO: 169)
mRANKL-1: 5'-ATATATGCTAGCAAAGCCTGAGGCCCAGCCATTTG3';

(SEQ ID NO: 170)
mRANKL-2: 5'-ATATATCTCGAGGTCTATGTCCTGAACTTTGAAAG3'.
```

Expression and Purification of RANKL-C

Competent *Escherichia coli* BL21 (DE3) Gold pLys cells were transformed with the plasmid pMod-GST-EK-mRANKL-C1. Single colonies from ampicillin-containing agar plates were expanded in 100 ml liquid culture (LB medium, 200 µg/ml ampicillin) and incubated at 30° C. with 220 rpm shaking overnight. One litre of medium (SB with 150 mM MOPS, pH 7.0, 200 µ/ml Amp) was then inoculated 1:100 v/v with the overnight culture and grown at 30° C. with 125 rpm shaking to $OD_{600}$=2.5. Cultures were then shifted to 18° C. and protein expression was induced after 30 min by addition of 0.1 mM IPTG. Bacteria were harvested after overnight culture at 18° C. by centrifugation (SLA-3000, 15 min, 4° C., 6000 rpm), resuspended in 40 ml lysis buffer (10 mM $Na_2HPO_4$, 30 mM NaCl, 10 mM EDTA and 0.25% Tween-20) and incubated for 30 min on ice with 0.8 mg/ml lysozyme. Bacteria were then lysed by sonication and incubated for 30 min at RT with 0.2 M $MgCl_2$ and 8 µl Benzonase. The lysate was cleared from unsoluble material by centrifugation (SS-34, 30 min, 4° C., 20000 rpm) and used immediately for glutathione sepharose affinity chromatography.

A GST-Trap FF column of 5 ml (Amersham Pharmacia) was therefore equilibrated with lysis buffer (10 mM $Na_2HPO_4$, 30 mM NaCl, 10 mM EDTA and 0.25% Tween-20) and loaded with the cleared lysate at a constant flow rate of 0.5 ml/min. The column was then washed three times with 5 column volumes of lysis buffer and the protein GST-EK-RANKL-C was eluted in 9 fractions of 1 ml elution buffer (50 mM Tris-HCl, pH 8.0, 10 mM reduced glutathione) each. The purification, shown in FIG. 2A, resulted in GST-EK-RANKL-C fusion protein of about 45 kDa with small proportion of GST-EK.

Elution fractions were pooled and the purified GST-EK-RANKL-C protein was digested using EnterokinaseMax™ (Invitrogen). The digestion was performed at 4° C. for 16 hours using 10 units EnterokinaseMax per mg of purified GST-EK-RANKL-C. FIG. 2B shows that the cleavage reaction lead to RANKL-C with an apparent MW of about 16 kDa.

After cleavage the protein solution was dialysed against PBS pH 7.2 (140 mM NaCl, 2.7 mM KCl, 10 mM $Na_2HPO_4$, 1.8 mM $KH_2PO_4$) and the glutathione S transferase was removed by a second glutathione sepharose affinity chromatography. Therefore a GST-Trap FF column of 5 ml was equilibrated with PBS pH 7.2, and the protein solution was loaded on the column at a constant flow rate of 0.5 ml/min. Protein fractions were analysed before and after glutathione sepharose chromatography on SDS gels. As shown in FIG. 2C the cleaved RANKL-C protein (SEQ ID NO:99) was contained in the flow through in high purity, while the GST-EK protein remained bound to the column.

EXAMPLE 14

Coupling of C-RANKL to Qβ Capsid Protein

A solution of 1.48 ml of 6 mg/ml Qβ capsid protein in 20 mM Hepes, 150 mM NaCl pH 7.2 was reacted for 30 minutes with 14.8 µl of a SMPH (Pierce) (from a 100 mM stock solution dissolved in DMSO) at 25° C. The reaction solution was subsequently dialyzed twice for 3 hours against 2 l of 20 mM Hepes, 150 mM NaCl, pH 7.0 at 4° C. A solution of 230 µl of 9.8 mg/ml C-RANKL protein in 20 mM Hepes, 150 mM NaCl pH 7.2 was reacted for 30 min with 1.7 µl of a 100 mM solution of TCEP (Pierce) at 25° C. For coupling 80 µl of the derivatized and dialyzed Qβ was then mixed with 24 µl of reduced C-RANKL and 96 µl of 20 mM Hepes, 150 mM NaCl, pH 7.0 and incubated over night at 25° C.

Coupled products were analysed on 16% SDS-PAGE gels under reducing conditions. Gels were either stained with Coomassie Brilliant Blue or blotted onto nitrocellulose membranes. In the latter case membranes were blocked and incubated either with a polyclonal rabbit anti-Qβ antiserum (dilution 1:2000) followed by a horse radish peroxidase-conjugated goat anti-rabbit IgG (dilutions 1:5000), or a monoclonal mouse anti-RANKL antibody (dilution 1:2000) followed by a horse raddish peroxidase-conjugated goat anti mouse antibody (dilution 1:5000). Blots were then developed with the ECL™ Western Blotting Detection Reagents (Amersham Pharmacia). The results are shown in FIG. 3A and FIG. 3B. Coupled products could be detected in the Coomassie-stained gels (FIG. 3A) and by both anti-Qβ antiserum and the anti-RANKL antibody (FIG. 3B), clearly demonstrating the covalent coupling of C-RANKL to Qβ capsid protein.

EXAMPLE 15

Immunization of Mice with C-RANKL Coupled to Qβ Capsid Protein

A total of 8 female Balb/c mice were vaccinated with C-RANKL coupled to Qβ capsid protein. 25 μg of total protein of each sample was diluted in PBS to 200 μl and injected subcutaneously (100 μl on two ventral sides) on day 0, day 16 and day 64. Four mice received the vaccine without addition of adjuvants while the other four received the vaccine with the addition of alum. Mice were bled retroorbitally on day 0, 16, 23, 64, and 78 and their serum was analyzed using a RANKL-specific ELISA.

EXAMPLE 16

Detection of RANKL-Specific Antibodies in an ELISA

ELISA plates were coated with C-RANKL at a concentration of 10 μg/ml. The plates were blocked and then incubated with serially diluted mouse sera from day 16, 23, 64, and 78. Bound antibodies were detected with enzymatically labeled anti-mouse IgG antibody. As a control, preimmune serum of the same mice was also tested. FIG. 4 shows the average titers of RANKL-specific antibodies that could be detected in sera mice which had been immunized with Qβ-C-RANKL with or without alum. ELISA titers are expressed as serum dilutions which lead to half maximal OD in the ELISA assay. In mice immunized without alum an average titer of 28000 was reached, while the average titer in mice immunized with the addition of alum was 160000. Preimmune sera did not show any reactivity with C-RANKL. This clearly demonstrates that a RANKL-VLP conjugate is able to induce a high antibody titer against a selfprotein.

EXAMPLE 17

Inhibition of RANKL-RANK Interaction by Sera of Mice Immunized with Qb-C-RANKL

To test whether the antibodies generated in mice vaccinated with Qβ-C-RANKL have neutralizing activity, an in vitro binding assay for RANKL and its cognate receptor RANK was established. ELISA plates were therefore coated with C-RANKL protein at a concentration of 10 μg/ml and incubated with serial dilutions of a purified RANK-Fc fusion protein or an unrelated Fc-fusion protein as negative control. Binding proteins were detected with a horse raddish peroxidase conjugated anti-Fc antibody. FIG. 5A shows the result of this analysis. The purified RANK-Fc fusion protein was found to bind with a high affinity (half maximal binding at 1–3 nM) to its ligand RANKL, while virtually no binding was observed when the unrelated Fc-fused protein was used.

Sera of mice vaccinated with C-RANKL coupled to Qβ were then tested for their ability to inhibit the binding of RANKL to RANK-Fc. ELISA plates were therefore coated with C-RANKL protein at a concentration of 10 μg/ml, and co-incubated with serial dilutions of mouse sera from day 78 mixed with 1 nM RANK-Fc fusion protein. Binding of the RANK-Fc fusion protein to C-RANKL was detected with horse raddish peroxidase conjugated anti-Fc antibody. FIG. 5B shows that all 8 mice, that received the vaccine, produced antibodies that specifically inhibited binding of RANK-Fc to C-RANKL. On average, half maximal inhibition was achieved when sera dilutions of 1:90 were used. This clearly demonstrates that immunization with an RANKL-VLP conjugate does induce antibodies with high titers that are able to inhibit the interaction of RANKL with its receptor RANK. Thus, inhibition of the RANK-RANKL interaction by way of injecting the specific embodiment of this invention may reverse or prevent bone diseases characterized by increased bone resorption.

EXAMPLE 18

Expression and Purification of Recombinant AP205 VLP

A. Expression of Recombinant AP205 VLP

E.coli JM109 was transformed with plasmid pAP283-58.5 ml of LB liquid medium with 20 μg/ml ampicillin were inoculated with a single colony, and incubated at 37° C. for 16–24 h without shaking.

The prepared inoculum was diluted 1:100 in 100–300 ml of LB medium, containing 20 μg/ml ampicillin and incubated at 37° C. overnight without shaking. The resulting second inoculum was diluted 1:50 in 2TY medium, containing 0.2% glucose and phosphate for buffering, and incubated at 37° C. overnight on a shaker. Cells were harvested by centrifugation and frozen at −80° C.

B. Purification of Recombinant AP205 VLP

Solutions and buffers:

1. Lysis buffer 50 mM Tris-HCl pH 8.0 with 5 mM EDTA, 0.1% tritonX100 and PMSF at 5 micrograms per ml.

2. SAS

Saturated ammonium sulphate in water

3. Buffer NET.

20 mM Tris-HCl, pH 7.8 with 5 mM EDTA and 150 mM NaCl.

4. PEG

40% (w/v) polyethylenglycol 6000 in NET

Lysis:

Frozen cells were resuspended in lysis buffer at 2 ml/g cells. The mixture was sonicated with 22 kH five times for 15 seconds, with intervals of 1 min to cool the solution on ice. The lysate was then centrifuged for 20 minutes at 12 000 rpm, using a F34-6-38 rotor (Ependorf). The centrifugation steps described below were all performed using the same rotor, except otherwise stated. The supernatant was stored at 4° C., while cell debris were washed twice with lysis buffer. After centrifugation, the supernatants of the lysate and wash fractions were pooled.

Fractionation:

Ammonium-sulphate precipitation can be further used to purify AP205 VLP. In a first step, a concentration of ammonium-sulphate at which AP205 VLP does not precipitate is chosen. The resulting pellet is discarded. In the next step, an ammonium sulphate concentration at which AP205 VLP quantitatively precipitates is selected, and AP205 VLP is isolated from the pellet of this precipitation step by centrifugation (14 000 rpm, for 20 min). The obtained pellet is solubilised in NET buffer.

Chromatography:

The capsid protein from the pooled supernatants was loaded on a Sepharose 4B column (2.8×70 cm), and eluted with NET buffer, at 4 ml/hour/fraction. Fractions 28–40 were collected, and precipitated with ammonium sulphate at 60% saturation. The fractions were analyzed by SDS-PAGE and Western Blot with an antiserum specific for AP205 prior to precipitation (FIG. 6A and FIG. 6B). The pellet isolated by centrifugation was resolubilized in NET buffer, and loaded on a Sepharose 2B column (2.3×65 cm), eluted at 3 ml/h/fraction. Fractions were analysed by SDS-PAGE, and fractions 44–50 were collected, pooled and precipitated with ammonium sulphate at 60% saturation. The pellet isolated by centrifugation was resolubilized in NET buffer, and purified on a Sepharose 6B column (2.5×47 cm), eluted at 3 ml/hour/fraction. The fractions were analysed by SDS-PAGE. Fractions 23–27 were collected, the salt concentration adjusted to 0.5 M, and precipitated with PEG 6000, added from a 40% stock in water and to a final concentration of 13.3%. The pellet isolated by centrifugation was resolubilized in NET buffer, and loaded on the same Sepharose 2B column as above, eluted in the same manner. Analysis of the fractions by SDS-PAGE is shown in FIG. 6C. Fractions 43–53 were collected, and precipitated with ammonium sulphate at a saturation of 60%. The pellet isolated by centrifugation was resolubilized in water, and the obtained protein solution was extensively dialyzed against water. About 10 mg of purified protein per gram of cells could be isolated.

Examination of the virus-like particles in Electron microscopy showed that they were identical to the phage particles (FIGS. 7A and 7B).

FIG. 6A shows in the top panel, the silver-stained SDS-PAGE run under reducing conditions of the fractions of the first Sepharose 4B chromatography step. Lane 1–13 were loaded with every second fraction from fraction 20 to 44. Fraction 50 was loaded in lane 14. A second gel was loaded with the same fractions and analysed by Western blotting with an anti-serum specific for AP205, and is shown in the lower panel (FIG. 6B).

FIG. 6C shows the silver-stained SDS-PAGE run under reducing conditions of the fractions of the last Sepharose 2B chromatography step. Fractions 38–54 are loaded in Lane 1–16.

FIG. 7A shows an EM picture of AP205 phage particles, while an EM picture of self assembled particles of recombinant AP205 VLP is shown in FIG. 7B.

EXAMPLE 19

Inhibition of RANKL-Induced Osteoclast Formation by Sera of Mice Immunized with Qβ-C-RANKL To test whether the antibodies generated in mice immunized with Qβ-C-RANKL are able to inhibit the biological activity of RANKL, an in vitro osteoclast differentiation assay was established. Bone marrow cells were therefore isolated from Balb/c mice (4 weeks of age) and incubated at a density of $10^6$/ml with recombinant mouse M-CSF (5 ng/ml) in α-MEM/10% FCS for 16 hours. Floating cells were then collected and further cultivated with M-CSF (30 ng/ml), PGE2 (1 μM) and different concentrations of C-RANKL. On day 4 osteoclast formation was assessed by the number of multinucleated cells staining positive for tartrate resistant acid phosphatase (TRAP). C-RANKL was found to induce a significant number of TRAP positive multinucleated cells at a concentration of 100–1000 ng/ml.

Sera of mice vaccinated with Qβ-C-RANKL are then tested for their ability to inhibit the formation of osteoclasts from C-RANKL treated bone marrow cells. Osteoclast precursor cells are therefore isolated from Balb/c mice and incubated with M-CSF (30 ng/ml), $PGE_2$ (1 μM), C-RANKL (1000 ng/ml) and serial dilutions of sera derived from immunized mice in α-MEM/10% FCS for 4 days. Osteoclast formation is then assayed by counting the number of TRAP positive multinucleated cells and comparison to the controls incubated with C-RANKL alone and with C-RANKL and preimmune sera.

EXAMPLE 20

Inhibition of Bone Loss by Vaccination with Qβ-C-RANKL in a Murine Ovariectomy Model To test whether vaccination with Qβ-C-RANKL protects from bone loss induced by estrogen deficiency a mouse ovariectomy (ovx) model is established. A total of 40 C57/BL6 mice at the age of 12 weeks is therefore randomized into 4 groups and treated as follows: Group 1 is not immunized and subjected to sham operation, group 2 is not immunized and subjected to ovx, group 3 is immunized with 25 μg of Qβ-C-RANKL without Alum and subjected to ovx, and group 4 is immunized with 25 μg of Qβ-C-RANKL with Alum and also subjected to ovx. Animals from group 3 and 4 receive immunizations at days 0, 14, 21, and 42 and all animals are operated (either sham or ovx) on day 28 and sacrificed on day 63. Body weight is measured at days 0, 28, and 63 and blood samples are collected on days 0, 14, 21, 28, 42 and 63. Antibody titres as well as bone formation and bone degradation markers are monitored continuously and bone mineral density is assessed after scarification of the animals by DXA scan of the excised vertebrae columns and pQCT scanning of excised femurs at one distal and one midshaft site.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A composition comprising:
   (a) a virus-like particle of an RNA bacteriophage; and
   (b) at least one antigen or antigenic determinant, wherein said antigen or said antigenic determinant is a RANKL protein, RANKL fragment or RANKL peptide, and wherein said at least one antigen or antigenic determinant is bound to said virus-like particle by at least one non-peptide bond.

2. The composition of claim 1, wherein said virus-like particle is a recombinant virus-like particle.

3. The composition of claim 1, wherein said virus-like particle comprises recombinant proteins, or fragments thereof, of an RNA bacteriophage.

4. The composition of claim 3, wherein said RNA bacteriophage is selected from the group consisting of:
   (a) bacteriophage Qβ;
   (b) bacteriophage R17;
   (c) bacteriophage fr;
   (d) bacteriophage GA;
   (e) bacteriophage SP;
   (f) bacteriophage MS2;
   (g) bacteriophage M11;
   (h) bacteriophage MX1;
   (i) bacteriophage NL95;
   (j) bacteriophage f2;
   (k) bacteriophage PP7; and
   (l) bacteriophage AP205.

5. The composition of claim 1, wherein said virus-like particle comprises recombinant proteins, or fragments thereof, of RNA bacteriophage Qβ.

6. The composition of claim 1, wherein said virus-like particle comprises recombinant proteins, or fragments thereof, of RNA bacteriophage fr.

7. The composition of claim 1, wherein said virus-like particle comprises recombinant proteins, or fragments thereof, of RNA bacteriophage AP205.

8. The composition of claim 1, wherein said at least one antigen or antigenic determinant is bound to said virus-like particle by at least one non-peptide covalent bond.

9. The composition of claim 1, wherein said antigen or antigenic determinant is a RANKL protein or RANKL fragment.

10. The composition of claim 1, wherein said antigen or antigenic determinant is a human RANKL protein or a human RANKL fragment.

11. The composition of claim 1, wherein said antigen or antigenic determinant has an amino acid sequence selected from the group consisting of:
    (a) the amino acid sequence of SEQ ID NO:79;
    (b) the amino acid sequence of SEQ ID NO:80;
    (c) the amino acid sequence of SEQ ID NO:81;
    (d) the amino acid sequence of SEQ ID NO:82;
    (e) the amino acid sequence of SEQ ID NO:83;
    (f) the amino acid sequence of SEQ ID NO:84
    (g) the amino acid sequence of SEQ ID NO: 100
    (h) the amino acid sequence of SEQ ID NO: 101; and
    (i) the amino acid sequence of a fragment of any one of SEQ ID NOs:79–84, 100 and 101.

12. The composition of claim 1, wherein said antigen or antigenic determinant is a RANKL peptide.

13. The composition of claim 12, wherein said RANKL peptide is a human RANKL peptide.

14. The composition of claim 1, wherein said antigen or antigenic determinant is a RANKL peptide comprising an amino acid sequence selected from the group consisting of:
    (a) the amino acid sequence of SEQ ID NO:87;
    (b) the amino acid sequence of SEQ ID NO:88;
    (c) the amino acid sequence of SEQ ID NO:89;
    (d) the amino acid sequence of SEQ ID NO:90;
    (e) the amino acid sequence of SEQ ID NO:91;
    (f) the amino acid sequence of SEQ ID NO:92;
    (g) the amino acid sequence of SEQ ID NO:93; and
    (h) the amino acid sequence of a fragment of any one of SEQ ID NOs:87–93.

15. The composition of claim 1, wherein said RNA bacteriophage comprises at least one first attachment site, and wherein said antigen or antigenic determinant comprises at least one second attachment site selected from the group consisting of:
  (i) an attachment site not naturally occurring with said antigen or antigenic determinant; and
  (ii) an attachment site naturally occurring with said antigen or antigenic determinant.

16. The composition of claim 15, wherein said antigen or antigenic determinant with said at least second attachment site comprises an amino acid sequence selected from the group consisting of:
  (a) the amino acid sequence of SEQ ID NO:104;
  (b) the amino acid sequence of SEQ ID NO:105;
  (c) the amino acid sequence of SEQ ID NO:106;
  (d) the amino acid sequence of SEQ ID NO:107;
  (e) the amino acid sequence of SEQ ID NO:108;
  (f) the amino acid sequence of SEQ ID NO:109;
  (g) the amino acid sequence of SEQ ID NO:110; and
  (h) the amino acid sequence of a fragment of any one of SEQ ID NOs:104–110.

17. A composition comprising:
  (a) a core particle with at least one first attachment site, wherein said core particle is a virus-like particle or a recombinant form thereof; and
  (b) at least one antigen or antigenic determinant with one or more second attachment sites;
  wherein said antigen or antigenic determinant is a RANKL protein, RANKL fragment or RANKL peptide, and wherein said one or more second attachment sites are selected from the group consisting of:
    (i) an attachment site not naturally occurring with said antigen or antigenic determinant; and
    (ii) an attachment site naturally occurring with said antigen or antigenic determinant,
  wherein only one of said second attachment sites associates with said first attachment site through at least one non-peptide covalent bond leading to a single and uniform type of binding of said antigen to said core particle, wherein said only one second attachment site that associates with said first attachment site is a sulfhydryl group, and wherein said antigen or antigenic determinant and said core particle interact through said association to form an ordered and repetitive antigen array.

18. The composition of claim 17, wherein said core particle is a virus-like particle of an RNA bacteriophage.

19. The composition of claim 17, wherein said virus-like particle is a recombinant virus-like particle.

20. The composition of claim 17, wherein said virus-like particle comprises recombinant proteins, or fragments thereof, selected from the group consisting of:
  (a) recombinant proteins of Hepatitis B virus;
  (b) recombinant proteins of measles virus;
  (c) recombinant proteins of Sindbis virus;
  (d) recombinant proteins of Rotavirus;
  (e) recombinant proteins of Foot-and-Mouth-Disease virus;
  (f) recombinant proteins of Retrovirus;
  (g) recombinant proteins of Norwalk virus;
  (h) recombinant proteins of Alphavirus;
  (i) recombinant proteins of human Papilloma virus;
  (j) recombinant proteins of Polyoma virus;
  (k) recombinant proteins of bacteriophages;
  (l) recombinant proteins of RNA bacteriophages;
  (m) recombinant proteins of Ty;
  (n) recombinant proteins of Qβ-phage;
  (o) recombinant proteins of GA-phage; and
  (p) recombinant proteins of fr-phage.

21. The composition of claim 17, wherein said virus-like particle comprises Hepatitis B virus core antigen.

22. The composition of claim 17, wherein said virus-like particle comprises recombinant proteins, or fragments thereof, of an RNA bacteriophage.

23. The composition of claim 22, wherein said RNA bacteriophage is selected from the group consisting of:
  (a) bacteriophage Qβ;
  (b) bacteriophage R17;
  (c) bacteriophage fr;
  (d) bacteriophage GA;
  (e) bacteriophage SP;
  (f) bacteriophage MS2;
  (g) bacteriophage M11;
  (h) bacteriophage MX1;
  (i) bacteriophage NL95;
  (j) bacteriophage f2;
  (k) bacteriophage PP7; and
  (l) bacteriophage AP205.

24. The composition of claim 17, wherein said virus-like particle comprises recombinant proteins, or fragments thereof, of RNA bacteriophage Qβ.

25. The composition of claim 17, wherein said virus-like particle comprises recombinant proteins, or fragments thereof, of RNA bacteriophage fr.

26. The composition of claim 17, wherein said virus-like particle comprises recombinant proteins, or fragments thereof, of RNA bacteriophage AP205.

27. The composition of claim 17, wherein said antigen or antigenic determinant is a RANKL protein or RANKL fragment.

28. The composition of claim 17, wherein said antigen or antigenic determinant is a human RANKL protein or a human RANKL fragment.

29. The composition of claim 17, wherein said antigen or antigenic determinant has an amino acid sequence selected from the group consisting of:
  (a) the amino acid sequence of SEQ ID NO:79;
  (b) the amino acid sequence of SEQ ID NO:80;
  (c) the amino acid sequence of SEQ ID NO:81;
  (d) the amino acid sequence of SEQ ID NO:82;
  (e) the amino acid sequence of SEQ ID NO:83;
  (f) the amino acid sequence of SEQ ID NO:84
  (g) the amino acid sequence of SEQ ID NO:100
  (h) the amino acid sequence of SEQ ID NO:101; and
  (i) the amino acid sequence of a fragment of any one of SEQ ID NOs:79–84, 100, and 101.

30. The composition of claim 17, wherein said antigen or antigenic determinant is a RANKL peptide.

31. The composition of claim 30, wherein said RANKL peptide is a human RANKL peptide.

32. The composition of claim 17, wherein said antigen or antigenic determinant is a RANKL peptide comprising an amino acid sequence selected from the group consisting of:
  (a) the amino acid sequence of SEQ ID NO:87;
  (b) the amino acid sequence of SEQ ID NO:88;
  (c) the amino acid sequence of SEQ ID NO:89;
  (d) the amino acid sequence of SEQ ID NO:90;
  (e) the amino acid sequence of SEQ ID NO:91;
  (f) the amino acid sequence of SEQ ID NO:92;
  (g) the amino acid sequence of SEQ ID NO:93; and
  (h) the amino acid sequence of a fragment of any one of SEQ ID NOs:87–93.

33. The composition of claim 17, wherein said antigen or antigenic determinant with said second attachment site comprises an amino acid sequence selected from the group consisting of:
(a) the amino acid sequence of SEQ ID NO:104;
(b) the amino acid sequence of SEQ ID NO:105;
(c) the amino acid sequence of SEQ ID NO:106;
(d) the amino acid sequence of SEQ ID NO:107;
(e) the amino acid sequence of SEQ ID NO:108;
(f) the amino acid sequence of SEQ ID NO:109;
(g) the amino acid sequence of SEQ ID NO:110; and
(h) the amino acid sequence of a fragment of any one of SEQ ID NOs:104–110.

34. A pharmaceutical composition comprising:
(a) the composition of claim 1; and
(b) a pharmaceutically acceptable carrier.

35. A pharmaceutical composition comprising:
(a) the composition of claim 17; and
(b) a pharmaceutically acceptable carrier.

36. A vaccine composition comprising the composition of claim 1 and an adjuvant.

37. A process for producing the composition of claim 1 comprising:
(a) providing a virus-like particle of an RNA bacteriophage;
(b) providing at least one antigen or antigenic determinant, wherein said antigen or antigenic determinant is a RANKL protein, RANKL fragment or RANKL peptide; and
(c) combining said virus-like particle and said antigen or antigenic determinant so that said antigen or antigenic determinant is bound to said virus-like particle by at least one non-peptide bond.

38. A process for producing the composition of claim 17 comprising:
(a) providing a core particle with at least one first attachment site, wherein said core particle is a virus-like particle or a recombinant form thereof;
(b) providing at least one antigen or antigenic determinant with one or more second attachment sites, wherein said antigen or antigenic determinant is a RANKL protein, RANKL fragment or RANKL peptide, and wherein said one or more second attachment sites are selected from the group consisting of:
(i) an attachment site not naturally occurring with said antigen or antigenic determinant; and
(ii) an attachment site naturally occurring with said antigen or antigenic determinant; and
(c) combining said core particle and said antigen or antigenic determinant, such that only one of said second attachment sites associates with said first attachment site through at least one non-peptide covalent bond leading to a single and uniform type of binding of said antigen to said core particle, wherein said only one second attachment site that associates with said first attachment site is a sulfhydryl group, and wherein said antigen or antigenic determinant and said core particle interact through said association to form an ordered and repetitive antigen array.

39. A method of immunizing an animal comprising administering the composition of claim 1 to an animal, wherein an immune response against said antigen or antigenic determinant is produced in said animal.

40. The method of immunization of claim 39, wherein said animal is a human.

41. A method of treating a bone disease comprising administering the composition of claim 1 to an animal, wherein an immune response against said antigen or antigenic determinant is produced in said animal.

42. A method of treating a bone disease comprising administering the composition of claim 17 to an animal, wherein an immune response against said antigen or antigenic determinant is produced in said animal.

43. A method of treating a bone disease comprising administering the composition of claim 1 to an animal, wherein said composition is administered in combination with at least one additional medicament suitable to treat bone diseases.

44. A method of treating a bone disease comprising administering the composition of claim 17 to an animal, wherein said composition is administered in combination with at least one additional medicament suitable to treat bone diseases.

45. The method of any one of claims 41–44, wherein said animal is a human.

46. The composition of claim 1, wherein said antigen or antigenic determinant is bound to said virus-like particle to form an ordered and repetitive antigen array.

47. The composition of claim 15, wherein said first attachment site associates with said second attachment site to form an ordered and repetitive antigen array.

48. The composition of claim 15, wherein said first attachment site comprises an amino group.

49. The composition of claim 15, wherein said second attachment site comprises a sulfhydryl group.

50. The composition of claim 15, wherein said first attachment site comprises an amino group and wherein said second attachment site comprises a sulfhydryl group.

51. The composition of claim 15 or claim 17, wherein said first attachment site is not a sulfhydryl group of a cysteine.

52. The composition of claim 17, wherein said first attachment site comprises an amino group.

53. A vaccine composition comprising the composition of claim 17 and an adjuvant.

54. A method of immunizing an animal comprising administering the composition of claim 17 to an animal, wherein an immune response against said antigen or antigenic determinant is produced in said animal.

55. The method of claim 54, wherein said animal is human.

* * * * *

SEQUENCE LISTING

<160> NUMBER OF SEQ ID NOS: 170

<210> SEQ ID NO 1
<211> LENGTH: 212
<212> TYPE: PRT
<213> ORGANISM: Haemophilus influenzae

<400> SEQUENCE: 1

Met Lys Lys Thr Leu Leu Gly Ser Leu Ile Leu Ala Phe Ala Gly
1               5                   10                  15

Asn Val Gln Ala Ala Asn Ala Asp Thr Ser Gly Thr Val Thr Phe
                20                  25                  30

Phe Gly Lys Val Val Glu Asn Thr Cys Gln Val Asn Gln Asp Ser Glu
            35                  40                  45

Tyr Glu Cys Asn Leu Asn Asp Val Gly Lys Asn His Leu Ser Gln Gln
    50                  55                  60

Gly Tyr Thr Ala Met Gln Thr Pro Phe Thr Ile Thr Leu Glu Asn Cys
65                  70                  75                  80

Asn Val Thr Thr Thr Asn Asn Lys Pro Lys Ala Thr Lys Val Gly Val
                85                  90                  95

Tyr Phe Tyr Ser Trp Glu Ile Ala Asp Lys Asp Asn Lys Tyr Thr Leu
            100                 105                 110

Lys Asn Ile Lys Glu Asn Thr Gly Thr Asn Asp Ser Ala Asn Lys Val
        115                 120                 125

Asn Ile Gln Leu Leu Glu Asp Asn Gly Thr Ala Glu Ile Lys Val Val
    130                 135                 140

Gly Lys Thr Thr Thr Asp Phe Thr Ser Glu Asn His Asn Gly Ala Gly
145                 150                 155                 160

Ala Asp Pro Val Ala Thr Asn Lys His Ile Ser Ser Leu Thr Pro Leu
                165                 170                 175

Asn Asn Gln Asn Ser Ile Asn Leu His Tyr Ile Ala Gln Tyr Tyr Ala
            180                 185                 190

Thr Gly Val Ala Glu Ala Gly Lys Val Pro Ser Ser Val Asn Ser Gln
        195                 200                 205

Ile Ala Tyr Glu
    210

<210> SEQ ID NO 2
<211> LENGTH: 139
<212> TYPE: PRT
<213> ORGANISM: Pseudomonas stutzeri

<400> SEQUENCE: 2

Met Lys Ala Gln Met Gln Lys Gly Phe Thr Leu Ile Glu Leu Met Ile
1               5                   10                  15

Val Val Ala Ile Ile Gly Ile Leu Ala Ala Ile Ala Leu Pro Ala Tyr
                20                  25                  30

Gln Asp Tyr Thr Val Arg Ser Asn Ala Ala Ala Leu Ala Glu Ile
            35                  40                  45

Thr Pro Gly Lys Ile Gly Phe Glu Gln Ala Ile Asn Glu Gly Lys Thr
    50                  55                  60

Pro Ser Leu Thr Ser Thr Asp Glu Gly Tyr Ile Gly Ile Thr Asp Ser
65                  70                  75                  80

Thr Ser Tyr Cys Asp Val Asp Leu Asp Thr Ala Ala Asp Gly His Ile
                85                  90                  95

```
Glu Cys Thr Ala Lys Gly Gly Asn Ala Gly Lys Phe Asp Gly Lys Thr
                100                 105                 110

Ile Thr Leu Asn Arg Thr Ala Asp Gly Glu Trp Ser Cys Ala Ser Thr
            115                 120                 125

Leu Asp Ala Lys Tyr Lys Pro Gly Lys Cys Ser
        130                 135
```

<210> SEQ ID NO 3
<211> LENGTH: 59
<212> TYPE: PRT
<213> ORGANISM: Caulobacter crescentus

<400> SEQUENCE: 3

```
Met Thr Lys Phe Val Thr Arg Phe Leu Lys Asp Glu Ser Gly Ala Thr
1               5                   10                  15

Ala Ile Glu Tyr Gly Leu Ile Val Ala Leu Ile Ala Val Val Ile Val
            20                  25                  30

Thr Ala Val Thr Thr Leu Gly Thr Asn Leu Arg Thr Ala Phe Thr Lys
        35                  40                  45

Ala Gly Ala Ala Val Ser Thr Ala Ala Gly Thr
    50                  55
```

<210> SEQ ID NO 4
<211> LENGTH: 173
<212> TYPE: PRT
<213> ORGANISM: Escherichia coli

<400> SEQUENCE: 4

```
Met Ala Val Val Ser Phe Gly Val Asn Ala Ala Pro Thr Ile Pro Gln
1               5                   10                  15

Gly Gln Gly Lys Val Thr Phe Asn Gly Thr Val Val Asp Ala Pro Cys
            20                  25                  30

Ser Ile Ser Gln Lys Ser Ala Asp Gln Ser Ile Asp Phe Gly Gln Leu
        35                  40                  45

Ser Lys Ser Phe Leu Glu Ala Gly Gly Val Ser Lys Pro Met Asp Leu
    50                  55                  60

Asp Ile Glu Leu Val Asn Cys Asp Ile Thr Ala Phe Lys Gly Gly Asn
65                  70                  75                  80

Gly Ala Gln Lys Gly Thr Val Lys Leu Ala Phe Thr Gly Pro Ile Val
                85                  90                  95

Asn Gly His Ser Asp Glu Leu Asp Thr Asn Gly Gly Thr Gly Thr Ala
            100                 105                 110

Ile Val Val Gln Gly Ala Gly Lys Asn Val Val Phe Asp Gly Ser Glu
        115                 120                 125

Gly Asp Ala Asn Thr Leu Lys Asp Gly Glu Asn Val Leu His Tyr Thr
    130                 135                 140

Ala Val Val Lys Lys Ser Ser Ala Val Gly Ala Ala Val Thr Glu Gly
145                 150                 155                 160

Ala Phe Ser Ala Val Ala Asn Phe Asn Leu Thr Tyr Gln
                165                 170
```

<210> SEQ ID NO 5
<211> LENGTH: 173
<212> TYPE: PRT
<213> ORGANISM: Escherichia coli

<400> SEQUENCE: 5

-continued

```
Met Ala Val Val Ser Phe Gly Val Asn Ala Ala Pro Thr Ile Pro Gln
1               5                   10                  15

Gly Gln Gly Lys Val Thr Phe Asn Gly Thr Val Asp Ala Pro Cys
                20                  25                  30

Ser Ile Ser Gln Lys Ser Ala Asp Gln Ser Ile Asp Phe Gly Gln Leu
            35                  40                  45

Ser Lys Ser Phe Leu Glu Ala Gly Val Ser Lys Pro Met Asp Leu
50                  55                  60

Asp Ile Glu Leu Val Asn Cys Asp Ile Thr Ala Phe Lys Gly Gly Asn
65                  70                  75                  80

Gly Ala Gln Lys Gly Thr Val Lys Leu Ala Phe Thr Gly Pro Ile Val
                85                  90                  95

Asn Gly His Ser Asp Glu Leu Asp Thr Asn Gly Gly Thr Gly Thr Ala
                100                 105                 110

Ile Val Val Gln Gly Ala Gly Lys Asn Val Val Phe Asp Gly Ser Glu
            115                 120                 125

Gly Asp Ala Asn Thr Leu Lys Asp Gly Glu Asn Val Leu His Tyr Thr
130                 135                 140

Ala Val Val Lys Lys Ser Ser Ala Val Gly Ala Ala Val Thr Glu Gly
145                 150                 155                 160

Ala Phe Ser Ala Val Ala Asn Phe Asn Leu Thr Tyr Gln
                165                 170
```

<210> SEQ ID NO 6
<211> LENGTH: 181
<212> TYPE: PRT
<213> ORGANISM: Escherichia coli

<400> SEQUENCE: 6

```
Met Lys Ile Lys Thr Leu Ala Ile Val Val Leu Ser Ala Leu Ser Leu
1               5                   10                  15

Ser Ser Thr Ala Ala Leu Ala Ala Thr Thr Val Asn Gly Gly Thr
                20                  25                  30

Val His Phe Lys Gly Glu Val Val Asn Ala Ala Cys Ala Val Asp Ala
            35                  40                  45

Gly Ser Val Asp Gln Thr Val Gln Leu Gly Gln Val Arg Thr Ala Ser
50                  55                  60

Leu Ala Gln Glu Gly Ala Thr Ser Ser Ala Val Gly Phe Asn Ile Gln
65                  70                  75                  80

Leu Asn Asp Cys Asp Thr Asn Val Ala Ser Lys Ala Ala Val Ala Phe
                85                  90                  95

Leu Gly Thr Ala Ile Asp Ala Gly His Thr Asn Val Leu Ala Leu Gln
                100                 105                 110

Ser Ser Ala Ala Gly Ser Ala Thr Asn Val Gly Val Gln Ile Leu Asp
            115                 120                 125

Arg Thr Gly Ala Ala Leu Thr Leu Asp Gly Ala Thr Phe Ser Ser Glu
130                 135                 140

Thr Thr Leu Asn Asn Gly Thr Asn Thr Ile Pro Phe Gln Ala Arg Tyr
145                 150                 155                 160

Phe Ala Gly Ala Ala Thr Pro Gly Ala Ala Asn Ala Asp Ala Thr Phe
                165                 170                 175

Lys Val Gln Tyr Gln
                180
```

<210> SEQ ID NO 7

```
<211> LENGTH: 172
<212> TYPE: PRT
<213> ORGANISM: Escherichia coli

<400> SEQUENCE: 7

Met Ala Val Val Ser Phe Gly Val Asn Ala Ala Pro Thr Thr Pro Gln
1               5                   10                  15

Gly Gln Gly Arg Val Thr Phe Asn Gly Thr Val Asp Ala Pro Cys
            20                  25                  30

Ser Ile Ser Gln Lys Ser Ala Asp Gln Ser Ile Asp Phe Gly Gln Leu
        35                  40                  45

Ser Lys Ser Phe Leu Ala Asn Asp Gly Gln Ser Lys Pro Met Asn Leu
    50                  55                  60

Asp Ile Glu Leu Val Asn Cys Asp Ile Thr Ala Phe Lys Asn Gly Asn
65                  70                  75                  80

Ala Lys Thr Gly Ser Val Lys Leu Ala Phe Thr Gly Pro Thr Val Ser
                85                  90                  95

Gly His Pro Ser Glu Leu Ala Thr Asn Gly Gly Pro Gly Thr Ala Ile
            100                 105                 110

Met Ile Gln Ala Ala Gly Lys Asn Val Pro Phe Asp Gly Thr Glu Gly
        115                 120                 125

Asp Pro Asn Leu Leu Lys Asp Gly Asp Asn Val Leu His Tyr Thr Thr
    130                 135                 140

Val Gly Lys Lys Ser Ser Asp Gly Asn Ala Gln Ile Thr Glu Gly Ala
145                 150                 155                 160

Phe Ser Gly Val Ala Thr Phe Asn Leu Ser Tyr Gln
                165                 170

<210> SEQ ID NO 8
<211> LENGTH: 182
<212> TYPE: PRT
<213> ORGANISM: Escherichia coli

<400> SEQUENCE: 8

Met Lys Ile Lys Thr Leu Ala Ile Val Val Leu Ser Ala Leu Ser Leu
1               5                   10                  15

Ser Ser Thr Thr Ala Leu Ala Ala Thr Thr Val Asn Gly Gly Thr
            20                  25                  30

Val His Phe Lys Gly Glu Val Val Asn Ala Ala Cys Ala Val Asp Ala
        35                  40                  45

Gly Ser Val Asp Gln Thr Val Gln Leu Gly Gln Val Arg Thr Ala Ser
    50                  55                  60

Leu Ala Gln Glu Gly Ala Thr Ser Ser Ala Val Gly Phe Asn Ile Gln
65                  70                  75                  80

Leu Asn Asp Cys Asp Thr Asn Val Ala Ser Lys Ala Ala Val Ala Phe
                85                  90                  95

Leu Gly Thr Ala Ile Asp Ala Gly His Thr Asn Val Leu Ala Leu Gln
            100                 105                 110

Ser Ser Ala Ala Gly Ser Ala Thr Asn Val Gly Val Gln Ile Leu Asp
        115                 120                 125

Arg Thr Gly Ala Ala Leu Thr Leu Asp Gly Ala Thr Phe Ser Ser Glu
    130                 135                 140

Thr Thr Leu Asn Asn Gly Thr Asn Thr Ile Pro Phe Gln Ala Arg Tyr
145                 150                 155                 160

Phe Ala Thr Gly Ala Ala Thr Pro Gly Ala Ala Asn Ala Asp Ala Thr
                165                 170                 175
```

Phe Lys Val Gln Tyr Gln
          180

<210> SEQ ID NO 9
<211> LENGTH: 853
<212> TYPE: DNA
<213> ORGANISM: Escherichia coli

<400> SEQUENCE: 9

| acgtttctgt | ggctcgacgc | atcttcctca | ttcttctctc | caaaaaccac | ctcatgcaat | 60 |
| ataaacatct | ataaataaag | ataacaaata | gaatattaag | ccaacaaata | aactgaaaaa | 120 |
| gtttgtccgc | gatgctttac | ctctatgagt | caaaatggcc | ccaatgtttc | atcttttggg | 180 |
| ggaaactgtg | cagtgttggc | agtcaaactc | gttgacaaac | aaagtgtaca | gaacgactgc | 240 |
| ccatgtcgat | ttagaaatag | ttttttgaaa | ggaaagcagc | atgaaaatta | aaactctggc | 300 |
| aatcgttgtt | ctgtcggctc | tgtccctcag | ttctacgacg | gctctggccg | ctgccacgac | 360 |
| ggttaatggt | gggaccgttc | actttaaagg | ggaagttgtt | aacgccgctt | gcgcagttga | 420 |
| tgcaggctct | gttgatcaaa | ccgttcagtt | aggacaggtt | cgtaccgcat | cgctggcaca | 480 |
| ggaaggagca | accagttctg | ctgtcggttt | aacattcag | ctgaatgatt | gcgataccaa | 540 |
| tgttgcatct | aaagccgctg | ttgcctttt | aggtacggcg | attgatgcgg | gtcataccaa | 600 |
| cgttctggct | ctgcagagtt | cagctgcggg | tagcgcaaca | aacgttggtg | tgcagatcct | 660 |
| ggacagaacg | ggtgctgcgc | tgacgctgga | tggtgcgaca | tttagttcag | aaacaaccct | 720 |
| gaataacgga | accaatacca | ttccgttcca | ggcgcgttat | tttgcaaccg | ggccgcaac | 780 |
| cccgggtgct | gctaatgcgg | atgcgacctt | caaggttcag | tatcaataac | ctacctaggt | 840 |
| tcagggacgt | tca | | | | | 853 |

<210> SEQ ID NO 10
<211> LENGTH: 132
<212> TYPE: PRT
<213> ORGANISM: Bacteriophage Q-beta

<400> SEQUENCE: 10

Ala Lys Leu Glu Thr Val Thr Leu Gly Asn Ile Gly Lys Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Ala Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 11

```
<211> LENGTH: 329
<212> TYPE: PRT
<213> ORGANISM: Bacteriophage Q-beta

<400> SEQUENCE: 11

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Ala Val Pro Ala Leu Glu Lys Arg
        35                  40                  45

Val Thr Val Ser Val Ser Gln Pro Ser Arg Asn Arg Lys Asn Tyr Lys
50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Asp Glu Glu Arg Ala Phe Val Arg Thr Glu
            100                 105                 110

Leu Ala Ala Leu Leu Ala Ser Pro Leu Leu Ile Asp Ala Ile Asp Gln
        115                 120                 125

Leu Asn Pro Ala Tyr Trp Thr Leu Leu Ile Ala Gly Gly Gly Ser Gly
130                 135                 140

Ser Lys Pro Asp Pro Val Ile Pro Asp Pro Pro Ile Asp Pro Pro Pro
145                 150                 155                 160

Gly Thr Gly Lys Tyr Thr Cys Pro Phe Ala Ile Trp Ser Leu Glu Glu
                165                 170                 175

Val Tyr Glu Pro Pro Thr Lys Asn Arg Pro Trp Pro Ile Tyr Asn Ala
            180                 185                 190

Val Glu Leu Gln Pro Arg Glu Phe Asp Val Ala Leu Lys Asp Leu Leu
        195                 200                 205

Gly Asn Thr Lys Trp Arg Asp Trp Asp Ser Arg Leu Ser Tyr Thr Thr
210                 215                 220

Phe Arg Gly Cys Arg Gly Asn Gly Tyr Ile Asp Leu Asp Ala Thr Tyr
225                 230                 235                 240

Leu Ala Thr Asp Gln Ala Met Arg Asp Gln Lys Tyr Asp Ile Arg Glu
                245                 250                 255

Gly Lys Lys Pro Gly Ala Phe Gly Asn Ile Glu Arg Phe Ile Tyr Leu
            260                 265                 270

Lys Ser Ile Asn Ala Tyr Cys Ser Leu Ser Asp Ile Ala Ala Tyr His
        275                 280                 285

Ala Asp Gly Val Ile Val Gly Phe Trp Arg Asp Pro Ser Ser Gly Gly
        290                 295                 300

Ala Ile Pro Phe Asp Phe Thr Lys Phe Asp Lys Thr Lys Cys Pro Ile
305                 310                 315                 320

Gln Ala Val Ile Val Val Pro Arg Ala
                325

<210> SEQ ID NO 12
<211> LENGTH: 129
<212> TYPE: PRT
<213> ORGANISM: Bacteriophage R17

<400> SEQUENCE: 12

Ala Ser Asn Phe Thr Gln Phe Val Leu Val Asn Asp Gly Gly Thr Gly
1               5                   10                  15
```

```
Asn Val Thr Val Ala Pro Ser Asn Phe Ala Asn Gly Val Ala Glu Trp
             20                  25                  30
Ile Ser Ser Asn Ser Arg Ser Gln Ala Tyr Lys Val Thr Cys Ser Val
         35                  40                  45
Arg Gln Ser Ser Ala Gln Asn Arg Lys Tyr Thr Ile Lys Val Glu Val
     50                  55                  60
Pro Lys Val Ala Thr Gln Thr Val Gly Gly Val Glu Leu Pro Val Ala
 65                  70                  75                  80
Ala Trp Arg Ser Tyr Leu Asn Met Glu Leu Thr Ile Pro Ile Phe Ala
                 85                  90                  95
Thr Asn Ser Asp Cys Glu Leu Ile Val Lys Ala Met Gln Gly Leu Leu
             100                 105                 110
Lys Asp Gly Asn Pro Ile Pro Ser Ala Ile Ala Ala Asn Ser Gly Ile
         115                 120                 125
Tyr

<210> SEQ ID NO 13
<211> LENGTH: 130
<212> TYPE: PRT
<213> ORGANISM: Bacteriophage fr

<400> SEQUENCE: 13

Met Ala Ser Asn Phe Glu Glu Phe Val Leu Val Asp Asn Gly Gly Thr
 1               5                  10                  15
Gly Asp Val Lys Val Ala Pro Ser Asn Phe Ala Asn Gly Val Ala Glu
             20                  25                  30
Trp Ile Ser Ser Asn Ser Arg Ser Gln Ala Tyr Lys Val Thr Cys Ser
         35                  40                  45
Val Arg Gln Ser Ser Ala Asn Asn Arg Lys Tyr Thr Val Lys Val Glu
     50                  55                  60
Val Pro Lys Val Ala Thr Gln Val Gln Gly Gly Val Glu Leu Pro Val
 65                  70                  75                  80
Ala Ala Trp Arg Ser Tyr Met Asn Met Glu Leu Thr Ile Pro Val Phe
                 85                  90                  95
Ala Thr Asn Asp Asp Cys Ala Leu Ile Val Lys Ala Leu Gln Gly Thr
             100                 105                 110
Phe Lys Thr Gly Asn Pro Ile Ala Thr Ala Ile Ala Ala Asn Ser Gly
         115                 120                 125
Ile Tyr
     130

<210> SEQ ID NO 14
<211> LENGTH: 130
<212> TYPE: PRT
<213> ORGANISM: Bacteriophage GA

<400> SEQUENCE: 14

Met Ala Thr Leu Arg Ser Phe Val Leu Val Asp Asn Gly Gly Thr Gly
 1               5                  10                  15
Asn Val Thr Val Val Pro Val Ser Asn Ala Asn Gly Val Ala Glu Trp
             20                  25                  30
Leu Ser Asn Asn Ser Arg Ser Gln Ala Tyr Arg Val Thr Ala Ser Tyr
         35                  40                  45
Arg Ala Ser Gly Ala Asp Lys Arg Lys Tyr Ala Ile Lys Leu Glu Val
     50                  55                  60
```

```
Pro Lys Ile Val Thr Gln Val Val Asn Gly Val Glu Leu Pro Gly Ser
 65                  70                  75                  80

Ala Trp Lys Ala Tyr Ala Ser Ile Asp Leu Thr Pro Ile Phe Ala
                 85                  90                  95

Ala Thr Asp Asp Val Thr Val Ile Ser Lys Ser Leu Ala Gly Leu Phe
            100                 105                 110

Lys Val Gly Asn Pro Ile Ala Glu Ala Ile Ser Ser Gln Ser Gly Phe
        115                 120                 125

Tyr Ala
    130

<210> SEQ ID NO 15
<211> LENGTH: 132
<212> TYPE: PRT
<213> ORGANISM: Bacteriophage SP

<400> SEQUENCE: 15

Met Ala Lys Leu Asn Gln Val Thr Leu Ser Lys Ile Gly Lys Asn Gly
 1               5                  10                  15

Asp Gln Thr Leu Thr Leu Thr Pro Arg Gly Val Asn Pro Thr Asn Gly
             20                  25                  30

Val Ala Ser Leu Ser Glu Ala Gly Ala Val Pro Ala Leu Glu Lys Arg
         35                  40                  45

Val Thr Val Ser Val Ala Gln Pro Ser Arg Asn Arg Lys Asn Phe Lys
     50                  55                  60

Val Gln Ile Lys Leu Gln Asn Pro Thr Ala Cys Thr Arg Asp Ala Cys
 65                  70                  75                  80

Asp Pro Ser Val Thr Arg Ser Ala Phe Ala Asp Val Thr Leu Ser Phe
                 85                  90                  95

Thr Ser Tyr Ser Thr Asp Glu Glu Arg Ala Leu Ile Arg Thr Glu Leu
            100                 105                 110

Ala Ala Leu Leu Ala Asp Pro Leu Ile Val Asp Ala Ile Asp Asn Leu
        115                 120                 125

Asn Pro Ala Tyr
    130

<210> SEQ ID NO 16
<211> LENGTH: 329
<212> TYPE: PRT
<213> ORGANISM: Bacteriophage SP A1 protein

<400> SEQUENCE: 16

Ala Lys Leu Asn Gln Val Thr Leu Ser Lys Ile Gly Lys Asn Gly Asp
 1               5                  10                  15

Gln Thr Leu Thr Leu Thr Pro Arg Gly Val Asn Pro Thr Asn Gly Val
             20                  25                  30

Ala Ser Leu Ser Glu Ala Gly Ala Val Pro Ala Leu Glu Lys Arg Val
         35                  40                  45

Thr Val Ser Val Ala Gln Pro Ser Arg Asn Arg Lys Asn Phe Lys Val
     50                  55                  60

Gln Ile Lys Leu Gln Asn Pro Thr Ala Cys Thr Arg Asp Ala Cys Asp
 65                  70                  75                  80

Pro Ser Val Thr Arg Ser Ala Phe Ala Asp Val Thr Leu Ser Phe Thr
                 85                  90                  95

Ser Tyr Ser Thr Asp Glu Glu Arg Ala Leu Ile Arg Thr Glu Leu Ala
            100                 105                 110
```

Ala Leu Leu Ala Asp Pro Leu Ile Val Asp Ala Ile Asp Asn Leu Asn
            115                 120                 125

Pro Ala Tyr Trp Ala Ala Leu Leu Val Ala Ser Ser Gly Gly Gly Asp
130                 135                 140

Asn Pro Ser Asp Pro Asp Val Pro Val Pro Asp Val Lys Pro Pro
145                 150                 155                 160

Asp Gly Thr Gly Arg Tyr Lys Cys Pro Phe Ala Cys Tyr Arg Leu Gly
                165                 170                 175

Ser Ile Tyr Glu Val Gly Lys Glu Gly Ser Pro Asp Ile Tyr Glu Arg
                180                 185                 190

Gly Asp Glu Val Ser Val Thr Phe Asp Tyr Ala Leu Glu Asp Phe Leu
            195                 200                 205

Gly Asn Thr Asn Trp Arg Asn Trp Asp Gln Arg Leu Ser Asp Tyr Asp
            210                 215                 220

Ile Ala Asn Arg Arg Cys Arg Gly Asn Gly Tyr Ile Asp Leu Asp
225                 230                 235                 240

Ala Thr Ala Met Gln Ser Asp Asp Phe Val Leu Ser Gly Arg Tyr Gly
                245                 250                 255

Val Arg Lys Val Lys Phe Pro Gly Ala Phe Gly Ser Ile Lys Tyr Leu
                260                 265                 270

Leu Asn Ile Gln Gly Asp Ala Trp Leu Asp Leu Ser Glu Val Thr Ala
            275                 280                 285

Tyr Arg Ser Tyr Gly Met Val Ile Gly Phe Trp Thr Asp Ser Lys Ser
            290                 295                 300

Pro Gln Leu Pro Thr Asp Phe Thr Gln Phe Asn Ser Ala Asn Cys Pro
305                 310                 315                 320

Val Gln Thr Val Ile Ile Pro Ser
                325

<210> SEQ ID NO 17
<211> LENGTH: 130
<212> TYPE: PRT
<213> ORGANISM: Bacteriophage MS2

<400> SEQUENCE: 17

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
                20                  25                  30

Trp Ile Ser Ser Asn Ser Arg Ser Gln Ala Tyr Lys Val Thr Cys Ser
            35                  40                  45

Val Arg Gln Ser Ser Ala Gln Asn Arg Lys Tyr Thr Ile Lys Val Glu
        50                  55                  60

Val Pro Lys Val Ala Thr Gln Thr Val Gly Gly Val Glu Leu Pro Val
65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
                100                 105                 110

Leu Lys Asp Gly Asn Pro Ile Pro Ser Ala Ile Ala Ala Asn Ser Gly
            115                 120                 125

Ile Tyr
    130

<210> SEQ ID NO 18

```
<211> LENGTH: 133
<212> TYPE: PRT
<213> ORGANISM: Bacteriophage M11

<400> SEQUENCE: 18

Met Ala Lys Leu Gln Ala Ile Thr Leu Ser Gly Ile Gly Lys Lys Gly
1               5                   10                  15

Asp Val Thr Leu Asp Leu Asn Pro Arg Gly Val Asn Pro Thr Asn Gly
            20                  25                  30

Val Ala Ala Leu Ser Glu Ala Gly Ala Val Pro Ala Leu Glu Lys Arg
        35                  40                  45

Val Thr Ile Ser Val Ser Gln Pro Ser Arg Asn Arg Lys Asn Tyr Lys
50                  55                  60

Val Gln Val Lys Ile Gln Asn Pro Thr Ser Cys Thr Ala Ser Gly Thr
65                  70                  75                  80

Cys Asp Pro Ser Val Thr Arg Ser Ala Tyr Ser Asp Val Thr Phe Ser
                85                  90                  95

Phe Thr Gln Tyr Ser Thr Val Glu Glu Arg Ala Leu Val Arg Thr Glu
                100                 105                 110

Leu Gln Ala Leu Leu Ala Asp Pro Met Leu Val Asn Ala Ile Asp Asn
            115                 120                 125

Leu Asn Pro Ala Tyr
    130

<210> SEQ ID NO 19
<211> LENGTH: 133
<212> TYPE: PRT
<213> ORGANISM: Bacteriophage MX1

<400> SEQUENCE: 19

Met Ala Lys Leu Gln Ala Ile Thr Leu Ser Gly Ile Gly Lys Asn Gly
1               5                   10                  15

Asp Val Thr Leu Asn Leu Asn Pro Arg Gly Val Asn Pro Thr Asn Gly
            20                  25                  30

Val Ala Ala Leu Ser Glu Ala Gly Ala Val Pro Ala Leu Glu Lys Arg
        35                  40                  45

Val Thr Ile Ser Val Ser Gln Pro Ser Arg Asn Arg Lys Asn Tyr Lys
50                  55                  60

Val Gln Val Lys Ile Gln Asn Pro Thr Ser Cys Thr Ala Ser Gly Thr
65                  70                  75                  80

Cys Asp Pro Ser Val Thr Arg Ser Ala Tyr Ala Asp Val Thr Phe Ser
                85                  90                  95

Phe Thr Gln Tyr Ser Thr Asp Glu Glu Arg Ala Leu Val Arg Thr Glu
                100                 105                 110

Leu Lys Ala Leu Leu Ala Asp Pro Met Leu Ile Asp Ala Ile Asp Asn
            115                 120                 125

Leu Asn Pro Ala Tyr
    130

<210> SEQ ID NO 20
<211> LENGTH: 330
<212> TYPE: PRT
<213> ORGANISM: Bacteriophage NL95

<400> SEQUENCE: 20

Met Ala Lys Leu Asn Lys Val Thr Leu Thr Gly Ile Gly Lys Ala Gly
1               5                   10                  15
```

-continued

```
Asn Gln Thr Leu Thr Leu Thr Pro Arg Gly Val Asn Pro Thr Asn Gly
            20                  25                  30

Val Ala Ser Leu Ser Glu Ala Gly Ala Val Pro Ala Leu Glu Lys Arg
        35                  40                  45

Val Thr Val Ser Val Ala Gln Pro Ser Arg Asn Arg Lys Asn Tyr Lys
    50                  55                  60

Val Gln Ile Lys Leu Gln Asn Pro Thr Ala Cys Thr Lys Asp Ala Cys
65                  70                  75                  80

Asp Pro Ser Val Thr Arg Ser Gly Ser Arg Asp Val Thr Leu Ser Phe
                85                  90                  95

Thr Ser Tyr Ser Thr Glu Arg Glu Arg Ala Leu Ile Arg Thr Glu Leu
            100                 105                 110

Ala Ala Leu Leu Lys Asp Asp Leu Ile Val Asp Ala Ile Asp Asn Leu
        115                 120                 125

Asn Pro Ala Tyr Trp Ala Ala Leu Leu Ala Ala Ser Pro Gly Gly Gly
    130                 135                 140

Asn Asn Pro Tyr Pro Gly Val Pro Asp Ser Pro Asn Val Lys Pro Pro
145                 150                 155                 160

Gly Gly Thr Gly Thr Tyr Arg Cys Pro Phe Ala Cys Tyr Arg Arg Gly
                165                 170                 175

Glu Leu Ile Thr Glu Ala Lys Asp Gly Ala Cys Ala Leu Tyr Ala Cys
            180                 185                 190

Gly Ser Glu Ala Leu Val Glu Phe Glu Tyr Ala Leu Glu Asp Phe Leu
        195                 200                 205

Gly Asn Glu Phe Trp Arg Asn Trp Asp Gly Arg Leu Ser Lys Tyr Asp
    210                 215                 220

Ile Glu Thr His Arg Arg Cys Arg Gly Asn Gly Tyr Val Asp Leu Asp
225                 230                 235                 240

Ala Ser Val Met Gln Ser Asp Glu Tyr Val Leu Ser Gly Ala Tyr Asp
                245                 250                 255

Val Val Lys Met Gln Pro Pro Gly Thr Phe Asp Ser Pro Arg Tyr Tyr
            260                 265                 270

Leu His Leu Met Asp Gly Ile Tyr Val Asp Leu Ala Glu Val Thr Ala
        275                 280                 285

Tyr Arg Ser Tyr Gly Met Val Ile Gly Phe Trp Thr Asp Ser Lys Ser
    290                 295                 300

Pro Gln Leu Pro Thr Asp Phe Thr Arg Phe Asn Arg His Asn Cys Pro
305                 310                 315                 320

Val Gln Thr Val Ile Val Ile Pro Ser Leu
                325                 330

<210> SEQ ID NO 21
<211> LENGTH: 129
<212> TYPE: PRT
<213> ORGANISM: Bacteriophage F2

<400> SEQUENCE: 21

Ala Ser Asn Phe Thr Gln Phe Val Leu Val Asn Asp Gly Gly Thr Gly
1               5                   10                  15

Asn Val Thr Val Ala Pro Ser Asn Phe Ala Asn Gly Val Ala Glu Trp
            20                  25                  30

Ile Ser Ser Asn Ser Arg Ser Gln Ala Tyr Lys Val Thr Cys Ser Val
        35                  40                  45

Arg Gln Ser Ser Ala Gln Asn Arg Lys Tyr Thr Ile Lys Val Glu Val
    50                  55                  60
```

-continued

```
Pro Lys Val Ala Thr Gln Thr Val Gly Gly Val Glu Leu Pro Val Ala
 65                  70                  75                  80

Ala Trp Arg Ser Tyr Leu Asn Leu Glu Leu Thr Ile Pro Ile Phe Ala
                 85                  90                  95

Thr Asn Ser Asp Cys Glu Leu Ile Val Lys Ala Met Gln Gly Leu Leu
            100                 105                 110

Lys Asp Gly Asn Pro Ile Pro Ser Ala Ile Ala Ala Asn Ser Gly Ile
        115                 120                 125

Tyr

<210> SEQ ID NO 22
<211> LENGTH: 128
<212> TYPE: PRT
<213> ORGANISM: Bacteriophage PP7

<400> SEQUENCE: 22

Met Ser Lys Thr Ile Val Leu Ser Val Gly Glu Ala Thr Arg Thr Leu
 1               5                  10                  15

Thr Glu Ile Gln Ser Thr Ala Asp Arg Gln Ile Phe Glu Glu Lys Val
                20                  25                  30

Gly Pro Leu Val Gly Arg Leu Arg Leu Thr Ala Ser Leu Arg Gln Asn
             35                 40                  45

Gly Ala Lys Thr Ala Tyr Arg Val Asn Leu Lys Leu Asp Gln Ala Asp
         50                  55                  60

Val Val Asp Cys Ser Thr Ser Val Cys Gly Glu Leu Pro Lys Val Arg
 65                  70                  75                  80

Tyr Thr Gln Val Trp Ser His Asp Val Thr Ile Val Ala Asn Ser Thr
                 85                  90                  95

Glu Ala Ser Arg Lys Ser Leu Tyr Asp Leu Thr Lys Ser Leu Val Ala
            100                 105                 110

Thr Ser Gln Val Glu Asp Leu Val Asn Leu Val Pro Leu Gly Arg
        115                 120                 125

<210> SEQ ID NO 23
<211> LENGTH: 132
<212> TYPE: PRT
<213> ORGANISM: Artificial Sequence
<220> FEATURE:
<223> OTHER INFORMATION: Q-beta 240 mutant

<400> SEQUENCE: 23

Ala Lys Leu Glu Thr Val Thr Leu Gly Asn Ile Gly Arg Asp Gly Lys
 1               5                  10                  15

Gln Thr Leu Val Leu Asn Pro Arg Gly Val Asn Pro Thr Asn Gly Val
                20                  25                  30

Ala Ser Leu Ser Gln Ala Gly Ala Val Pro Ala Leu Glu Lys Arg Val
             35                 40                  45

Thr Val Ser Val Ser Gln Pro Ser Arg Asn Arg Lys Asn Tyr Lys Val
         50                  55                  60

Gln Val Lys Ile Gln Asn Pro Thr Ala Cys Thr Ala Asn Gly Ser Cys
 65                  70                  75                  80

Asp Pro Ser Val Thr Arg Gln Lys Tyr Ala Asp Val Thr Phe Ser Phe
                 85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
```

```
                    115                 120                 125
Asn Pro Ala Tyr
    130

<210> SEQ ID NO 24
<211> LENGTH: 132
<212> TYPE: PRT
<213> ORGANISM: Artificial Sequence
<220> FEATURE:
<223> OTHER INFORMATION: Q-beta 243 mutant

<400> SEQUENCE: 24

Ala Lys Leu Glu Thr Val Thr Leu Gly Lys Ile Gly Lys Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 25
<211> LENGTH: 132
<212> TYPE: PRT
<213> ORGANISM: Artificial Sequence
<220> FEATURE:
<223> OTHER INFORMATION: Q-beta 250 mutant

<400> SEQUENCE: 25

Ala Arg Leu Glu Thr Val Thr Leu Gly Asn Ile Gly Arg Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130
```

```
<210> SEQ ID NO 26
<211> LENGTH: 132
<212> TYPE: PRT
<213> ORGANISM: Artificial Sequence
<220> FEATURE:
<223> OTHER INFORMATION: Q-beta 251 mutant

<400> SEQUENCE: 26

Ala Lys Leu Glu Thr Val Thr Leu Gly Asn Ile Gly Lys Asp Gly Arg
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 27
<211> LENGTH: 132
<212> TYPE: PRT
<213> ORGANISM: Artificial Sequence
<220> FEATURE:
<223> OTHER INFORMATION: Q-beta 259 mutant

<400> SEQUENCE: 27

Ala Arg Leu Glu Thr Val Thr Leu Gly Asn Ile Gly Lys Asp Gly Arg
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 28
<211> LENGTH: 185
<212> TYPE: PRT
<213> ORGANISM: Hepatitis B virus
```

```
<400> SEQUENCE: 28

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Arg Ser Gln Ser Pro Arg Arg Arg
                165                 170                 175

Arg Ser Gln Ser Arg Glu Ser Gln Cys
            180                 185

<210> SEQ ID NO 29
<211> LENGTH: 183
<212> TYPE: PRT
<213> ORGANISM: Hepatitis B virus

<400> SEQUENCE: 29

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Gly Asn Leu Glu Asp Pro Ile
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175
```

```
Gln Ser Arg Gly Ser Gln Cys
            180

<210> SEQ ID NO 30
<211> LENGTH: 183
<212> TYPE: PRT
<213> ORGANISM: Hepatitis B virus

<400> SEQUENCE: 30

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Gly Asn Leu Glu Asp Pro Thr
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Thr Asn Ala Pro Ile Leu Ser Thr Leu Pro
    130                 135                 140

Glu Thr Cys Val Ile Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Gly Ser Gln Cys
            180

<210> SEQ ID NO 31
<211> LENGTH: 212
<212> TYPE: PRT
<213> ORGANISM: Hepatitis B virus

<400> SEQUENCE: 31

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Gly Asn Leu Glu Asp Pro Ile Ser Arg Asp
            100                 105                 110

Leu Val Val Ser Tyr Val Asn Thr Asn Met Gly Leu Lys Phe Arg Gln
        115                 120                 125
```

```
Leu Leu Trp Phe His Ile Ser Cys Leu Thr Phe Gly Arg Glu Thr Val
        130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Thr Pro Ser Pro
            180                 185                 190

Arg Arg Arg Arg Ser Gln Ser Pro Arg Arg Arg Ser Gln Ser Arg
            195                 200                 205

Glu Ser Gln Cys
        210

<210> SEQ ID NO 32
<211> LENGTH: 212
<212> TYPE: PRT
<213> ORGANISM: Hepatitis B virus

<400> SEQUENCE: 32

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Asn Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Gly Asn Leu Glu Asp Pro Ile Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
        130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Thr Pro Ser Pro
            180                 185                 190

Arg Arg Arg Arg Ser Gln Ser Pro Arg Arg Arg Ser Gln Ser Arg
            195                 200                 205

Glu Ser Gln Cys
        210

<210> SEQ ID NO 33
<211> LENGTH: 183
<212> TYPE: PRT
<213> ORGANISM: Hepatitis B virus

<400> SEQUENCE: 33

Met Asp Ile Asp Pro Tyr Lys Glu Phe Gly Ala Thr Val Glu Leu Leu
1               5                   10                  15
```

```
Ser Phe Leu Pro Thr Asp Phe Phe Pro Ser Val Arg Asp Leu Leu Asp
             20                  25                  30

Thr Ala Ser Ala Leu Tyr Arg Glu Ala Leu Glu Ser Pro Glu His Cys
         35                  40                  45

Ser Pro His His Thr Ala Leu Arg Gln Ala Ile Leu Cys Trp Gly Glu
     50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                 85                  90                  95

Phe Arg Gln Leu Leu Trp Phe His Ile Ser Cys Leu Thr Phe Gly Arg
             100                 105                 110

Glu Thr Val Ile Glu Tyr Leu Val Ser Phe Gly Val Trp Ile Arg Thr
         115                 120                 125

Pro Pro Ala Tyr Arg Pro Pro Asn Ala Pro Ile Leu Ser Thr Leu Pro
     130                 135                 140

Glu Thr Cys Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                 165                 170                 175

Gln Ser Arg Glu Ser Gln Cys
             180

<210> SEQ ID NO 34
<211> LENGTH: 212
<212> TYPE: PRT
<213> ORGANISM: Hepatitis B virus

<400> SEQUENCE: 34

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
             20                  25                  30

Asp Pro Tyr Lys Glu Phe Gly Ala Thr Val Glu Leu Leu Ser Phe Leu
         35                  40                  45

Pro Ser Asp Phe Phe Pro Ser Val Arg Asp Leu Leu Asp Thr Ala Ser
     50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Thr
                 85                  90                  95

Leu Ala Thr Trp Val Gly Gly Asn Leu Glu Asp Pro Val Ser Arg Asp
             100                 105                 110

Leu Val Val Ser Tyr Val Asn Thr Asn Val Gly Leu Lys Phe Arg Gln
         115                 120                 125

Leu Leu Trp Phe His Ile Ser Cys Leu Thr Phe Gly Arg Glu Thr Val
     130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                 165                 170                 175

Val Val Arg Arg Arg Gly Arg Ser Pro Arg Arg Arg Thr Pro Ser Pro
             180                 185                 190

Arg Arg Arg Arg Ser Gln Ser Pro Arg Arg Arg Arg Ser Gln Ser Arg
```

-continued

```
                195                 200                 205
Glu Ser Gln Cys
    210

<210> SEQ ID NO 35
<211> LENGTH: 212
<212> TYPE: PRT
<213> ORGANISM: Hepatitis B virus

<400> SEQUENCE: 35

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Asp Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Thr
                85                  90                  95

Leu Ala Thr Trp Val Gly Gly Asn Leu Glu Asp Pro Val Ser Arg Asp
            100                 105                 110

Leu Val Val Ser Tyr Val Asn Thr Asn Val Gly Leu Lys Phe Arg Gln
        115                 120                 125

Leu Leu Trp Phe His Ile Ser Cys Leu Thr Phe Gly Arg Glu Thr Val
130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210

<210> SEQ ID NO 36
<211> LENGTH: 212
<212> TYPE: PRT
<213> ORGANISM: Hepatitis B virus

<400> SEQUENCE: 36

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
50                  55                  60

Ala Leu Tyr Arg Glu Ala Leu Glu Ser Pro Glu His Cys Ser Pro Gln
65                  70                  75                  80

His Thr Ala Leu Arg Gln Ala Ile Leu Cys Trp Gly Glu Leu Met Thr
```

```
                    85                  90                  95
Leu Ala Thr Trp Val Gly Gly Asn Leu Glu Asp Pro Ile Ser Arg Asp
                100                 105                 110
Leu Val Val Ser Tyr Val Asn Thr Asn Met Gly Leu Lys Phe Arg Gln
            115                 120                 125
Leu Leu Trp Phe His Ile Ser Cys Leu Thr Phe Gly Arg Glu Thr Val
        130                 135                 140
Ile Glu Tyr Leu Val Ser Phe Gly Val Trp Ile Arg Thr Pro Pro Ala
145                 150                 155                 160
Tyr Arg Pro Pro Asn Ala Pro Ile Leu Ser Thr Leu Pro Glu Thr Thr
                165                 170                 175
Val Val Arg Arg Arg Gly Arg Ser Pro Arg Arg Arg Thr Pro Ser Pro
            180                 185                 190
Arg Arg Arg Arg Ser Gln Ser Pro Arg Arg Arg Arg Ser Gln Ser Arg
        195                 200                 205
Glu Ser Gln Cys
    210

<210> SEQ ID NO 37
<211> LENGTH: 212
<212> TYPE: PRT
<213> ORGANISM: Hepatitis B virus

<400> SEQUENCE: 37

Met Gln Leu Phe His Leu Cys Leu Ile Ile Ser Cys Ser Cys Pro Thr
1               5                   10                  15
Val Gln Ala Ser Lys Leu Cys Leu Gly Trp Leu Trp Gly Met Asp Ile
            20                  25                  30
Asp Pro Tyr Lys Glu Phe Gly Ala Thr Val Glu Leu Leu Ser Phe Leu
        35                  40                  45
Pro Ser Asp Phe Phe Pro Ser Val Arg Asp Leu Leu Asp Thr Ala Ser
    50                  55                  60
Ala Leu Tyr Arg Glu Ala Leu Glu Ser Pro Glu His Cys Ser Pro His
65                  70                  75                  80
His Thr Ala Leu Arg Gln Ala Ile Leu Cys Trp Gly Glu Leu Met Thr
                85                  90                  95
Leu Ala Thr Trp Val Gly Val Asn Leu Glu Asp Pro Ala Ser Arg Asp
                100                 105                 110
Leu Val Val Ser Tyr Val Asn Thr Asn Met Gly Leu Lys Phe Arg Gln
            115                 120                 125
Leu Leu Trp Phe His Ile Ser Cys Leu Thr Phe Gly Arg Glu Thr Val
        130                 135                 140
Ile Glu Tyr Leu Val Ser Phe Gly Val Trp Ile Arg Thr Pro Pro Ala
145                 150                 155                 160
Tyr Lys Pro Pro Asn Ala Pro Ile Leu Ser Thr Leu Pro Glu Thr Thr
                165                 170                 175
Val Val Arg Arg Arg Gly Arg Ser Pro Arg Arg Arg Thr Pro Ser Pro
            180                 185                 190
Arg Arg Arg Arg Ser Gln Ser Pro Arg Arg Arg Arg Ser Gln Ser Arg
        195                 200                 205
Gly Ser Gln Cys
    210

<210> SEQ ID NO 38
<211> LENGTH: 183
```

```
<212> TYPE: PRT
<213> ORGANISM: Hepatitis B virus

<400> SEQUENCE: 38

Met Asp Ile Asp Pro Tyr Lys Glu Phe Gly Ala Thr Val Glu Leu Leu
1               5                   10                  15

Ser Phe Leu Pro Ser Asp Phe Pro Ser Val Arg Asp Leu Leu Asp
            20                  25                  30

Thr Ala Ser Ala Leu Phe Arg Asp Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Gly Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Asp Thr Val Ile Glu Tyr Leu Val Ser Phe Gly Val Trp Ile Arg Thr
            115                 120                 125

Pro Pro Ala Tyr Arg Pro Ser Asn Ala Pro Ile Leu Ser Thr Leu Pro
        130                 135                 140

Glu Thr Cys Val Val Arg Arg Gly Arg Ser Pro Arg Arg Arg Thr
145                 150                 155                 160

Pro Ser Pro Arg Arg Arg Ser Gln Ser Pro Arg Arg Arg Ser
                165                 170                 175

Gln Ser Arg Glu Ser Gln Cys
            180

<210> SEQ ID NO 39
<211> LENGTH: 183
<212> TYPE: PRT
<213> ORGANISM: Hepatitis B virus

<400> SEQUENCE: 39

Met Asp Ile Asp Pro Tyr Lys Glu Phe Gly Ala Thr Val Glu Leu Leu
1               5                   10                  15

Ser Phe Leu Pro Ser Asp Phe Pro Ser Val Arg Asp Leu Leu Asp
            20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Arg Arg Arg Gly Arg Ser Pro Arg Arg Arg Thr
145                 150                 155                 160
```

```
Pro Ser Pro Arg Arg Arg Ser Gln Ser Pro Arg Arg Arg Ser
            165                 170                 175
Gln Ser Arg Glu Ser Gln Cys
            180
```

<210> SEQ ID NO 40
<211> LENGTH: 212
<212> TYPE: PRT
<213> ORGANISM: Hepatitis B virus

<400> SEQUENCE: 40

```
Met Gln Leu Phe His Leu Cys Leu Ile Ile Ser Cys Ser Cys Pro Thr
1               5                   10                  15
Val Gln Ala Ser Lys Leu Cys Leu Gly Trp Leu Trp Gly Met Asp Ile
                20                  25                  30
Asp Pro Tyr Lys Glu Phe Gly Ala Thr Val Glu Leu Leu Ser Phe Leu
            35                  40                  45
Pro Ser Asp Phe Phe Pro Ser Val Arg Asp Leu Leu Asp Thr Ala Ser
    50                  55                  60
Ala Leu Tyr Arg Glu Ala Leu Glu Ser Pro Glu His Cys Ser Pro His
65                  70                  75                  80
His Thr Ala Leu Arg His Ala Ile Leu Cys Trp Gly Asp Leu Arg Thr
                85                  90                  95
Leu Ala Thr Trp Val Gly Gly Asn Leu Glu Asp Pro Ile Ser Arg Asp
            100                 105                 110
Leu Val Val Ser Tyr Val Asn Thr Asn Met Gly Leu Lys Phe Arg Gln
        115                 120                 125
Leu Leu Trp Phe His Ile Ser Cys Leu Thr Phe Gly Arg Glu Thr Val
    130                 135                 140
Ile Glu Tyr Leu Val Ser Phe Gly Val Trp Ile Arg Thr Pro Pro Ala
145                 150                 155                 160
Tyr Arg Pro Pro Asn Ala Pro Ile Leu Ser Thr Leu Pro Glu Thr Thr
                165                 170                 175
Val Val Arg Arg Arg Gly Arg Ser Pro Arg Arg Arg Thr Pro Ser Pro
            180                 185                 190
Arg Arg Arg Arg Ser Gln Ser Pro Arg Arg Arg Arg Ser Gln Ser Arg
        195                 200                 205
Glu Ser Gln Cys
    210
```

<210> SEQ ID NO 41
<211> LENGTH: 212
<212> TYPE: PRT
<213> ORGANISM: Hepatitis B virus

<400> SEQUENCE: 41

```
Met Gln Leu Phe His Leu Cys Leu Ile Ile Ser Cys Ser Cys Pro Thr
1               5                   10                  15
Val Gln Ala Ser Lys Leu Cys Leu Gly Trp Leu Trp Asp Met Asp Ile
                20                  25                  30
Asp Pro Tyr Lys Glu Phe Gly Ala Thr Val Glu Leu Leu Ser Phe Leu
            35                  40                  45
Pro Ser Asp Phe Phe Pro Ser Val Arg Asp Leu Leu Asp Thr Ala Ser
    50                  55                  60
Ala Leu Phe Arg Asp Ala Leu Glu Ser Pro Glu His Cys Ser Pro His
65                  70                  75                  80
```

-continued

```
His Thr Ala Leu Arg Gln Ala Ile Leu Cys Trp Gly Glu Leu Met Thr
                85                  90                  95

Leu Ala Thr Trp Val Gly Ala Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
130                 135                 140

Ile Glu Tyr Leu Val Ser Phe Gly Val Trp Ile Arg Thr Pro Gln Ala
145                 150                 155                 160

Tyr Arg Pro Pro Asn Ala Pro Ile Leu Ser Thr Leu Pro Glu Thr Cys
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210

<210> SEQ ID NO 42
<211> LENGTH: 183
<212> TYPE: PRT
<213> ORGANISM: Artificial sequence
<220> FEATURE:
<223> OTHER INFORMATION: Synthetic human Hepatitus B construct

<400> SEQUENCE: 42

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu T

```
<400> SEQUENCE: 43

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Ser
                85                  90                  95

Leu Ala Thr Trp Val Gly Val Asn Leu Glu Asp Pro Ile Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
            195                 200                 205

Glu Ser Gln Cys
    210

<210> SEQ ID NO 44
<211> LENGTH: 183
<212> TYPE: PRT
<213> ORGANISM: Hepatitis B virus

<400> SEQUENCE: 44

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
130                 135                 140
```

-continued

```
Glu Thr Thr Val Val Arg Arg Gly Arg Ser Pro Arg Arg Thr
145                 150                 155                 160

Pro Ser Pro Arg Arg Arg Ser Gln Ser Pro Arg Arg Arg Ser
                165                 170                 175

Gln Ser Arg Glu Ser Gln Cys
            180

<210> SEQ ID NO 45
<211> LENGTH: 183
<212> TYPE: PRT
<213> ORGANISM: Hepatitis B virus

<400> SEQUENCE: 45

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Gly Arg Ser Pro Arg Arg Arg Thr
145                 150                 155                 160

Pro Ser Pro Arg Arg Arg Ser Gln Ser Pro Arg Arg Arg Ser
                165                 170                 175

Gln Ser Arg Glu Ser Gln Cys
            180

<210> SEQ ID NO 46
<211> LENGTH: 183
<212> TYPE: PRT
<213> ORGANISM: Hepatitis B virus

<400> SEQUENCE: 46

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Ala Asn Leu Glu Asp Pro Ala
65                  70                  75                  80

Ser Arg Asp Leu Val Val Ser Tyr Val Asn Thr Asn Met Gly Leu Lys
                85                  90                  95
```

```
Phe Arg Gln Leu Leu Trp Phe His Ile Ser Cys Leu Thr Phe Gly Arg
                100                 105                 110

Glu Thr Val Ile Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Arg Arg Arg Gly Arg Thr Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

<210> SEQ ID NO 47
<211> LENGTH: 212
<212> TYPE: PRT
<213> ORGANISM: Hepatitis B virus

<400> SEQUENCE: 47

```
Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Asp Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210
```

<210> SEQ ID NO 48
<211> LENGTH: 212
<212> TYPE: PRT
<213> ORGANISM: Hepatitis B virus

<400> SEQUENCE: 48

```
Met Gln Leu Phe His Leu Cys Leu Ile Ile Ser Cys Ser Cys Pro Thr
1               5                   10                  15
```

-continued

```
Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
 50                  55                  60

Ala Leu Tyr Arg Glu Ala Leu Glu Ser Pro Glu His Cys Ser Pro His
 65                  70                  75                  80

His Thr Ala Leu Arg Gln Ala Ile Leu Cys Trp Gly Asp Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
            115                 120                 125

Leu Leu Trp Phe His Ile Ser Cys Leu Thr Phe Gly Arg Glu Thr Val
 130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
            195                 200                 205

Glu Ser Gln Cys
    210

<210> SEQ ID NO 49
<211> LENGTH: 212
<212> TYPE: PRT
<213> ORGANISM: Hepatitis B virus

<400> SEQUENCE: 49

Met Gln Leu Phe His Leu Cys Leu Ile Ile Ser Cys Thr Cys Pro Thr
 1               5                  10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
 50                  55                  60

Ala Leu Tyr Arg Glu Ala Leu Glu Ser Pro Glu His Cys Ser Pro His
 65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
            115                 120                 125

Leu Leu Trp Phe His Ile Ser Cys Leu Thr Phe Gly Arg Glu Thr Val
 130                 135                 140

Ile Glu Tyr Leu Val Ala Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175
```

-continued

```
Val Val Arg Arg Arg Gly Arg Ser Pro Arg Arg Thr Pro Ser Pro
            180                 185                 190

Arg Arg Arg Arg Ser Gln Ser Pro Arg Arg Arg Ser Gln Ser Arg
            195                 200                 205

Glu Ser Gln Cys
    210

<210> SEQ ID NO 50
<211> LENGTH: 212
<212> TYPE: PRT
<213> ORGANISM: Hepatitis B virus

<400> SEQUENCE: 50

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Phe Glu Cys Ser Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Gly Asn Leu Glu Asp Pro Ile Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Thr Pro Ser Pro
            180                 185                 190

Arg Arg Arg Arg Ser Gln Ser Pro Arg Arg Arg Ser Gln Ser Arg
            195                 200                 205

Glu Ser Gln Cys
    210

<210> SEQ ID NO 51
<211> LENGTH: 212
<212> TYPE: PRT
<213> ORGANISM: Hepatitis B virus
<220> FEATURE:
<221> NAME/KEY: MISC_FEATURE
<222> LOCATION: (28)..(28)
<223> OTHER INFORMATION: May be any amino acid

<400> SEQUENCE: 51

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Xaa Asp Met Asp Ile
            20                  25                  30

Asp Pro Tyr Lys Glu Phe Gly Ala Thr Val Glu Leu Leu Ser Phe Leu
```

```
                35                  40                  45
Pro Ser Asp Phe Phe Pro Ser Val Arg Asp Leu Leu Asp Thr Ala Ser
         50                  55                  60
Ala Leu Tyr Arg Glu Ala Leu Glu Ser Pro Glu His Cys Ser Pro His
 65                  70                  75                  80
His Thr Ala Leu Arg Gln Ala Ile Leu Cys Trp Gly Asp Leu Ile Thr
                 85                  90                  95
Leu Ser Thr Trp Val Gly Gly Asn Leu Glu Asp Pro Thr Ser Arg Asp
                100                 105                 110
Leu Val Val Ser Tyr Val Asn Thr Asn Met Gly Leu Lys Phe Arg Gln
                115                 120                 125
Leu Leu Trp Phe His Ile Ser Cys Leu Thr Phe Gly Arg Glu Thr Val
            130                 135                 140
Ile Glu Tyr Leu Val Ser Phe Gly Val Trp Ile Arg Thr Pro Pro Ala
145                 150                 155                 160
Tyr Arg Pro Pro Asn Ala Pro Ile Leu Ser Thr Leu Pro Glu Thr Thr
                165                 170                 175
Val Val Arg Arg Arg Gly Arg Ser Pro Arg Arg Arg Thr Pro Ser Pro
                180                 185                 190
Arg Arg Arg Arg Ser Gln Ser Pro Arg Arg Arg Arg Thr Gln Ser Arg
                195                 200                 205
Glu Ser Gln Cys
        210

<210> SEQ ID NO 52
<211> LENGTH: 212
<212> TYPE: PRT
<213> ORGANISM: Hepatitis B virus

<400> SEQUENCE: 52

Met Gln Leu Phe His Leu Cys Leu Ile Ile Ser Cys Ser Cys Pro Thr
 1               5                  10                  15
Val Gln Ala Ser Lys Leu Cys Leu Gly Trp Leu Trp Gly Met Asp Ile
                 20                  25                  30
Asp Pro Tyr Lys Glu Phe Gly Ala Thr Val Glu Leu Leu Ser Phe Leu
             35                  40                  45
Pro Ser Asp Phe Phe Pro Ser Val Arg Asp Leu Leu Asp Asn Ala Ser
         50                  55                  60
Ala Leu Tyr Arg Glu Ala Leu Glu Ser Pro Glu His Cys Ser Pro His
 65                  70                  75                  80
His Thr Ala Leu Arg Gln Ala Ile Leu Cys Trp Gly Glu Leu Met Thr
                 85                  90                  95
Leu Ala Thr Trp Val Gly Val Asn Leu Glu Asp Pro Ala Ser Arg Asp
                100                 105                 110
Leu Val Val Ser Tyr Val Asn Thr Asn Met Gly Leu Lys Phe Arg Gln
                115                 120                 125
Leu Leu Trp Phe His Ile Ser Cys Leu Thr Phe Gly Arg Glu Thr Val
            130                 135                 140
Ile Glu Tyr Leu Val Ser Phe Gly Val Trp Ile Arg Thr Pro Pro Ala
145                 150                 155                 160
Tyr Arg Pro Pro Asn Ala Pro Ile Leu Ser Thr Leu Pro Glu Thr Thr
                165                 170                 175
Val Val Arg Arg Arg Gly Arg Ser Pro Arg Arg Arg Thr Pro Ser Pro
                180                 185                 190
```

```
Arg Arg Arg Arg Ser Gln Ser Pro Arg Arg Arg Ser Gln Ser Arg
        195                 200                 205
Glu Ser Gln Cys
    210

<210> SEQ ID NO 53
<211> LENGTH: 212
<212> TYPE: PRT
<213> ORGANISM: Hepatitis B virus

<400> SEQUENCE: 53

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Cys Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Ser Gln Ser Arg
        195                 200                 205

Glu Ser Gln Cys
    210

<210> SEQ ID NO 54
<211> LENGTH: 212
<212> TYPE: PRT
<213> ORGANISM: Hepatitis B virus

<400> SEQUENCE: 54

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80
```

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
            115                 120                 125

Leu Leu Trp Phe His Ile Ser Cys Leu Thr Phe Gly Arg Glu Thr Val
        130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Pro Gln Cys
    210

<210> SEQ ID NO 55
<211> LENGTH: 212
<212> TYPE: PRT
<213> ORGANISM: Hepatitis B virus

<400> SEQUENCE: 55

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Ser Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
            115                 120                 125

Leu Leu Trp Phe His Ile Ser Cys Leu Thr Phe Gly Arg Glu Thr Val
        130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210

<210> SEQ ID NO 56

<211> LENGTH: 212
<212> TYPE: PRT
<213> ORGANISM: Hepatitis B virus

<400> SEQUENCE: 56

```
Met Gln Leu Phe His Leu Cys Leu Ile Ile Ser Cys Ser Cys Pro Thr
1               5                   10                  15
Val Gln Ala Ser Lys Leu Cys Leu Gly Trp Leu Trp Gly Met Asp Ile
            20                  25                  30
Asp Pro Tyr Lys Glu Phe Gly Ala Thr Val Glu Leu Leu Ser Phe Leu
        35                  40                  45
Pro Ser Asp Phe Phe Pro Ser Val Arg Asp Leu Leu Asp Thr Ala Ser
    50                  55                  60
Ala Leu Tyr Arg Glu Ala Leu Glu Ser Pro Glu His Cys Ser Pro His
65                  70                  75                  80
His Thr Ala Leu Arg Gln Ala Ile Leu Cys Trp Gly Glu Leu Met Thr
                85                  90                  95
Leu Ala Thr Trp Val Gly Val Asn Leu Glu Asp Pro Ala Ser Arg Asp
            100                 105                 110
Leu Val Val Ser Tyr Val Asn Thr Asn Met Gly Leu Lys Phe Arg Gln
        115                 120                 125
Leu Leu Trp Phe His Ile Ser Cys Leu Thr Phe Gly Arg Glu Thr Val
    130                 135                 140
Ile Glu Tyr Leu Val Ser Phe Gly Val Trp Ile Arg Thr Pro Pro Ala
145                 150                 155                 160
Tyr Arg Pro Pro Asn Ala Pro Ile Leu Leu Thr Leu Pro Glu Thr Thr
                165                 170                 175
Val Val Arg Arg Arg Gly Arg Ser Pro Arg Arg Arg Thr Pro Ser Pro
            180                 185                 190
Arg Arg Arg Arg Ser Gln Ser Pro Arg Arg Arg Arg Ser Gln Ser Arg
        195                 200                 205
Glu Ser Gln Cys
    210
```

<210> SEQ ID NO 57
<211> LENGTH: 212
<212> TYPE: PRT
<213> ORGANISM: Hepatitis B virus

<400> SEQUENCE: 57

```
Met Gln Leu Phe His Leu Cys Leu Ile Ile Ser Cys Ser Cys Pro Thr
1               5                   10                  15
Val Gln Ala Ser Lys Leu Cys Leu Gly Trp Leu Trp Gly Met Asp Ile
            20                  25                  30
Asp Pro Tyr Lys Glu Phe Gly Ala Thr Val Glu Leu Leu Ser Phe Leu
        35                  40                  45
Pro Ser Asp Phe Phe Pro Ser Val Arg Asp Leu Leu Asp Thr Ala Ser
    50                  55                  60
Ala Leu Tyr Arg Glu Ala Leu Glu Ser Pro Glu His Cys Ser Pro His
65                  70                  75                  80
His Thr Ala Leu Arg Gln Ala Ile Leu Cys Trp Gly Asp Leu Met Thr
                85                  90                  95
Leu Ala Thr Trp Val Gly Val Asn Leu Glu Asp Pro Ala Ser Arg Asp
            100                 105                 110
Leu Val Val Ser Tyr Val Asn Thr Asn Met Gly Leu Lys Phe Lys Gln
        115                 120                 125
```

```
Leu Leu Trp Phe His Ile Ser Cys Leu Thr Phe Gly Arg Glu Thr Val
        130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Thr Pro Ser Pro
            180                 185                 190

Arg Arg Arg Arg Ser Gln Ser Pro Arg Arg Arg Ser Gln Ser Arg
            195                 200                 205

Glu Ser Gln Cys
        210

<210> SEQ ID NO 58
<211> LENGTH: 212
<212> TYPE: PRT
<213> ORGANISM: Hepatitis B virus

<400> SEQUENCE: 58

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ala
    50                  55                  60

Ala Leu Tyr Arg Asp Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Thr Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
        130                 135                 140

Leu Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Thr Pro Ser Pro
            180                 185                 190

Arg Arg Arg Arg Ser Gln Ser Pro Arg Arg Arg Ser Gln Ser Arg
            195                 200                 205

Glu Ser Gln Cys
        210

<210> SEQ ID NO 59
<211> LENGTH: 183
<212> TYPE: PRT
<213> ORGANISM: Hepatitis B virus

<400> SEQUENCE: 59

Met Asp Ile Asp Pro Tyr Lys Glu Phe Gly Ala Ser Met Glu Leu Leu
1               5                   10                  15
```

```
Ser Phe Leu Pro Ser Asp Phe Tyr Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Thr Pro His His Thr Ala Leu Arg Gln Ala Ile Leu Cys Trp Gly Glu
    50                  55                  60

Leu Met Thr Leu Ala Thr Trp Val Gly Gly Asn Leu Gln Asp Pro Thr
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Val Ser Cys Leu Thr Phe Gly Arg
            100                 105                 110

Glu Thr Val Val Glu Tyr Leu Val Ser Phe Gly Val Trp Ile Arg Thr
        115                 120                 125

Pro Gln Ala Tyr Arg Pro Pro Asn Ala Pro Ile Leu Ser Thr Leu Pro
    130                 135                 140

Glu Thr Cys Val Val Arg Arg Gly Arg Ser Pro Arg Arg Arg Thr
145                 150                 155                 160

Pro Ser Pro Arg Arg Arg Arg Ser Gln Ser Pro Arg Arg Arg Ser
                165                 170                 175

Gln Ser Arg Glu Ser Gln Cys
            180

<210> SEQ ID NO 60
<211> LENGTH: 183
<212> TYPE: PRT
<213> ORGANISM: Hepatitis B virus

<400> SEQUENCE: 60

Met Asp Ile Asp Pro Tyr Lys Glu Phe Gly Ala Thr Val Glu Leu Leu
1               5                   10                  15

Ser Phe Leu Pro Ser Asp Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg His Val Phe Leu Cys Trp Gly Asp
    50                  55                  60

Leu Met Thr Leu Ala Thr Trp Val Gly Gly Asn Leu Glu Asp Pro Thr
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Gly Arg Ser Pro Arg Arg Arg Thr
145                 150                 155                 160

Pro Ser Pro Arg Arg Arg Arg Ser Gln Ser Pro Arg Arg Arg Ser
                165                 170                 175

Gln Ser Arg Glu Ser Gln Cys
            180
```

```
<210> SEQ ID NO 61
<211> LENGTH: 212
<212> TYPE: PRT
<213> ORGANISM: Hepatitis B virus

<400> SEQUENCE: 61

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Thr Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210

<210> SEQ ID NO 62
<211> LENGTH: 212
<212> TYPE: PRT
<213> ORGANISM: Hepatitis B virus

<400> SEQUENCE: 62

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Asp Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
```

```
                115                 120                 125
Leu Leu Trp Phe His Ile Ser Cys Leu Ile Phe Gly Arg Glu Thr Val
        130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Ser Gln Ser Arg
        195                 200                 205

Glu Ser Gln Cys
    210

<210> SEQ ID NO 63
<211> LENGTH: 183
<212> TYPE: PRT
<213> ORGANISM: Hepatitis B virus

<400> SEQUENCE: 63

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Val Asn Leu Glu Asp Pro Val
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Ala Arg Arg Arg Ser Gln Ser Pro Arg Arg Arg Arg Ser
                165                 170                 175

Gln Ser Arg Glu Ser Gln Cys
            180

<210> SEQ ID NO 64
<211> LENGTH: 212
<212> TYPE: PRT
<213> ORGANISM: Hepatitis B virus

<400> SEQUENCE: 64

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
```

```
                35                  40                  45
Pro Ser Asp Phe Phe Pro Ser Val Arg Asp Leu Leu Asp Thr Ala Ser
         50                  55                  60

Ala Leu Tyr Arg Glu Ala Leu Glu Ser Pro Glu His Cys Ser Pro His
 65                  70                  75                  80

His Thr Ala Leu Arg Gln Ala Ile Leu Cys Trp Gly Asp Leu Met Asn
                 85                  90                  95

Leu Ala Thr Trp Val Gly Gly Asn Leu Glu Asp Pro Val Ser Arg Asp
                100                 105                 110

Leu Val Val Gly Tyr Val Asn Thr Thr Val Gly Leu Lys Phe Arg Gln
            115                 120                 125

Leu Leu Trp Phe His Ile Ser Cys Leu Thr Phe Gly Arg Glu Thr Val
        130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
            195                 200                 205

Glu Ser Gln Cys
        210

<210> SEQ ID NO 65
<211> LENGTH: 183
<212> TYPE: PRT
<213> ORGANISM: Hepatitis B virus

<400> SEQUENCE: 65

Met Asp Ile Asp Pro Tyr Lys Glu Phe Gly Ala Thr Val Glu Leu Leu
 1               5                  10                  15

Ser Phe Leu Pro Ser Asp Phe Phe Pro Ser Val Arg Asp Leu Leu Asp
                20                  25                  30

Thr Ala Ser Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
        50                  55                  60

Leu Met Thr Leu Ala Thr Trp Val Gly Val Asn Leu Glu Asp Pro Ala
 65                  70                  75                  80

Ser Arg Asp Leu Val Val Ser Tyr Val Asn Thr Asn Met Gly Leu Lys
                 85                  90                  95

Phe Arg Gln Leu Leu Trp Phe His Ile Ser Cys Leu Thr Phe Gly Arg
                100                 105                 110

Glu Thr Val Ile Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val Arg Arg Gly Arg Thr Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180
```

```
<210> SEQ ID NO 66
<211> LENGTH: 212
<212> TYPE: PRT
<213> ORGANISM: Hepatitis B virus

<400> SEQUENCE: 66

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Ala Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Ile Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210

<210> SEQ ID NO 67
<211> LENGTH: 212
<212> TYPE: PRT
<213> ORGANISM: Hepatitis B virus

<400> SEQUENCE: 67

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Thr
                85                  90                  95

Leu Ala Thr Trp Val Gly Val Asn Leu Glu Asp Pro Ala Thr Arg Asp
            100                 105                 110
```

```
Leu Val Val Ser Tyr Val Asn Thr Asn Val Gly Leu Lys Phe Arg Gln
        115                 120                 125

Leu Leu Trp Phe His Ile Ser Cys Leu Thr Phe Gly Arg Glu Thr Val
        130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
                180                 185                 190

Arg Arg Arg Arg Ser Gln Ser Pro Arg Arg Arg Arg Ser Gln Ser Arg
        195                 200                 205

Glu Ser Gln Cys
    210

<210> SEQ ID NO 68
<211> LENGTH: 212
<212> TYPE: PRT
<213> ORGANISM: Hepatitis B virus

<400> SEQUENCE: 68

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Arg Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
        130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
                180                 185                 190

Arg Arg Arg Arg Ser Gln Ser Pro Arg Arg Arg Thr Arg Ser Gln Ser Arg
        195                 200                 205

Glu Ser Gln Cys
    210

<210> SEQ ID NO 69
<211> LENGTH: 212
<212> TYPE: PRT
<213> ORGANISM: Hepatitis B virus

<400> SEQUENCE: 69
```

-continued

```
Met Gln Leu Phe His Leu Cys Leu Val Ile Ser Cys Ser Cys Pro Thr
1               5                   10                  15

Val Gln Ala Ser Lys Leu Cys Leu Gly Trp Leu Trp Gly Met Asp Ile
                20                  25                  30

Asp Pro Tyr Lys Glu Phe Gly Ala Thr Val Glu Leu Leu Ser Phe Leu
            35                  40                  45

Pro Ser Asp Phe Phe Pro Ser Val Arg Asp Leu Leu Asp Thr Ala Ala
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Asn Asn Leu Glu Asp Pro Ala Ser Arg Asp
                100                 105                 110

Leu Val Val Asn Tyr Val Asn Thr Asn Met Gly Leu Lys Ile Arg Gln
            115                 120                 125

Leu Leu Trp Phe His Ile Ser Cys Leu Thr Phe Gly Arg Glu Thr Val
    130                 135                 140

Leu Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Thr Pro Ser Pro
                180                 185                 190

Arg Arg Arg Arg Ser Gln Ser Pro Arg Arg Arg Ser Gln Ser Arg
    195                 200                 205

Glu Ser Gln Cys
    210

<210> SEQ ID NO 70
<211> LENGTH: 212
<212> TYPE: PRT
<213> ORGANISM: Hepatitis B virus

<400> SEQUENCE: 70

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
                20                  25                  30

Asp Pro Tyr Lys Glu Phe Gly Ala Thr Val Glu Leu Leu Ser Phe Leu
            35                  40                  45

Pro Ser Ala Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Asp Leu Met Thr
                85                  90                  95

Leu Ala Thr Trp Val Gly Val Asn Leu Glu Asp Pro Ala Ser Arg Asp
                100                 105                 110

Leu Val Val Ser Tyr Val Asn Thr Asn Met Gly Leu Lys Phe Arg Gln
            115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160
```

```
Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Thr Pro Ser Pro
            180                 185                 190

Arg Arg Arg Arg Ser Gln Ser Pro Arg Arg Arg Arg Ser Gln Ser Arg
            195                 200                 205

Glu Ser Gln Cys
        210

<210> SEQ ID NO 71
<211> LENGTH: 183
<212> TYPE: PRT
<213> ORGANISM: Hepatitis B virus

<400> SEQUENCE: 71

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 72
<211> LENGTH: 183
<212> TYPE: PRT
<213> ORGANISM: Hepatitis B virus

<400> SEQUENCE: 72

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Gly Asn Leu Glu Asp Pro Ile
65                  70                  75                  80
```

```
Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Cys Val Val Arg Arg Gly Arg Ser Pro Arg Arg Arg Thr
145                 150                 155                 160

Pro Ser Pro Arg Arg Arg Ser Gln Ser Pro Arg Arg Arg Ser
                165                 170                 175

Gln Ser Arg Gly Ser Gln Cys
            180

<210> SEQ ID NO 73
<211> LENGTH: 188
<212> TYPE: PRT
<213> ORGANISM: Woodchuck Hepatitis B virus

<400> SEQUENCE: 73

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
            20                  25                  30

Thr Ala Thr Ala Leu Tyr Glu Glu Leu Thr Gly Arg Glu His Cys
        35                  40                  45

Ser Pro His His Thr Ala Ile Arg Gln Ala Leu Val Cys Trp Asp Glu
    50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
            100                 105                 110

His Thr Val Gln Glu Phe Leu Val Ser Phe Gly Val Trp Ile Arg Thr
        115                 120                 125

Pro Ala Pro Tyr Arg Pro Pro Asn Ala Pro Ile Leu Ser Thr Leu Pro
    130                 135                 140

Glu His Thr Val Ile Arg Arg Gly Gly Ala Arg Ala Ser Arg Ser
145                 150                 155                 160

Pro Arg Arg Arg Thr Pro Ser Pro Arg Arg Arg Ser Gln Ser Pro
                165                 170                 175

Arg Arg Arg Arg Ser Gln Ser Pro Ser Thr Asn Cys
            180                 185

<210> SEQ ID NO 74
<211> LENGTH: 217
<212> TYPE: PRT
<213> ORGANISM: Ground squirrel hepatitis virus

<400> SEQUENCE: 74

Met Tyr Leu Phe His Leu Cys Leu Val Phe Ala Cys Val Pro Cys Pro
1               5                   10                  15

Thr Val Gln Ala Ser Lys Leu Cys Leu Gly Trp Leu Trp Asp Met Asp
            20                  25                  30
```

```
Ile Asp Pro Tyr Lys Glu Phe Gly Ser Ser Tyr Gln Leu Leu Asn Phe
        35                  40                  45

Leu Pro Leu Asp Phe Phe Pro Asp Leu Asn Ala Leu Val Asp Thr Ala
    50                  55                  60

Ala Ala Leu Tyr Glu Glu Leu Thr Gly Arg Glu His Cys Ser Pro
65                  70                  75                  80

His His Thr Ala Ile Arg Gln Ala Leu Val Cys Trp Glu Glu Leu Thr
                85                  90                  95

Arg Leu Ile Thr Trp Met Ser Glu Asn Thr Thr Glu Glu Val Arg Arg
                100                 105                 110

Ile Ile Val Asp His Val Asn Asn Thr Trp Gly Leu Lys Val Arg Gln
                115                 120                 125

Thr Leu Trp Phe His Leu Ser Cys Leu Thr Phe Gly Gln His Thr Val
                130                 135                 140

Gln Glu Phe Leu Val Ser Phe Gly Val Trp Ile Arg Thr Pro Ala Pro
145                 150                 155                 160

Tyr Arg Pro Pro Asn Ala Pro Ile Leu Ser Thr Leu Pro Glu His Thr
                165                 170                 175

Val Ile Arg Arg Arg Gly Gly Ser Arg Ala Ala Arg Ser Pro Arg Arg
                180                 185                 190

Arg Thr Pro Ser Pro Arg Arg Arg Ser Gln Ser Pro Arg Arg Arg
                195                 200                 205

Arg Ser Gln Ser Pro Ala Ser Asn Cys
    210                 215

<210> SEQ ID NO 75
<211> LENGTH: 262
<212> TYPE: PRT
<213> ORGANISM: Snow Goose Hepatitis B virus

<400> SEQUENCE: 75

Met Asp Val Asn Ala Ser Arg Ala Leu Ala Asn Val Tyr Asp Leu Pro
1               5                   10                  15

Asp Asp Phe Phe Pro Lys Ile Glu Asp Leu Val Arg Asp Ala Lys Asp
                20                  25                  30

Ala Leu Glu Pro Tyr Trp Lys Ser Asp Ser Ile Lys Lys His Val Leu
        35                  40                  45

Ile Ala Thr His Phe Val Asp Leu Ile Glu Asp Phe Trp Gln Thr Thr
    50                  55                  60

Gln Gly Met His Glu Ile Ala Glu Ala Ile Arg Ala Val Ile Pro Pro
65                  70                  75                  80

Thr Thr Ala Pro Val Pro Ser Gly Tyr Leu Ile Gln His Asp Glu Ala
                85                  90                  95

Glu Glu Ile Pro Leu Gly Asp Leu Phe Lys Glu Gln Glu Glu Arg Ile
                100                 105                 110

Val Ser Phe Gln Pro Asp Tyr Pro Ile Thr Ala Arg Ile His Ala His
                115                 120                 125

Leu Lys Ala Tyr Ala Lys Ile Asn Glu Glu Ser Leu Asp Arg Ala Arg
                130                 135                 140

Arg Leu Leu Trp Trp His Tyr Asn Cys Leu Leu Trp Gly Glu Ala Thr
145                 150                 155                 160

Val Thr Asn Tyr Ile Ser Arg Leu Arg Thr Trp Leu Ser Thr Pro Glu
                165                 170                 175

Lys Tyr Arg Gly Arg Asp Ala Pro Thr Ile Glu Ala Ile Thr Arg Pro
```

-continued

```
                180                 185                 190
Ile Gln Val Ala Gln Gly Gly Arg Lys Thr Ser Thr Ala Thr Arg Lys
            195                 200                 205

Pro Arg Gly Leu Glu Pro Arg Arg Lys Val Lys Thr Thr Val Val
        210                 215                 220

Tyr Gly Arg Arg Arg Ser Lys Ser Arg Glu Arg Arg Ala Ser Ser Pro
225                 230                 235                 240

Gln Arg Ala Gly Ser Pro Leu Pro Arg Ser Ser Ser His His Arg
                245                 250                 255

Ser Pro Ser Pro Arg Lys
            260

<210> SEQ ID NO 76
<211> LENGTH: 305
<212> TYPE: PRT
<213> ORGANISM: Duck Hepatitis B virus

<400> SEQUENCE: 76

Met Trp Asp Leu Arg Leu His Pro Ser Pro Phe Gly Ala Ala Cys Gln
1               5                   10                  15

Gly Ile Phe Thr Ser Ser Leu Leu Phe Leu Val Thr Val Pro Leu
            20                  25                  30

Val Cys Thr Ile Val Tyr Asp Ser Cys Leu Cys Met Asp Ile Asn Ala
                35                  40                  45

Ser Arg Ala Leu Ala Asn Val Tyr Asp Leu Pro Asp Asp Phe Phe Pro
        50                  55                  60

Lys Ile Asp Asp Leu Val Arg Asp Ala Lys Asp Ala Leu Glu Pro Tyr
65                  70                  75                  80

Trp Arg Asn Asp Ser Ile Lys Lys His Val Leu Ile Ala Thr His Phe
                85                  90                  95

Val Asp Leu Ile Glu Asp Phe Trp Gln Thr Thr Gln Gly Met His Glu
            100                 105                 110

Ile Ala Glu Ala Leu Arg Ala Ile Ile Pro Ala Thr Thr Ala Pro Val
        115                 120                 125

Pro Gln Gly Phe Leu Val Gln His Glu Glu Ala Glu Glu Ile Pro Leu
    130                 135                 140

Gly Glu Leu Phe Arg Tyr Gln Glu Glu Arg Leu Thr Asn Phe Gln Pro
145                 150                 155                 160

Asp Tyr Pro Val Thr Ala Arg Ile His Ala His Leu Lys Ala Tyr Ala
                165                 170                 175

Lys Ile Asn Glu Glu Ser Leu Asp Arg Ala Arg Arg Leu Leu Trp Trp
            180                 185                 190

His Tyr Asn Cys Leu Leu Trp Gly Glu Pro Asn Val Thr Asn Tyr Ile
        195                 200                 205

Ser Arg Leu Arg Thr Trp Leu Ser Thr Pro Glu Lys Tyr Arg Gly Lys
    210                 215                 220

Asp Ala Pro Thr Ile Glu Ala Ile Thr Arg Pro Ile Gln Val Ala Gln
225                 230                 235                 240

Gly Gly Arg Asn Lys Thr Gln Gly Val Arg Lys Ser Arg Gly Leu Glu
                245                 250                 255

Pro Arg Arg Arg Arg Val Lys Thr Thr Ile Val Tyr Gly Arg Arg Arg
            260                 265                 270

Ser Lys Ser Arg Glu Arg Arg Ala Pro Thr Pro Gln Arg Ala Gly Ser
        275                 280                 285
```

```
Pro Leu Pro Arg Thr Ser Arg Asp His His Arg Ser Pro Ser Pro Arg
    290                 295                 300

Glu
305

<210> SEQ ID NO 77
<211> LENGTH: 185
<212> TYPE: PRT
<213> ORGANISM: Hepatitis B virus

<400> SEQUENCE: 77

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Arg Ser Gln Ser Pro Arg Arg Arg
                165                 170                 175

Arg Ser Gln Ser Arg Glu Ser Gln Cys
            180                 185

<210> SEQ ID NO 78
<211> LENGTH: 152
<212> TYPE: PRT
<213> ORGANISM: Hepatitis B

<400> SEQUENCE: 78

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Gly Gly
65                  70                  75                  80

Lys Gly Gly Ser Arg Asp Leu Val Val Ser Tyr Val Asn Thr Asn Val
                85                  90                  95

Gly Leu Lys Phe Arg Gln Leu Leu Trp Phe His Ile Ser Cys Leu Thr
            100                 105                 110
```

```
Phe Gly Arg Glu Thr Val Leu Glu Tyr Leu Val Ser Phe Gly Val Trp
        115                 120                 125
Ile Arg Thr Pro Pro Ala Tyr Arg Pro Pro Asn Ala Pro Ile Leu Ser
130                 135                 140
Thr Leu Pro Glu Thr Thr Val Val
145                 150

<210> SEQ ID NO 79
<211> LENGTH: 317
<212> TYPE: PRT
<213> ORGANISM: Homo sapiens

<400> SEQUENCE: 79

Met Arg Arg Ala Ser Arg Asp Tyr Thr Lys Tyr Leu Arg Gly Ser Glu
1               5                   10                  15
Glu Met Gly Gly Gly Pro Gly Ala Pro His Glu Gly Pro Leu His Ala
                20                  25                  30
Pro Pro Pro Ala Pro His Gln Pro Ala Ala Ser Arg Ser Met
            35                  40                  45
Phe Val Ala Leu Leu Gly Leu Gly Leu Gly Gln Val Val Cys Ser Val
50                  55                  60
Ala Leu Phe Phe Tyr Phe Arg Ala Gln Met Asp Pro Asn Arg Ile Ser
65                  70                  75                  80
Glu Asp Gly Thr His Cys Ile Tyr Arg Ile Leu Arg Leu His Glu Asn
                85                  90                  95
Ala Asp Phe Gln Asp Thr Thr Leu Glu Ser Gln Asp Thr Lys Leu Ile
            100                 105                 110
Pro Asp Ser Cys Arg Arg Ile Lys Gln Ala Phe Gln Gly Ala Val Gln
        115                 120                 125
Lys Glu Leu Gln His Ile Val Gly Ser Gln His Ile Arg Ala Glu Lys
130                 135                 140
Ala Met Val Asp Gly Ser Trp Leu Asp Leu Ala Lys Arg Ser Lys Leu
145                 150                 155                 160
Glu Ala Gln Pro Phe Ala His Leu Thr Ile Asn Ala Thr Asp Ile Pro
                165                 170                 175
Ser Gly Ser His Lys Val Ser Leu Ser Ser Trp Tyr His Asp Arg Gly
            180                 185                 190
Trp Ala Lys Ile Ser Asn Met Thr Phe Ser Asn Gly Lys Leu Ile Val
        195                 200                 205
Asn Gln Asp Gly Phe Tyr Tyr Leu Tyr Ala Asn Ile Cys Phe Arg His
210                 215                 220
His Glu Thr Ser Gly Asp Leu Ala Thr Glu Tyr Leu Gln Leu Met Val
225                 230                 235                 240
Tyr Val Thr Lys Thr Ser Ile Lys Ile Pro Ser Ser His Thr Leu Met
                245                 250                 255
Lys Gly Gly Ser Thr Lys Tyr Trp Ser Gly Asn Ser Glu Phe His Phe
            260                 265                 270
Tyr Ser Ile Asn Val Gly Gly Phe Phe Lys Leu Arg Ser Gly Glu Glu
        275                 280                 285
Ile Ser Ile Glu Val Ser Asn Pro Ser Leu Leu Asp Pro Asp Gln Asp
290                 295                 300
Ala Thr Tyr Phe Gly Ala Phe Lys Val Arg Asp Ile Asp
305                 310                 315

<210> SEQ ID NO 80
```

-continued

```
<211> LENGTH: 270
<212> TYPE: PRT
<213> ORGANISM: Homo sapiens

<400> SEQUENCE: 80

Met Phe Val Ala Leu Leu Gly Leu Gly Leu Gln Val Val Cys Ser
1               5                   10                  15

Val Ala Leu Phe Phe Tyr Phe Arg Ala Gln Met Asp Pro Asn Arg Ile
            20                  25                  30

Ser Glu Asp Gly Thr His Cys Ile Tyr Arg Ile Leu Arg Leu His Glu
        35                  40                  45

Asn Ala Asp Phe Gln Asp Thr Thr Leu Glu Ser Gln Asp Thr Lys Leu
    50                  55                  60

Ile Pro Asp Ser Cys Arg Arg Ile Lys Gln Ala Phe Gln Gly Ala Val
65                  70                  75                  80

Gln Lys Glu Leu Gln His Ile Val Gly Ser Gln His Ile Arg Ala Glu
                85                  90                  95

Lys Ala Met Val Asp Gly Ser Trp Leu Asp Leu Ala Lys Arg Ser Lys
            100                 105                 110

Leu Glu Ala Gln Pro Phe Ala His Leu Thr Ile Asn Ala Thr Asp Ile
        115                 120                 125

Pro Ser Gly Ser His Lys Val Ser Leu Ser Ser Trp Tyr His Asp Arg
    130                 135                 140

Gly Trp Ala Lys Ile Ser Asn Met Thr Phe Ser Asn Gly Lys Leu Ile
145                 150                 155                 160

Val Asn Gln Asp Gly Phe Tyr Tyr Leu Tyr Ala Asn Ile Cys Phe Arg
                165                 170                 175

His His Glu Thr Ser Gly Asp Leu Ala Thr Glu Tyr Leu Gln Leu Met
            180                 185                 190

Val Tyr Val Thr Lys Thr Ser Ile Lys Ile Pro Ser Ser His Thr Leu
        195                 200                 205

Met Lys Gly Gly Ser Thr Lys Tyr Trp Ser Gly Asn Ser Glu Phe His
    210                 215                 220

Phe Tyr Ser Ile Asn Val Gly Gly Phe Phe Lys Leu Arg Ser Gly Glu
225                 230                 235                 240

Glu Ile Ser Ile Glu Val Ser Asn Pro Ser Leu Leu Asp Pro Asp Gln
                245                 250                 255

Asp Ala Thr Tyr Phe Gly Ala Phe Lys Val Arg Asp Ile Asp
            260                 265                 270

<210> SEQ ID NO 81
<211> LENGTH: 244
<212> TYPE: PRT
<213> ORGANISM: Homo sapiens

<400> SEQUENCE: 81

Met Asp Pro Asn Arg Ile Ser Glu Asp Gly Thr His Cys Ile Tyr Arg
1               5                   10                  15

Ile Leu Arg Leu His Glu Asn Ala Asp Phe Gln Asp Thr Thr Leu Glu
            20                  25                  30

Ser Gln Asp Thr Lys Leu Ile Pro Asp Ser Cys Arg Arg Ile Lys Gln
        35                  40                  45

Ala Phe Gln Gly Ala Val Gln Lys Glu Leu Gln His Ile Val Gly Ser
    50                  55                  60

Gln His Ile Arg Ala Glu Lys Ala Met Val Asp Gly Ser Trp Leu Asp
65                  70                  75                  80
```

```
Leu Ala Lys Arg Ser Lys Leu Glu Ala Gln Pro Phe Ala His Leu Thr
                85                  90                  95

Ile Asn Ala Thr Asp Ile Pro Ser Gly Ser His Lys Val Ser Leu Ser
            100                 105                 110

Ser Trp Tyr His Asp Arg Gly Trp Ala Lys Ile Ser Asn Met Thr Phe
            115                 120                 125

Ser Asn Gly Lys Leu Ile Val Asn Gln Asp Gly Phe Tyr Tyr Leu Tyr
        130                 135                 140

Ala Asn Ile Cys Phe Arg His His Glu Thr Ser Gly Asp Leu Ala Thr
145                 150                 155                 160

Glu Tyr Leu Gln Leu Met Val Tyr Val Thr Lys Thr Ser Ile Lys Ile
                165                 170                 175

Pro Ser Ser His Thr Leu Met Lys Gly Ser Thr Lys Tyr Trp Ser
            180                 185                 190

Gly Asn Ser Glu Phe His Phe Tyr Ser Ile Asn Val Gly Gly Phe Phe
        195                 200                 205

Lys Leu Arg Ser Gly Glu Glu Ile Ser Ile Glu Val Ser Asn Pro Ser
210                 215                 220

Leu Leu Asp Pro Asp Gln Asp Ala Thr Tyr Phe Gly Ala Phe Lys Val
225                 230                 235                 240

Arg Asp Ile Asp

<210> SEQ ID NO 82
<211> LENGTH: 249
<212> TYPE: PRT
<213> ORGANISM: Homo sapiens

<400> SEQUENCE: 82

Tyr Phe Arg Ala Gln Met Asp Pro Asn Arg Ile Ser Glu Asp Gly Thr
1               5                   10                  15

His Cys Ile Tyr Arg Ile Leu Arg Leu His Glu Asn Ala Asp Phe Gln
                20                  25                  30

Asp Thr Thr Leu Glu Ser Gln Asp Thr Lys Leu Ile Pro Asp Ser Cys
            35                  40                  45

Arg Arg Ile Lys Gln Ala Phe Gln Gly Ala Val Gln Lys Glu Leu Gln
        50                  55                  60

His Ile Val Gly Ser Gln His Ile Arg Ala Glu Lys Ala Met Val Asp
65                  70                  75                  80

Gly Ser Trp Leu Asp Leu Ala Lys Arg Ser Lys Leu Glu Ala Gln Pro
                85                  90                  95

Phe Ala His Leu Thr Ile Asn Ala Thr Asp Ile Pro Ser Gly Ser His
            100                 105                 110

Lys Val Ser Leu Ser Ser Trp Tyr His Asp Arg Gly Trp Ala Lys Ile
        115                 120                 125

Ser Asn Met Thr Phe Ser Asn Gly Lys Leu Ile Val Asn Gln Asp Gly
    130                 135                 140

Phe Tyr Tyr Leu Tyr Ala Asn Ile Cys Phe Arg His His Glu Thr Ser
145                 150                 155                 160

Gly Asp Leu Ala Thr Glu Tyr Leu Gln Leu Met Val Tyr Val Thr Lys
                165                 170                 175

Thr Ser Ile Lys Ile Pro Ser Ser His Thr Leu Met Lys Gly Gly Ser
            180                 185                 190

Thr Lys Tyr Trp Ser Gly Asn Ser Glu Phe His Phe Tyr Ser Ile Asn
        195                 200                 205
```

```
Val Gly Gly Phe Phe Lys Leu Arg Ser Gly Glu Ile Ser Ile Glu
        210                 215                 220

Val Ser Asn Pro Ser Leu Leu Asp Pro Asp Gln Asp Ala Thr Tyr Phe
225                 230                 235                 240

Gly Ala Phe Lys Val Arg Asp Ile Asp
                245

<210> SEQ ID NO 83
<211> LENGTH: 178
<212> TYPE: PRT
<213> ORGANISM: Homo sapiens

<400> SEQUENCE: 83

Ile Arg Ala Glu Lys Ala Met Val Asp Gly Ser Trp Leu Asp Leu Ala
1               5                   10                  15

Lys Arg Ser Lys Leu Glu Ala Gln Pro Phe Ala His Leu Thr Ile Asn
                20                  25                  30

Ala Thr Asp Ile Pro Ser Gly Ser His Lys Val Ser Leu Ser Ser Trp
            35                  40                  45

Tyr His Asp Arg Gly Trp Ala Lys Ile Ser Asn Met Thr Phe Ser Asn
        50                  55                  60

Gly Lys Leu Ile Val Asn Gln Asp Gly Phe Tyr Tyr Leu Tyr Ala Asn
65                  70                  75                  80

Ile Cys Phe Arg His His Glu Thr Ser Gly Asp Leu Ala Thr Glu Tyr
                85                  90                  95

Leu Gln Leu Met Val Tyr Val Thr Lys Thr Ser Ile Lys Ile Pro Ser
                100                 105                 110

Ser His Thr Leu Met Lys Gly Gly Ser Thr Lys Tyr Trp Ser Gly Asn
            115                 120                 125

Ser Glu Phe His Phe Tyr Ser Ile Asn Val Gly Gly Phe Phe Lys Leu
        130                 135                 140

Arg Ser Gly Glu Glu Ile Ser Ile Glu Val Ser Asn Pro Ser Leu Leu
145                 150                 155                 160

Asp Pro Asp Gln Asp Ala Thr Tyr Phe Gly Ala Phe Lys Val Arg Asp
                165                 170                 175

Ile Asp

<210> SEQ ID NO 84
<211> LENGTH: 159
<212> TYPE: PRT
<213> ORGANISM: Homo sapiens

<400> SEQUENCE: 84

Lys Leu Glu Ala Gln Pro Phe Ala His Leu Thr Ile Asn Ala Thr Asp
1               5                   10                  15

Ile Pro Ser Gly Ser His Lys Val Ser Leu Ser Ser Trp Tyr His Asp
                20                  25                  30

Arg Gly Trp Ala Lys Ile Ser Asn Met Thr Phe Ser Asn Gly Lys Leu
            35                  40                  45

Ile Val Asn Gln Asp Gly Phe Tyr Tyr Leu Tyr Ala Asn Ile Cys Phe
        50                  55                  60

Arg His His Glu Thr Ser Gly Asp Leu Ala Thr Glu Tyr Leu Gln Leu
65                  70                  75                  80

Met Val Tyr Val Thr Lys Thr Ser Ile Lys Ile Pro Ser Ser His Thr
                85                  90                  95
```

```
Leu Met Lys Gly Gly Ser Thr Lys Tyr Trp Ser Gly Asn Ser Glu Phe
            100                 105                 110

His Phe Tyr Ser Ile Asn Val Gly Phe Phe Lys Leu Arg Ser Gly
        115                 120                 125

Glu Glu Ile Ser Ile Glu Val Ser Asn Pro Ser Leu Leu Asp Pro Asp
    130                 135                 140

Gln Asp Ala Thr Tyr Phe Gly Ala Phe Lys Val Arg Asp Ile Asp
145                 150                 155
```

<210> SEQ ID NO 85
<211> LENGTH: 247
<212> TYPE: PRT
<213> ORGANISM: Mus sp.

<400> SEQUENCE: 85

```
Tyr Phe Arg Ala Gln Met Asp Pro Asn Arg Ile Ser Glu Asp Ser Thr
1               5                   10                  15

His Cys Phe Tyr Arg Ile Leu Arg Leu His Glu Asn Ala Gly Leu Gln
            20                  25                  30

Asp Ser Thr Leu Glu Ser Glu Asp Thr Leu Pro Asp Ser Cys Arg Arg
        35                  40                  45

Met Lys Gln Ala Phe Gln Gly Ala Val Gln Lys Glu Leu Gln His Ile
    50                  55                  60

Val Gly Pro Gln Arg Phe Ser Gly Ala Pro Ala Met Met Glu Gly Ser
65                  70                  75                  80

Trp Leu Asp Val Ala Gln Arg Gly Lys Pro Glu Ala Gln Pro Phe Ala
                85                  90                  95

His Leu Thr Ile Asn Ala Ala Ser Ile Pro Ser Gly Ser His Lys Val
            100                 105                 110

Thr Leu Ser Ser Trp Tyr His Asp Arg Gly Trp Ala Lys Ile Ser Asn
        115                 120                 125

Met Thr Leu Ser Asn Gly Lys Leu Arg Val Asn Gln Asp Gly Phe Tyr
    130                 135                 140

Tyr Leu Tyr Ala Asn Ile Cys Phe Arg His His Glu Thr Ser Gly Ser
145                 150                 155                 160

Val Pro Thr Asp Tyr Leu Gln Leu Met Val Tyr Val Lys Thr Ser
                165                 170                 175

Ile Lys Ile Pro Ser Ser His Asn Leu Met Lys Gly Gly Ser Thr Lys
            180                 185                 190

Asn Trp Ser Gly Asn Ser Glu Phe His Phe Tyr Ser Ile Asn Val Gly
        195                 200                 205

Gly Phe Phe Lys Leu Arg Ala Gly Glu Glu Ile Ser Ile Gln Val Ser
    210                 215                 220

Asn Pro Ser Leu Leu Asp Pro Asp Gln Asp Ala Thr Tyr Phe Gly Ala
225                 230                 235                 240

Phe Lys Val Gln Asp Ile Asp
                245
```

<210> SEQ ID NO 86
<211> LENGTH: 199
<212> TYPE: PRT
<213> ORGANISM: Mus sp.

<400> SEQUENCE: 86

```
Met Lys Gln Ala Phe Gln Gly Ala Val Gln Lys Glu Leu Gln His Ile
1               5                   10                  15
```

-continued

```
Val Gly Pro Gln Arg Phe Ser Gly Ala Pro Ala Met Met Glu Gly Ser
             20                  25                  30
Trp Leu Asp Val Ala Gln Arg Gly Lys Pro Glu Ala Gln Pro Phe Ala
         35                  40                  45
His Leu Thr Ile Asn Ala Ala Ser Ile Pro Ser Gly Ser His Lys Val
     50                  55                  60
Thr Leu Ser Ser Trp Tyr His Asp Arg Gly Trp Ala Lys Ile Ser Asn
 65                  70                  75                  80
Met Thr Leu Ser Asn Gly Lys Leu Arg Val Asn Gln Asp Gly Phe Tyr
                 85                  90                  95
Tyr Leu Tyr Ala Asn Ile Cys Phe Arg His His Glu Thr Ser Gly Ser
            100                 105                 110
Val Pro Thr Asp Tyr Leu Gln Leu Met Val Tyr Val Val Lys Thr Ser
        115                 120                 125
Ile Lys Ile Pro Ser Ser His Asn Leu Met Lys Gly Gly Ser Thr Lys
130                 135                 140
Asn Trp Ser Gly Asn Ser Glu Phe His Phe Tyr Ser Ile Asn Val Gly
145                 150                 155                 160
Gly Phe Phe Lys Leu Arg Ala Gly Glu Glu Ile Ser Ile Gln Val Ser
                165                 170                 175
Asn Pro Ser Leu Leu Asp Pro Asp Gln Asp Ala Thr Tyr Phe Gly Ala
            180                 185                 190
Phe Lys Val Gln Asp Ile Asp
        195

<210> SEQ ID NO 87
<211> LENGTH: 24
<212> TYPE: PRT
<213> ORGANISM: Artificial Sequence
<220> FEATURE:
<223> OTHER INFORMATION: RANKL peptides AA" loop

<400> SEQUENCE: 87

Asn Ala Thr Asp Ile Pro Ser Gly Ser His Lys Val Ser Leu Ser Ser
 1               5                  10                  15
Trp Tyr His Asp Arg Gly Trp Ala
             20

<210> SEQ ID NO 88
<211> LENGTH: 8
<212> TYPE: PRT
<213> ORGANISM: Artificial Sequence
<220> FEATURE:
<223> OTHER INFORMATION: RANKL peptides DE loop

<400> SEQUENCE: 88

Ser Ile Lys Ile Pro Ser Ser His
 1               5

<210> SEQ ID NO 89
<211> LENGTH: 11
<212> TYPE: PRT
<213> ORGANISM: Artificial Sequence
<220> FEATURE:
<223> OTHER INFORMATION: RANKL peptide b-strand D

<400> SEQUENCE: 89

Tyr Leu Gln Leu Met Val Tyr Val Thr Lys Thr
 1               5                  10
```

<210> SEQ ID NO 90
<211> LENGTH: 10
<212> TYPE: PRT
<213> ORGANISM: Artificial Sequence
<220> FEATURE:
<223> OTHER INFORMATION: RANKL peptide CD loop

<400> SEQUENCE: 90

His Glu Thr Ser Gly Asp Leu Ala Thr Glu
1               5                   10

<210> SEQ ID NO 91
<211> LENGTH: 11
<212> TYPE: PRT
<213> ORGANISM: Artificial Sequence
<220> FEATURE:
<223> OTHER INFORMATION: RANKL peptide EF loop

<400> SEQUENCE: 91

Lys Tyr Trp Ser Gly Asn Ser Glu Phe His Phe
1               5                   10

<210> SEQ ID NO 92
<211> LENGTH: 8
<212> TYPE: PRT
<213> ORGANISM: Artificial Sequence
<220> FEATURE:
<223> OTHER INFORMATION: RANKL peptide B strand-B'B loop

<400> SEQUENCE: 92

Thr Phe Ser Asn Gly Lys Leu Ile
1               5

<210> SEQ ID NO 93
<211> LENGTH: 6
<212> TYPE: PRT
<213> ORGANISM: Artificial Sequence
<220> FEATURE:
<223> OTHER INFORMATION: RANKL peptide GH loop

<400> SEQUENCE: 93

Asp Pro Asp Gln Asp Ala
1               5

<210> SEQ ID NO 94
<211> LENGTH: 1269
<212> TYPE: DNA
<213> ORGANISM: Artificial Sequence
<220> FEATURE:
<223> OTHER INFORMATION: GST-PS-C-RANKL cDNA sequence (mouse RANKL)

<400> SEQUENCE: 94

```
atgtcccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaagtttga attgggtttg agtttccca atcttcctta ttatattgat      180
ggtgatgtta aattaacaca gtctatggcc atcatacgtt atatagctga caagcacaac    240
atgttgggtg gttgtccaaa agagcgtgca gagatttcaa tgcttgaagg agcggttttg    300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttatatga cgctcttgat    480
gttgttttat acatggaccc aatgtgcctg gatgcgttcc caaaattagt ttgtttttaa    540
```

```
aaacgtattg aagctatccc acaaattgat aagtacttga atccagcaa gtatatagca    600 tggcctttgc agggctggca agccacgttt ggtggtggcg accatcctcc aaaatcggat    660
ctggaagttc tgttccaggg gcccgggtgc ggcggtggcc atcatcacca ccatcaccag    720
cgcttctcag gagctccagc tatgatggaa ggctcatggt tggatgtggc ccagcgaggc    780
aagcctgagg cccagccatt tgcacacctc accatcaatg ctgccagcat cccatcgggt    840
tcccataaag tcactctgtc ctcttggtac cacgatcgag gctgggccaa gatctctaac    900
atgacgttaa gcaacggaaa actaaggggtt aaccaagatg gcttctatta cctgtacgcc    960
aacatttgct ttcggcatca tgaaacatcg ggaagcgtac ctacagacta tcttcagctg   1020
atggtgtatg tcgttaaaac cagcatcaaa atcccaagtt ctcataacct gatgaaagga   1080
gggagcacga aaaactggtc gggcaattct gaattccact tttattccat aaatgttggg   1140
ggatttttca agctccgagc tggtgaagaa attagcattc aggtgtccaa cccttccctg   1200
ctggatccgg atcaagatgc gacgtacttt ggggctttca agttcagga catagactaa   1260 ctcgagcgg                                                           1269
```

<210> SEQ ID NO 95
<211> LENGTH: 418
<212> TYPE: PRT
<213> ORGANISM: Artificial Sequence
<220> FEATURE:
<223> OTHER INFORMATION: GST-PS-C-RANKL protein sequence (mouse RANKL)

<400> SEQUENCE: 95

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Lys Tyr Glu Glu His Leu Tyr
            20                  25                  30

Glu Arg Asp Glu Gly Asp Lys Trp Arg Asn Lys Lys Phe Glu Leu Gly
        35                  40                  45

Leu Glu Phe Pro Asn Leu Pro Tyr Tyr Ile Asp Gly Asp Val Lys Leu
    50                  55                  60

Thr Gln Ser Met Ala Ile Ile Arg Tyr Ile Ala Asp Lys His Asn Met
65                  70                  75                  80

Leu Gly Gly Cys Pro Lys Glu Arg Ala Glu Ile Ser Met Leu Glu Gly
                85                  90                  95

Ala Val Leu Asp Ile Arg Tyr Gly Val Ser Arg Ile Ala Tyr Ser Lys
            100                 105                 110

Asp Phe Glu Thr Leu Lys Val Asp Phe Leu Ser Lys Leu Pro Glu Met
        115                 120                 125

Leu Lys Met Phe Glu Asp Arg Leu Cys His Lys Thr Tyr Leu Asn Gly
    130                 135                 140

Asp His Val Thr His Pro Asp Phe Met Leu Tyr Asp Ala Leu Asp Val
145                 150                 155                 160

Val Leu Tyr Met Asp Pro Met Cys Leu Asp Ala Phe Pro Lys Leu Val
                165                 170                 175

Cys Phe Lys Lys Arg Ile Glu Ala Ile Pro Gln Ile Asp Lys Tyr Leu
            180                 185                 190

Lys Ser Ser Lys Tyr Ile Ala Trp Pro Leu Gln Gly Trp Gln Ala Thr
        195                 200                 205

Phe Gly Gly Gly Asp His Pro Pro Lys Ser Asp Leu Glu Val Leu Phe
    210                 215                 220

Gln Gly Pro Gly Cys Gly Gly Gly His His His His His His Gln Arg
```

```
                225                 230                 235                 240
Phe Ser Gly Ala Pro Ala Met Met Glu Gly Ser Trp Leu Asp Val Ala
                245                 250                 255
Gln Arg Gly Lys Pro Glu Ala Gln Pro Phe Ala His Leu Thr Ile Asn
            260                 265                 270
Ala Ala Ser Ile Pro Ser Gly Ser His Lys Val Thr Leu Ser Ser Trp
        275                 280                 285
Tyr His Asp Arg Gly Trp Ala Lys Ile Ser Asn Met Thr Leu Ser Asn
    290                 295                 300
Gly Lys Leu Arg Val Asn Gln Asp Gly Phe Tyr Tyr Leu Tyr Ala Asn
305                 310                 315                 320
Ile Cys Phe Arg His His Glu Thr Ser Gly Ser Val Pro Thr Asp Tyr
                325                 330                 335
Leu Gln Leu Met Val Tyr Val Val Lys Thr Ser Ile Lys Ile Pro Ser
                340                 345                 350
Ser His Asn Leu Met Lys Gly Gly Ser Thr Lys Asn Trp Ser Gly Asn
            355                 360                 365
Ser Glu Phe His Phe Tyr Ser Ile Asn Val Gly Gly Phe Phe Lys Leu
        370                 375                 380
Arg Ala Gly Glu Glu Ile Ser Ile Gln Val Ser Asn Pro Ser Leu Leu
385                 390                 395                 400
Asp Pro Asp Gln Asp Ala Thr Tyr Phe Gly Ala Phe Lys Val Gln Asp
                405                 410                 415
Ile Asp

<210> SEQ ID NO 96
<211> LENGTH: 193
<212> TYPE: PRT
<213> ORGANISM: Mus sp.

<400> SEQUENCE: 96

Gly Pro Gly Cys Gly Gly Gly His His His His His Gln Arg Phe
1               5                   10                  15
Ser Gly Ala Pro Ala Met Met Glu Gly Ser Trp Leu Asp Val Ala Gln
            20                  25                  30
Arg Gly Lys Pro Glu Ala Gln Pro Phe Ala His Leu Thr Ile Asn Ala
        35                  40                  45
Ala Ser Ile Pro Ser Gly Ser His Lys Val Thr Leu Ser Ser Trp Tyr
    50                  55                  60
His Asp Arg Gly Trp Ala Lys Ile Ser Asn Met Thr Leu Ser Asn Gly
65                  70                  75                  80
Lys Leu Arg Val Asn Gln Asp Gly Phe Tyr Tyr Leu Tyr Ala Asn Ile
                85                  90                  95
Cys Phe Arg His His Glu Thr Ser Gly Ser Val Pro Thr Asp Tyr Leu
            100                 105                 110
Gln Leu Met Val Tyr Val Val Lys Thr Ser Ile Lys Ile Pro Ser Ser
        115                 120                 125
His Asn Leu Met Lys Gly Gly Ser Thr Lys Asn Trp Ser Gly Asn Ser
    130                 135                 140
Glu Phe His Phe Tyr Ser Ile Asn Val Gly Gly Phe Phe Lys Leu Arg
145                 150                 155                 160
Ala Gly Glu Glu Ile Ser Ile Gln Val Ser Asn Pro Ser Leu Leu Asp
                165                 170                 175
Pro Asp Gln Asp Ala Thr Tyr Phe Gly Ala Phe Lys Val Gln Asp Ile
```

```
                          180             185              190
Asp

<210> SEQ ID NO 97
<211> LENGTH: 1221
<212> TYPE: DNA
<213> ORGANISM: Artificial Sequence
<220> FEATURE:
<223> OTHER INFORMATION: GST-EK-RANKL-C cDNA sequence (mouse RANKL)

<400> SEQUENCE: 97
atggatccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg agtttcccca atcttcctta ttatattgat     180
ggtgatgtta aattaacaca gtctatggcc atcatacgtt atatagctga caagcacaac     240
atgttgggtg ttgtccaaa agagcgtgca gagatttcaa tgcttgaagg agcggttttg     300
gatattagat acgtgtttc gagaattgca tatagtaaag actttgaaac tctcaaagtt     360
gattttctta gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg atgcgttcc caaaattagt ttgttttaaa     540
aaacgtattg aagctatccc acaaattgat aagtacttga atccagcaa gtatatagca     600 tggcctttgc agggctggca agccacgttt ggtggtggcg accatcctcc aaaagctagt     660
atgactggtg gacagcaaat gggtcgggat ctgtacgacg atgacgataa gctagcaaag     720
cctgaggccc agccatttgc acacctcacc atcaatgctg ccagcatccc atcgggttcc     780
cataaagtca ctctgtcctc ttggtaccac gatcgaggct gggccaagat ctctaacatg     840
acgttaagca acggaaaact aagggttaac caagatggct tctattacct gtacgccaac     900
atttgctttc ggcatcatga acatcggga agcgtaccta cagactatct tcagctgatg     960
gtgtatgtcg ttaaaaccag catcaaaatc ccaagttctc ataacctgat gaaaggaggg    1020
agcacgaaaa actggtcggg caattctgaa ttccactttt attccataaa tgttggggga    1080
tttttcaagc tccgagctgg tgaagaaatt agcattcagg tgtccaaccc ttccctgctg    1140
gatccggatc aagatgcgac gtactttggg gctttcaaag ttcaggacat agacctcgag    1200
ggtggtggtg gtggttgcgg t                                              1221

<210> SEQ ID NO 98
<211> LENGTH: 407
<212> TYPE: PRT
<213> ORGANISM: Artificial Sequence
<220> FEATURE:
<223> OTHER INFORMATION: GST-EK-RANKL-C protein sequence (mouse RANKL)

<400> SEQUENCE: 98

Met Asp Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
```

```
                65                  70                  75                  80
Met Leu Gly Gly Cys Pro Lys Glu Arg Ala Glu Ile Ser Met Leu Glu
                    85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
                115                 120                 125

Met Leu Lys Met Phe Glu Asp Arg Leu Cys His Lys Thr Tyr Leu Asn
            130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
                195                 200                 205

Thr Phe Gly Gly Asp His Pro Pro Lys Ala Ser Met Thr Gly Gly
            210                 215                 220

Gln Gln Met Gly Arg Asp Leu Tyr Asp Asp Asp Lys Leu Ala Lys
225                 230                 235                 240

Pro Glu Ala Gln Pro Phe Ala His Leu Thr Ile Asn Ala Ala Ser Ile
                245                 250                 255

Pro Ser Gly Ser His Lys Val Thr Leu Ser Ser Trp Tyr His Asp Arg
                260                 265                 270

Gly Trp Ala Lys Ile Ser Asn Met Thr Leu Ser Asn Gly Lys Leu Arg
                275                 280                 285

Val Asn Gln Asp Gly Phe Tyr Tyr Leu Tyr Ala Asn Ile Cys Phe Arg
            290                 295                 300

His His Glu Thr Ser Gly Ser Val Pro Thr Asp Tyr Leu Gln Leu Met
305                 310                 315                 320

Val Tyr Val Val Lys Thr Ser Ile Lys Ile Pro Ser Ser His Asn Leu
                325                 330                 335

Met Lys Gly Gly Ser Thr Lys Asn Trp Ser Gly Asn Ser Glu Phe His
                340                 345                 350

Phe Tyr Ser Ile Asn Val Gly Gly Phe Phe Lys Leu Arg Ala Gly Glu
            355                 360                 365

Glu Ile Ser Ile Gln Val Ser Asn Pro Ser Leu Leu Asp Pro Asp Gln
            370                 375                 380

Asp Ala Thr Tyr Phe Gly Ala Phe Lys Val Gln Asp Ile Asp Leu Glu
385                 390                 395                 400

Gly Gly Gly Gly Gly Cys Gly
                405

<210> SEQ ID NO 99
<211> LENGTH: 170
<212> TYPE: PRT
<213> ORGANISM: Mus sp.

<400> SEQUENCE: 99

Leu Ala Lys Pro Glu Ala Gln Pro Phe Ala His Leu Thr Ile Asn Ala
1               5                   10                  15

Ala Ser Ile Pro Ser Gly Ser His Lys Val Thr Leu Ser Ser Trp Tyr
            20                  25                  30
```

-continued

```
His Asp Arg Gly Trp Ala Lys Ile Ser Asn Met Thr Leu Ser Asn Gly
        35                  40                  45

Lys Leu Arg Val Asn Gln Asp Gly Phe Tyr Tyr Leu Tyr Ala Asn Ile
    50                  55                  60

Cys Phe Arg His His Glu Thr Ser Gly Ser Val Pro Thr Asp Tyr Leu
65                  70                  75                  80

Gln Leu Met Val Tyr Val Lys Thr Ser Ile Lys Ile Pro Ser Ser
                85                  90                  95

His Asn Leu Met Lys Gly Gly Ser Thr Lys Asn Trp Ser Gly Asn Ser
                100                 105                 110

Glu Phe His Phe Tyr Ser Ile Asn Val Gly Gly Phe Lys Leu Arg
            115                 120                 125

Ala Gly Glu Glu Ile Ser Ile Gln Val Ser Asn Pro Ser Leu Leu Asp
        130                 135                 140

Pro Asp Gln Asp Ala Thr Tyr Phe Gly Ala Phe Lys Val Gln Asp Ile
145                 150                 155                 160

Asp Leu Glu Gly Gly Gly Gly Cys Gly
                165                 170
```

<210> SEQ ID NO 100
<211> LENGTH: 180
<212> TYPE: PRT
<213> ORGANISM: Homo sapiens

<400> SEQUENCE: 100

```
Gln His Ile Arg Ala Glu Lys Ala Met Val Asp Gly Ser Trp Leu Asp
1               5                   10                  15

Leu Ala Lys Arg Ser Lys Leu Glu Ala Gln Pro Phe Ala His Leu Thr
            20                  25                  30

Ile Asn Ala Thr Asp Ile Pro Ser Gly Ser His Lys Val Ser Leu Ser
        35                  40                  45

Ser Trp Tyr His Asp Arg Gly Trp Ala Lys Ile Ser Asn Met Thr Phe
    50                  55                  60

Ser Asn Gly Lys Leu Ile Val Asn Gln Asp Gly Phe Tyr Tyr Leu Tyr
65                  70                  75                  80

Ala Asn Ile Cys Phe Arg His His Glu Thr Ser Gly Asp Leu Ala Thr
                85                  90                  95

Glu Tyr Leu Gln Leu Met Val Tyr Val Thr Lys Thr Ser Ile Lys Ile
            100                 105                 110

Pro Ser Ser His Thr Leu Met Lys Gly Gly Ser Thr Lys Tyr Trp Ser
        115                 120                 125

Gly Asn Ser Glu Phe His Phe Tyr Ser Ile Asn Val Gly Gly Phe Phe
    130                 135                 140

Lys Leu Arg Ser Gly Glu Glu Ile Ser Ile Glu Val Ser Asn Pro Ser
145                 150                 155                 160

Leu Leu Asp Pro Asp Gln Asp Ala Thr Tyr Phe Gly Ala Phe Lys Val
                165                 170                 175

Arg Asp Ile Asp
180
```

<210> SEQ ID NO 101
<211> LENGTH: 158
<212> TYPE: PRT
<213> ORGANISM: Homo sapiens

<400> SEQUENCE: 101

```
Leu Glu Ala Gln Pro Phe Ala His Leu Thr Ile Asn Ala Thr Asp Ile
1               5                   10                  15

Pro Ser Gly Ser His Lys Val Ser Leu Ser Ser Trp Tyr His Asp Arg
            20                  25                  30

Gly Trp Ala Lys Ile Ser Asn Met Thr Phe Ser Asn Gly Lys Leu Ile
        35                  40                  45

Val Asn Gln Asp Gly Phe Tyr Tyr Leu Tyr Ala Asn Ile Cys Phe Arg
50                      55                  60

His His Glu Thr Ser Gly Asp Leu Ala Thr Glu Tyr Leu Gln Leu Met
65                  70                  75                  80

Val Tyr Val Thr Lys Thr Ser Ile Lys Ile Pro Ser Ser His Thr Leu
                85                  90                  95

Met Lys Gly Gly Ser Thr Lys Tyr Trp Ser Gly Asn Ser Glu Phe His
            100                 105                 110

Phe Tyr Ser Ile Asn Val Gly Gly Phe Phe Lys Leu Arg Ser Gly Glu
        115                 120                 125

Glu Ile Ser Ile Glu Val Ser Asn Pro Ser Leu Leu Asp Pro Asp Gln
    130                 135                 140

Asp Ala Thr Tyr Phe Gly Ala Phe Lys Val Arg Asp Ile Asp
145                 150                 155

<210> SEQ ID NO 102
<211> LENGTH: 187
<212> TYPE: PRT
<213> ORGANISM: Artificial Sequence
<220> FEATURE:
<223> OTHER INFORMATION: Human-C-RANKL with linker corresponding to
      mouse C-RANKL 96

<400> SEQUENCE: 102

Gly Cys Gly Gly Gly Gly Gln His Ile Arg Ala Glu Lys Ala Met
1               5                   10                  15

Val Asp Gly Ser Trp Leu Asp Leu Ala Lys Arg Ser Lys Leu Glu Ala
            20                  25                  30

Gln Pro Phe Ala His Leu Thr Ile Asn Ala Thr Asp Ile Pro Ser Gly
        35                  40                  45

Ser His Lys Val Ser Leu Ser Ser Trp Tyr His Asp Arg Gly Trp Ala
50                  55                  60

Lys Ile Ser Asn Met Thr Phe Ser Asn Gly Lys Leu Ile Val Asn Gln
65                  70                  75                  80

Asp Gly Phe Tyr Tyr Leu Tyr Ala Asn Ile Cys Phe Arg His His Glu
                85                  90                  95

Thr Ser Gly Asp Leu Ala Thr Glu Tyr Leu Gln Leu Met Val Tyr Val
            100                 105                 110

Thr Lys Thr Ser Ile Lys Ile Pro Ser Ser His Thr Leu Met Lys Gly
        115                 120                 125

Gly Ser Thr Lys Tyr Trp Ser Gly Asn Ser Glu Phe His Phe Tyr Ser
    130                 135                 140

Ile Asn Val Gly Gly Phe Phe Lys Leu Arg Ser Gly Glu Glu Ile Ser
145                 150                 155                 160

Ile Glu Val Ser Asn Pro Ser Leu Leu Asp Pro Asp Gln Asp Ala Thr
                165                 170                 175

Tyr Phe Gly Ala Phe Lys Val Arg Asp Ile Asp
            180                 185

<210> SEQ ID NO 103
```

```
<211> LENGTH: 165
<212> TYPE: PRT
<213> ORGANISM: Artificial Sequence
<220> FEATURE:
<223> OTHER INFORMATION: Human-C-RANKL with linker corresponding to
      mouse RANKL-C 99

<400> SEQUENCE: 103
```

Leu Glu Ala Gln Pro Phe Ala His Leu Thr Ile Asn Ala Thr Asp Ile
1               5                   10                  15

Pro Ser Gly Ser His Lys Val Ser Leu Ser Ser Trp Tyr His Asp Arg
            20                  25                  30

Gly Trp Ala Lys Ile Ser Asn Met Thr Phe Ser Asn Gly Lys Leu Ile
        35                  40                  45

Val Asn Gln Asp Gly Phe Tyr Tyr Leu Tyr Ala Asn Ile Cys Phe Arg
    50                  55                  60

His His Glu Thr Ser Gly Asp Leu Ala Thr Glu Tyr Leu Gln Leu Met
65                  70                  75                  80

Val Tyr Val Thr Lys Thr Ser Ile Lys Ile Pro Ser Ser His Thr Leu
                85                  90                  95

Met Lys Gly Gly Ser Thr Lys Tyr Trp Ser Gly Asn Ser Glu Phe His
            100                 105                 110

Phe Tyr Ser Ile Asn Val Gly Gly Phe Phe Lys Leu Arg Ser Gly Glu
        115                 120                 125

Glu Ile Ser Ile Glu Val Ser Asn Pro Ser Leu Leu Asp Pro Asp Gln
    130                 135                 140

Asp Ala Thr Tyr Phe Gly Ala Phe Lys Val Arg Asp Ile Asp Gly Gly
145                 150                 155                 160

Gly Gly Gly Cys Gly
                165

```
<210> SEQ ID NO 104
<211> LENGTH: 27
<212> TYPE: PRT
<213> ORGANISM: Artificial Sequence
<220> FEATURE:
<223> OTHER INFORMATION: RANKL peptides AA" loop

<400> SEQUENCE: 104
```

Cys Gly Gly Asn Ala Thr Asp Ile Pro Ser Gly Ser His Lys Val Ser
1               5                   10                  15

Leu Ser Ser Trp Tyr His Asp Arg Gly Trp Ala
            20                  25

```
<210> SEQ ID NO 105
<211> LENGTH: 11
<212> TYPE: PRT
<213> ORGANISM: RANKL peptides DE loop

<400> SEQUENCE: 105
```

Cys Gly Gly Ser Ile Lys Ile Pro Ser Ser His
1               5                   10

```
<210> SEQ ID NO 106
<211> LENGTH: 15
<212> TYPE: PRT
<213> ORGANISM: Artificial Sequence
<220> FEATURE:
<223> OTHER INFORMATION: RANKL peptide b-strand D

<400> SEQUENCE: 106
```

```
Cys Gly Gly Gly Tyr Leu Gln Leu Met Val Tyr Val Thr Lys Thr
1               5                   10                  15

<210> SEQ ID NO 107
<211> LENGTH: 13
<212> TYPE: PRT
<213> ORGANISM: Artificial Sequence
<220> FEATURE:
<223> OTHER INFORMATION: RANKL peptide CD loop

<400> SEQUENCE: 107

Cys Gly Gly His Glu Thr Ser Gly Asp Leu Ala Thr Glu
1               5                   10

<210> SEQ ID NO 108
<211> LENGTH: 14
<212> TYPE: PRT
<213> ORGANISM: Artificial Sequence
<220> FEATURE:
<223> OTHER INFORMATION: RANKL peptide EF loop

<400> SEQUENCE: 108

Cys Gly Gly Lys Tyr Trp Ser Gly Asn Ser Glu Phe His Phe
1               5                   10

<210> SEQ ID NO 109
<211> LENGTH: 11
<212> TYPE: PRT
<213> ORGANISM: Artificial Sequence
<220> FEATURE:
<223> OTHER INFORMATION: RANKL peptide B strand-B'B loop

<400> SEQUENCE: 109

Cys Gly Gly Thr Phe Ser Asn Gly Lys Leu Ile
1               5                   10

<210> SEQ ID NO 110
<211> LENGTH: 9
<212> TYPE: PRT
<213> ORGANISM: Artificial Sequence
<220> FEATURE:
<223> OTHER INFORMATION: RANKL peptide GH loop

<400> SEQUENCE: 110

Cys Gly Gly Asp Pro Asp Gln Asp Ala
1               5

<210> SEQ ID NO 111
<211> LENGTH: 3635
<212> TYPE: DNA
<213> ORGANISM: Artificial Sequence
<220> FEATURE:
<223> OTHER INFORMATION: pAP283-58

<400> SEQUENCE: 111
cgagctcgcc cctggcttat cgaaattaat acgactcact ataggagac cggaattcga      60 gctcgcccgg ggatcctcta gaattttctg cgcacccatc ccgggtggcg cccaaagtga    120
ggaaaatcac atggcaaata agccaatgca accgatcaca tctacagcaa ataaaattgt    180
gtggtcggat ccaactcgtt tatcaactac attttcagca agtctgttac gccaacgtgt    240
taaagttggt atagccgaac tgaataatgt ttcaggtcaa tatgtatctg tttataagcg    300
tcctgcacct aaaccggaag gttgtgcaga tgcctgtgtc attatgccga atgaaaacca    360
atccattcgc acagtgattt cagggtcagc cgaaaacttg gctaccttaa aagcagaatg    420
```

```
ggaaactcac aaacgtaacg ttgacacact cttcgcgagc ggcaacgccg gtttgggttt      480
ccttgaccct actgcggcta tcgtatcgtc tgatactact gcttaagctt gtattctata      540
gtgtcaccta atcgtatgt gtatgataca taaggttatg tattaattgt agccgcgttc      600
taacgacaat atgtacaagc ctaattgtgt agcatctggc ttactgaagc agaccctatc      660
atctctctcg taaactgccg tcagagtcgg tttggttgga cgaaccttct gagtttctgg      720
taacgccgtt ccgcaccccg gaaatggtca ccgaaccaat cagcagggtc atcgctagcc      780
agatcctcta cgccggacgc atcgtggccg gcatcaccgg cgccacaggt gcggttgctg      840
gcgcctatat cgccgacatc accgatgggg aagatcgggc tcgccacttc gggctcatga      900
gcgcttgttt cggcgtgggt atggtggcag gccccgtggc cggggggactg ttgggcgcca      960 tctccttgca tgcaccattc cttgcggcgg cggtgctcaa cggcctcaac ctactactgg     1020
gctgcttcct aatgcaggag tcgcataagg gagagcgtcg atatggtgca ctctcagtac     1080
aatctgctct gatgccgcat agttaagcca actccgctat cgctacgtga ctgggtcatg     1140
gctgcgcccc gacacccgcc aacacccgct gacgcgccct gacgggcttg tctgctcccg     1200
gcatccgctt acagacaagc tgtgaccgtc tccgggagct gcatgtgtca gaggttttca     1260
ccgtcatcac cgaaacgcgc gaggcagctt gaagacgaaa gggcctcgtg atacgcctat     1320 tttataggt taatgtcatg ataataatgg tttcttagac gtcaggtggc acttttcggg     1380
gaaatgtgcg cggaacccct atttgtttat ttttctaaat acattcaaat atgtatccgc     1440
tcatgagaca ataaccctga taaatgcttc aataatattg aaaaggaag agtatgagta     1500 ttcaacattt ccgtgtcgcc cttattccct tttttgcggc attttgcctt cctgtttttg     1560
ctcacccaga aacgctggtg aaagtaaaag atgctgaaga tcagttgggt gcacgagtgg     1620
gttacatcga actggatctc aacagcggta agatccttga gagttttcgc cccgaagaac     1680
gttttccaat gatgagcact tttaaagttc tgctatgtgg cgcggtatta tcccgtattg     1740
acgccgggca agagcaactc ggtcgccgca tacactattc tcagaatgac ttggttgagt     1800
actcaccagt cacagaaaag catcttacgg atggcatgac agtaagagaa ttatgcagtg     1860
ctgccataac catgagtgat aacactgcgg ccaacttact tctgacaacg atcggaggac     1920
cgaaggagct aaccgctttt ttgcacaaca tgggggatca tgtaactcgc cttgatcgtt     1980
gggaaccgga gctgaatgaa gccataccaa acgacgagcg tgacaccacg atgcctgtag     2040
caatggcaac aacgttgcgc aaactattaa ctggcgaact acttactcta gcttcccggc     2100
aacaattaat agactggatg gaggcggata agttgcagg accacttctg cgctcggccc     2160
ttccggctgg ctggtttatt gctgataaat ctggagccgg tgagcgtggg tctcgcggta     2220
tcattgcagc actggggcca gatggtaagc cctcccgtat cgtagttatc tacacgacgg     2280
ggagtcaggc aactatggat gaacgaaata gacagatcgc tgagataggt gcctcactga     2340
ttaagcattg gtaactgtca gaccaagttt actcatatat actttagatt gatttaaaac     2400 ttcatttta atttaaaagg atctaggtga agatcctttt tgataatctc atgaccaaaa     2460
tcccttaacg tgagttttcg ttccactgag cgtcagaccc cgtagaaaag atcaaaggat     2520
cttcttgaga tcctttttt ctgcgcgtaa tctgctgctt gcaaacaaaa aaaccaccgc     2580
taccagcggt ggtttgtttg ccggatcaag agctaccaac tcttttccg aagtaactg     2640 gcttcagcag agcgcagata ccaaatactg tccttctagt gtagccgtag ttaggccacc     2700
acttcaagaa ctctgtagca ccgcctacat acctcgctct gctaatcctg ttaccagtgg     2760
ctgctgccag tggcgataag tcgtgtctta ccgggttgga ctcaagacga tagttaccgg     2820
```

-continued

```
ataaggcgca gcggtcgggc tgaacggggg gttcgtgcac acagcccagc ttggagcgaa    2880
cgacctacac cgaactgaga tacctacagc gcgagcattg agaaagcgcc acgcttcccg    2940
aagggagaaa ggcggacagg tatccggtaa gcggcaggt cggaacagga gagcgcacga    3000
gggagcttcc aggggaaac gcctggtatc tttatagtcc tgtcgggttt cgccacctct    3060
gacttgagcg tcgattttg tgatgctcgt caggggggcg gagcctatgg aaaaacgcca    3120
gcaacgcggc ctttttacgg ttcctggcct tttgctggcc ttttgctcac atgttctttc    3180
ctgcgttatc ccctgattct gtggataacc gtattaccgc ctttgagtga gctgataccg    3240
ctcgccgcag ccgaacgacc gagcgcagcg agtcagtgag cgaggaagcg gaagagcgcc    3300
caatacgcaa accgcctctc cccgcgcgtt ggccgattca ttaatgcagc tgtggtgtca    3360
tggtcggtga tcgccagggt gccgacgcgc atctcgactg catggtgcac caatgcttct    3420
ggcgtcaggc agccatcgga agctgtggta tggccgtgca ggtcgtaaat cactgcataa    3480
ttcgtgtcgc tcaaggcgca ctcccgttct ggataatgtt ttttgcgccg acatcataac    3540
ggttctggca aatattctga aatgagctgt tgacaattaa tcatcgaact agttaactag    3600
tacgcaagtt cacgtaaaaa gggtatcgcg gaatt                              3635
```

<210> SEQ ID NO 112
<211> LENGTH: 131
<212> TYPE: PRT
<213> ORGANISM: Artificial Sequence
<220> FEATURE:
<223> OTHER INFORMATION: AP205 coat protein
<400> SEQUENCE: 112

Met Ala Asn Lys Pro Met Gln Pro Ile Thr Ser Thr Ala Asn Lys Ile
1               5                   10                  15

Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
        35                  40                  45

Gly Gln Tyr Val Ser Val Tyr Lys Arg Pro Ala Pro Lys Pro Glu Gly
    50                  55                  60

Cys Ala Asp Ala Cys Val Ile Met Pro Asn Glu Asn Gln Ser Ile Arg
65                  70                  75                  80

Thr Val Ile Ser Gly Ser Ala Glu Asn Leu Ala Thr Leu Lys Ala Glu
                85                  90                  95

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
        115                 120                 125

Thr Thr Ala
    130

<210> SEQ ID NO 113
<211> LENGTH: 131
<212> TYPE: PRT
<213> ORGANISM: Artificial Sequence
<220> FEATURE:
<223> OTHER INFORMATION: AP205 coat protein
<400> SEQUENCE: 113

Met Ala Asn Lys Thr Met Gln Pro Ile Thr Ser Thr Ala Asn Lys Ile
1               5                   10                  15

```
Val Trp Ser Asp Pro Thr Arg Leu Ser Thr Thr Phe Ser Ala Ser Leu
         20                  25                  30

Leu Arg Gln Arg Val Lys Val Gly Ile Ala Glu Leu Asn Asn Val Ser
     35                  40                  45

Gly Gln Tyr Val Ser Val Tyr Lys Arg Pro Ala Pro Lys Pro Glu Gly
 50                  55                  60

Cys Ala Asp Ala Cys Val Ile Met Pro Asn Glu Asn Gln Ser Ile Arg
 65                  70                  75                  80

Thr Val Ile Ser Gly Ser Ala Glu Asn Leu Ala Thr Leu Lys Ala Glu
             85                  90                  95

Trp Glu Thr His Lys Arg Asn Val Asp Thr Leu Phe Ala Ser Gly Asn
                100                 105                 110

Ala Gly Leu Gly Phe Leu Asp Pro Thr Ala Ala Ile Val Ser Ser Asp
            115                 120                 125

Thr Thr Ala
    130

<210> SEQ ID NO 114
<211> LENGTH: 3613
<212> TYPE: DNA
<213> ORGANISM: Artificial Sequence
<220> FEATURE:
<223> OTHER INFORMATION: pAP281-32

<400> SEQUENCE: 114
cgagctcgcc cctggcttat cgaaattaat acgactcact atagggagac cggaattcga      60
gctcgcccgg ggatcctcta gattaaccca acgcgtagga gtcaggccat ggcaaataag     120
acaatgcaac cgatcacatc tacagcaaat aaaattgtgt ggtcggatcc aactcgttta     180
tcaactacat tttcagcaag tctgttacgc caacgtgtta agttggtat  agccgaactg     240 aataatgttt caggtcaata tgtatctgtt tataagcgtc ctgcacctaa accggaaggt     300
tgtgcagatg cctgtgtcat tatgccgaat gaaaaccaat ccattcgcac agtgatttca     360
gggtcagccg aaaacttggc taccttaaaa gcagaatggg aaactcacaa acgtaacgtt     420
gacacactct cgcgagcgg  caacgccggt ttgggtttcc ttgaccctac tgcggctatc     480
gtatcgtctg atactactgc ttaagcttgt attctatagt gtcacctaaa tcgtatgtgt     540
atgatacata aggttatgta ttaattgtag ccgcgttcta acgacaatat gtacaagcct     600
aattgtgtag catctggctt actgaagcag accctatcat ctctctcgta aactgccgtc     660
agagtcggtt tggttggacg aaccttctga gtttctggta acgccgttcc gcaccccgga     720
aatggtcacc gaaccaatca gcagggtcat cgctagccag atcctctacg ccggacgcat     780
cgtggccggc atcaccggcg ccacaggtgc ggttgctggc gcctatatcg ccgacatcac     840
cgatggggaa gatcgggctc gccacttcgg gctcatgagc gcttgtttcg gcgtgggtat     900
ggtggcaggc cccgtggccg ggggactgtt ggcgccatc  tccttgcatg caccattcct     960
tgcggcggcg gtgctcaacg gcctcaacct actactgggc tgcttcctaa tgcaggagtc    1020
gcataaggga gagcgtcgat atggtgcact ctcagtacaa tctgctctga tgccgcatag    1080
ttaagccaac tccgctatcg ctacgtgact gggtcatggc tgcgccccga cacccgccaa    1140
cacccgctga cgcgccctga cgggcttgtc tgctcccggc atccgcttac agacaagctg    1200
tgaccgtctc cgggagctgc atgtgtcaga ggttttcacc gtcatcaccg aaacgcgcga    1260
ggcagcttga agacgaaagg gcctcgtgat acgcctattt ttataggtta atgtcatgat    1320
aataatggtt tcttagacgt caggtggcac ttttcgggga atgtgcgcg  gaacccctat    1380
```

```
ttgtttattt ttctaaatac attcaaatat gtatccgctc atgagacaat aaccctgata   1440
aatgcttcaa taatattgaa aaaggaagag tatgagtatt caacatttcc gtgtcgccct   1500
tattcccttt tttgcggcat tttgccttcc tgttttgct cacccagaaa cgctggtgaa    1560
agtaaaagat gctgaagatc agttgggtgc acgagtgggt tacatcgaac tggatctcaa   1620
cagcggtaag atccttgaga gttttcgccc cgaagaacgt tttccaatga tgagcacttt   1680
taaagttctg ctatgtggcg cggtattatc ccgtattgac gccgggcaag agcaactcgg   1740
tcgccgcata cactattctc agaatgactt ggttgagtac tcaccagtca cagaaaagca   1800
tcttacggat ggcatgacag taagagaatt atgcagtgct gccataacca tgagtgataa   1860
cactgcggcc aacttacttc tgacaacgat cggaggaccg aaggagctaa ccgcttttt    1920 gcacaacatg ggggatcatg taactcgcct tgatcgttgg gaaccggagc tgaatgaagc   1980
cataccaaac gacgagcgtg acaccacgat gcctgtagca atggcaacaa cgttgcgcaa   2040
actattaact ggcgaactac ttactctagc ttcccggcaa caattaatag actggatgga   2100
ggcggataaa gttgcaggac cacttctgcg ctcggccctt ccggctggct ggtttattgc   2160
tgataaatct ggagccggtg agcgtgggtc tcgcggtatc attgcagcac tggggccaga   2220
tggtaagccc tcccgtatcg tagttatcta cacgacgggg agtcaggcaa ctatggatga   2280
acgaaataga cagatcgctg agataggtgc ctcactgatt aagcattggt aactgtcaga   2340
ccaagtttac tcatatatac tttagattga tttaaaactt catttttaat ttaaaaggat   2400
ctaggtgaag atccttttg ataatctcat gaccaaaatc ccttaacgtg agttttcgtt    2460
ccactgagcg tcagaccccg tagaaaagat caaaggatct tcttgagatc cttttttct    2520 gcgcgtaatc tgctgcttgc aaacaaaaaa accaccgcta ccagcggtgg tttgtttgcc   2580
ggatcaagag ctaccaactc ttttccgaa ggtaactggc ttcagcagag cgcagatacc     2640
aaatactgtc cttctagtgt agccgtagtt aggccaccac ttcaagaact ctgtagcacc   2700
gcctacatac ctcgctctgc taatcctgtt accagtggct gctgccagtg gcgataagtc   2760
gtgtcttacc gggttggact caagacgata gttaccggat aaggcgcagc ggtcgggctg   2820
aacggggggt tcgtgcacac agcccagctt ggagcgaacg acctacaccg aactgagata   2880
cctacagcgc gagcattgag aaagcgccac gcttcccgaa gggagaaagg cggacaggta   2940
tccggtaagc ggcagggtcg aacaggaga gcgcacgagg gagcttccag ggggaaacgc    3000
ctggtatctt tatagtcctg tcgggtttcg ccacctctga cttgagcgtc gattttgtg    3060 atgctcgtca ggggggcgga gcctatggaa aaacgccagc aacgcggcct ttttacggtt   3120
cctggccttt tgctggcctt tgctcacat gttctttcct gcgttatccc ctgattctgt    3180
ggataaccgt attaccgcct ttgagtgagc tgataccgct cgccgcagcc gaacgaccga   3240
gcgcagcgag tcagtgagcg aggaagcgga agagcgccca atacgcaaac cgcctctccc   3300
cgcgcgttgg ccgattcatt aatgcagctg tggtgtcatg gtcggtgatc gccagggtgc   3360
cgacgcgcat ctcgactgca tggtgcacca atgcttctgg cgtcaggcag ccatcggaag   3420
ctgtggtatg gccgtgcagg tcgtaaatca ctgcataatt cgtgtcgctc aaggcgcact   3480
cccgttctgg ataatgtttt ttgcgccgac atcataacgg ttctggcaaa tattctgaaa   3540
tgagctgttg acaattaatc atcgaactag ttaactagta cgcaagttca cgtaaaaagg   3600
gtatcgcgga att                                                      3613
```

<210> SEQ ID NO 115

```
<211> LENGTH: 57
<212> TYPE: DNA
<213> ORGANISM: Artificial Sequence
<220> FEATURE:
<223> OTHER INFORMATION: Putative ribosomal binding site in pAP283-58

<400> SEQUENCE: 115
tctagaattt tctgcgcacc catcccgggt ggcgcccaaa gtgaggaaaa tcacatg      57

<210> SEQ ID NO 116
<211> LENGTH: 35
<212> TYPE: DNA
<213> ORGANISM: Artificial Sequence
<220> FEATURE:
<223> OTHER INFORMATION: Shine Dalgarno sequence in pQb185

<400> SEQUENCE: 116
tctagattaa cccaacgcgt aggagtcagg ccatg                              35

<210> SEQ ID NO 117
<211> LENGTH: 5
<212> TYPE: PRT
<213> ORGANISM: Artificial Sequence
<220> FEATURE:
<223> OTHER INFORMATION: Peptide sequence used to mediate binding of
      RANKL protein

<400> SEQUENCE: 117

Gly Gly Lys Gly Gly
1               5

<210> SEQ ID NO 118
<211> LENGTH: 9
<212> TYPE: PRT
<213> ORGANISM: Artificial Sequence
<220> FEATURE:
<223> OTHER INFORMATION: Linker peptide
<220> FEATURE:
<221> NAME/KEY: REPEAT
<222> LOCATION: (1)..(1)
<223> OTHER INFORMATION: May be repeated 0 to 5 times
<220> FEATURE:
<221> NAME/KEY: REPEAT
<222> LOCATION: (3)..(3)
<223> OTHER INFORMATION: May be repeated 0 to 10 times
<220> FEATURE:
<221> NAME/KEY: REPEAT
<222> LOCATION: (4)..(4)
<223> OTHER INFORMATION: May be repeated 0 to 2 times
<220> FEATURE:
<221> NAME/KEY: REPEAT
<222> LOCATION: (5)..(9)
<223> OTHER INFORMATION: May be repeated 0 to 3 times

<400> SEQUENCE: 118

Gly Cys Gly Ser Gly Gly Gly Gly Ser
1               5

<210> SEQ ID NO 119
<211> LENGTH: 10
<212> TYPE: PRT
<213> ORGANISM: Artificial Sequence
<220> FEATURE:
<223> OTHER INFORMATION: Linker peptide
<220> FEATURE:
<221> NAME/KEY: REPEAT
<222> LOCATION: (1)..(1)
<223> OTHER INFORMATION: May be repeated 0-10 times
<220> FEATURE:
<221> NAME/KEY: REPEAT
<222> LOCATION: (2)..(2)
```

```
<223> OTHER INFORMATION: May be repeated 0-2 times
<220> FEATURE:
<221> NAME/KEY: REPEAT
<222> LOCATION: (3)..(7)
<223> OTHER INFORMATION: May be repeated 0-3 times
<220> FEATURE:
<221> NAME/KEY: REPEAT
<222> LOCATION: (8)..(8)
<223> OTHER INFORMATION: May be repeated 0-8 times
<220> FEATURE:
<221> NAME/KEY: REPEAT
<222> LOCATION: (10)..(10)
<223> OTHER INFORMATION: May be repeated 0-5 times

<400> SEQUENCE: 119

Gly Ser Gly Gly Gly Gly Ser Gly Cys Gly
1               5                   10

<210> SEQ ID NO 120
<211> LENGTH: 5
<212> TYPE: PRT
<213> ORGANISM: Artificial Sequence
<220> FEATURE:
<223> OTHER INFORMATION: Glycine serine linker
<220> FEATURE:
<221> NAME/KEY: REPEAT
<222> LOCATION: (1)..(5)
<223> OTHER INFORMATION: May be repeated

<400> SEQUENCE: 120

Gly Gly Gly Gly Ser
1               5

<210> SEQ ID NO 121
<211> LENGTH: 10
<212> TYPE: PRT
<213> ORGANISM: Artificial Sequence
<220> FEATURE:
<223> OTHER INFORMATION: N-terminal gamma 1 amino acid linker

<400> SEQUENCE: 121

Cys Gly Asp Lys Thr His Thr Ser Pro Pro
1               5                   10

<210> SEQ ID NO 122
<211> LENGTH: 10
<212> TYPE: PRT
<213> ORGANISM: Artificial Sequence
<220> FEATURE:
<223> OTHER INFORMATION: C-terminal  gamma 1 amino acid linker

<400> SEQUENCE: 122

Asp Lys Thr His Thr Ser Pro Pro Cys Gly
1               5                   10

<210> SEQ ID NO 123
<211> LENGTH: 17
<212> TYPE: PRT
<213> ORGANISM: Artificial Sequence
<220> FEATURE:
<223> OTHER INFORMATION: N-terminal gamma 3 amino acid linker

<400> SEQUENCE: 123

Cys Gly Gly Pro Lys Pro Ser Thr Pro Pro Gly Ser Ser Gly Gly Ala
1               5                   10                  15

Pro

<210> SEQ ID NO 124
```

```
<211> LENGTH: 18
<212> TYPE: PRT
<213> ORGANISM: Artificial Sequence
<220> FEATURE:
<223> OTHER INFORMATION: C-terminal gamma 3 amino acid linker

<400> SEQUENCE: 124

Pro Lys Pro Ser Thr Pro Pro Gly Ser Ser Gly Gly Ala Pro Gly Gly
1               5                   10                  15

Cys Gly

<210> SEQ ID NO 125
<211> LENGTH: 6
<212> TYPE: PRT
<213> ORGANISM: Artificial Sequence
<220> FEATURE:
<223> OTHER INFORMATION: N-terminal glycine linker

<400> SEQUENCE: 125

Gly Cys Gly Gly Gly Gly
1               5

<210> SEQ ID NO 126
<211> LENGTH: 6
<212> TYPE: PRT
<213> ORGANISM: Artificial Sequence
<220> FEATURE:
<223> OTHER INFORMATION: C-terminal glycine linker

<400> SEQUENCE: 126

Gly Gly Gly Gly Cys Gly
1               5

<210> SEQ ID NO 127
<211> LENGTH: 6
<212> TYPE: PRT
<213> ORGANISM: Artificial Sequence
<220> FEATURE:
<223> OTHER INFORMATION: C-terminal glycine-lysine linker

<400> SEQUENCE: 127

Gly Gly Lys Lys Gly Cys
1               5

<210> SEQ ID NO 128
<211> LENGTH: 6
<212> TYPE: PRT
<213> ORGANISM: Artificial Sequence
<220> FEATURE:
<223> OTHER INFORMATION: N-terminal glycine-lysine linker

<400> SEQUENCE: 128

Cys Gly Lys Lys Gly Gly
1               5

<210> SEQ ID NO 129
<211> LENGTH: 37
<212> TYPE: DNA
<213> ORGANISM: Artificial Sequence
<220> FEATURE:
<223> OTHER INFORMATION: Oligonucleotide inverse PCR primer

<400> SEQUENCE: 129
ggtaacatcg gtcgagatgg aaaacaaact ctggtcc                        37

<210> SEQ ID NO 130
```

```
<211> LENGTH: 37
<212> TYPE: DNA
<213> ORGANISM: Artificial Sequence
<220> FEATURE:
<223> OTHER INFORMATION: Oligonucleotide inverse PCR primer

<400> SEQUENCE: 130
ggaccagagt ttgttttcca tctcgaccga tgttacc                    37

<210> SEQ ID NO 131
<211> LENGTH: 22
<212> TYPE: DNA
<213> ORGANISM: Artificial Sequence
<220> FEATURE:
<223> OTHER INFORMATION: Oligonucleotide PCR primer

<400> SEQUENCE: 131
agctcgcccg gggatcctct ag                                    22

<210> SEQ ID NO 132
<211> LENGTH: 40
<212> TYPE: DNA
<213> ORGANISM: Artificial Sequence
<220> FEATURE:
<223> OTHER INFORMATION: Oligonucleotide PCR primer

<400> SEQUENCE: 132
cgatgcattt catccttagt tatcaatacg ctgggttcag                 40

<210> SEQ ID NO 133
<211> LENGTH: 36
<212> TYPE: DNA
<213> ORGANISM: Artificial Sequence
<220> FEATURE:
<223> OTHER INFORMATION: Oligonucleotide inverse PCR primer

<400> SEQUENCE: 133
ggcaaaatta gagactgtta ctttaggtaa gatcgg                     36

<210> SEQ ID NO 134
<211> LENGTH: 36
<212> TYPE: DNA
<213> ORGANISM: Artificial Sequence
<220> FEATURE:
<223> OTHER INFORMATION: Oligonucleotide inverse PCR primer

<400> SEQUENCE: 134
ccgatcttac ctaaagtaac agtctctaat tttgcc                     36

<210> SEQ ID NO 135
<211> LENGTH: 22
<212> TYPE: DNA
<213> ORGANISM: Artificial Sequence
<220> FEATURE:
<223> OTHER INFORMATION: Oligonucleotide PCR primer

<400> SEQUENCE: 135
agctcgcccg gggatcctct ag                                    22

<210> SEQ ID NO 136
<211> LENGTH: 40
<212> TYPE: DNA
<213> ORGANISM: Artificial Sequence
<220> FEATURE:
<223> OTHER INFORMATION: Oligonucleotide PCR primer

<400> SEQUENCE: 136
```
cgatgcattt catccttagt tatcaatacg ctgggttcag                             40

<210> SEQ ID NO 137
<211> LENGTH: 33
<212> TYPE: DNA
<213> ORGANISM: Artificial Sequence
<220> FEATURE:
<223> OTHER INFORMATION: Site-directed mutagenesis oligonucleotide

<400> SEQUENCE: 137
ggccatggca cgactcgaga ctgttacttt agg                                    33

<210> SEQ ID NO 138
<211> LENGTH: 19
<212> TYPE: DNA
<213> ORGANISM: Artificial Sequence
<220> FEATURE:
<223> OTHER INFORMATION: Site-directed mutagenesis oligonucleotide

<400> SEQUENCE: 138
gatttaggtg acactatag                                                    19

<210> SEQ ID NO 139
<211> LENGTH: 37
<212> TYPE: DNA
<213> ORGANISM: Artificial Sequence
<220> FEATURE:
<223> OTHER INFORMATION: Oligonucleotide inverse PCR primer

<400> SEQUENCE: 139
gatggacgtc aaactctggt cctcaatccg cgtgggg                                37

<210> SEQ ID NO 140
<211> LENGTH: 37
<212> TYPE: DNA
<213> ORGANISM: Artificial Sequence
<220> FEATURE:
<223> OTHER INFORMATION: Oligonucleotide inverse PCR primer

<400> SEQUENCE: 140
ccccacgcgg attgaggacc agagtttgac gtccatc                                37

<210> SEQ ID NO 141
<211> LENGTH: 22
<212> TYPE: DNA
<213> ORGANISM: Artificial Sequence
<220> FEATURE:
<223> OTHER INFORMATION: Oligonucleotide PCR primer

<400> SEQUENCE: 141
agctcgcccg gggatcctct ag                                                22

<210> SEQ ID NO 142
<211> LENGTH: 40
<212> TYPE: DNA
<213> ORGANISM: Artificial Sequence
<220> FEATURE:
<223> OTHER INFORMATION: Oligonucleotide PCR primer

<400> SEQUENCE: 142
cgatgcattt catccttagt tatcaatacg ctgggttcag                             40

<210> SEQ ID NO 143
<211> LENGTH: 33
<212> TYPE: DNA

```
<213> ORGANISM: Artificial Sequence
<220> FEATURE:
<223> OTHER INFORMATION: Site-directed mutagenesis oligonucleotide
      primer

<400> SEQUENCE: 143
ggccatggca cgactcgaga ctgttacttt agg                             33

<210> SEQ ID NO 144
<211> LENGTH: 19
<212> TYPE: DNA
<213> ORGANISM: Artificial Sequence
<220> FEATURE:
<223> OTHER INFORMATION: Site-directed mutagenesis oligonucleotide
      primer

<400> SEQUENCE: 144
gatttaggtg acactatag                                              19

<210> SEQ ID NO 145
<211> LENGTH: 31
<212> TYPE: DNA
<213> ORGANISM: Artificial Sequence
<220> FEATURE:
<223> OTHER INFORMATION: EcoRIHBcAg(s) oligonucleotide primer

<400> SEQUENCE: 145
ccggaattca tggacattga cccttataaa g                                31

<210> SEQ ID NO 146
<211> LENGTH: 51
<212> TYPE: DNA
<213> ORGANISM: Artificial Sequence
<220> FEATURE:
<223> OTHER INFORMATION: Lys-HBcAg(as) oligonucleotide primer

<400> SEQUENCE: 146
cctagagcca cctttgccac catcttctaa attagtaccc acccaggtag c          51

<210> SEQ ID NO 147
<211> LENGTH: 48
<212> TYPE: DNA
<213> ORGANISM: Artificial Sequence
<220> FEATURE:
<223> OTHER INFORMATION: Lys-HBcAg(s) oligonucleotide primer

<400> SEQUENCE: 147
gaagatggtg gcaaaggtgg ctctagggac ctagtagtca gttatgtc              48

<210> SEQ ID NO 148
<211> LENGTH: 38
<212> TYPE: DNA
<213> ORGANISM: Artificial Sequence
<220> FEATURE:
<223> OTHER INFORMATION: HBcAg(1-149)Hind(as) oligonucleotide primer

<400> SEQUENCE: 148
cgcgtcccaa gcttctaaac aacagtagtc tccggaag                         38

<210> SEQ ID NO 149
<211> LENGTH: 37
<212> TYPE: DNA
<213> ORGANISM: Artificial Sequence
<220> FEATURE:
<223> OTHER INFORMATION: 48as oligonucleotide primer

<400> SEQUENCE: 149
```

```
gtgcagtatg gtgaggtgag gaatgctcag gagactc                              37

<210> SEQ ID NO 150
<211> LENGTH: 37
<212> TYPE: DNA
<213> ORGANISM: Artificial Sequence
<220> FEATURE:
<223> OTHER INFORMATION: 48s oligonucleotide primer

<400> SEQUENCE: 150
gsgtctcctg agcattcctc acctcaccat actgcac                              37

<210> SEQ ID NO 151
<211> LENGTH: 33
<212> TYPE: DNA
<213> ORGANISM: Artificial Sequence
<220> FEATURE:
<223> OTHER INFORMATION: 107as oligonucleotide primer

<400> SEQUENCE: 151
cttccaaaag tgagggaaga aatgtgaaac cac                                  33

<210> SEQ ID NO 152
<211> LENGTH: 47
<212> TYPE: DNA
<213> ORGANISM: Artificial Sequence
<220> FEATURE:
<223> OTHER INFORMATION: HBcAg149hind-as oligonucleotide primer

<400> SEQUENCE: 152
cgcgtcccaa gcttctaaac aacagtagtc tccggaagcg ttgatag                   47

<210> SEQ ID NO 153
<211> LENGTH: 33
<212> TYPE: DNA
<213> ORGANISM: Artificial Sequence
<220> FEATURE:
<223> OTHER INFORMATION: 107s oligonucleotide primer

<400> SEQUENCE: 153
gtggtttcac atttcttccc tcacttttgg aag                                  33

<210> SEQ ID NO 154
<211> LENGTH: 38
<212> TYPE: DNA
<213> ORGANISM: Artificial Sequence
<220> FEATURE:
<223> OTHER INFORMATION: HBcAgwtHindIIII oligonucleotide primer

<400> SEQUENCE: 154
cgcgtcccaa gcttctaaca ttgagattcc cgagattg                             38

<210> SEQ ID NO 155
<211> LENGTH: 10
<212> TYPE: PRT
<213> ORGANISM: Artificial Sequence
<220> FEATURE:
<223> OTHER INFORMATION: C-epsilon H3 epitope

<400> SEQUENCE: 155

Val Asn Leu Thr Trp Ser Arg Ala Ser Gly
1               5                   10

<210> SEQ ID NO 156
<211> LENGTH: 51
```

```
<212> TYPE: DNA
<213> ORGANISM: Artificial Sequence
<220> FEATURE:
<223> OTHER INFORMATION: C-epsilon H3fwd oligonucleotide primer

<400> SEQUENCE: 156
gttaacttga cctggtctcg tgcttctggt gcatccaggg atctagtagt c          51

<210> SEQ ID NO 157
<211> LENGTH: 17
<212> TYPE: PRT
<213> ORGANISM: Artificial Sequence
<220> FEATURE:
<223> OTHER INFORMATION: C-epsilon  H3fwd primer encoded amino acid
      sequence

<400> SEQUENCE: 157

Val Asn Leu Thr Trp Ser Arg Ala Ser Gly Ala Ser Arg Asp Leu Val
1               5                  10                  15
Val

<210> SEQ ID NO 158
<211> LENGTH: 51
<212> TYPE: DNA
<213> ORGANISM: Artificial Sequence
<220> FEATURE:
<223> OTHER INFORMATION: C-epsilon H3rev oligonucleotide primer

<400> SEQUENCE: 158
accagaagca cgagaccagg tcaagttaac atcttccaaa ttattaccca c          51

<210> SEQ ID NO 159
<211> LENGTH: 7
<212> TYPE: PRT
<213> ORGANISM: Artificial Sequence
<220> FEATURE:
<223> OTHER INFORMATION: C-epsilon H3rev oligonucleotide encoded peptide

<400> SEQUENCE: 159

Asp Glu Leu Asn Asn Gly Val
1               5

<210> SEQ ID NO 160
<211> LENGTH: 31
<212> TYPE: DNA
<213> ORGANISM: Artificial Sequence
<220> FEATURE:
<223> OTHER INFORMATION: HBcAg-wt EcoRI fwd oligonucleotide primer

<400> SEQUENCE: 160
ccggaattca tggacattga cccttataaa g                               31

<210> SEQ ID NO 161
<211> LENGTH: 38
<212> TYPE: DNA
<213> ORGANISM: Artificial Sequence
<220> FEATURE:
<223> OTHER INFORMATION: HBcAg-wt Hind III rev oligonucleotide primer

<400> SEQUENCE: 161
cgcgtcccaa gcttctaaca ttgagattcc cgagattg                        38

<210> SEQ ID NO 162
<211> LENGTH: 8
<212> TYPE: PRT
<213> ORGANISM: Artificial Sequence
```

```
<220> FEATURE:
<223> OTHER INFORMATION: RANKL epitope

<400> SEQUENCE: 162

Ser Ile Lys Ile Pro Ser Ser His
1               5

<210> SEQ ID NO 163
<211> LENGTH: 62
<212> TYPE: DNA
<213> ORGANISM: Artificial Sequence
<220> FEATURE:
<223> OTHER INFORMATION: RANKL-UP oligonucleotide primer

<400> SEQUENCE: 163
ctgccagggg cccgggtgcg gcggtggcca tcatcaccac catcaccagc gcttctcagg      60
ag                                                                    62

<210> SEQ ID NO 164
<211> LENGTH: 35
<212> TYPE: DNA
<213> ORGANISM: Artificial Sequence
<220> FEATURE:
<223> OTHER INFORMATION: RANKL-DOWN oligonucleotide primer

<400> SEQUENCE: 164
ccgctcgagt tagtctatgt cctgaacttt gaaag                                 35

<210> SEQ ID NO 165
<211> LENGTH: 7
<212> TYPE: PRT
<213> ORGANISM: Artificial Sequence
<220> FEATURE:
<223> OTHER INFORMATION: Cysteine-containing amno acid linker

<400> SEQUENCE: 165

Gly Pro Gly Cys Gly Gly Gly
1               5

<210> SEQ ID NO 166
<211> LENGTH: 74
<212> TYPE: DNA
<213> ORGANISM: Artificial Sequence
<220> FEATURE:
<223> OTHER INFORMATION: pMod00 MCS

<400> SEQUENCE: 166
gtttaacttt aagaaggaga tatacatatg gatccggcta gcgctcgagg gtttaaacgg      60
cggccgcatg cacc                                                       74

<210> SEQ ID NO 167
<211> LENGTH: 33
<212> TYPE: DNA
<213> ORGANISM: Artificial Sequence
<220> FEATURE:
<223> OTHER INFORMATION: GST-UP oligonucleotide primer

<400> SEQUENCE: 167
atatatggat cctatactag gttattggaa aat                                  33

<210> SEQ ID NO 168
<211> LENGTH: 27
<212> TYPE: DNA
<213> ORGANISM: Artificial Sequence
<220> FEATURE:
```

-continued

```
<223> OTHER INFORMATION: GST-EK oligonucleotide primer

<400> SEQUENCE: 168
atatatgcta gcttatcgtc atcgtcg                                          27

<210> SEQ ID NO 169
<211> LENGTH: 35
<212> TYPE: DNA
<213> ORGANISM: Artificial Sequence
<220> FEATURE:
<223> OTHER INFORMATION: mRANKL-1 oligonucleotide primer

<400> SEQUENCE: 169
atatatgcta gcaaagcctg aggcccagcc atttg                                 35

<210> SEQ ID NO 170
<211> LENGTH: 35
<212> TYPE: DNA
<213> ORGANISM: Artificial Sequence
<220> FEATURE:
<223> OTHER INFORMATION: mRANKL-2 oligonucleotide primer

<400> SEQUENCE: 170
atatatctcg aggtctatgt cctgaacttt gaaag                                 35
```